(12) United States Patent
Fleckenstein et al.

(10) Patent No.: US 7,339,030 B2
(45) Date of Patent: Mar. 4, 2008

(54) HUMAN SEMAPHORIN L (H-SEMAL) AND CORRESPONDING SEMAPHORINS IN OTHER SPECIES

(75) Inventors: Bernhard Fleckenstein, Wiesenthau (DE); Armin Ensser, Nürnberg (DE)

(73) Assignee: Sanofi-Aventis Deutschland GmbH

( * ) Notice: Subject to any disclaimer, the term of this patent is extended or adjusted under 35 U.S.C. 154(b) by 27 days.

(21) Appl. No.: 10/933,746

(22) Filed: Sep. 3, 2004

(65) Prior Publication Data

US 2006/0029998 A1 Feb. 9, 2006

Related U.S. Application Data

(63) Continuation of application No. 09/836,077, filed on Apr. 16, 2001, now abandoned, which is a continuation of application No. 09/112,904, filed on Jul. 9, 1998, now abandoned.

(30) Foreign Application Priority Data

| Jul. 9, 1997 | (DE) | ................................. 197 29 211 |
| Feb. 11, 1998 | (DE) | ................................. 198 05 371 |

(51) Int. Cl.
*A61K 38/16* (2006.01)
*C07K 14/00* (2006.01)

(52) U.S. Cl. .......................................... 530/350; 514/2
(58) Field of Classification Search ................ 530/350
See application file for complete search history.

(56) References Cited

U.S. PATENT DOCUMENTS

| 5,416,197 | A | * | 5/1995 | Raper ......................... 530/387 |
| 5,639,856 | A | | 6/1997 | Goodman et al. |
| 5,807,826 | A | | 9/1998 | Goodman et al. |
| 5,935,865 | A | | 8/1999 | Goodman et al. |
| 6,225,285 | B1 | * | 5/2001 | Luo et al. ...................... 514/12 |
| 6,670,135 | B1 | * | 12/2003 | Spriggs ....................... 435/7.1 |

FOREIGN PATENT DOCUMENTS

| WO | WO 95/07706 | 3/1995 |
| WO | WO 99/38885 | 8/1999 |
| WO | WO 99/45114 | 9/1999 |
| WO | WO 99/58676 | 11/1999 |
| WO | 01/77137 | * 10/2001 |

OTHER PUBLICATIONS

Skolnick et al. Trends in Biotech., 18(1):34-39, 2000.*
Pushel et al. Neuron, 14, 941-948, 1995.*
Applied Cytogenetics 21 (6), 1995 entitled "Direct Preparation of Uncultured EDTA-Treated or Heparinized Blood for Interphase FISH Analysis", by Liehr et al., pp. 185-188.
Adams et al. (1996) Mech. Dev. 57: 33-45.
Altschul et al. (1990) J. Mol. Biol. 215, 403-410.
Comeau et al. (1998) Immunity, vol. 8, 473-482.
Ensser et al (1997), J. of Virol. 71: 6517-6525.
Ensser u. Flechenstein (1995), J. General Virol. 76: 1063-1067.
Feinberg (1983) Anal. Biochem. 132: 6-13.
Furuyama et al. (1996) J. Biol. Chem. 271: 33376-33381.
Galtier et al. (1996) Comput. Appl. Biosci 12, 543-548.
Giger et al. (1996) J. Comp. Neurol. 375: 378-392.
Gish und States (1993) Nat. Genet. 3, 266-272.
Goshima et al. (1995) Nature 376: 509-514.
Hall et al. (1996) Proc. Natl. Acad. Sci. USA 39: 11780-11785.
Hamajima et al. (1996) Gene 180: 157-163.
Ingaki et al. (1995 FEBS Letters 370: 269-272.
Keyna et al. (1995) J. Imunol. 155, 5536-5542.
Kolodkin et al. (1993) Cell 75: 1389-1399.
Kraus et al. (1994) Genomics 23, 272-274.
Luo et al. (1995) Neuron 14: 1131-1140.
Messerschmidt et al. (1995) Neuron 14: 949-959.
Neilsen H. et al. (1997) Protein Engineering 10: 1-6.
Pearson und Lipman (1988) Proc. Natl. Acad. Sci. 85, 2444-2448.
Puschel et al. (1995) Neuron 14: 941-948.
Roche et al. (1996) Onkogene 12: 1289-1297.
Sekido et al. (1996) Proc.Natl. Acad. Sci. USA 93: 4120-4125.
Thompson J.D. et al. (1994) Nucleic Acids Res. 22: 4673-4680.
Wang et al. (1996) Neurosci, 16: 6197-6207.
Xiang et al. (1996) Genomics 32: 39-48.
The Journel of Biological Chemistry 273 (1988) by Xu et al, pp. 22428-22434.
Database EMBL Online Accession No. AF 176670, Sep. 7, 1999, XP002125535.
Database EMBL Online Accession No. AB017532, Mar. 15, 1999, XP002125536.
Database EMBL Online Accession No. A260340, Mar. 19, 1997, XP002125534.
Database EMBL Online Accession No. H03806, Jun. 22, 1995, XP002125533.
Xu, et al. (1998) J. Biological Chemistry, vol. 273, No. 35, pp. 22428-22434.
Essner et al. (1995) J. of General Virology, 76, pp. 1063-1067, XP002113888.
Lange et al. (1998) Genomics, 51, pp. 340-350, XP00213887.
Yamada et al. (1999) J. of Immunology, No. 162, pp. 4094-4100, XP002123609.

* cited by examiner

*Primary Examiner*—Michael Borin
(74) *Attorney, Agent, or Firm*—Frommer Lawrence & Haug LLP

(57) ABSTRACT

The invention relates to novel semaphorins which are distinguished by a particular domain structure and derivatives thereof, nucleic acids (DNA, RNA, cDNA) which code for these semaphorins, and derivatives thereof, and the use thereof.

The present invention relates to semaphorins which have a novel, as yet undisclosed and unexpected domain structure and which possess a biochemical function in the immune system (immunomodulating semaphorins). The novel semaphorins are referred to as type L semaphorins (SemaL). They comprise an N-terminal signal peptide, a characteristic Sema domain and, in the C-terminal region of the protein, an immunoglobulin-like domain and a hydrophobic domain which represents a potential transmembrane domain.

4 Claims, 18 Drawing Sheets

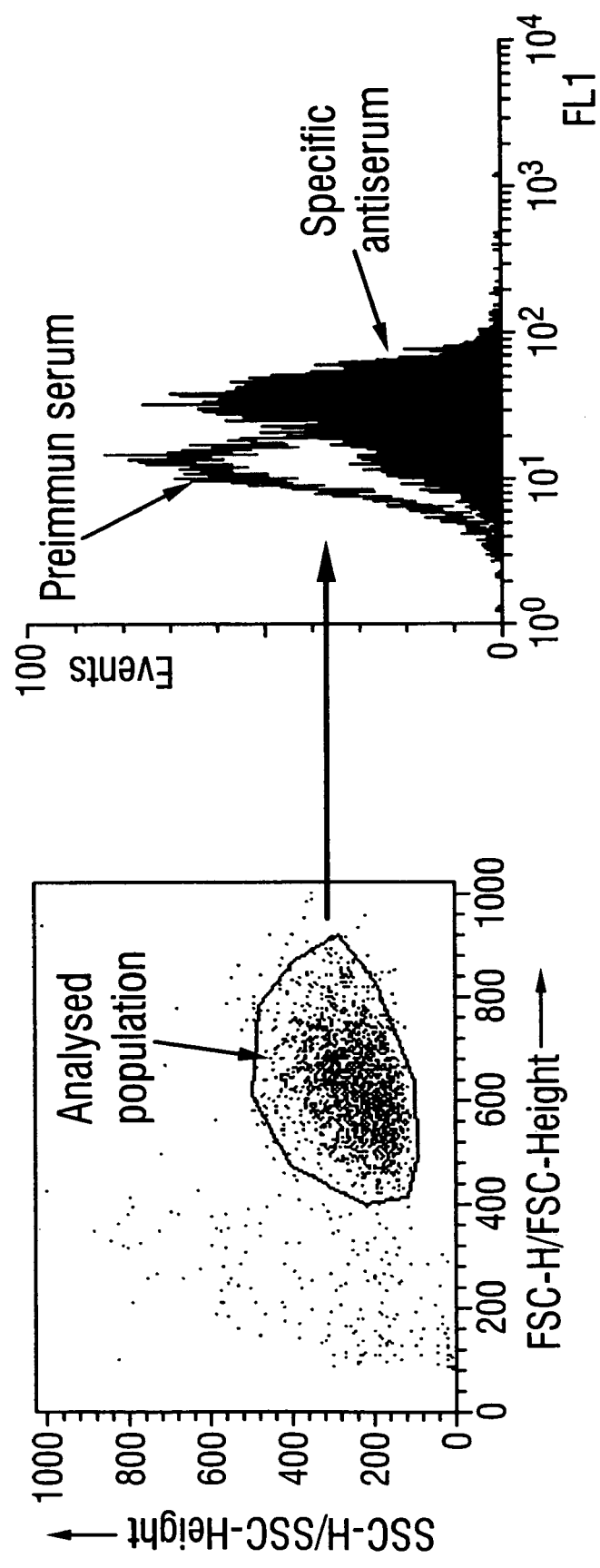
Fig. 4a (U937)

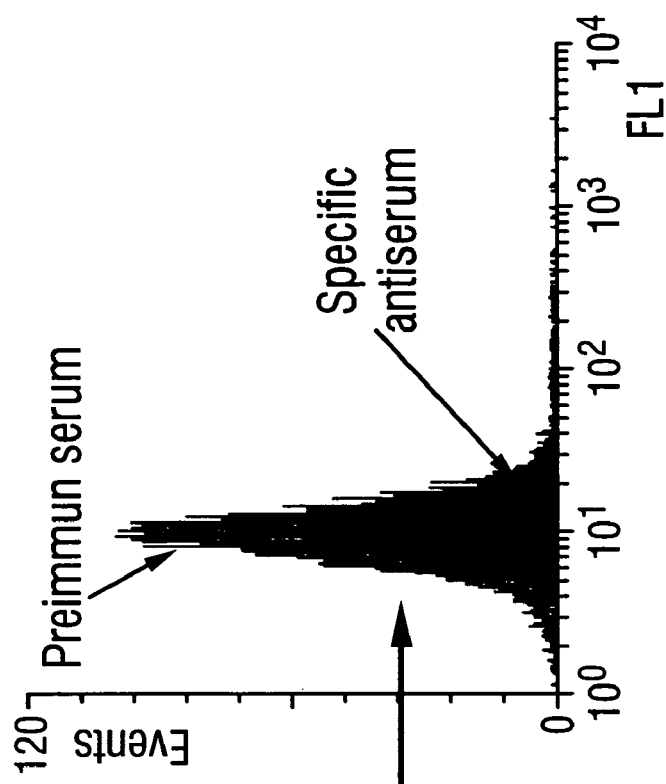
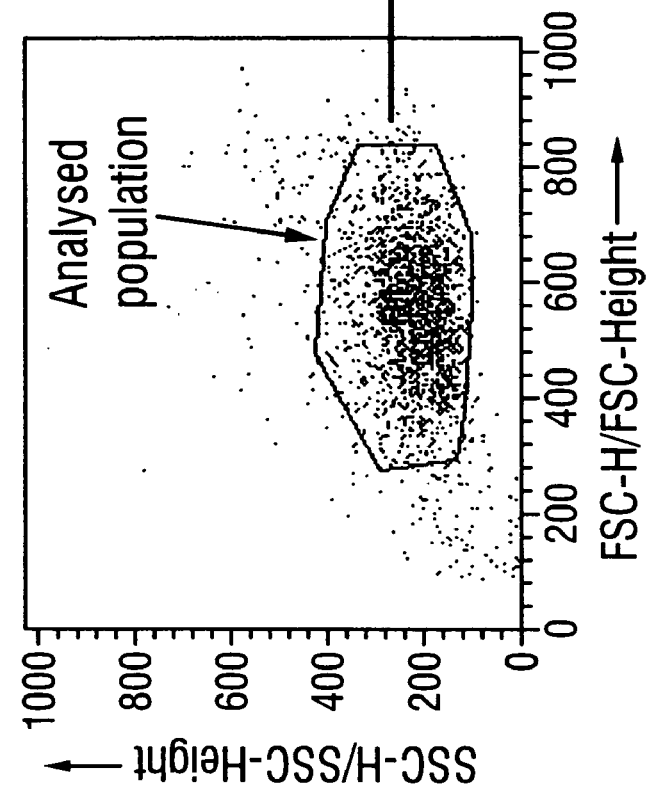
Fig. 4b (THP-1)

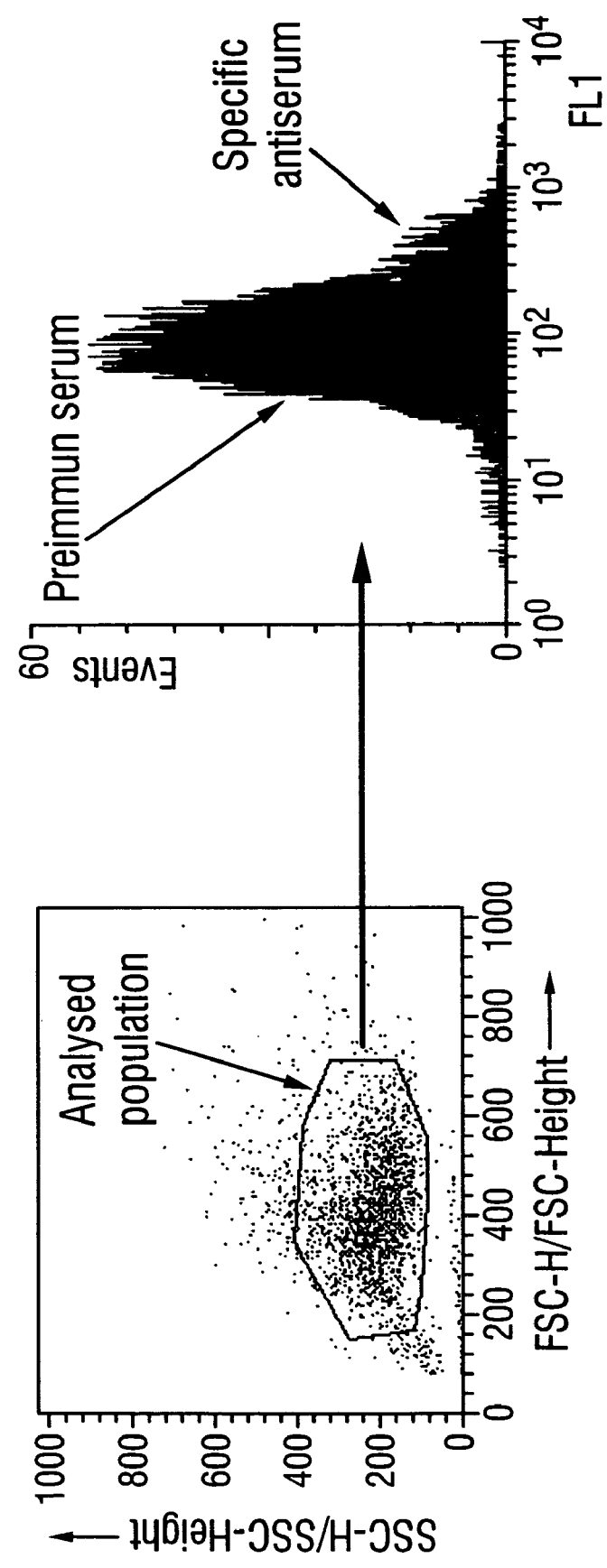
Fig. 4c (K562)

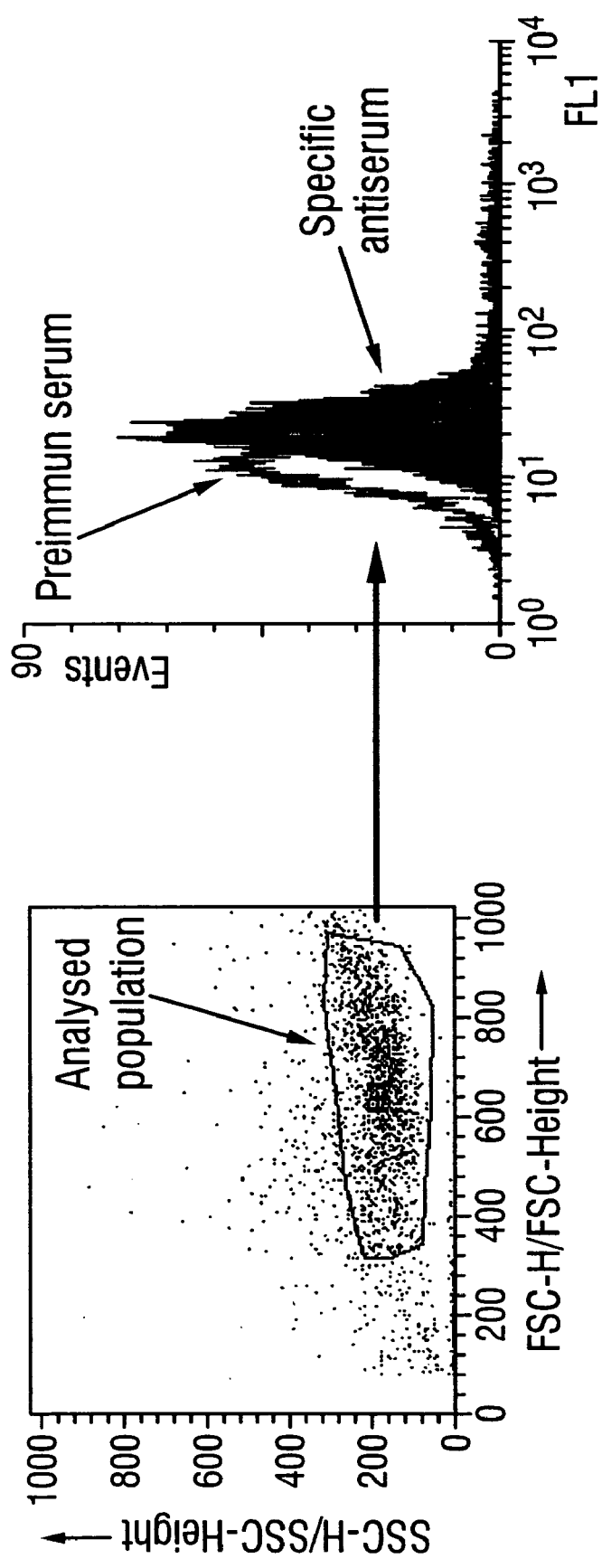
Fig. 4d (L-428)

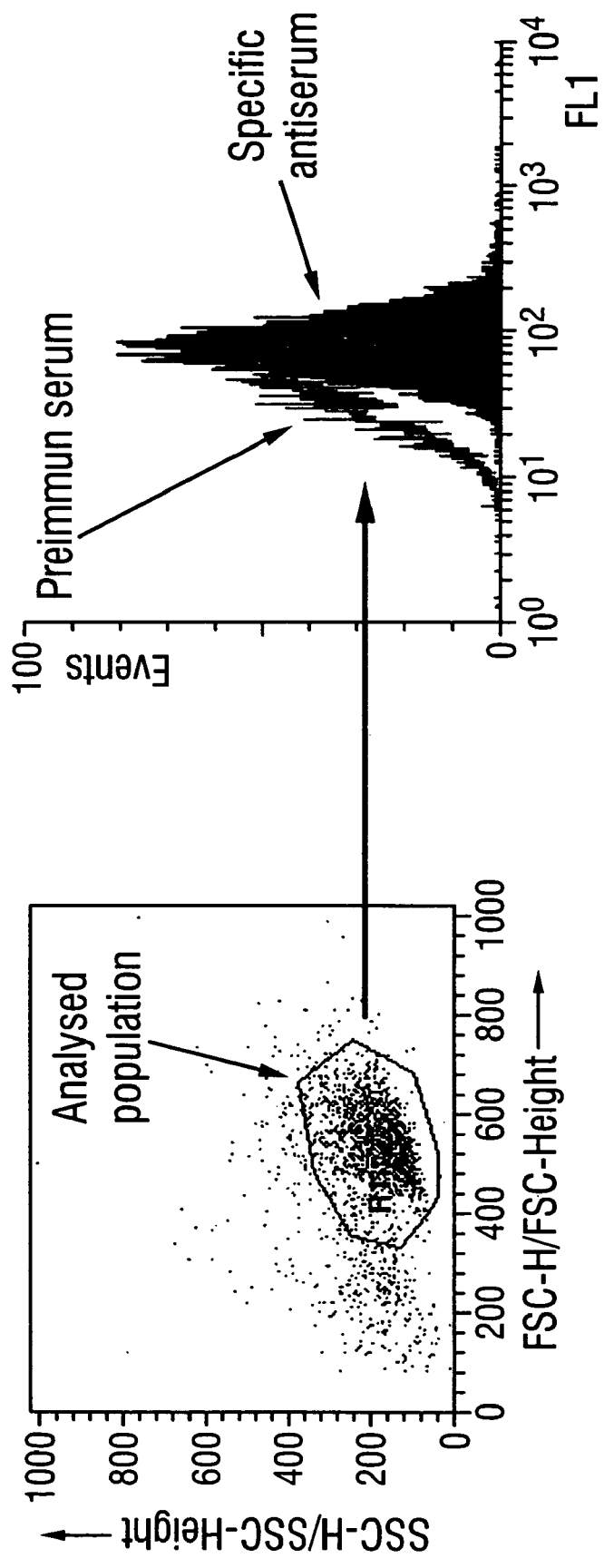
Fig. 4e (Jurkat)

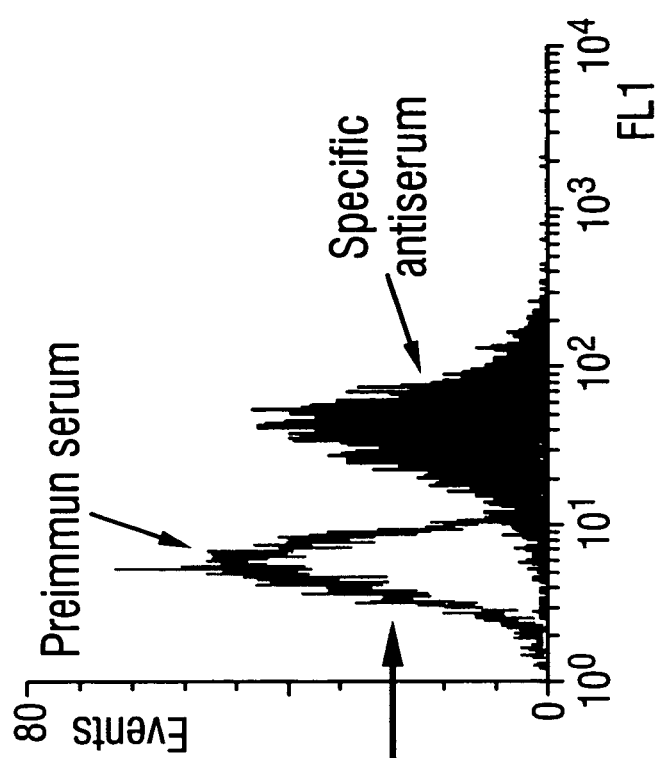
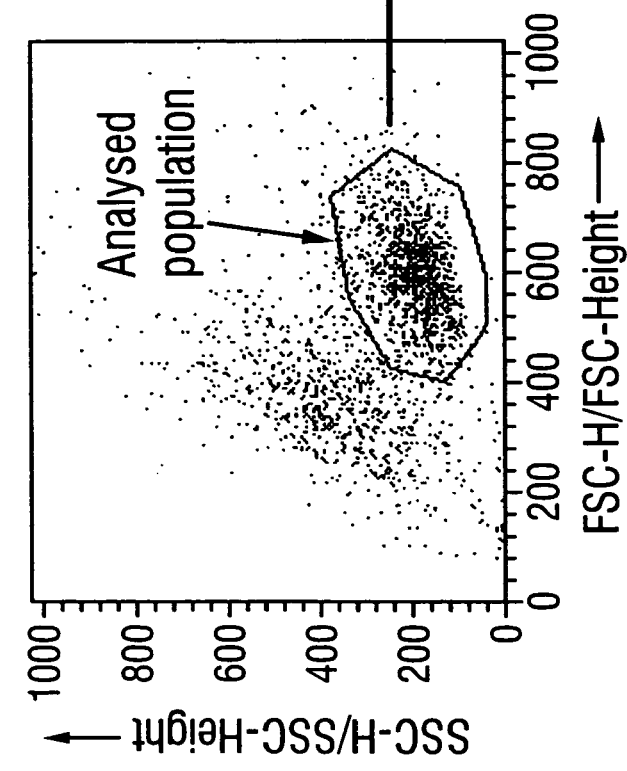
Fig. 4f (Daudi)

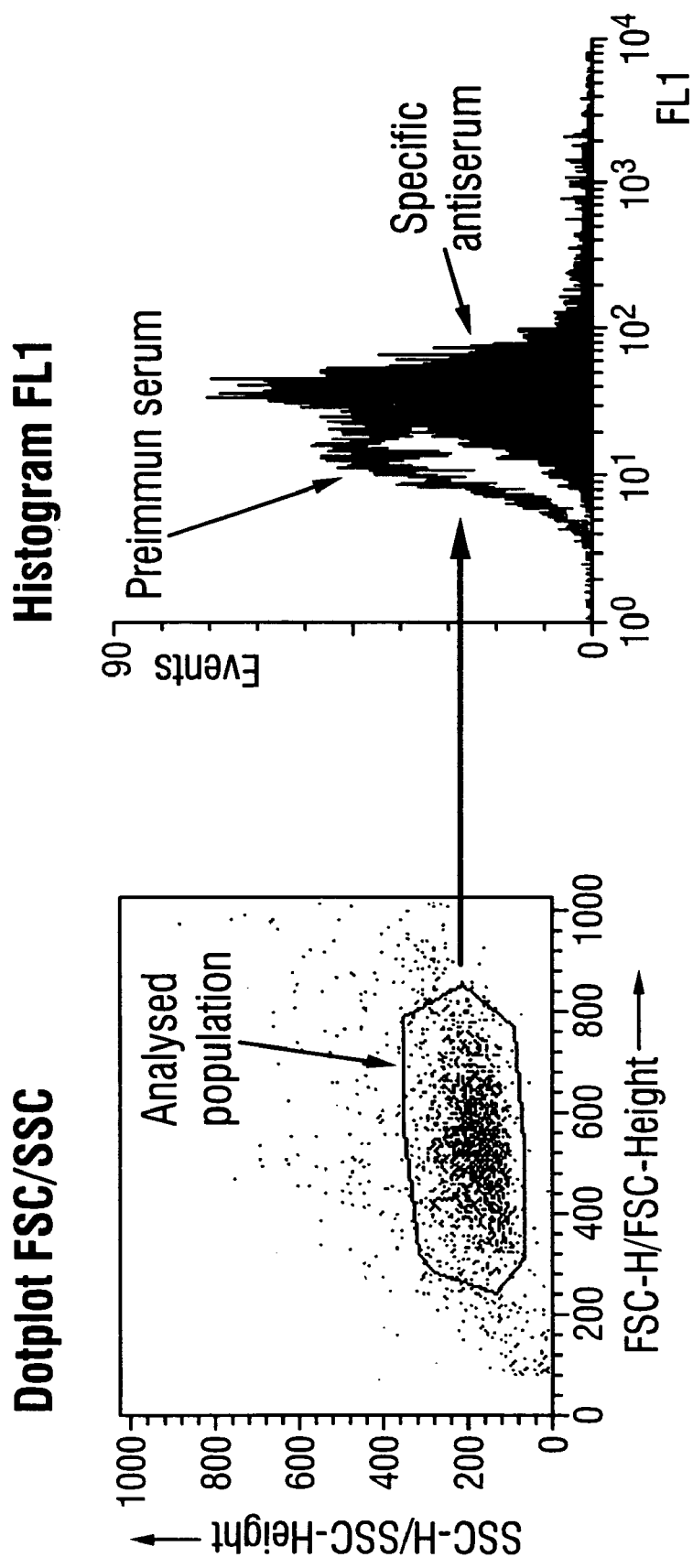
Fig. 4g (LCL EBV-Transformed B-cells)

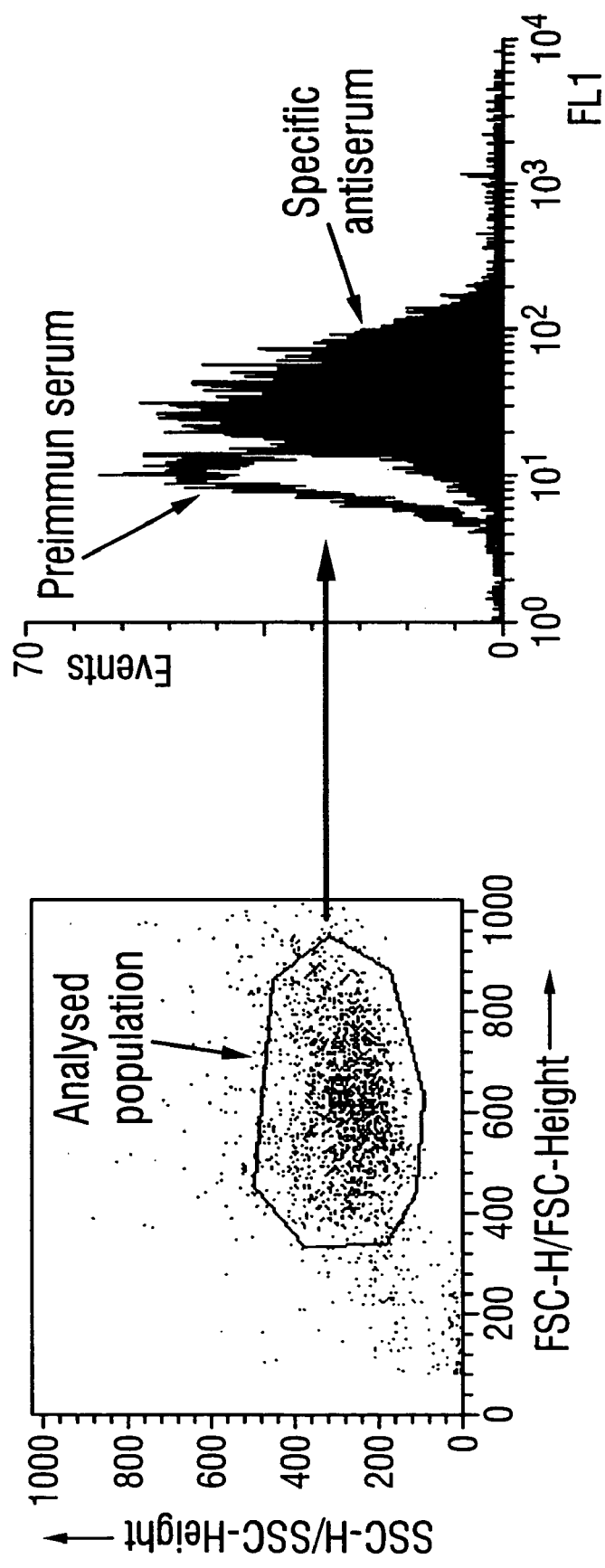
Fig. 4h (Jiyoye)

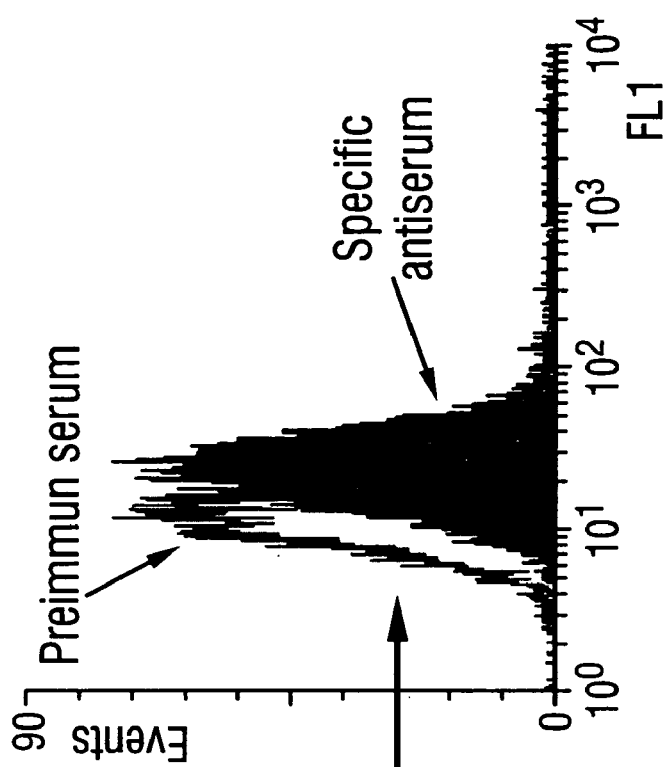
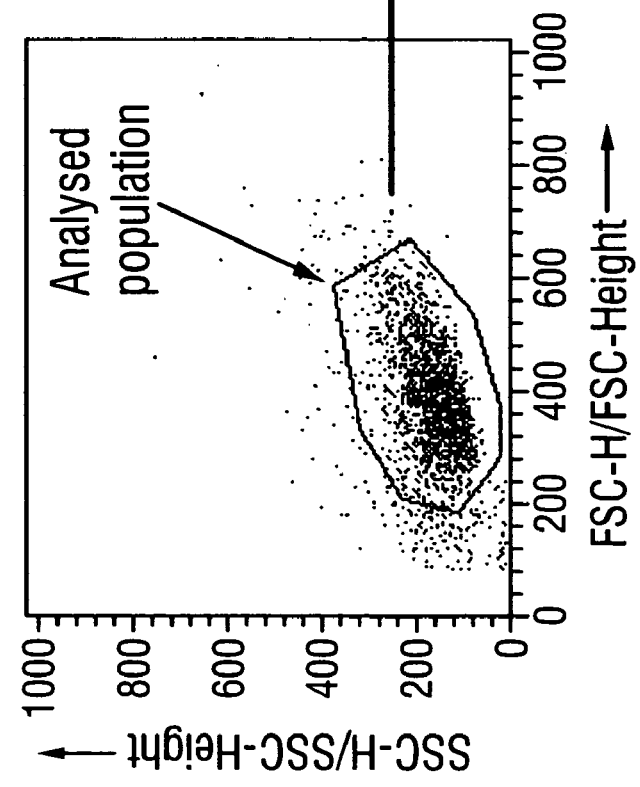
Fig. 4i (CBL-Mix57)

Fig. 4k (CBL-Mix59)
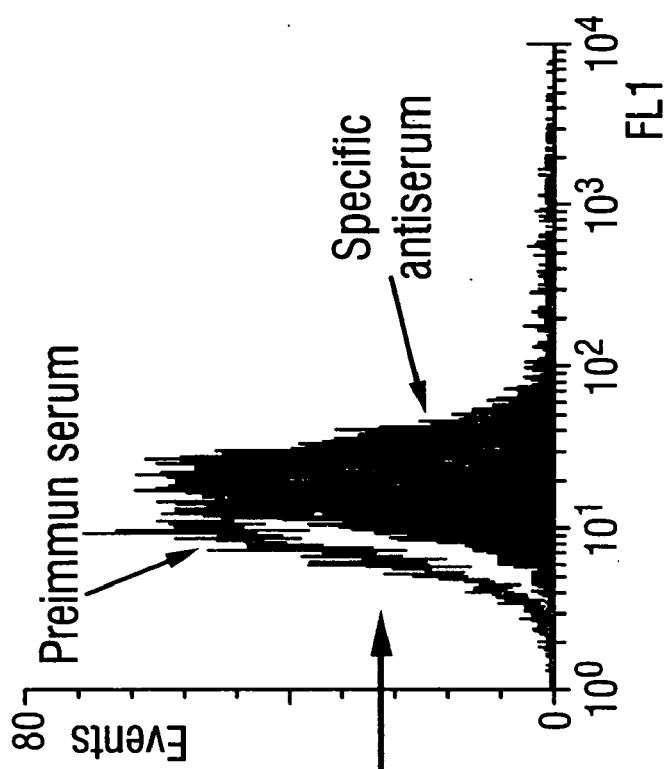
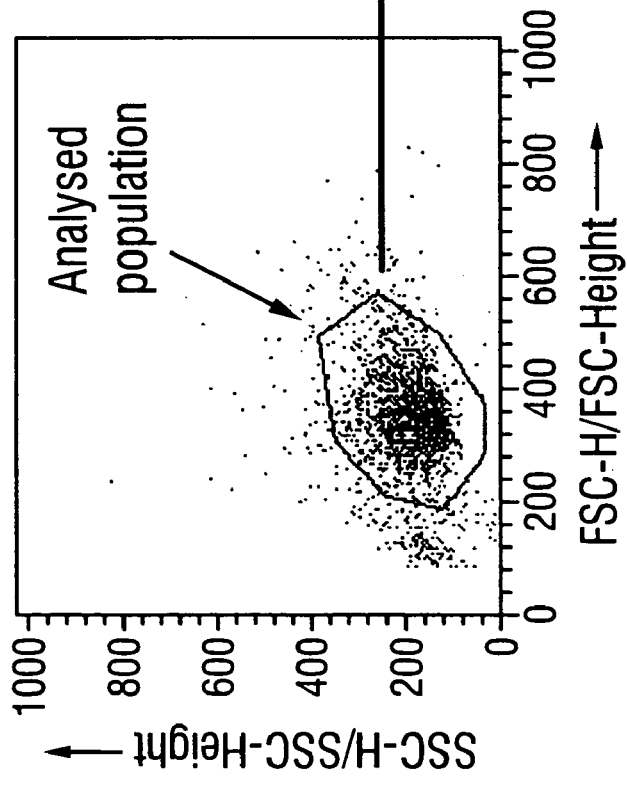

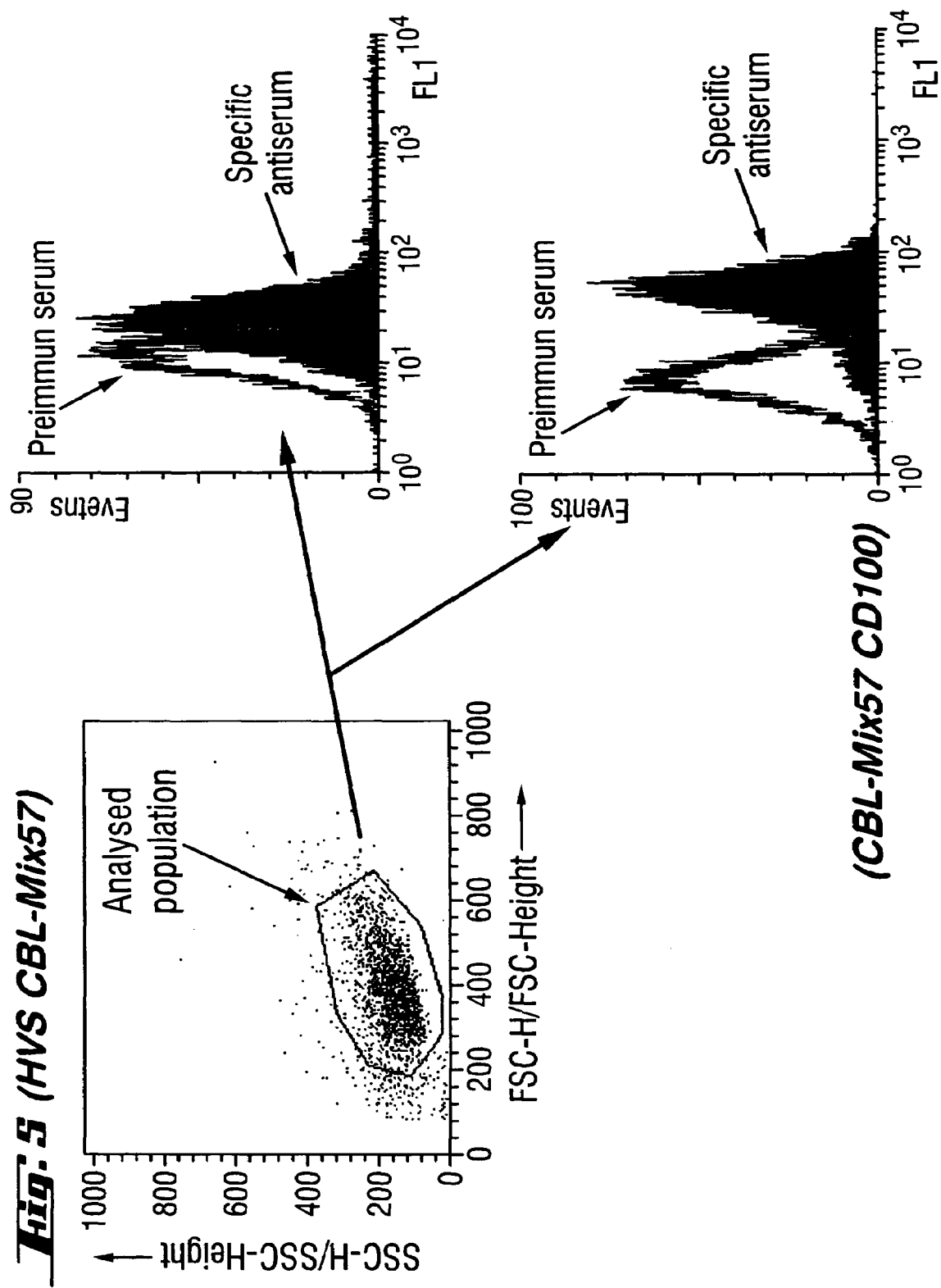

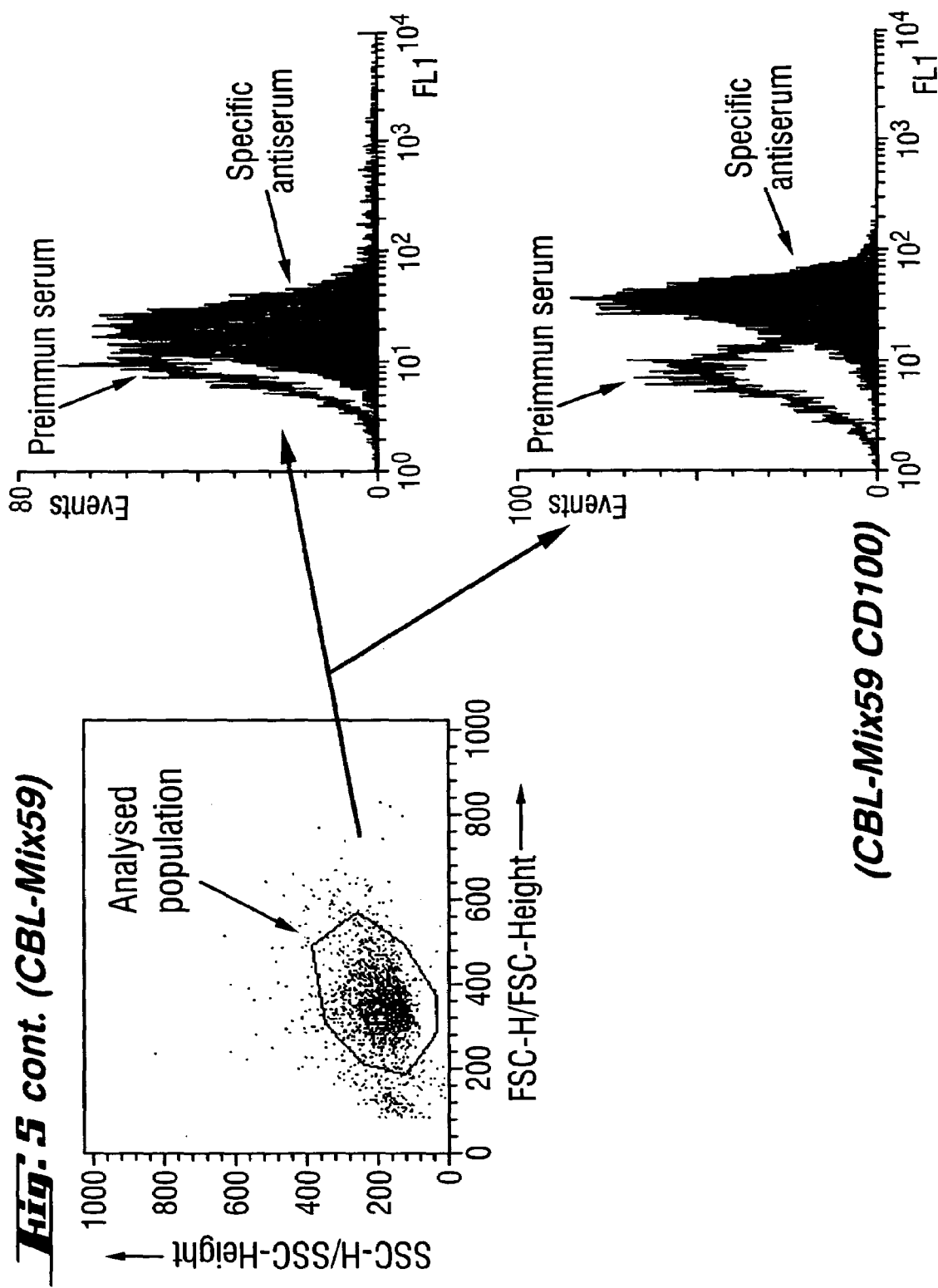

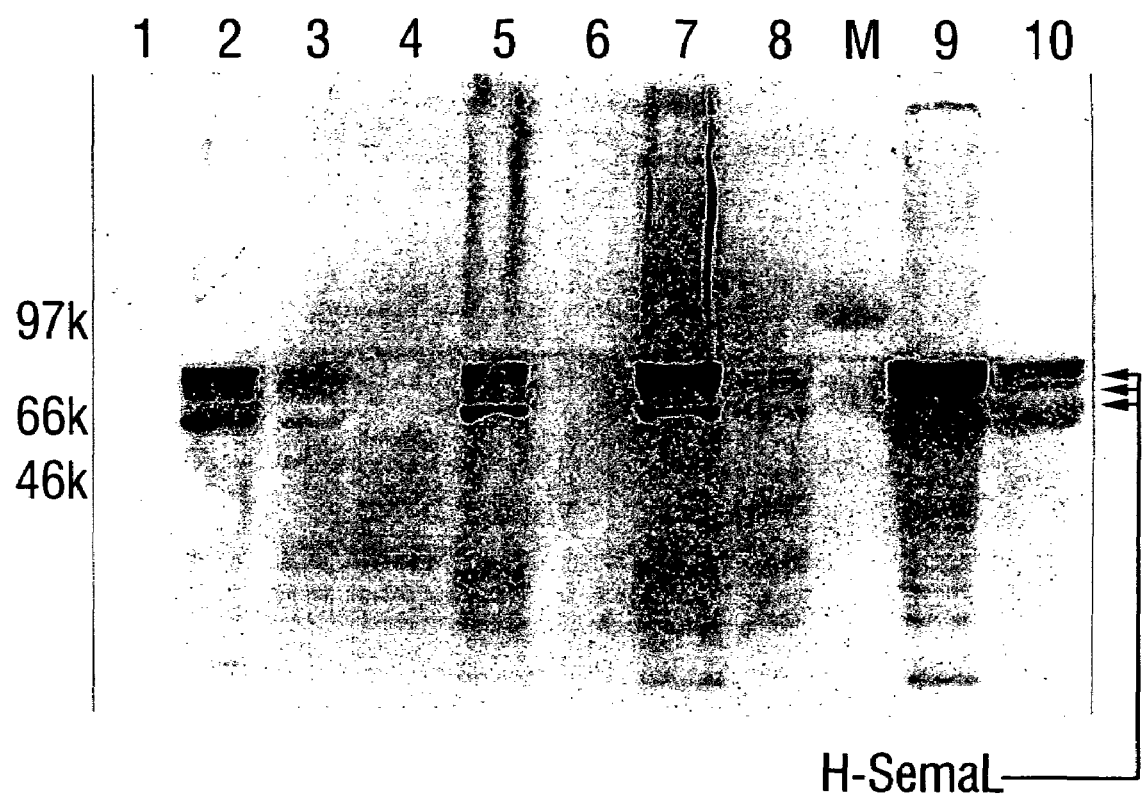

H-SemaL →

```
                           SEQUENCE LISTING (1) GENERAL INFORMATION:

(iii) NUMBER OF SEQUENCES: 44

(2) INFORMATION FOR SEQ ID NO: 1:

(i) SEQUENCE CHARACTERISTICS:
          (A) LENGTH: 2636 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 1:

CGGGGCCACG GGATGACGCC TCCTCCGCCC GGACGTGCCG CCCCCAGCGC ACCGCGCGCC      60

CGCGTCCCTG GCCCGCCGGC TCGGTTGGGG CTTCCGCTGC GGCTGCGGCT GCTGCTGCT     120

CTCTGGGCGG CCGCCGCCTC CGCCCAGGGC CACCTAAGGA GCGGACCCCG CATCTTCGC     180

GTCTGGAAAG GCCATGTAGG GCAGGACCGG GTGGACTTTG GCCAGACTGA GCCGCACAC     240

GTGCTTTTCC ACGAGCCAGG CAGCTCCTCT GTGTGGGTGG GAGGACGTGG CAAGGTCTA     300

CTCTTTGACT TCCCCGAGGG CAAGAACGCA TCTGTGCGCA CGGTGAATAT CGGCTCCAC     360

AAGGGGTCCT GTCTGGATAA GCGGGACTGC GAGAACTACA TCACTCTCCT GGAGAGGCG     420

AGTGAGGGGC TGCTGGCCTG TGGCACCAAC GCCCGGCACC CCAGCTGCTG GAACCTGGT     480

AATGGCACTG TGGTGCCACT TGGCGAGATG AGAGGCTACG CCCCCTTCAG CCCGGACGA     540

AACTCCCTGG TTCTGTTTGA AGGGGACGAG GTGTATTCCA CCATCCGGAA GCAGGAATA     600

AATGGGAAGA TCCCTCGGTT CCGCCGCATC CGGGGCGAGA GTGAGCTGTA CACCAGTGA     660

ACTGTCATGC AGAACCCACA GTTCATCAAA GCCACCATCG TGCACCAAGA CCAGGCTTA     720

GATGACAAGA TCTACTACTT CTTCCGAGAG GACAATCCTG ACAAGAATCC TGAGGCTCC     780

CTCAATGTGT CCCGTGTGGC CCAGTTGTGC AGGGGGGACC AGGGTGGGGA AAGTTCACT     840

TCAGTCTCCA AGTGGAACAC TTTTCTGAAA GCCATGCTGG TATGCAGTGA TGCTGCCAC     900

AACAAGAACT TCAACAGGCT GCAAGACGTC TTCCTGCTCC CTGACCCCAG CGGCCAGTG     960

AGGGACACCA GGGTCTATGG TGTTTTCTCC AACCCCTGGA ACTACTCAGC CGTCTGTG    1020

TATTCCCTCG GTGACATTGA CAAGGTCTTC CGTACCTCCT CACTCAAGGG CTACCACT    1080

AGCCTTCCCA ACCCGCGGCC TGGCAAGTGC CTCCCAGACC AGCAGCCGAT ACCCACAG    1140

ACCTTCCAGG TGGCTGACCG TCACCCAGAG GTGGCGCAGA GGGTGGAGCC CATGGGGC    1200

CTGAAGACGC CATTGTTCCA CTCTAAATAC CACTACCAGA AAGTGGCCGT TCACCGCA    1260

CAAGCCAGCC ACGGGGAGAC CTTTCATGTG CTTTACCTAA CTACAGACAG GGGCACTA    1320

CACAAGGTGG TGGAACCGGG GGAGCAGGAG CACAGCTTCG CCTTCAACAT CATGGAGA    1380

CAGCCCTTCC GCCGCGCGGC TGCCATCCAG ACCATGTCGC TGGATGCTGA GCGGAGGA    1440

CTGTATGTGA GCTCCCAGTG GGAGGTGAGC CAGGTGCCCC TGGACCTGTG TGAGGTCT    1500

GGCGGGGGCT GCCACGGTTG CCTCATGTCC CGAGACCCCT ACTGCGGCTG GGACCAGG    1560

CGCTGCATCT CCATCTACAG CTCCGAACGG TCAGTGCTGC AATCCATTAA TCCAGCCG    1620
```

```
CCACACAAGG AGTGTCCCAA CCCCAAACCA GACAAGGCCC CACTGCAGAA GGTTTCCC       1680

GCCCCAAACT CTCGCTACTA CCTGAGCTGC CCCATGGAAT CCCGCCACGC CACCTACT       1740

TGGCGCCACA AGGAGAACGT GGAGCAGAGC TGCGAACCTG GTCACCAGAG CCCCAACT       1800

ATCCTGTTCA TCGAGAACCT CACGGCGCAG CAGTACGGCC ACTACTTCTG CGAGGCCC       1860

GAGGGCTCCT ACTTCCGCGA GGCTCAGCAC TGGCAGCTGC TGCCCGAGGA CGGCATCA       1920

GCCGAGCACC TGCTGGGTCA TGCCTGTGCC CTGGCTGCCT CCCTCTGGCT GGGGGTGC       1980

CCCACACTCA CTCTTGGCTT GCTGGTCCAC TAGGGCCTCC CGAGGCTGGG CATGCCTC       2040

GCTTCTGCAG CCCAGGGCAC TAGAACGTCT CACACTCAGA GCCGGCTGGC CCGGGAGC       2100

CTTGCCTGCC ACTTCTTCCA GGGGACAGAA TAACCCAGTG GAGGATGCCA GGCCTGGA       2160

CGTCCAGCCG CAGGCGGCTG CTGGGCCCCA GGTGGCGCAC GGATGGTGAG GGGCTGAG       2220

TGAGGGCACC GACTGTGAAG CTGGGGCATC GATGACCCAA GACTTTATCT TCTGGAAA       2280

ATTTTTCAGA CTCCTCAAAC TTGACTAAAT GCAGCGATGC TCCCAGCCCA AGAGCCCA       2340

GGTCGGGGAG TGGGTTTGGA TAGGAGAGCT GGGACTCCAT CTCGACCCTG GGGCTGAG       2400

CTGAGTCCTT CTGGACTCTT GGTACCCACA TTGCCTCCTT CCCCTCCCTC TCTCATGG       2460

GGGTGGCTGG TGTTCCTGAA GACCCAGGGC TACCCTCTGT CCAGCCCTGT CCTCTGCA       2520

TCCCTCTCTG GTCCTGGGTC CCACAGGACA GCCGCCTTGC ATGTTTATTG AAGGATGT       2580

GCTTTCCGGA CGGAAGGACG GAAAAAGCTC TGAAAAAAAA AAAAAAAAAA AAAAAA        2636

(2) INFORMATION FOR SEQ ID NO: 2:

(i) SEQUENCE CHARACTERISTICS:
        (A) LENGTH: 1195 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

CGGGGCTGCG GGATGACGCC TCCTCCTCCC GGACGTGCCG CCCCCAGCGC ACCGCGCGCC       60

CGCGTCCTCA GCCTGCCGGC TCGGTTCGGG CTCCCGCTGC GGCTGCGGCT TCTGCTGGT      120

TTCTGGGTGG CCGCCGCCTC CGCCCAAGGC CACTCGAGGA GCGGACCCCG CATCTCCGC      180

GTCTGGAAAG GGCAGGACCA TGTGGACTTT AGCCAGCCTG AGCCACACAC CGTGCTTTT      240

CATGAGCCGG GCAGCTTCTC TGTCTGGGTG GGTGGACGTG GCAAGGTCTA CCACTTCAA      300

TTCCCCGAGG GCAAGAATGC CTCTGTGCGC ACGGTGAACA TCGGCTCCAC AAAGGGGTC      360

TGTCAGGACA AACAGGACTG TGGGAATTAC ATCACTCTTC TAGAAAGGCG GGGTAATGG      420

CTGCTGGTCT GTGGCACCAA TGCCCGGAAG CCCAGCTGCT GGAACTTGGT GAATGACAG      480

GTGGTGATGT CACTTGGTGA GATGAAAGGC TATGCCCCCT TCAGCCCGGA TGAGAACTC      540

CTGGTTCTGT TTGAAGGAGA TGAAGTGTAC TCTACCATCC GGAAGCAGGA ATACAACGG      600

AAGATCCCTC GGTTTCGACG CATTCGGGGC GAGAGTGAAC TGTACACAAG TGATACAGT      660

ATGCAGAACC CACAGTTCAT CAAGGCCACC ATTGTGCACC AAGACCAAGC CTATGATGA      720

AAGATCTACT ACTTCTTCCG AGAAGACAAC CCTGACAAGA ACCCCGAGGC TCCTCTCAA      780

GTGTCCCGAG TAGCCCAGTT GTGCAGGGGG ACCAGGGTG GTGAGAGTTC GTTGTCTGT       840

TCCAAGTGGA ACACCTTCCT GAAAGCCATG TTGGTCTGCA GCGATGCAGC CACCAACAG      900

AACTTCAATC GGCTGCAAGA TGTCTTCCTG CTCCCTGACC CCAGTGGCCA GTGGAGAGA      960
```

```
ACCAGGGTCT ATGGCGTTTT CTCCAACCCC TGGAACTACT CAGCTGTCTG CGTGTATT    1020

CTTGGTGACA TTGACAGAGT CTTCCGTACC TCATCGCTCA AAGGCTACCA CATGGGCC    1080

TCCAACCCTC GACCTGGCAT GTGCCTCCCA AAAAAGCAGC CCATACCCAC AGAAACCT    1140

CAGGTAGCTG ATAGTCACCC AGAGGTGGCT CAGAGGGTGG AACCTATGGG GCCCC       1195
```

(2) INFORMATION FOR SEQ ID NO: 3:

(i) SEQUENCE CHARACTERISTICS:
        (A) LENGTH: 666 amino acids
        (B) TYPE: amino acid
        (C) STRANDEDNESS: n/a
        (D) TOPOLOGY: linear (ii) MOLECULE TYPE: amino acid (xi) SEQUENCE DESCRIPTION: SEQ ID NO: 3:

```
Met Thr Pro Pro Pro Gly Arg Ala Ala Pro Ser Ala Pro Arg Ala
1               5                   10                  15

Arg Val Pro Gly Pro Pro Ala Arg Leu Gly Leu Pro Leu Arg Leu Arg
            20                  25                  30

Leu Leu Leu Leu Leu Trp Ala Ala Ala Ser Ala Gln Gly His Leu
        35                  40                  45

Arg Ser Gly Pro Arg Ile Phe Ala Val Trp Lys Gly His Val Gly Gln
50                  55                  60

Asp Arg Val Asp Phe Gly Gln Thr Glu Pro His Thr Val Leu Phe His
65                  70                  75                  80

Glu Pro Gly Ser Ser Val Trp Val Gly Gly Arg Gly Lys Val Tyr
                85                  90                  95

Leu Phe Asp Phe Pro Glu Gly Lys Asn Ala Ser Val Arg Thr Val Asn
                100                 105                 110

Ile Gly Ser Thr Lys Gly Ser Cys Leu Asp Lys Arg Asp Cys Glu Asn
            115                 120                 125

Tyr Ile Thr Leu Leu Glu Arg Arg Ser Glu Gly Leu Leu Ala Cys Gly
    130                 135                 140

Thr Asn Ala Arg His Pro Ser Cys Trp Asn Leu Val Asn Gly Thr Val
145                 150                 155                 160

Val Pro Leu Gly Glu Met Arg Gly Tyr Ala Pro Phe Ser Pro Asp Glu
                165                 170                 175

Asn Ser Leu Val Leu Phe Glu Gly Asp Glu Val Tyr Ser Thr Ile Arg
            180                 185                 190

Lys Gln Glu Tyr Asn Gly Lys Ile Pro Arg Phe Arg Arg Ile Arg Gly
        195                 200                 205

Glu Ser Glu Leu Tyr Thr Ser Asp Thr Val Met Gln Asn Pro Gln Phe
    210                 215                 220

Ile Lys Ala Thr Ile Val His Gln Asp Gln Ala Tyr Asp Asp Lys Ile
225                 230                 235                 240

Tyr Tyr Phe Phe Arg Glu Asp Asn Pro Asp Lys Asn Pro Glu Ala Pro
                245                 250                 255

Leu Asn Val Ser Arg Val Ala Gln Leu Cys Arg Gly Asp Gln Gly Gly
            260                 265                 270

Glu Ser Ser Leu Ser Val Ser Lys Trp Asn Thr Phe Leu Lys Ala Met
        275                 280                 285

Leu Val Cys Ser Asp Ala Ala Thr Asn Lys Asn Phe Asn Arg Leu Gln
    290                 295                 300
```

-continued

```
Asp Val Phe Leu Leu Pro Asp Pro Ser Gly Gln Trp Arg Asp Thr Arg
305                 310                 315                 320

Val Tyr Gly Val Phe Ser Asn Pro Trp Asn Tyr Ser Ala Val Cys Val
                325                 330                 335

Tyr Ser Leu Gly Asp Ile Asp Lys Val Phe Arg Thr Ser Ser Leu Lys
            340                 345                 350

Gly Tyr His Ser Ser Leu Pro Asn Pro Arg Pro Gly Lys Cys Leu Pro
        355                 360                 365

Asp Gln Gln Pro Ile Pro Thr Glu Thr Phe Gln Val Ala Asp Arg His
    370                 375                 380

Pro Glu Val Ala Gln Arg Val Glu Pro Met Gly Pro Leu Lys Thr Pro
385                 390                 395                 400

Leu Phe His Ser Lys Tyr His Tyr Gln Lys Val Ala Val His Arg Met
                405                 410                 415

Gln Ala Ser His Gly Glu Thr Phe His Val Leu Tyr Leu Thr Thr Asp
            420                 425                 430

Arg Gly Thr Ile His Lys Val Val Glu Pro Gly Glu Gln Glu His Ser
        435                 440                 445

Phe Ala Phe Asn Ile Met Glu Ile Gln Pro Phe Arg Arg Ala Ala Ala
    450                 455                 460

Ile Gln Thr Met Ser Leu Asp Ala Glu Arg Arg Lys Leu Tyr Val Ser
465                 470                 475                 480

Ser Gln Trp Glu Val Ser Gln Val Pro Leu Asp Leu Cys Glu Val Tyr
                485                 490                 495

Gly Gly Gly Cys His Gly Cys Leu Met Ser Arg Asp Pro Tyr Cys Gly
            500                 505                 510

Trp Asp Gln Gly Arg Cys Ile Ser Ile Tyr Ser Ser Glu Arg Ser Val
        515                 520                 525

Leu Gln Ser Ile Asn Pro Ala Glu Pro His Lys Glu Cys Pro Asn Pro
    530                 535                 540

Lys Pro Asp Lys Ala Pro Leu Gln Lys Val Ser Leu Ala Pro Asn Ser
545                 550                 555                 560

Arg Tyr Tyr Leu Ser Cys Pro Met Glu Ser Arg His Ala Thr Tyr Ser
                565                 570                 575

Trp Arg His Lys Glu Asn Val Gln Ser Cys Glu Pro Gly His Gln Gln
            580                 585                 590

Ser Pro Asn Cys Ile Leu Phe Ile Glu Asn Leu Thr Ala Gln Gln Tyr
        595                 600                 605

Gly His Tyr Phe Cys Glu Ala Gln Glu Gly Ser Tyr Phe Arg Glu Ala
    610                 615                 620

Gln His Trp Gln Leu Leu Pro Glu Asp Gly Ile Met Ala Glu His Leu
625                 630                 635                 640

Leu Gly His Ala Cys Ala Leu Ala Ala Ser Leu Trp Leu Gly Val Leu
                645                 650                 655

Pro Thr Leu Thr Leu Gly Leu Leu Val His
            660                 665
```

(2) INFORMATION FOR SEQ ID NO: 4:

(i) SEQUENCE CHARACTERISTICS:
        (A) LENGTH: 394 amino acids
        (B) TYPE: amino acid
        (C) STRANDEDNESS: n/a
        (D) TOPOLOGY: linear (ii) MOLECULE TYPE: amino acid (xi) SEQUENCE DESCRIPTION: SEQ ID NO: 4:

```
Met Thr Pro Pro Pro Gly Arg Ala Ala Pro Ser Ala Pro Arg Ala
 1               5                  10                  15

Arg Val Leu Ser Leu Pro Ala Arg Phe Gly Leu Pro Leu Arg Leu Arg
                20                  25                  30

Leu Leu Leu Val Phe Trp Val Ala Ala Ser Ala Gln Gly His Ser
            35                  40                  45

Arg Ser Gly Pro Arg Ile Ser Ala Val Trp Lys Gly Gln Asp His Val
 50                  55                  60

Asp Phe Ser Gln Pro Glu Pro His Thr Val Leu Phe His Glu Pro Gly
 65                  70                  75                  80

Ser Phe Ser Val Trp Val Gly Arg Gly Lys Val Tyr His Phe Asn
                85                  90                  95

Phe Pro Glu Gly Lys Asn Ala Ser Val Arg Thr Val Asn Ile Gly Ser
                100                 105                 110

Thr Lys Gly Ser Cys Gln Asp Lys Gln Asp Cys Gly Asn Tyr Ile Thr
                115                 120                 125

Leu Leu Glu Arg Arg Gly Asn Gly Leu Leu Val Cys Gly Thr Asn Ala
            130                 135                 140

Arg Lys Pro Ser Cys Trp Asn Leu Val Asn Asp Ser Val Val Met Ser
145                 150                 155                 160

Leu Gly Glu Met Lys Gly Tyr Ala Pro Phe Ser Pro Asp Glu Asn Ser
                165                 170                 175

Leu Val Leu Phe Glu Gly Asp Glu Val Tyr Ser Thr Ile Arg Lys Gln
                180                 185                 190

Glu Tyr Asn Gly Lys Ile Pro Arg Phe Arg Arg Ile Arg Gly Glu Ser
                195                 200                 205

Glu Leu Tyr Thr Ser Asp Thr Val Met Gln Asn Pro Gln Phe Ile Lys
            210                 215                 220

Ala Thr Ile Val His Gln Asp Gln Ala Tyr Asp Asp Lys Ile Tyr Tyr
225                 230                 235                 240

Phe Phe Arg Glu Asp Asn Pro Asp Lys Asn Pro Glu Ala Pro Leu Asn
                245                 250                 255

Val Ser Arg Val Ala Gln Leu Cys Arg Gly Asp Gln Gly Gly Glu Ser
                260                 265                 270

Ser Leu Ser Val Ser Lys Trp Asn Thr Phe Leu Lys Ala Met Leu Val
            275                 280                 285

Cys Ser Asp Ala Ala Thr Asn Arg Asn Phe Asn Arg Leu Gln Asp Val
            290                 295                 300

Phe Leu Leu Pro Asp Pro Ser Gly Gln Trp Arg Asp Thr Arg Val Tyr
305                 310                 315                 320

Gly Val Phe Ser Asn Pro Trp Asn Tyr Ser Ala Val Cys Val Tyr Ser
                325                 330                 335

Leu Gly Asp Ile Asp Arg Val Phe Arg Thr Ser Ser Leu Lys Gly Tyr
                340                 345                 350

His Met Gly Leu Ser Asn Pro Arg Pro Gly Met Cys Leu Pro Lys Lys
            355                 360                 365

Gln Pro Ile Pro Thr Glu Thr Phe Gln Val Ala Asp Ser His Pro Glu
            370                 375                 380

Val Ala Gln Arg Val Glu Pro Met Gly Pro
385                 390
```

```
(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ACTCACTATA GGGCTCGAGC GGC                                             23

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AGCCGCACAC GGTGCTTTTC                                                 20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCACAGATGC GTTCTTGCCC                                                 20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

ACCATAGACC CTGGTGTCCC                                                 20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GCAGTGATGC TGCCACCAAC                                                 20

(2) INFORMATION FOR SEQ ID NO: 10:

(i) SEQUENCE CHARACTERISTICS:
        (A) LENGTH: 20 base pairs
```

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CCAGACCATG TCGCTGGATG                                                   20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

ACATGAGGCA ACCGTGGCAG                                                   20

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CCATCCTAAT ACGACTCACT ATAGGGC                                           27

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

AGGTAGACCT TGCCACGTCC                                                   20

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GAACTTCAAC AGGCTGCAAG ACG                                               23

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 15:

ATGCTGAGCG GAGGAAGCTG                                                     20

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

CCGCCATACA CCTCACACAG                                                     20

(2) INFORMATION FOR SEQ ID NO: 17:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 17:

CTGGAAGCTT TCTGTGGGTA TCGGCTGC                                            28

(2) INFORMATION FOR SEQ ID NO: 18:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 18:

TTTGGATCCC TGGTTCTGTT TGAAG                                               25

(2) INFORMATION FOR SEQ ID NO: 19:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 19:

TTCTAGAATT CAGCGGCCGC TTTTTTTTTT TTTTTTTTTT TTTTTTTTTT                    50

(2) INFORMATION FOR SEQ ID NO: 20:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 20:

```
GGGGAAAGTT CACTGTCAGT CTCCAAG                                                 27

(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GGGAATACAC ACAGACGGCT GAGTAG                                                  26

(2) INFORMATION FOR SEQ ID NO: 22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

AGCAAGTTCA GCCTGGTTAA GT                                                      22

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

TTATGAGTAT TCTTCCAGG G                                                        21

(2) INFORMATION FOR SEQ ID NO: 24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

CCATTAATCC AGCCGAGCCA CACAAG                                                  26

(2) INFORMATION FOR SEQ ID NO: 25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

CATCTACAGC TCCGAACGGT CAGTG                                                   25

(2) INFORMATION FOR SEQ ID NO: 26:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

CAGCGGAAGC CCCAACCGAG                                               20

(2) INFORMATION FOR SEQ ID NO: 27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

GGGATGACGC CTCCTCCGCC CGG                                           23

(2) INFORMATION FOR SEQ ID NO: 28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

AAGCTTCACG TGGACCAGCA AGCCAAGAGT G                                  31

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

AAGCTTTTTC CGTCCTTCCG TCCGG                                         25

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

ATGGTGAGCA AGGGCGAGGA GCTG                                          24

(2) INFORMATION FOR SEQ ID NO: 31:

(i) SEQUENCE CHARACTERISTICS:
        (A) LENGTH: 24 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO: 31:

CTTGTACAGC TCGTCCATGC CGAG                                              24

(2) INFORMATION FOR SEQ ID NO: 32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

GGGTGGTGAG AGTTCGTTGT CTGTC                                             25

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

GAGCGATGAG GTACGGAAGA CTCTG                                             25

(2) INFORMATION FOR SEQ ID NO: 34:

(i) SEQUENCE CHARACTERISTICS:
        (A) LENGTH: 5856 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

AGCGCCCAAT ACGCAAACCG CCTCTCCCCG CGCGTTGGCC GATTCATTAA TGCAGCTGGC        60

ACGACAGGTT TCCCGACTGG AAAGCGGGCA GTGAGCGCAA CGCAATTAAT GTGAGTTAG        120

TCACTCATTA GGCACCCCAG GCTTTACACT TTATGCTTCC GGCTCGTATG TTGTGTGGA        180

TTGTGAGCGG ATAACAATTT CACACAGGAA ACAGCTATGA CCATGATTAC GCCAAGCTT        240

ACGTGGACCA GCAAGCCAAG AGTGAGTGTG GGCAGCACCC CCAGCCAGAG GGAGGCAGC        300

AGGGCACAGG CATGACCCAG CAGGTGCTCG GCCATGATGC CGTCCTCGGG CAGCAGCTG        360

CAGTGCTGAG CCTCGCGGAA GTAGGAGCCC TCCTGGGCCT CGCAGAAGTA GTGGCCGTA        420

TGCTGCGCCG TGAGGTTCTC GATGAACAGG ATGCAGTTGG GGCTCTGGTG ACCAGGTTC        480

CAGCTCTGCT CCACGTTCTC CTTGTGGCGC CATGAGTAGG TGGCGTGGCG GGATTCCAT        540

GGGCAGCTCA GGTAGTAGCG AGAGTTTGGG GCCAGGGAAA CCTTCTGCAG TGGGGCCTT        600

TCTGGTTTGG GGTTGGGACA CTCCTTGTGT GGCTCGGCTG GATTAATGGA TTGCAGCAC        660

GACCGTTCGG AGCTGTAGAT GGAGATGCAG CGGCCCTGGT CCCAGCCGCA GTAGGGGTC        720

CGGGACATGA GGCAACCGTG GCAGCCCCCG CCATAGACCT CACACAGGTC CAGGGGCAC        780

TGGCTCACCT CCCACTGGGA GCTCACATAC AGCTTCCTCC GCTCAGCATC CAGCGACAT        840

```
GTCTGGATGG CAGCCGCGCG GCGGAAGGGC TGGATCTCCA TGATGTTGAA GGCGAAGCT       900
TGCTCCTGCT CCCCCGGTTC CACCACCTTG TGGATAGTGC CCCTGTCTGT AGTTAGGTA       960
AGCACATGAA AGGTCTCCCC GTGGCTGGCT TGCATGCGGT GAACGGCCAC TTTCTGGT       1020
TGGTATTTAG AGTGGAACAA TGGCGTCTTC AGAGGCCCCA TGGGCTCCAC CCTCTGCG       1080
ACCTCTGGGT GACGGTCAGC CACCTGGAAG GTCTCTGTGG GTATCGGCTG CTGGTCTG       1140
AGGCACTTGC CAGGCCGCGG GTTGGGAAGG CTTGAGTGGT AGCCCTTGAG TGAGGAGG       1200
CGGAAGACCT TGTCAATGTC ACCGAGGGAA TACACACAGA CGGCTGAGTA GTTCCAGG       1260
TTGGAGAAAA CACCATAGAC CCTGGTGTCC CTCCACTGGC CGCTGGGGTC AGGGAGCA       1320
AAGACGTCTT GCAGCCTGTT GAAGTTCTTG TTGGTGGCAG CATCACTGCA TACCAGCA       1380
GCTTTCAGAA AAGTGTTCCA CTTGGAGACT GACAGTGAAC TTTCCCCACC CTGGTCCC       1440
CTGCACAACT GGGCCACACG GGACACATTG AGAGGAGCCT CAGGATTCTT GTCAGGAT       1500
TCCTCTCGGA AGAAGTAGTA GATCTTGTCA TCGTAAGCCT GGTCTTGGTG CACGATGG       1560
GCTTTGATGA ACTGTGGGTT CTGCATGACA GTATCACTGG TGTACAGCTC ACTCTCGC       1620
CGGATGCGGC GGAACCGAGG GATCTTCCCA TTGTATTCCT GCTTCCGGAT GGTGGAAT       1680
ACCTCGTCCC CTTCAAACAG AACCAGGGAG TTCTCGTCCG GGCTGAAGGG GGCGTAGC       1740
CTCATCTCGC CAAGTGGCAC CACAGTGCCA TTCACCAGGT TCCAGCAGCT GGGGTGCC       1800
GCGTTGGTGC CACAGGCCAG CAGCCCCTCA CTCCGCCTCT CCAGGAGAGT GATGTAGT       1860
TCGCAGTCCC GCTTATCCAG ACAGGACCCC TTTGTGGAGC CGATATTCAC CGTGCGCA       1920
GATGCGTTCT TGCCCTCGGG GAAGTCAAAG AGGTAGACCT TGCCACGTCC TCCCACCC       1980
ACAGAGGAGC TGCCTGGCTC GTGGAAAAGC ACCGTGTGCG GCTCAGTCTG GCCAAAGT       2040
ACCCGGTCCT GCCCTACATG GCCTTTCCAG ACGGCGAAGA TGCGGGGTCC GCTCCTTA       2100
TGGCCCTGGG CGGAGGCGGC GGCCGCCCAG AGCAGCAGCA GCAGCCGCAG CCGCAGCG       2160
AGCCCCAACC GAGCCGGCGG GCCAGGGACG CGGGCGCGCG GTGCGCTGGG GGCGGCAC       2220
CCGGGCGGAG GAGGCGTCAT CCCAAGCCGA ATTCTGCAGA TATCCATCAC ACTGGCGG       2280
GCTCGAGCAT GCATCTAGAG GGCCCAATTC GCCCTATAGT GAGTCGTATT ACAATTCA       2340
GGCCGTCGTT TTACAACGTC GTGACTGGGA AAACCCTGGC GTTACCCAAC TTAATCGC       2400
TGCAGCACAT CCCCCTTTCG CCAGCTGGCG TAATAGCGAA GAGGCCCGCA CCGATCGC       2460
TTCCCAACAG TTGCGCAGCC TGAATGGCGA ATGGGACGCG CCCTGTAGCG GCGCATTA       2520
CGCGGCGGGT GTGGTGGTTA CGCGCAGCGT GACCGCTACA CTTGCCAGCG CCCTAGCG       2580
CGCTCCTTTC GCTTTCTTCC CTTCCTTTCT CGCCACGTTC GCCGGCTTTC CCCGTCAA       2640
TCTAAATCGG GGGCTCCCTT TAGGGTTCCG ATTTAGAGCT TTACGGCACC TCGACCGC       2700
AAAACTTGAT TTGGGTGATG GTTCACGTAG TGGGCCATCG CCCTGATAGA CGGTTTTT       2760
CCCTTTGACG TTGGAGTCCA CGTTCTTTAA TAGTGGACTC TTGTTCCAAA CTGGAACA       2820
ACTCAACCCT ATCGCGGTCT ATTCTTTTGA TTTATAAGGG ATTTTGCCGA TTTCGGCC       2880
TTGGTTAAAA AATGAGCTGA TTTAACAAAT TCAGGGCGCA AGGGCTGCTA AAGGAACC       2940
AACACGTAGA AAGCCAGTCC GCAGAAACGG TGCTGACCCC GGATGAATGT CAGCTACT       3000
GCTATCTGGA CAAGGGAAAA CGCAAGCGCA AAGAGAAAGC AGGTAGCTTG CAGTGGGC       3060
ACATGGCGAT AGCTAGACTG GCGGTTTTA TGGACAGCAA GCGAACCGGA ATTGCCAG       3120
GGGGCGCCCT CTGGTAAGGT TGGGAAGCCC TGCAAAGTAA ACTGGATGGC TTTCTTGC       3180
```

```
CCAAGGATCT GATGGCGCAG GGGATCAAGA TCTGATCAAG AGACAGGATG AGGATCGT      3240

CGCATGATTG AACAAGATGG ATTGCACGCA GGTTCTCCGG CCGCTTGGGT GGAGAGGC      3300

TTCGGCTATG ACTGGGCACA ACAGACAATC GGCTGCTCTG ATGCCGCCGT GTTCCGGC      3360

TCAGCGCAGG GGCGCCCGGT TCTTTTTGTC AAGACCGACC TGTCCGGTGC CCTGAATG      3420

CTGCAGGACG AGGCAGCGCG GCTATCGTGG CTGGCCACGA CGGGCGTTCC TTGCGCAG      3480

GTGCTCGACG TTGTCACTGA AGCGGGAAGG GACTGGCTGC TATTGGGCGA AGTGCCGG      3540

CAGGATCTCC TGTCATCTCG CCTTGCTCCT GCCGAGAAAG TATCCATCAT GGCTGATG      3600

ATGCGGCGGC TGCATACGCT TGATCCGGCT ACCTGCCCAT TCGACCACCA AGCGAAAC      3660

CGCATCGAGC GAGCACGTAC TCGGATGGAA GCCGGTCTTG TCGATCAGGA TGATCTGG      3720

GAAGAGCATC AGGGGCTCGC GCCAGCCGAA CTGTTCGCCA GGCTCAAGGC GCGCATGC      3780

GACGGCGAGG ATCTCGTCGT GATCCATGGC GATGCCTGCT TGCCGAATAT CATGGTGG      3840

AATGGCCGCT TTTCTGGATT CAACGACTGT GGCCGGCTGG GTGTGGCGGA CCGCTATC      3900

GACATAGCGT TGGATACCCG TGATATTGCT GAAGAGCTTG GCGGCGAATG GCTGACC      3960

TTCCTCGTGC TTTACGGTAT CGCCGCTCCC GATTCGCAGC GCATCGCCTT CTATCGCC      4020

CTTGACGAGT TCTTCTGAAT TGAAAAAGGA AGAGTATGAG TATTCAACAT TTCCGTGT      4080

CCCTTATTCC CTTTTTTGCG GCATTTTGCC TTCCTGTTTT TGCTCACCCA GAAACGCT      4140

TGAAAGTAAA AGATGCTGAA GATCAGTTGG GTGCACGAGT GGGTTACATC GAACTGGA      4200

TCAACAGCGG TAAGATCCTT GAGAGTTTTC GCCCCGAAGA ACGTTTTCCA ATGATGAG      4260

CTTTTAAAGT TCTGCTATGT CATACACTAT TATCCCGTAT TGACGCCGGG CAAGAGCA      4320

TCGGTCGCCG GGCGCGGTAT TCTCAGAATG ACTTGGTTGA GTACTCACCA GTCACAGA      4380

AGCATCTTAC GGATGGCATG ACAGTAAGAG AATTATGCAG TGCTGCCATA ACCATGAG      4440

ATAACACTGC GGCCAACTTA CTTCTGACAA CGATCGGAGG ACCGAAGGAG CTAACCGC      4500

TTTTGCACAA CATGGGGGAT CATGTAACTC GCCTTGATCG TTGGGAACCG GAGCTGAA      4560

AAGCCATACC AAACGACGAG AGTGACACCA CGATGCCTGT AGCAATGCCA ACAACGTT      4620

GCAAACTATT AACTGGCGAA CTACTTACTC TAGCTTCCCG GCAACAATTA ATAGACTG      4680

TGGAGGCGGA TAAAGTTGCA GGACCACTTC TGCGCTCGGC CCTTCCGGCT GGCTGGTT      4740

TTGCTGATAA ATCTGGAGCC GGTGAGCGTG GGTCTCGCGG TATCATTGCA GCACTGGG      4800

CAGATGGTAA GCCCTCCCGT ATCGTAGTTA TCTACACGAC GGGGAGTCAG GCAACTAT      4860

ATGAACGAAA TAGACAGATC GCTGAGATAG GTGCCTCACT GATTAAGCAT TGGTAACT      4920

CAGACCAAGT TTACTCATAT ATACTTTAGA TTGATTTAAA ACTTCATTTT TAATTTAA      4980

GGATCTAGGT GAAGATCCTT TTTGATAATC TCATGACCAA AATCCCTTAA CGTGAGTT      5040

CGTTCCACTG AGCGTCAGAC CCCGTAGAAA AGATCAAAGG ATCTTCTTGA GATCCTTT      5100

TTCTGCGCGT AATCTGCTGC TTGCAAACAA AAAAACCACC GCTACCAGCG GTGGTTTG      5160

TGCCGGATCA AGAGCTACCA ACTCTTTTTC CGAAGGTAAC TGGCTTCAGC AGAGCGCA      5220

TACCAAATAC TGTCCTTCTA GTGTAGCCGT AGTTAGGCCA CCACTTCAAG AACTCTGT      5280

CACCGCCTAC ATACCTCGCT CTGCTAATCC TGTTACCAGT GGCTGCTGCC AGTGGCGA      5340

AGTCGTGTCT TACCGGGTTG GACTCAAGAC GATAGTTACC GGATAAGGCG CAGCGGTC      5400

GCTGAACGGG GGGTTCGTGC ACACAGCCCA GCTTGGAGCG AACGACCTAC ACCGAACT      5460

GATACCTACA GCGTGAGCAT TGAGAAAGCG CCACGCTTCC CGAAGGGAGA AAGGCGGA      5520

GGTATCCGGT AAGCGGCAGG GTCGGAACAG GAGAGCGCAC GAGGGAGCTT CCAGGGGG      5580
```

```
ACGCCTGGTA TCTTTATAGT CCTGTCGGGT TTCGCCACCT CTGACTTGAG CGTCGATT      5640

TGTGATGCTC GTCAGGGGGG CGGAGCCTAT GGAAAAACGC CAGCAACGCG GCCTTTTT      5700

GGTTCCTGGC CTTTTGCTGG CCTTTTGCTC ACATGTTCTT TCCTGCGTTA TCCCCTGA      5760

CTGTGGATAA CCGTATTACC GCCTTTGAGT GAGCTGATAC CGCTCGCCGC AGCCGAAC      5820

CCGAGCGCAG CGAGTCAGTG AGCGAGGAAG CGGAAG                              5856

(2) INFORMATION FOR SEQ ID NO: 35:

(i) SEQUENCE CHARACTERISTICS:
        (A) LENGTH: 7475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

GACGGATCGG GAGATCTCCC GATCCCCTAT GGTCGACTCT CAGTACAATC TGCTCTGATG      60

CCGCATAGTT AAGCCAGTAT CTGCTCCCTG CTTGTGTGTT GGAGGTCGCT GAGTAGTGC     120

CGAGCAAAAT TTAAGCTACA ACAAGGCAAG GCTTGACCGA CAATTGCATG AAGAATCTG     180

TTAGGGTTAG GCGTTTTGCG CTGCTTCGCG ATGTACGGGC CAGATATACG CGTTGACAT     240

GATTATTGAC TAGTTATTAA TAGTAATCAA TTACGGGGTC ATTAGTTCAT AGCCCATAT     300

TGGAGTTCCG CGTTACATAA CTTACGGTAA ATGGCCCGCC TGGCTGACCG CCCAACGAC     360

CCCGCCCATT GACGTCAATA ATGACGTATG TTCCCATAGT AACGCCAATA GGGACTTTC     420

ATTGACGTCA ATGGGTGGAC TATTTACGGT AAACTGCCCA CTTGGCAGTA CATCAAGTG     480

ATCATATGCC AAGTACGCCC CCTATTGACG TCAATGACGG TAAATGGCCC GCCTGGCAT     540

ATGCCCAGTA CATGACCTTA TGGGACTTTC CTACTTGGCA GTACATCTAC GTATTAGTC     600

TCGCTATTAC CATGGTGATG CGGTTTTGGC AGTACATCAA TGGGCGTGGA TAGCGGTTT     660

ACTCACGGGG ATTTCCAAGT CTCCACCCCA TTGACGTCAA TGGGAGTTTG TTTTGGCAC     720

AAAATCAACG GGACTTTCCA AAATGTCGTA ACAACTCCGC CCCATTGACG CAAATGGGC     780

GTAGGCGTGT ACGGTGGGAG GTCTATATAA GCAGAGCTCT CTGGCTAACT AGAGAACCC     840

CTGCTTACTG GCTTATCGAA ATTAATACGA CTCACTATAG GGAGACCCAA GCTGGCTAG     900

GTTTAAACGG GCCCTCTAGA CTCGAGCGGC CGCCACTGTG CTGGATATCT GCAGAATTC     960

GCTTGGGATG ACGCCTCCTC CGCCCGGACG TGCCGCCCCC AGCGCACCGC GCGCCCGC     1020

CCCTGGCCCG CCGGCTCGGT TGGGGCTTCC GCTGCGGCTG CGGCTGCTGC TGCTGCTC     1080

GGCGGCCGCC GCCTCCGCCC AGGGCCACCT AAGGAGCGGA CCCCGCATCT TCGCCGTC     1140

GAAAGGCCAT GTAGGGCAGG ACCGGGTGGA CTTTGGCCAG ACTGAGCCGC ACACGGTG     1200

TTTCCACGAG CCAGGCAGCT CCTCTGTGTG GGTGGGAGGA CGTGGCAAGG TCTACCTC     1260

TGACTTCCCC GAGGGCAAGA ACGCATCTGT GCGCACGGTG AATATCGGCT CCACAAAG     1320

GTCCTGTCTG GATAAGCGGG ACTGCGAGAA CTACATCACT CTCCTGGAGA GGCGGAGT     1380

GGGGCTGCTG GCCTGTGGCA CCAACGCCCG GCACCCCAGC TGCTGGAACC TGGTGAAT     1440

CACTGTGGTG CCACTTGGCG AGATGAGAGG CTACGCCCCC TTCAGCCCGG ACGAGAAC     1500

CCTGGTTCTG TTTGAAGGGG ACGAGGTGTA TTCCACCATC CGGAAGCAGG AATACAAT     1560

GAAGATCCCT CGGTTCCGCC GCATCCGGGG CGAGAGTGAG CTGTACACCA GTGATACT     1620

CATGCAGAAC CCACAGTTCA TCAAAGCCAC CATCGTGCAC AAGACCAGG CTTACGAT     1680
```

| | |
|---|---|
| CAAGATCTAC TACTTCTTCC GAGAGGACAA TCCTGACAAG AATCCTGAGG CTCCTCTC | 1740 |
| TGTGTCCCGT GTGGCCCAGT TGTGCAGGGG GGACCAGGGT GGGGAAAGTT CACTGTCA | 1800 |
| CTCCAAGTGG AACACTTTTC TGAAAGCCAT GCTGGTATGC AGTGATGCTG CCACCAAC | 1860 |
| GAACTTCAAC AGGCTGCAAG ACGTCTTCCT GCTCCCTGAC CCCAGCGGCC AGTGGAGG | 1920 |
| CACCAGGGTC TATGGTGTTT TCTCCAACCC CTGGAACTAC TCAGCCGTCT GTGTGTAT | 1980 |
| CCTCGGTGAC ATTGACAAGG TCTTCCGTAC CTCCTCACTC AAGGGCTACC ACTCAAGC | 2040 |
| TCCCAACCCG CGGCCTGGCA AGTGCCTCCC AGACCAGCAG CCGATACCCA CAGAGACC | 2100 |
| CCAGGTGGCT GACCGTCACC CAGAGGTGGC GCAGAGGGTG GAGCCCATGG GGCCTCTG | 2160 |
| GACGCCATTG TTCCACTCTA AATACCACTA CCAGAAAGTG GCCGTTCACC GCATGCAA | 2220 |
| CAGCCACGGG GAGACCTTTC ATGTGCTTTA CCTAACTACA GACAGGGGCA CTATCCAC | 2280 |
| GGTGGTGGAA CCGGGGGAGC AGGAGCACAG CTTCGCCTTC AACATCATGG AGATCCAG | 2340 |
| CTTCCGCCGC GCGGCTGCCA TCCAGACCAT GTCGCTGGAT GCTGAGCGGA GGAAGCTG | 2400 |
| TGTGAGCTCC CAGTGGGAGG TGAGCCAGGT GCCCCTGGAC CTGTGTGAGG TCTATGGC | 2460 |
| GGGCTGCCAC GGTTGCCTCA TGTCCCGAGA CCCCTACTGC GGCTGGGACC AGGGCCGC | 2520 |
| CATCTCCATC TACAGCTCCG AACGGTCAGT GCTGCAATCC ATTAATCCAG CCGAGCCA | 2580 |
| CAAGGAGTGT CCCAACCCCA AACCAGACAA GGCCCCACTG CAGAAGGTTT CCCTGGCC | 2640 |
| AAACTCTCGC TACTACCTGA GCTGCCCCAT GGAATCCCGC CACGCCACCT ACTCATGG | 2700 |
| CCACAAGGAG AACGTGGAGC AGAGCTGCGA ACCTGGTCAC CAGAGCCCCA ACTGCATC | 2760 |
| GTTCATCGAG AACCTCACGG CGCAGCAGTA CGGCCACTAC TTCTGCGAGG CCCAGGAG | 2820 |
| CTCCTACTTC CGCGAGGCTC AGCACTGGCA GCTGCTGCCC GAGGACGGCA TCATGGCC | 2880 |
| GCACCTGCTG GGTCATGCCT GTGCCCTGGC TGCCTCCCTC TGGCTGGGGG TGCTGCCC | 2940 |
| ACTCACTCTT GGCTTGCTGG TCCACGTGAA GCTTGGGCCC GAACAAAAAC TCATCTCA | 3000 |
| AGAGGATCTG AATAGCGCCG TCGACCATCA TCATCATCAT CATTGAGTTT AAACCGCT | 3060 |
| TCAGCCTCGA CTGTGCCTTC TAGTTGCCAG CCATCTGTTG TTTGCCCCTC CCCCGTGC | 3120 |
| TCCTTGACCC TGGAAGGTGC CACTCCCACT GTCCTTTCCT AATAAAATGA GGAAATTG | 3180 |
| TCGCATTGTC TGAGTAGGTG TCATTCTATT CTGGGGGGTG GGGTGGGGCA GGACAGCA | 3240 |
| GGGGAGGATT GGGAAGACAA TAGCAGGCAT GCTGGGGATG CGGTGGGCTC TATGGCTT | 3300 |
| GAGGCGGAAA GAACCAGCTG GGGCTCTAGG GGGTATCCCC ACGCGCCCTG TAGCGGCG | 3360 |
| TTAAGCGCGG CGGGTGTGGT GGTTACGCGC AGCGTGACCG CTACACTTGC CAGCGCCC | 3420 |
| GCGCCCGCTC CTTTCGCTTT CTTCCCTTCC TTTCTCGCCA CGTTCGCCGG CTTTCCCC | 3480 |
| CAAGCTCTAA ATCGGGCAT CCCTTTAGGG TTCCGATTTA GTGCTTTACG GCACCTCG | 3540 |
| CCCAAAAAAC TTGATTAGGG TGATGGTTCA CGTAGTGGGC CATCGCCCTG ATAGACGG | 3600 |
| TTTCGCCCTT TGACGTTGGA GTCCACGTTC TTTAATAGTG GACTCTTGTT CCAAACTG | 3660 |
| ACAACACTCA ACCCTATCTC GGTCTATTCT TTTGATTTAT AAGGGATTTT GGGGATTT | 3720 |
| GCCTATTGGT TAAAAAATGA GCTGATTTAA CAAAAATTTA ACGCGAATTA ATTCTGTG | 3780 |
| ATGTGTGTCA GTTAGGGTGT GGAAAGTCCC CAGGCTCCCC AGGCAGGCAG AAGTATGC | 3840 |
| AGCATGCATC TCAATTAGTC AGCAACCAGG TGTGGAAAGT CCCCAGGCTC CCCAGCAG | 3900 |
| AGAAGTATGC AAAGCATGCA TCTCAATTAG TCAGCAACCA TAGTCCCGCC CCTAACTC | 3960 |
| CCCATCCCGC CCCTAACTCC GCCCAGTTCC GCCCATTCTC CGCCCCATGG CTGACTAA | 4020 |

```
TTTTTTATTT ATGCAGAGGC CGAGGCCGCC TCTGCCTCTG AGCTATTCCA GAAGTAGT    4080
GGAGGCTTTT TTGGAGGCCT AGGCTTTTGC AAAAAGCTCC CGGGAGCTTG TATATCCA    4140
TTCGGATCTG ATCAAGAGAC AGGATGAGGA TCGTTTCGCA TGATTGAACA AGATGGAT    4200
CACGCAGGTT CTCCGGCCGC TTGGGTGGAG AGGCTATTCG GCTATGACTG GGCACAAC    4260
ACAATCGGCT GCTCTGATGC CGCCGTGTTC CGGCTGTCAG CGCAGGGGCG CCCGGTTC    4320
TTTGTCAAGA CCGACCTGTC CGGTGCCCTG AATGAACTGC AGGACGAGGC AGCGCGGC    4380
TCGTGGCTGG CCACGACGGG CGTTCCTTGC GCAGCTGTGC TCGACGTTGT CACTGAAG    4440
GGAAGGGACT GGCTGCTATT GGGCGAAGTG CCGGGGCAGG ATCTCCTGTC ATCTCACC    4500
GCTCCTGCCG AGAAAGTATC CATCATGGCT GATGCAATGC GGCGGCTGCA TACGCTTG    4560
CCGGCTACCT GCCCATTCGA CCACCAAGCG AAACATCGCA TCGAGCGAGC ACGTACTC    4620
ATGGAAGCCG GTCTTGTCGA TCAGGATGAT CTGGACGAAG AGCATCAGGG GCTCGCGC    4680
GCCGAACTGT TCGCCAGGCT CAAGGCGCGC ATGCCCGACG GCGAGGATCT CGTCGTGA    4740
CATGGCGATG CCTGCTTGCC GAATATCATG GTGGAAAATG GCCGCTTTTC TGGATTCA    4800
GACTGTGGCC GGCTGGGTGT GGCGGACCGC TATCAGGACA TAGCGTTGGC TACCCGTG    4860
ATTGCTGAAG AGCTTGGCGG CGAATGGGCT GACCGCTTCC TCGTGCTTTA CGGTATCG    4920
GCTCCCGATT CGCAGCGCAT CGCCTTCTAT CGCCTTCTTG ACGAGTTCTT CTGAGCGG    4980
CTCTGGGGTT CGAAATGACC GACCAAGCGA CGCCCAACCT GCCATCACGA GATTTCGA    5040
CCACCGCCGC CTTCTATGAA AGGTTGGGCT TCGGAATCGT TTTCCGGGAC GCCGGCTG    5100
TGATCCTCCA GCGCGGGGAT CTCATGCTGG AGTTCTTCGC CCACCCCAAC TTGTTTAT    5160
CAGCTTATAA TGGTTACAAA TAAAGCAATA GCATCACAAA TTTCACAAAT AAAGCATT    5220
TTTCACTGCA TTCTAGTTGT GGTTTGTCCA AACTCATCAA TGTATCTTAT CATGTCTG    5280
TACCGTCGAC CTCTAGCTAG AGCTTGGCGT AATCATGGTC ATAGCTGTTT CCTGTGTG    5340
ATTGTTATCC GCTCACAATT CCACACAACA TACGAGCCGG AAGCATAAAG TGTAAAGC    5400
GGGGTGCCTA ATGAGTGAGC TAACTCACAT TAATTGCGTT GCGCTCACTG CCCGCTTT    5460
AGTCGGGAAA CCTGTCGTGC CAGCTGCATT AATGAATCGG CCAACGCGCG GGGAGAGG    5520
GTTTGCGTAT TGGGCGCTCT TCCGCTTCCT CGCTCACTGA CTCGCTGCGC TCGGTCGT    5580
GGCTGCGGCG AGCGGTATCA GCTCACTCAA AGGCGGTAAT ACGGTTATCC ACAGAATC    5640
GGGATAACGC AGGAAAGAAC ATGTGAGCAA AAGGCCAGCA AAAGGCCAGG AACCGTAA    5700
AGGCCGCGTT GCTGGCGTTT TTCCATAGGC TCCGCCCCCC TGACGAGCAT CACAAAAA    5760
GACGCTCAAG TCAGAGGTGG CGAAACCCGA CAGGACTATA AAGATACCAG GCGTTTCC    5820
CTGGAAGCTC CCTCGTGCGC TCTCCTGTTC CGACCCTGCC GCTTACCGGA TACCTGTC    5880
CCTTTCTCCC TTCGGGAAGC GTGGCGCTTT CTCAATGCTC ACGCTGTAGG TATCTCAG    5940
CGGTGTAGGT CGTTCGCTCC AAGCTGGGCT GTGTGCACGA ACCCCCCGTT CAGCCCGA    6000
GCTGCGCCTT ATCCGGTAAC TATCGTCTTG AGTCCAACCC GGTAAGACAC GACTTATC    6060
CACTGGCAGC AGCCACTGGT AACAGGATTA GCAGAGCGAG GTATGTAGGC GGTGCTAC    6120
AGTTCTTGAA GTGGTGGCCT AACTACGGCT ACACTAGAAG GACAGTATTT GGTATCTG    6180
CTCTGCTGAA GCCAGTTACC TTCGGAAAAA GAGTTGGTAG CTCTTGATCC GGCAAACA    6240
CCACCGCTGG TAGCGGTGGT TTTTTTGTTT GCAAGCAGCA GATTACGCGC AGAAAAAA    6300
GATCTCAAGA AGATCCTTTG ATCTTTTCTA CGGGGTCTGA CGCTCAGTGG AACGAAAA    6360
CACGTTAAGG GATTTTGGTC ATGAGATTAT CAAAAAGGAT CTTCACCTAG ATCCTTTT    6420
```

```
ATTAAAAATG AAGTTTTAAA TCAATCTAAA GTATATATGA GTAAACTTGG TCTGACAG       6480

ACCAATGCTT AATCAGTGAG GCACCTATCT CAGCGATCTG TCTATTTCGT TCATCCAT       6540

TTGCCTGACT CCCCGTCGTG TAGATAACTA CGATACGGGA GGGCTTACCA TCTGGCCC       6600

GTGCTGCAAT GATACCGCGA GACCCACGCT CACCGGCTCC AGATTTATCA GCAATAAA       6660

AGCCAGCCGG AAGGGCCGAG CGCAGAAGTG GTCCTGCAAC TTTATCCGCC TCCATCCA       6720

CTATTAATTG TTGCCGGGAA GCTAGAGTAA GTAGTTCGCC AGTTAATAGT TTGCGCAA       6780

TTGTTGCCAT TGCTACAGGC ATCGTGGTGT CACGCTCGTC GTTTGGTATG GCTTCATT       6840

GCTCCGGTTC CCAACGATCA AGGCGAGTTA CATGATCCCC CATGTTGTGC AAAAAAGC       6900

TTAGCTCCTT CGGTCCTCCG ATCGTTGTCA GAAGTAAGTT GGCCGCAGTG TTATCACT       6960

TGGTTATGGC AGCACTGCAT AATTCTCTTA CTGTCATGCC ATCCGTAAGA TGCTTTTC       7020

TGACTGGTGA GTACTCAACC AAGTCATTCT GAGAATAGTG TATGCGGCGA CCGAGTTG       7080

CTTGCCCGGC GTCAATACGG GATAATACCG CGCCACATAG CAGAACTTTA AAAGTGCT       7140

TCATTGGAAA ACGTTCTTCG GGGCGAAAAC TCTCAAGGAT CTTACCGCTG TTGAGATC       7200

GTTCGATGTA ACCCACTCGT GCACCCAACT GATCTTCAGC ATCTTTTACT TTCACCAG       7260

TTTCTGGGTG AGCAAAAACA GGAAGGCAAA ATGCCGCAAA AAAGGGAATA AGGGCGAC       7320

GGAAATGTTG AATACTCATA CTCTTCCTTT TTCAATATTA TTGAAGCATT TATCAGGG       7380

ATTGTCTCAT GAGCGGATAC ATATTTGAAT GTATTTAGAA AATAAACAA  ATAGGGGT       7440

CGCGCACATT TCCCCGAAAA GTGCCACCTG ACGTC                               7475

(2) INFORMATION FOR SEQ ID NO: 36:

(i) SEQUENCE CHARACTERISTICS:
        (A) LENGTH: 8192 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

GACGGATCGG GAGATCTCCC GATCCCCTAT GGTCGACTCT CAGTACAATC TGCTCTGATG        60

CCGCATAGTT AAGCCAGTAT CTGCTCCCTG CTTGTGTGTT GGAGGTCGCT GAGTAGTGC        120

CGAGCAAAAT TTAAGCTACA ACAAGGCAAG GCTTGACCGA CAATTGCATG AAGAATCTG        180

TTAGGGTTAG GCGTTTTGCG CTGCTTCGCG ATGTACGGGC CAGATATACG CGTTGACAT        240

GATTATTGAC TAGTTATTAA TAGTAATCAA TTACGGGGTC ATTAGTTCAT AGCCCATAT        300

TGGAGTTCCG CGTTACATAA CTTACGGTAA ATGGCCCGCC TGGCTGACCG CCCAACGAC        360

CCCGCCCATT GACGTCAATA ATGACGTATG TTCCCATAGT AACGCCAATA GGGACTTTC        420

ATTGACGTCA ATGGGTGGAC TATTTACGGT AAACTGCCCA CTTGGCAGTA CATCAAGTG        480

ATCATATGCC AAGTACGCCC CCTATTGACG TCAATGACGG TAAATGGCCC GCCTGGCAT        540

ATGCCCAGTA CATGACCTTA TGGGACTTTC CTACTTGGCA GTACATCTAC GTATTAGTC        600

TCGCTATTAC CATGGTGATG CGGTTTTGGC AGTACATCAA TGGGCGTGGA TAGCGGTTT        660

ACTCACGGGG ATTTCCAAGT CTCCACCCCA TTGACGTCAA TGGGAGTTTG TTTTGGCAC        720

AAAATCAACG GGACTTTCCA AAATGTCGTA ACAACTCCGC CCCATTGACG CAAATGGGC        780

GTAGGCGTGT ACGGTGGGAG GTCTATATAA GCAGAGCTCT CTGGCTAACT AGAGAACCC        840

CTGCTTACTG GCTTATCGAA ATTAATACGA CTCACTATAG GGAGACCCAA GCTGGCTAG        900
```

```
GTTTAAACGG GCCCTCTAGA CTCGAGCGGC CGCCACTGTG CTGGATATCT GCAGAATTC     960

GCTTGGGATG ACGCCTCCTC CGCCCGGACG TGCCGCCCCC AGCGCACCGC GCGCCCGC     1020

CCCTGGCCCG CCGGCTCGGT TGGGGCTTCC GCTGCGGCTG CGGCTGCTGC TGCTGCTC     1080

GGCGGCCGCC GCCTCCGCCC AGGGCCACCT AAGGAGCGGA CCCCGCATCT TCGCCGTC     1140

GAAAGGCCAT GTAGGGCAGG ACCGGGTGGA CTTTGGCCAG ACTGAGCCGC ACACGGTG     1200

TTTCCACGAG CCAGGCAGCT CCTCTGTGTG GGTGGGAGGA CGTGGCAAGG TCTACCTC     1260

TGACTTCCCC GAGGGCAAGA ACGCATCTGT GCGCACGGTG AATATCGGCT CCACAAAG     1320

GTCCTGTCTG GATAAGCGGG ACTGCGAGAA CTACATCACT CTCCTGGAGA GGCGGAGT     1380

GGGGCTGCTG GCCTGTGGCA CCAACGCCCG GCACCCCAGC TGCTGGAACC TGGTGAAT     1440

CACTGTGGTG CCACTTGGCG AGATGAGAGG CTACGCCCCC TTCAGCCCGG ACGAGAAC     1500

CCTGGTTCTG TTTGAAGGGG ACGAGGTGTA TTCCACCATC CGGAAGCAGG AATACAAT     1560

GAAGATCCCT CGGTTCCGCC GCATCCGGGG CGAGAGTGAG CTGTACACCA GTGATACT     1620

CATGCAGAAC CCACAGTTCA TCAAAGCCAC CATCGTGCAC CAAGACCAGG CTTACGAT     1680

CAAGATCTAC TACTTCTTCC GAGAGGACAA TCCTGACAAG AATCCTGAGG CTCCTCTC     1740

TGTGTCCCGT GTGGCCCAGT TGTGCAGGGG GGACCAGGGT GGGGAAAGTT CACTGTCA     1800

CTCCAAGTGG AACACTTTTC TGAAAGCCAT GCTGGTATGC AGTGATGCTG CCACCAAC     1860

GAACTTCAAC AGGCTGCAAG ACGTCTTCCT GCTCCCTGAC CCCAGCGGCC AGTGGAGG     1920

CACCAGGGTC TATGGTGTTT CTCCAACCCC CTGGAACTAC TCAGCCGTCT GTGTGTAT     1980

CCTCGGTGAC ATTGACAAGG TCTTCCGTAC CTCCTCACTC AAGGGCTACC ACTCAAGC     2040

TCCCAACCCG CGGCCTGGCA AGTGCCTCCC AGACCAGCAG CCGATACCCA CAGAGACC     2100

CCAGGTGGCT GACCGTCACC AGAGGTGGC GCAGAGGGTG GAGCCCATGG GGCCTCTG     2160

GACGCCATTG TTCCACTCTA AATACCACTA CCAGAAAGTG GCCGTTCACC GCATGCAA     2220

CAGCCACGGG GAGACCTTTC ATGTGCTTTA CCTAACTACA GACAGGGGCA CTATCCAC     2280

GGTGGTGGAA CCGGGGGAGC AGGAGCACAG CTTCGCCTTC AACATCATGG AGATCCAG     2340

CTTCCGCCGC GCGGCTGCCA TCCAGACCAT GTCGCTGGAT GCTGAGCGGA GGAAGCTG     2400

TGTGAGCTCC CAGTGGGAGG TGAGCCAGGT GCCCCTGGAC CTGTGTGAGG TCTATGGC     2460

GGGCTGCCAC GGTTGCCTCA TGTCCCGAGA CCCCTACTGC GGCTGGGACC AGGGCCGC     2520

CATCTCCATC TACAGCTCCG AACGGTCAGT GCTGCAATCC ATTAATCCAG CCAGCCA     2580

CAAGGAGTGT CCCAACCCCA AACCAGACAA GGCCCCACTG CAGAAGGTTT CCCTGGCC     2640

AAACTCTCGC TACTACCTGA GCTGCCCCAT GGAATCCCGC CACGCCACCT ACTCATGG     2700

CCACAAGGAG AACGTGGAGC AGAGCTGCGA ACCTGGTCAC CAGAGCCCCA ACTGCATC     2760

GTTCATCGAG AACCTCACGG CGCAGCAGTA CGGCCACTAC TTCTGCGAGG CCCAGGAG     2820

CTCCTACTTC CGCGAGGCTC AGCACTGGCA GCTGCTGCCC GAGGACGGCA TCATGGCC     2880

GCACCTGCTG GGTCATGCCT GTGCCCTGGC TGCCTCCCTC TGGCTGGGGG TGCTGCCC     2940

ACTCACTCTT GGCTTGCTGG TCCACATGGT GAGCAAGGGC GAGGAGCTGT TCACCGGG     3000

GGTGCCCATC CTGGTCGAGC TGGACGGCGA CGTAAACGGC CACAAGTTCA GCGTGTCC     3060

CGAGGGCGAG GGCGATGCCA CCTACGGCAA GCTGACCCTG AAGTTCATCT GCACCACC     3120

CAAGCTGCCC GTGCCCTGGC CCACCCTCGT GACCACCCTG ACCTACGGCG TGCAGTGC     3180

CAGCCGCTAC CCCGACCACA TGAAGCAGCA CGACTTCTTC AAGTCCGCCA TGCCCGAA     3240
```

```
CTACGTCCAG GAGCGCACCA TCTTCTTCAA GGACGACGGC AACTACAAGA CCCGCGCC      3300

GGTGAAGTTC GAGGGCGACA CCCTGGTGAA CCGCATCGAG CTGAAGGGCA TCGACTTC      3360

GGAGGACGGC AACATCCTGG GGCACAAGCT GGAGTACAAC TACAACAGCC ACAACGTC      3420

TATCATGGCC GACAAGCAGA AGAACGGCAT CAAGGTGAAC TTCAAGATCC GCCACAAC      3480

CGAGGACGGC AGCGTGCAGC TCGCCGACCA CTACCAGCAG AACACCCCCA TCGGCGAC      3540

CCCCGTGCTG CTGCCCGACA ACCACTACCT GAGCACCCAG TCCGCCCTGA GCAAAGAC      3600

CAACGAGAAG CGCGATCACA TGGTCCTGCT GGAGTTCGTG ACCGCCGCCG GGATCACT      3660

CGGCATGGAC GAGCTGTACA AGGTGAAGCT TGGGCCCGAA CAAAAACTCA TCTCAGAA      3720

GGATCTGAAT AGCGCCGTCG ACCATCATCA TCATCATCAT TGAGTTTAAA CCGCTGAT      3780

GCCTCGACTG TGCCTTCTAG TTGCCAGCCA TCTGTTGTTT GCCCCTCCCC CGTGCCTT      3840

TTGACCCTGG AAGGTGCCAC TCCCACTGTC CTTTCCTAAT AAAATGAGGA AATTGCAT      3900

CATTGTCTGA GTAGGTGTCA TTCTATTCTG GGGGTGGGG TGGGGCAGGA CAGCAAGG       3960

GAGGATTGGG AAGACAATAG CAGGCATGCT GGGGATGCGG TGGGCTCTAT GGCTTCTG      4020

GCGGAAAGAA CCAGCTGGGG CTCTAGGGGG TATCCCCACG CGCCCTGTAG CGGCGCAT      4080

AGCGCGGCGG GTGTGGTGGT TACGCGCAGC GTGACCGCTA CACTTGCCAG CGCCCTAG      4140

CCCGCTCCTT TCGCTTTCTT CCCTTCCTTT CTCGCCACGT TCGCCGGCTT TCCCCGTC      4200

GCTCTAAATC GGGGCATCCC TTTAGGGTTC CGATTTAGTG CTTTACGGCA CCTCGACC      4260

AAAAAACTTG ATTAGGGTGA TGGTTCACGT AGTGGGCCAT CGCCCTGATA GACGGTTT      4320

CGCCCTTTGA CGTTGGAGTC CACGTTCTTT AATAGTGGAC TCTTGTTCCA AACTGGAA      4380

ACACTCAACC CTATCTCGGT CTATTCTTTT GATTTATAAG GGATTTTGGG GATTTCGG      4440

TATTGGTTAA AAAATGAGCT GATTTAACAA AAATTTAACG CGAATTAATT CTGTGGAA      4500

TGTGTCAGTT AGGGTGTGGA AAGTCCCCAG GCTCCCCAGG CAGGCAGAAG TATGCAAA      4560

ATGCATCTCA ATTAGTCAGC AACCAGGTGT GGAAAGTCCC CAGGCTCCCC AGCAGGCA      4620

AGTATGCAAA GCATGCATCT CAATTAGTCA GCAACCATAG TCCCGCCCCT AACTCCGC      4680

ATCCCGCCCC TAACTCCGCC CAGTTCCGCC CATTCTCCGC CCCATGGCTG ACTAATTT      4740

TTTATTTATG CAGAGGCCGA GGCCGCCTCT GCCTCTGAGC TATTCCAGAA GTAGTGAG      4800

GCTTTTTTG GAGGCCTAGG CTTTTGCAAA AAGCTCCCGG GAGCTTGTAT ATCCATTT      4860

GGATCTGATC AAGAGACAGG ATGAGGATCG TTTCGCATGA TTGAACAAGA TGGATTGC      4920

GCAGGTTCTC CGGCCGCTTG GGTGGAGAGG CTATTCGGCT ATGACTGGGC ACAACAGA      4980

ATCGGCTGCT CTGATGCCGC CGTGTTCCGG CTGTCAGCGC AGGGGCGCCC GGTTCTTT      5040

GTCAAGACCG ACCTGTCCGG TGCCCTGAAT GAACTGCAGG ACGAGGCAGC GCGGCTAT      5100

TGGCTGGCCA CGACGGGCGT TCCTTGCGCA GCTGTGCTCG ACGTTGTCAC TGAAGCGG      5160

AGGGACTGGC TGCTATTGGG CGAAGTGCCG GGGCAGGATC TCCTGTCATC TCACCTTG      5220

CCTGCCGAGA AAGTATCCAT CATGGCTGAT GCAATGCGGC GGCTGCATAC GCTTGATC      5280

GCTACCTGCC CATTCGACCA CCAAGCGAAA CATCGCATCG AGCGAGCACG TACTCGGA      5340

GAAGCCGGTC TTGTCGATCA GGATGATCTG GACGAAGAGC ATCAGGGGCT CGCGCCAG      5400

GAACTGTTCG CCAGGCTCAA GGCGCGCATG CCCGACGGCG AGGATCTCGT CGTGACCC      5460

GGCGATGCCT GCTTGCCGAA TATCATGGTG GAAAATGGCC GCTTTTCTGG ATTCATCG      5520

TGTGGCCGGC TGGGTGTGGC GGACCGCTAT CAGGACATAG CGTTGGCTAC CCGTGATA      5580

GCTGAAGAGC TTGGCGGCGA ATGGGCTGAC CGCTTCCTCG TGCTTTACGG TATCGCCG      5640
```

```
CCCGATTCGC AGCGCATCGC CTTCTATCGC CTTCTTGACG AGTTCTTCTG AGCGGGAC     5700
TGGGGTTCGA AATGACCGAC CAAGCGACGC CCAACCTGCC ATCACGAGAT TTCGATTC     5760
CCGCCGCCTT CTATGAAAGG TTGGGCTTCG GAATCGTTTT CCGGGACGCC GGCTGGAT     5820
TCCTCCAGCG CGGGGATCTC ATGCTGGAGT TCTTCGCCCA CCCCAACTTG TTTATTGC     5880
CTTATAATGG TTACAAATAA AGCAATAGCA TCACAAATTT CACAAATAAA GCATTTTT     5940
CACTGCATTC TAGTTGTGGT TTGTCCAAAC TCATCAATGT ATCTTATCAT GTCTGTAT     6000
CGTCGACCTC TAGCTAGAGC TTGGCGTAAT CATGGTCATA GCTGTTTCCT GTGTGAAA     6060
GTTATCCGCT CACAATTCCA CACAACATAC GAGCCGGAAG CATAAAGTGT AAAGCCTG     6120
GTGCCTAATG AGTGAGCTAA CTCACATTAA TTGCGTTGCG CTCACTGCCC GCTTTCCA     6180
CGGGAAACCT GTCGTGCCAG CTGCATTAAT GAATCGGCCA ACGCGCGGGG AGAGGCGG     6240
TGCGTATTGG GCGCTCTTCC GCTTCCTCGC TCACTGACTC GCTGCGCTCG GTCGTTCG     6300
TGCGGCGAGC GGTATCAGCT CACTCAAAGG CGGTAATACG GTTATCCACA GAATCAGG     6360
ATAACGCAGG AAAGAACATG TGAGCAAAAG GCCAGCAAAA GGCCAGGAAC CGTAAAAA     6420
CCGCGTTGCT GGCGTTTTTC CATAGGCTCC GCCCCCCTGA CGAGCATCAC AAAAATCG     6480
GCTCAAGTCA GAGGTGGCGA AACCCGACAG GACTATAAAG ATACCAGGCG TTTCCCCC     6540
GAAGCTCCCT CGTGCGCTCT CCTGTTCCGA CCCTGCCGCT TACCGGATAC CTGTCCGC     6600
TTCTCCCTTC GGGAAGCGTG GCGCTTTCTC AATGCTCACG CTGTAGGTAT CTCAGTTC     6660
TGTAGGTCGT TCGCTCCAAG CTGGGCTGTG TGCACGAACC CCCCGTTCAG CCCGACCG     6720
GCGCCTTATC CGGTAACTAT CGTCTTGAGT CCAACCCGGT AAGACACGAC TTATCGCC     6780
TGGCAGCAGC CACTGGTAAC AGGATTAGCA GAGCGAGGTA TGTAGGCGGT GCTACAGA     6840
TCTTGAAGTG GTGGCCTAAC TACGGCTACA CTAGAAGGAC AGTATTTGGT ATCTGCGC     6900
TGCTGAAGCC AGTTACCTTC GGAAAAAGAG TTGGTAGCTC TTGATCCGGC AAACAAAC     6960
CCGCTGGTAG CGGTGGTTTT TTTGTTTGCA AGCAGCAGAT TACGCGCAGA AAAAAAGG     7020
CTCAAGAAGA TCCTTTGATC TTTTCTACGG GGTCTGACGC TCAGTGGAAC GAAAACTC     7080
GTTAAGGGAT TTTGGTCATG AGATTATCAA AAAGGATCTT CACCTAGATC CTTTTAAA     7140
AAAAATGAAG TTTTAAATCA ATCTAAAGTA TATATGAGTA AACTTGGTCT GACAGTTA     7200
AATGCTTAAT CAGTGAGGCA CCTATCTCAG CGATCTGTCT ATTTCGTTCA TCCATAGT     7260
CCTGACTCCC CGTCGTGTAG ATAACTACGA TACGGGAGGG CTTACCATCT GGCCCCAG     7320
CTGCAATGAT ACCGCGAGAC CCACGCTCAC CGGCTCCAGA TTTATCAGCA ATAAACCA     7380
CAGCCGGAAG GGCCGAGCGC AGAAGTGGTC CTGCAACTTT ATCCGCCTCC ATCCAGTC     7440
TTAATTGTTG CCGGGAAGCT AGAGTAAGTA GTTCGCCAGT TAATAGTTTG CGCAACGT     7500
TTGCCATTGC TACAGGCATC GTGGTGTCAC GCTCGTCGTT TGGTATGGCT TCATTCAG     7560
CCGGTTCCCA ACGATCAAGG CGAGTTACAT GATCCCCCAT GTTGTGCAAA AAAGCGGT     7620
GCTCCTTCGG TCCTCCGATC GTTGTCAGAA GTAAGTTGGC CGCAGTGTTA TCACTCAT     7680
TTATGGCAGC ACTGCATAAT TCTCTTACTG TCATGCCATC CGTAAGATGC TTTTCTGT     7740
CTGGTGAGTA CTCAACCAAG TCATTCTGAG AATAGTGTAT GCGGCGACCG AGTTGCTC     7800
GCCCGGCGTC AATACGGGAT AATACCGCGC CACATAGCAG AACTTTAAAA GTGCTCAT     7860
TTGGAAAACG TTCTTCGGGG CGAAAACTCT CAAGGATCTT ACCGCTGTTG AGATCCAG     7920
CGATGTAACC CACTCGTGCA CCCAACTGAT CTTCAGCATC TTTTACTTTC ACCAGCGT     7980
```

| | |
|---|---|
| CTGGGTGAGC AAAAACAGGA AGGCAAAATG CCGCAAAAAA GGGAATAAGG GCGACACG | 8040 |
| AATGTTGAAT ACTCATACTC TTCCTTTTTC AATATTATTG AAGCATTTAT CAGGGTTA | 8100 |
| GTCTCATGAG CGGATACATA TTTGAATGTA TTTAGAAAAA TAAACAAATA GGGGTTCC | 8160 |
| GCACATTTCC CCGAAAAGTG CCACCTGACG TC | 8192 |

(2) INFORMATION FOR SEQ ID NO: 37:

(i) SEQUENCE CHARACTERISTICS:
        (A) LENGTH: 7000 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

| | |
|---|---|
| AGATCTCGGC CGCATATTAA GTGCATTGTT CTCGATACCG CTAAGTGCAT TGTTCTCGTT | 60 |
| AGCTCGATGG ACAAGTGCAT TGTTCTCTTG CTGAAAGCTC GATGGACAAG TGCATTGTT | 120 |
| TCTTGCTGAA AGCTCGATGG ACAAGTGCAT TGTTCTCTTG CTGAAAGCTC AGTACCCGG | 180 |
| AGTACCCTCG ACCGCCGGAG TATAAATAGA GGCGCTTCGT CTACGGAGCG ACAATTCAA | 240 |
| TCAAACAAGC AAAGTGAACA CGTCGCTAAG CGAAAGCTAA GCAAATAAAC AAGCGCAGC | 300 |
| GAACAAGCTA ACAATCTGC AGTAAAGTGC AAGTTAAAGT GAATCAATTA AAAGTAACC | 360 |
| GCAACCAAGT AAATCAACTG CAACTACTGA AATCTGCCAA GAAGTAATTA TTGAATACA | 420 |
| GAAGAGAACT CTGAATACTT TCAACAAGTT ACCGAGAAAG AAGAACTCAC ACACAGCTA | 480 |
| CGTTTAAACT TAAGCTTGGT ACCGAGCTCG GATCCACTAG TCCAGTGTGG TGGAATTCG | 540 |
| CTTGGGATGA CGCCTCCTCC GCCCGGACGT GCCGCCCCCA GCGCACCGCG CGCCCGCGT | 600 |
| CCTGGCCCGC CGGCTCGGTT GGGGCTTCCG CTGCGGCTGC GGCTGCTGCT GCTGCTCTG | 660 |
| GCGGCCGCCG CCTCCGCCCA GGGCCACCTA AGGAGCGGAC CCCGCATCTT CGCCGTCTG | 720 |
| AAAGGCCATG TAGGGCAGGA CCGGGTGGAC TTTGGCCAGA CTGAGCCGCA CACGGTGCT | 780 |
| TTCCACGAGC CAGGCAGCTC CTCTGTGTGG GTGGAGGAC GTGGCAAGGT CTACCTCTT | 840 |
| GACTTCCCCG AGGGCAAGAA CGCATCTGTG CGCACGGTGA ATATCGGCTC CACAAAGGG | 900 |
| TCCTGTCTGG ATAAGCGGGA CTGCGAGAAC TACATCACTC TCCTGGAGAG GCGGAGTGA | 960 |
| GGGCTGCTGG CCTGTGGCAC CAACGCCCGG CACCCCAGCT GCTGGAACCT GGTGAATG | 1020 |
| ACTGTGGTGC CACTTGGCGA GATGAGAGGC TACGCCCCCT TCAGCCCGGA CGAGAACT | 1080 |
| CTGGTTCTGT TTGAAGGGGA CGAGGTGTAT TCCACCATCC GGAAGCAGGA ATACAATG | 1140 |
| AAGATCCCTC GGTTCCGCCG CATCCGGGGC GAGAGTGAGC TGTACACCAG TGATACTG | 1200 |
| ATGCAGAACC CACAGTTCAT CAAAGCCACC ATCGTGCACC AAGACCAGGC TTACGATG | 1260 |
| AAGATCTACT ACTTCTTCCG AGAGGACAAT CCTGACAAGA ATCCTGAGGC TCCTCTCA | 1320 |
| GTGTCCCGTG TGGCCCAGTT GTGCAGGGGG ACCAGGGTG GGGAAAGTTC ACTGTCAG | 1380 |
| TCCAAGTGGA ACACTTTTCT GAAAGCCATG CTGGTATGCA GTGATGCTGC CACCAACA | 1440 |
| AACTTCAACA GGCTGCAAGA CGTCTTCCTG CTCCCTGACC CCAGCGGCCA GTGGAGGG | 1500 |
| ACCAGGGTCT ATGGTGTTTT CTCCAACCCC TGGAACTACT CAGCCGTCTG TGTGTATT | 1560 |
| CTCGGTGACA TTGACAAGGT CTTCCGTACC TCCTCACTCA AGGGCTACCA CTCAAGCC | 1620 |
| CCCAACCCGC GGCCTGGCAA GTGCCTCCCA GACCAGCAGC CGATACCCAC AGAGACCT | 1680 |
| CAGGTGGCTG ACCGTCACCC AGAGGTGGCG CAGAGGGTGG AGCCCATGGG GCCTCTGA | 1740 |

| | |
|---|---|
| ACGCCATTGT TCCACTCTAA ATACCACTAC CAGAAAGTGG CCGTTCACCG CATGCAAG | 1800 |
| AGCCACGGGG AGACCTTTCA TGTGCTTTAC CTAACTACAG ACAGGGGCAC TATCCACA | 1860 |
| GTGGTGGAAC CGGGGGAGCA GGAGCACAGC TTCGCCTTCA ACATCATGGA GATCCAGC | 1920 |
| TTCCGCCGCG CGGCTGCCAT CCAGACCATG TCGCTGGATG CTGAGCGGAG GAAGCTGT | 1980 |
| GTGAGCTCCC AGTGGGAGGT GAGCCAGGTG CCCCTGGACC TGTGTGAGGT CTATGGCG | 2040 |
| GGCTGCCACG GTTGCCTCAT GTCCCGAGAC CCCTACTGCG GCTGGGACCA GGGCCGCT | 2100 |
| ATCTCCATCT ACAGCTCCGA ACGGTCAGTG CTGCAATCCA TTAATCCAGC CGAGCCAC | 2160 |
| AAGGAGTGTC CCAACCCCAA ACCAGACAAG GCCCCACTGC AGAAGGTTTC CCTGGCCC | 2220 |
| AACTCTCGCT ACTACCTGAG CTGCCCCATG GAATCCCGCC ACGCCACCTA CTCATGGC | 2280 |
| CACAAGGAGA ACGTGGAGCA GAGCTGCGAA CCTGGTCACC AGAGCCCCAA CTGCATCC | 2340 |
| TTCATCGAGA ACCTCACGGC GCAGCAGTAC GGCCACTACT TCTGCGAGGC CCAGGAGG | 2400 |
| TCCTACTTCC GCGAGGCTCA GCACTGGCAG CTGCTGCCCG AGGACGGCAT CATGGCCG | 2460 |
| CACCTGCTGG GTCATGCCTG TGCCCTGGCT GCCTCCCTCT GGCTGGGGGT GCTGCCCA | 2520 |
| CTCACTCTTG GCTTGCTGGT CCACGTGAAG CTTGGGCCCG TTTAAACCCG CTGATCAG | 2580 |
| TCGACTGTGC CTTCTAGTTG CCAGCCATCT GTTGTTTGCC CCTCCCCCGT GCCTTCCT | 2640 |
| ACCCTGGAAG GTGCCACTCC CACTGTCCTT TCCTAATAAA ATGAGGAAAT TGCATCGC | 2700 |
| TGTCTGAGTA GGTGTCATTC TATTCTGGGG GGTGGGGTGG GGCAGGACAG CAAGGGGG | 2760 |
| GATTGGGAAG ACAATAGCAG GCATGCTGGG GATGCGGTGG GCTCTATGGC TTCTGAGG | 2820 |
| GAAAGAACCA GCTGGGGCTC TAGGGGGTAT CCCCACGCGC CCTGTAGCGG CGCATTAA | 2880 |
| GCGGCGGGTG TGGTGGTTAC GCGCAGCGTG ACCGCTACAC TTGCCAGCGC CCTAGCGC | 2940 |
| GCTCCTTTCG CTTTCTTCCC TTCCTTTCTC GCCACGTTCG CCGGCTTTCC CCGTCAAG | 3000 |
| CTAAATCGGG GCATCCCTTT AGGGTTCCGA TTTAGTGCTT TACGGCACCT CGACCCCA | 3060 |
| AAACTTGATT AGGGTGATGG TTCACGTAGT GGGCCATCGC CCTGATAGAC GGTTTTTC | 3120 |
| CCTTTGACGT TGGAGTCCAC GTTCTTTAAT AGTGGACTCT TGTTCCAAAC TGGAACAA | 3180 |
| CTCAACCCTA TCTCGGTCTA TTCTTTTGAT TTATAAGGGA TTTTGGGGAT TTCGGCCT | 3240 |
| TGGTTAAAAA ATGAGCTGAT TTAACAAAAA TTTAACGCGA ATTAATTCTG TGGAATGT | 3300 |
| GTCAGTTAGG GTGTGGAAAG TCCCCAGGCT CCCCAGGCAG GCAGAAGTAT GCAAAGCA | 3360 |
| CATCTCAATT AGTCAGCAAC CAGGTGTGGA AAGTCCCCAG GCTCCCCAGC AGGCAGAA | 3420 |
| ATGCAAAGCA TGCATCTCAA TTAGTCAGCA ACCATAGTCC CGCCCCTAAC TCCGCCCA | 3480 |
| CCGCCCCTAA CTCCGCCCAG TTCCGCCCAT TCTCCGCCCC ATGGCTGACT AATTTTTT | 3540 |
| ATTTATGCAG AGGCCGAGGC CGCCTCTGCC TCTGAGCTAT TCCAGAAGTA GTGAGGAG | 3600 |
| TTTTTTGGAG GCCTAGGCTT TTGCAAAAAG CTCCCGGGAG CTTGTATATC CATTTTCG | 3660 |
| TCTGATCAAG AGACAGGATG AGGATCGTTT CGCATGATTG AACAAGATGG ATTGCACG | 3720 |
| GGTTCTCCGG CCGCTTGGGT GGAGAGGCTA TTCGGCTATG ACTGGGCACA ACAGACAA | 3780 |
| GGCTGCTCTG ATGCCGCCGT GTTCCGGCTG TCAGCGCAGG GGCGCCCGGT TCTTTTTG | 3840 |
| AAGACCGACC TGTCCGGTGC CCTGAATGAA CTGCAGGACG AGGCAGCGCG GCTATCGT | 3900 |
| CTGGCCACGA CGGGCGTTCC TTGCGCAGCT GTGCTCGACG TTGTCACTGA AGCGGGAA | 3960 |
| GACTGGCTGC TATTGGGCGA AGTGCCGGGG CAGGATCTCC TGTCATCTCA CCTTGCTC | 4020 |
| GCCGAGAAAG TATCCATCAT GGCTGATGCA ATGCGGCGGC TGCATACGCT TGATCCGG | 4080 |
| ACCTGCCCAT TCGACCACCA AGCGAAACAT CGCATCGAGC GAGCACGTAC TCGGATGG | 4140 |

```
GCCGGTCTTG TCGATCAGGA TGATCTGGAC GAAGAGCATC AGGGGCTCGC GCCAGCCG      4200

CTGTTCGCCA GGCTCAAGGC GCGCATGCCC GACGGCGAGG ATCTCGTCGT GACCCATG      4260

GATGCCTGCT TGCCGAATAT CATGGTGGAA AATGGCCGCT TTTCTGGATT CATCGACT      4320

GGCCGGCTGG GTGTGGCGGA CCGCTATCAG GACATAGCGT TGGCTACCCG TGATATTG      4380

GAAGAGCTTG GCGGCGAATG GGCTGACCGC TTCCTCGTGC TTTACGGTAT CGCCGCTC      4440

GATTCGCAGC GCATCGCCTT CTATCGCCTT CTTGACGAGT TCTTCTGAGC GGGACTCT      4500

GGTTCGAAAT GACCGACCAA GCGACGCCCA ACCTGCCATC ACGAGATTTC GATTCCAC      4560

CCGCCTTCTA TGAAAGGTTG GGCTTCGGAA TCGTTTTCCG GGACGCCGGC TGGATGAT      4620

TCCAGCGCGG GGATCTCATG CTGGAGTTCT TCGCCCACCC CAACTTGTTT ATTGCAGC      4680

ATAATGGTTA CAAATAAAGC AATAGCATCA CAAATTTCAC AAATAAAGCA TTTTTTTC      4740

TGCATTCTAG TTGTGGTTTG TCCAAACTCA TCAATGTATC TTATCATGTC TGTATACC      4800

CGACCTCTAG CTAGAGCTTG GCGTAATCAT GGTCATAGCT GTTTCCTGTG TGAAATTG      4860

ATCCGCTCAC AATTCCACAC AACATACGAG CCGGAAGCAT AAAGTGTAAA GCCTGGGG      4920

CCTAATGAGT GAGCTAACTC ACATTAATTG CGTTGCGCTC ACTGCCCGCT TTCCAGTC      4980

GAAACCTGTC GTGCCAGCTG CATTAATGAA TCGGCCAACG CGCGGGGAGA GGCGGTTT      5040

GTATTGGGCG CTCTTCCGCT TCCTCGCTCA CTGACTCGCT GCGCTCGGTC GTTCGGCT      5100

GGCGAGCGGT ATCAGCTCAC TCAAAGGCGG TAATACGGTT ATCCACAGAA TCAGGGGA      5160

ACGCAGGAAA GAACATGTGA GCAAAAGGCC AGCAAAAGGC CAGGAACCGT AAAAAGGC      5220

CGTTGCTGGC GTTTTTCCAT AGGCTCCGCC CCCCTGACGA GCATCACAAA AATCGACG      5280

CAAGTCAGAG GTGGCGAAAC CCGACAGGAC TATAAAGATA CCAGGCGTTT CCCCCTGG      5340

GCTCCCTCGT GCGCTCTCCT GTTCCGACCC TGCCGCTTAC CGGATACCTG TCCGCCTT      5400

TCCCTTCGGG AAGCGTGGCG CTTTCTCAAT GCTCACGCTG TAGGTATCTC AGTTCGGT      5460

AGGTCGTTCG CTCCAAGCTG GGCTGTGTGC ACGAACCCCC CGTTCAGCCC GACCGCTG      5520

CCTTATCCGG TAACTATCGT CTTGAGTCCA ACCCGGTAAG ACACGACTTA TCGCCACT      5580

CAGCAGCCAC TGGTAACAGG ATTAGCAGAG CGAGGTATGT AGGCGGTGCT ACAGAGTT      5640

TGAAGTGGTG GCCTAACTAC GGCTACACTA GAAGGACAGT ATTTGGTATC TGCGCTCT      5700

TGAAGCCAGT TACCTTCGGA AAAAGAGTTG GTAGCTCTTG ATCCGGCAAA CAAACCAC      5760

CTGGTAGCGG TGGTTTTTTT GTTTGCAAGC AGCAGATTAC GCGCAGAAAA AAGGATC      5820

AAGAAGATCC TTTGATCTTT TCTACGGGGT CTGACGCTCA GTGGAACGAA AACTCACG      5880

AAGGGATTTT GGTCATGAGA TTATCAAAAA GGATCTTCAC CTAGATCCTT TTAAATTA      5940

AATGAAGTTT TAAATCAATC TAAAGTATAT ATGAGTAAAC TTGGTCTGAC AGTTACCA      6000

GCTTAATCAG TGAGGCACCT ATCTCAGCGA TCTGTCTATT TCGTTCATCC ATAGTTGC      6060

GACTCCCCGT CGTGTAGATA ACTACGATAC GGGAGGGCTT ACCATCTGGC CCCAGTGC      6120

CAATGATACC GCGAGACCCA CGCTCACCGG CTCCAGATTT ATCAGCAATA AACCAGCC      6180

CCGGAAGGGC CGAGCGCAGA AGTGGTCCTG CAACTTTATC CGCCTCCATC CAGTCTAT      6240

ATTGTTGCCG GGAAGCTAGA GTAAGTAGTT CGCCAGTTAA TAGTTTGCGC AACGTTGT      6300

CCATTGCTAC AGGCATCGTG GTGTCACGCT CGTCGTTTGG TATGGCTTCA TTCAGCTC      6360

GTTCCCAACG ATCAAGGCGA GTTACATGAT CCCCCATGTT GTGCAAAAAA GCGGTTAG      6420

CCTTCGGTCC TCCGATCGTT GTCAGAAGTA AGTTGGCCGC AGTGTTATCA CTCATGGT      6480
```

```
TGGCAGCACT GCATAATTCT CTTACTGTCA TGCCATCCGT AAGATGCTTT TCTGTGAC       6540

GTGAGTACTC AACCAAGTCA TTCTGAGAAT AGTGTATGCG GCGACCGAGT TGCTCTTG       6600

CGGCGTCAAT ACGGGATAAT ACCGCGCCAC ATAGCAGAAC TTTAAAAGTG CTCATCAT       6660

GAAAACGTTC TTCGGGGCGA AAACTCTCAA GGATCTTACC GCTGTTGAGA TCCAGTTC       6720

TGTAACCCAC TCGTGCACCC AACTGATCTT CAGCATCTTT TACTTTCACC AGCGTTTC       6780

GGTGAGCAAA AACAGGAAGG CAAAATGCCG CAAAAAAGGG AATAAGGGCG ACACGGAA       6840

GTTGAATACT CATACTCTTC CTTTTTCAAT ATTATTGAAG CATTTATCAG GGTTATTG       6900

TCATGAGCGG ATACATATTT GAATGTATTT AGAAAAATAA ACAATAGGG GTTCCGCG        6960

CATTTCCCCG AAAAGTGCCA CCTGACGTCG ACGGATCGGG                           7000

(2) INFORMATION FOR SEQ ID NO: 38:

(i) SEQUENCE CHARACTERISTICS:
        (A) LENGTH: 7108 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

AGATCTCGGC CGCATATTAA GTGCATTGTT CTCGATACCG CTAAGTGCAT TGTTCTCGTT       60

AGCTCGATGG ACAAGTGCAT TGTTCTCTTG CTGAAAGCTC GATGGACAAG TGCATTGTT      120

TCTTGCTGAA AGCTCGATGG ACAAGTGCAT TGTTCTCTTG CTGAAAGCTC AGTACCCGG      180

AGTACCCTCG ACCGCCGGAG TATAAATAGA GGCGCTTCGT CTACGGAGCG ACAATTCAA      240

TCAAACAAGC AAAGTGAACA CGTCGCTAAG CGAAAGCTAA GCAAATAAAC AAGCGCAGC      300

GAACAAGCTA ACAATCTGC AGTAAAGTGC AAGTTAAAGT GAATCAATTA AAAGTAACC       360

GCAACCAAGT AAATCAACTG CAACTACTGA AATCTGCCAA GAAGTAATTA TTGAATACA      420

GAAGAGAACT CTGAATACTT TCAACAAGTT ACCGAGAAAG AAGAACTCAC ACACAGCTA      480

CGTTTAAACT TAAGCTTGGT ACCGAGCTCG GATCCACTAG TCCAGTGTGG TGGAATTCG      540

CTTGGGATGA CGCCTCCTCC GCCCGGACGT GCCGCCCCCA GCGCACCGCG CGCCCGCGT      600

CCTGGCCCGC CGGCTCGGTT GGGGCTTCCG CTGCGGCTGC GGCTGCTGCT GCTGCTCTG      660

GCGGCCGCCG CCTCCGCCCA GGGCCACCTA AGGAGCGGAC CCCGCATCTT CGCCGTCTG      720

AAAGGCCATG TAGGGCAGGA CCGGGTGGAC TTTGGCCAGA CTGAGCCGCA CACGGTGCT      780

TTCCACGAGC CAGGCAGCTC CTCTGTGTGG GTGGGAGGAC GTGGCAAGGT CTACCTCTT      840

GACTTCCCCG AGGGCAAGAA CGCATCTGTG CGCACGGTGA ATATCGGCTC CACAAAGGG      900

TCCTGTCTGG ATAAGCGGGA CTGCGAGAAC TACATCACTC TCCTGGAGAG GCGGAGTGA      960

GGGCTGCTGG CCTGTGGCAC CAACGCCCGG CACCCCAGCT GCTGGAACCT GGTGAATG      1020

ACTGTGGTGC CACTTGGCGA GATGAGAGGC TACGCCCCCT TCAGCCCGGA CGAGAACT      1080

CTGGTTCTGT TTGAAGGGGA CGAGGTGTAT TCCACCATCC GGAAGCAGGA ATACAATG      1140

AAGATCCCTC GGTTCCGCCG CATCCGGGGC GAGAGTGAGC TGTACACCAG TGATACTG      1200

ATGCAGAACC CACAGTTCAT CAAAGCCACC ATCGTGCACC AAGACCAGGC TTACGATG      1260

AAGATCTACT ACTTCTTCCG AGAGGACAAT CCTGACAAGA ATCCTGAGGC TCCTCTCA      1320

GTGTCCCGTG TGGCCCAGTT GTGCAGGGGA GACCAGGGTG GGGAAAGTTC ACTGTCAG      1380

TCCAAGTGGA ACACTTTTCT GAAAGCCATG CTGGTATGCA GTGATGCTGC CACCAACA      1440
```

-continued

| | |
|---|---|
| AACTTCAACA GGCTGCAAGA CGTCTTCCTG CTCCCTGACC CCAGCGGCCA GTGGAGGG | 1500 |
| ACCAGGGTCT ATGGTGTTTT CTCCAACCCC TGGAACTACT CAGCCGTCTG TGTGTATT | 1560 |
| CTCGGTGACA TTGACAAGGT CTTCCGTACC TCCTCACTCA AGGGCTACCA CTCAAGCC | 1620 |
| CCCAACCCGC GGCCTGGCAA GTGCCTCCCA GACCAGCAGC CGATACCCAC AGAGACCT | 1680 |
| CAGGTGGCTG ACCGTCACCC AGAGGTGGCG CAGAGGGTGG AGCCCATGGG GCCTCTGA | 1740 |
| ACGCCATTGT TCCACTCTAA ATACCACTAC CAGAAAGTGG CCGTTCACCG CATGCAAG | 1800 |
| AGCCACGGGG AGACCTTTCA TGTGCTTTAC CTAACTACAG ACAGGGGCAC TATCCACA | 1860 |
| GTGGTGGAAC CGGGGGAGCA GGAGCACAGC TTCGCCTTCA ACATCATGGA GATCCAGC | 1920 |
| TTCCGCCGCG CGGCTGCCAT CCAGACCATG TCGCTGGATG CTGAGCGGAG GAAGCTGT | 1980 |
| GTGAGCTCCC AGTGGGAGGT GAGCCAGGTG CCCCTGGACC TGTGTGAGGT CTATGGCG | 2040 |
| GGCTGCCACG GTTGCCTCAT GTCCCGAGAC CCCTACTGCG GCTGGGACCA GGGCCGCT | 2100 |
| ATCTCCATCT ACAGCTCCGA ACGGTCAGTG CTGCAATCCA TTAATCCAGC CGAGCCAC | 2160 |
| AAGGAGTGTC CCAACCCCAA ACCAGACAAG GCCCCACTGC AGAAGGTTTC CCTGGCCC | 2220 |
| AACTCTCGCT ACTACCTGAG CTGCCCCATG GAATCCCGCC ACGCCACCTA CTCATGGC | 2280 |
| CACAAGGAGA ACGTGGAGCA GAGCTGCGAA CCTGGTCACC AGAGCCCCAA CTGCATCC | 2340 |
| TTCATCGAGA ACCTCACGGC GCAGCAGTAC GGCCACTACT TCTGCGAGGC CCAGGAGG | 2400 |
| TCCTACTTCC GCGAGGCTCA GCACTGGCAG CTGCTGCCCG AGGACGGCAT CATGGCCG | 2460 |
| CACCTGCTGG GTCATGCCTG TGCCCTGGCT GCCTCCCTCT GGCTGGGGGT GCTGCCCA | 2520 |
| CTCACTCTTG GCTTGCTGGT CCACGTGAAG CTTGGGCCCG AACAAAAACT CATCTCAG | 2580 |
| GAGGATCTGA ATAGCGCCGT CGACCATCAT CATCATCATC ATTGAGTTTA TCCAGCAC | 2640 |
| TGGCGGCCGC TCGAGTCTAG AGGGCCCGTT TAAACCCGCT GATCAGCCTC GACTGTGC | 2700 |
| TCTAGTTGCC AGCCATCTGT TGTTTGCCCC TCCCCCGTGC CTTCCTTGAC CCTGGAAG | 2760 |
| GCCACTCCCA CTGTCCTTTC CTAATAAAAT GAGGAAATTG CATCGCATTG TCTGAGTA | 2820 |
| TGTCATTCTA TTCTGGGGGG TGGGGTGGGG CAGGACAGCA AGGGGGAGGA TTGGAAG | 2880 |
| AATAGCAGGC ATGCTGGGGA TGCGGTGGGC TCTATGGCTT CTGAGGCGGA AAGAACCA | 2940 |
| TGGGGCTCTA GGGGGTATCC CCACGCGCCC TGTAGCGGCG CATTAAGCGC GGCGGGTG | 3000 |
| GTGGTTACGC GCAGCGTGAC CGCTACACTT GCCAGCGCCC TAGCGCCCGC TCCTTTCG | 3060 |
| TTCTTCCCTT CCTTTCTCGC CACGTTCGCC GGCTTTCCCC GTCAAGCTCT AAATCGGG | 3120 |
| ATCCCTTTAG GGTTCCGATT TAGTGCTTTA CGGCACCTCG ACCCCAAAAA ACTTGATT | 3180 |
| GGTGATGGTT CACGTAGTGG GCCATCGCCC TGATAGACGG TTTTTCGCCC TTTGACGT | 3240 |
| GAGTCCACGT TCTTTAATAG TGGACTCTTG TTCCAAACTG GAACAACACT CAACCCTA | 3300 |
| TCGGTCTATT CTTTTGATTT ATAAGGGATT TTGGGGATTT CGGCCTATTG GTTAAAAA | 3360 |
| GAGCTGATTT AACAAAAATT TAACGCGAAT TAATTCTGTG GAATGTGTGT CAGTTAGG | 3420 |
| GTGGAAAGTC CCCAGGCTCC CCAGGCAGGC AGAAGTATGC AAAGCATGCA TCTCAATT | 3480 |
| TCAGCAACCA GGTGTGGAAA GTCCCCAGGC TCCCCAGCAG GCAGAAGTAT GCAAAGCA | 3540 |
| CATCTCAATT AGTCAGCAAC CATAGTCCCG CCCCTAACTC CGCCCATCCC GCCCCTAA | 3600 |
| CCGCCCAGTT CCGCCCATTC TCCGCCCCAT GGCTGACTAA TTTTTTTTAT TTATGCAG | 3660 |
| GCCGAGGCCG CCTCTGCCTC TGAGCTATTC CAGAAGTAGT GAGGAGGCTT TTTTGGAG | 3720 |
| CTAGGCTTTT GCAAAAAGCT CCCGGGAGCT TGTATATCCA TTTTCGGATC TGATCAAG | 3780 |
| ACAGGATGAG GATCGTTTCG CATGATTGAA CAAGATGGAT TGCACGCAGG TTCTCCGG | 3840 |

```
GCTTGGGTGG AGAGGCTATT CGGCTATGAC TGGGCACAAC AGACAATCGG CTGCTCTG      3900

GCCGCCGTGT TCCGGCTGTC AGCGCAGGGG CGCCCGGTTC TTTTTGTCAA GACCGACC      3960

TCCGGTGCCC TGAATGAACT GCAGGACGAG GCAGCGCGGC TATCGTGGCT GGCCACGA      4020

GGCGTTCCTT GCGCAGCTGT GCTCGACGTT GTCACTGAAG CGGGAAGGGA CTGGCTGC      4080

TTGGGCGAAG TGCCGGGGCA GGATCTCCTG TCATCTCACC TTGCTCCTGC CGAGAAAG      4140

TCCATCATGG CTGATGCAAT GCGGCGGCTG CATACGCTTG ATCCGGCTAC CTGCCCAT      4200

GACCACCAAG CGAAACATCG CATCGAGCGA GCACGTACTC GGATGGAAGC CGGTCTTG      4260

GATCAGGATG ATCTGGACGA AGAGCATCAG GGGCTCGCGC CAGCCGAACT GTTCGCCA      4320

CTCAAGGCGC GCATGCCCGA CGGCGAGGAT CTCGTCGTGA CCCATGGCGA TGCCTGCT      4380

CCGAATATCA TGGTGGAAAA TGGCCGCTTT TCTGGATTCA TCGACTGTGG CCGGCTGG      4440

GTGGCGGACC GCTATCAGGA CATAGCGTTG GCTACCCGTG ATATTGCTGA AGAGCTTG      4500

GGCGAATGGG CTGACCGCTT CCTCGTGCTT TACGGTATCG CCGCTCCCGA TTCGCAGC      4560

ATCGCCTTCT ATCGCCTTCT TGACGAGTTC TTCTGAGCGG GACTCTGGGG TTCGAAAT      4620

CCGACCAAGC GACGCCCAAC CTGCCATCAC GAGATTTCGA TTCCACCGCC GCCTTCTA      4680

AAAGGTTGGG CTTCGGAATC GTTTTCCGGG ACGCCGGCTG GATGATCCTC CAGCGCGG      4740

ATCTCATGCT GGAGTTCTTC GCCCACCCCA ACTTGTTTAT TGCAGCTTAT AATGGTTA      4800

AATAAAGCAA TAGCATCACA AATTTCACAA ATAAAGCATT TTTTTCACTG CATTCTAG      4860

GTGGTTTGTC CAAACTCATC AATGTATCTT ATCATGTCTG TATACCGTCG ACCTCTAG      4920

AGAGCTTGGC GTAATCATGG TCATAGCTGT TTCCTGTGTG AAATTGTTAT CCGCTCAC      4980

TTCCACACAA CATACGAGCC GGAAGCATAA AGTGTAAAGC CTGGGGTGCC TAATGAGT      5040

GCTAACTCAC ATTAATTGCG TTGCGCTCAC TGCCCGCTTT CCAGTCGGGA AACCTGTC      5100

GCCAGCTGCA TTAATGAATC GGCCAACGCG CGGGGAGAGG CGGTTTGCGT ATTGGGCG      5160

CTTCCGCTTC CTCGCTCACT GACTCGCTGC GCTCGGTCGT TCGGCTGCGG CGAGCGGT      5220

CAGCTCACTC AAAGGCGGTA ATACGGTTAT CCACAGAATC AGGGGATAAC GCAGGAAA      5280

ACATGTGAGC AAAAGGCCAG CAAAAGGCCA GGAACCGTAA AAAGGCCGCG TTGCTGGC      5340

TTTTCCATAG GCTCCGCCCC CCTGACGAGC ATCACAAAAA TCGACGCTCA AGTCAGAG      5400

GGCGAAACCC GACAGGACTA TAAAGATACC AGGCGTTTCC CCCTGGAAGC TCCCTCGT      5460

GCTCTCCTGT TCCGACCCTG CCGCTTACCG GATACCTGTC CGCCTTTCTC CCTTCGGG      5520

GCGTGGCGCT TTCTCAATGC TCACGCTGTA GGTATCTCAG TTCGGTGTAG GTCGTTCG      5580

CCAAGCTGGG CTGTGTGCAC GAACCCCCCG TTCAGCCCGA CCGCTGCGCC TTATCCGG      5640

ACTATCGTCT TGAGTCCAAC CCGGTAAGAC ACGACTTATC GCCACTGGCA GCAGCCAC      5700

GTAACAGGAT TAGCAGAGCG AGGTATGTAG GCGGTGCTAC AGAGTTCTTG AAGTGGTG      5760

CTAACTACGG CTACACTAGA AGGACAGTAT TTGGTATCTG CGCTCTGCTG AAGCCAGT      5820

CCTTCGGAAA AAGAGTTGGT AGCTCTTGAT CCGGCAAACA AACCACCGCT GGTAGCGG      5880

GTTTTTTTGT TTGCAAGCAG CAGATTACGC GCAGAAAAAA AGGATCTCAA GAAGATCC      5940

TGATCTTTTC TACGGGGTCT GACGCTCAGT GGAACGAAAA CTCACGTTAA GGGATTTT      6000

TCATGAGATT ATCAAAAGG ATCTTCACCT AGATCCTTTT AAATTAAAAA TGAAGTTT      6060

AATCAATCTA AAGTATATAT GAGTAAACTT GGTCTGACAG TTACCAATGC TTAATCAG      6120

AGGCACCTAT CTCAGCGATC TGTCTATTTC GTTCATCCAT AGTTGCCTGA CTCCCCGT      6180
```

| | | | | |
|---|---|---|---|---|
|TGTAGATAAC|TACGATACGG|GAGGGCTTAC|CATCTGGCCC|CAGTGCTGCA ATGATACC 6240|
|GAGACCCACG|CTCACCGGCT|CCAGATTTAT|CAGCAATAAA|CCAGCCAGCC GGAAGGGC 6300|
|AGCGCAGAAG|TGGTCCTGCA|ACTTTATCCG|CCTCCATCCA|GTCTATTAAT TGTTGCCG 6360|
|AAGCTAGAGT|AAGTAGTTCG|CCAGTTAATA|GTTTGCGCAA|CGTTGTTGCC ATTGCTAC 6420|
|GCATCGTGGT|GTCACGCTCG|TCGTTTGGTA|TGGCTTCATT|CAGCTCCGGT TCCCAACG 6480|
|CAAGGCGAGT|TACATGATCC|CCCATGTTGT|GCAAAAAAGC|GGTTAGCTCC TTCGGTCC 6540|
|CGATCGTTGT|CAGAAGTAAG|TTGGCCGCAG|TGTTATCACT|CATGGTTATG GCAGCACT 6600|
|ATAATTCTCT|TACTGTCATG|CCATCCGTAA|GATGCTTTTC|TGTGACTGGT GAGTACTC 6660|
|CCAAGTCATT|CTGAGAATAG|TGTATGCGGC|GACCGAGTTG|CTCTTGCCCG GCGTCAAT 6720|
|GGGATAATAC|CGCGCCACAT|AGCAGAACTT|TAAAAGTGCT|CATCATTGGA AAACGTTC 6780|
|CGGGGCGAAA|ACTCTCAAGG|ATCTTACCGC|TGTTGAGATC|CAGTTCGATG TAACCCAC 6840|
|GTGCACCCAA|CTGATCTTCA|GCATCTTTTA|CTTTCACCAG|CGTTTCTGGG TGAGCAAA 6900|
|CAGGAAGGCA|AAATGCCGCA|AAAAAGGGAA|TAAGGGCGAC|ACGGAAATGT TGAATACT 6960|
|TACTCTTCCT|TTTTCAATAT|TATTGAAGCA|TTTATCAGGG|TTATTGTCTC ATGAGCGG 7020|
|ACATATTTGA|ATGTATTTAG|AAAAATAAAC|AAATAGGGGT|TCCGCGCACA TTTCCCCG 7080|
|AAGTGCCACC|TGACGTCGAC|GGATCGGG|  |7108|

(2) INFORMATION FOR SEQ ID NO: 39:

(i) SEQUENCE CHARACTERISTICS:
        (A) LENGTH: 4019 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

| | | | | |
|---|---|---|---|---|
|CTCGAGAAAT|CATAAAAAAT|TTATTTGCTT|TGTGAGCGGA|TAACAATTAT AATAGATTCA 60|
|ATTGTGAGCG|GATAACAATT|TCACACAGAA|TTCATTAAAG|AGGAGAAATT AACTATGAG 120|
|GGATCGCATC|ACCATCACCA|TCACGGATCC|CTGGTTCTGT|TGAAGGGGA CGAGGTGTA 180|
|TCCACCATCC|GGAAGCAGGA|ATACAATGGG|AAGATCCCTC|GGTTCCGCCG CATCCGGGG 240|
|GAGAGTGAGC|TGTACACCAG|TGATACTGTC|ATGCAGAACC|CACAGTTCAT CAAAGCCAC 300|
|ATCGTGCACC|AAGACCAGGC|TTACGATGAC|AAGATCTACT|ACTTCTTCCG AGAGGACAA 360|
|CCTGACAAGA|ATCCTGAGGC|TCCTCTCAAT|GTGTCCCGTG|TGGCCCAGTT GTGCAGGGG 420|
|GACCAGGGTG|GGGAAAGTTC|ACTGTCAGTC|TCCAAGTGGA|ACACTTTTCT GAAAGCCAT 480|
|CTGGTATGCA|GTGATGCTGC|CACCAACAAG|AACTTCAACA|GGCTGCAAGA CGTCTTCCT 540|
|CTCCCTGACC|CCAGCGGCCA|GTGGAGGGAC|ACCAGGGTCT|ATGGTGTTTT CTCCAACCC 600|
|TGGAACTACT|CAGCCGTCTG|TGTGTATTCC|CTCGGTGACA|TTGACAAGGT CTTCCGTAC 660|
|TCCTCACTCA|AGGGCTACCA|CTCAAGCCTT|CCCAACCCGC|GGCCTGGCAA GTGCCTCCC 720|
|GACCAGCAGC|CGATACCCAC|AGAAAGCTTA|ATTAGCTGAG|CTTGGACTCC TGTTGATAG 780|
|TCCAGTAATG|ACCTCAGAAC|TCCATCTGGA|TTTGTTCAGA|ACGCTCGGTT GCCGCCGGG 840|
|GTTTTTTATT|GGTGAGAATC|CAAGCTAGCT|TGGCGAGATT|TTCAGGAGCT AAGGAAGCT 900|
|AAATGGAGAA|AAAATCACT|GGATATACCA|CCGTTGATAT|ATCCCAATGG CATCGTAAA 960|
|AACATTTTGA|GGCATTTCAG|TCAGTTGCTC|AATGTACCTA|TAACCAGACC GTTCAGCT 1020|

```
ATATTACGGC CTTTTTAAAG ACCGTAAAGA AAAATAAGCA CAAGTTTTAT CCGGCCTT    1080

TTCACATTCT TGCCCGCCTG ATGAATGCTC ATCCGGAATT TCGTATGGCA ATGAAAGA    1140

GTGAGCTGGT GATATGGGAT AGTGTTCACC CTTGTTACAC CGTTTTCCAT GAGCAAAC    1200

AAACGTTTTC ATCGCTCTGG AGTGAATACC ACGACGATTT CCGGCAGTTT CTACACAT    1260

ATTCGCAAGA TGTGGCGTGT TACGGTGAAA ACCTGGCCTA TTTCCCTAAA GGGTTTAT    1320

AGAATATGTT TTTCGTCTCA GCCAATCCCT GGGTGAGTTT CACCAGTTTT GATTTAAA    1380

TGGCCAATAT GGACAACTTC TTCGCCCCCG TTTTCACCAT GGGCAAATAT TATACGCA    1440

GCGACAAGGT GCTGATGCCG CTGGCGATTC AGGTTCATCA TGCCGTCTGT GATGGCTT    1500

ATGTCGGCAG AATGCTTAAT GAATTACAAC AGTACTGCGA TGAGTGGCAG GGCGGGGC    1560

AATTTTTTTA AGGCAGTTAT TGGTGCCCTT AAACGCCTGG GGTAATGACT CTCTAGCT    1620

AGGCATCAAA TAAAACGAAA GGCTCAGTCG AAAGACTGGG CCTTTCGTTT TATCTGTT    1680

TTGTCGGTGA ACGCTCTCCT GAGTAGGACA AATCCGCCGC TCTAGAGCTG CCTCGCGC    1740

TTCGGTGATG ACGGTGAAAA CCTCTGACAC ATGCAGCTCC CGGAGACGGT CACAGCTT    1800

CTGTAAGCGG ATGCCGGGAG CAGACAAGCC CGTCAGGGCG CGTCAGCGGG TGTTGGCG    1860

TGTCGGGGCG CAGCCATGAC CCAGTCACGT AGCGATAGCG GAGTGTATAC TGGCTTAA    1920

ATGCGGCATC AGAGCAGATT GTACTGAGAG TGCACCATAT GCGGTGTGAA ATACCGCA    1980

GATGCGTAAG GAGAAAATAC CGCATCAGGC GCTCTTCCGC TTCCTCGCTC ACTGACTC    2040

TGCGCTCGGT CTGTCGGCTG CGGCGAGCGG TATCAGCTCA CTCAAAGGCG GTAATACG    2100

TATCCACAGA ATCAGGGGAT AACGCAGGAA AGAACATGTG AGCAAAAGGC CAGCAAAA    2160

CCAGGAACCG TAAAAAGGCC GCGTTGCTGG CGTTTTTCCA TAGGCTCCGC CCCCCTGA    2220

AGCATCACAA AAATCGACGC TCAAGTCAGA GGTGGCGAAA CCCGACAGGA CTATAAAG    2280

ACCAGGCGTT TCCCCCTGGA AGCTCCCTCG TGCGCTCTCC TGTTCCGACC CTGCCGCT    2340

CCGGATACCT GTCCGCCTTT CTCCCTTCGG GAAGCGTGGC GCTTTCTCAA TGCTCACG    2400

GTAGGTATCT CAGTTCGGTG TAGGTCGTTC GCTCCAAGCT GGGCTGTGTG CACGAACC    2460

CCGTTCAGCC CGACCGCTGC GCCTTATCCG GTAACTATCG TCTTGAGTCC AACCCGGT    2520

GACACGACTT ATCGCCACTG GCAGCAGCCA CTGGTAACAG GATTAGCAGA GCGAGGTA    2580

TAGGCGGTGC TACAGAGTTC TTGAAGTGGT GGCCTAACTA CGGCTACACT AGAAGGAC    2640

TATTTGGTAT CTGCGCTCTG CTGAAGCCAG TTACCTTCGG AAAAAGAGTT GGTAGCTC    2700

GATCCGGCAA ACAAACCACC GCTGGTAGCG GTGGTTTTTT TGTTTGCAAG CAGCAGAT    2760

CGCGCAGAAA AAAAGGATCT CAAGAAGATC CTTTGATCTT TTCTACGGGG TCTGACGC    2820

AGTGGAACGA AAACTCACGT TAAGGGATTT TGGTCATGAG ATTATCAAAA AGGATCTT    2880

CCTAGATCCT TTTAAATTAA AAATGAAGTT TTAAATCAAT CTAAAGTATA TATGAGTA    2940

CTTGGTCTGA CAGTTACCAA TGCTTAATCA GTGAGGCACC TATCTCAGCG ATCTGTCT    3000

TTCGTTCATC CATAGCTGCC TGACTCCCCG TCGTGTAGAT AACTACGATA CGGGAGGG    3060

TACCATCTGG CCCCAGTGCT GCAATGATAC CGCGAGACCC ACGCTCACCG GCTCCAGA    3120

TATCAGCAAT AAACCAGCCA GCCGGAAGGG CCGAGCGCAG AAGTGGTCCT GCAACTTT    3180

CCGCCTCCAT CCAGTCTATT AATTGTTGCC GGGAAGCTAG AGTAAGTAGT TCGCCAGT    3240

ATAGTTTGCG CAACGTTGTT GCCATTGCTA CAGGCATCGT GGTGTCACGC TCGTCGTT    3300

GTATGGCTTC ATTCAGCTCC GGTTCCCAAC GATCAAGGCG AGTTACATGA TCCCCCAT    3360

TGTGCAAAAA AGCGGTTAGC TCCTTCGGTC CTCCGATCGT TGTCAGAAGT AAGTTGGC    3420
```

```
CAGTGTTATC ACTCATGGTT ATGGCAGCAC TGCATAATTC TCTTACTGTC ATGCCATC        3480

TAAGATGCTT TTCTGTGACT GGTGAGTACT CAACCAAGTC ATTCTGAGAA TAGTGTAT        3540

GGCGACCGAG TTGCTCTTGC CCGGCGTCAA TACGGGATAA TACCGCGCCA CATAGCAG        3600

CTTTAAAAGT GCTCATCATT GGAAAACGTT CTTCGGGGCG AAAACTCTCA AGGATCTT        3660

CGCTGTTGAG ATCCAGTTCG ATGTAACCCA CTCGTGCACC CAACTGATCT TCAGCATC        3720

TTACTTTCAC CAGCGTTTCT GGGTGAGCAA AAACAGGAAG GCAAAATGCC GCAAAAA         3780

GAATAAGGGC GACACGGAAA TGTTGAATAC TCATACTCTT CCTTTTTCAA TATTATTG        3840

GCATTTATCA GGGTTATTGT CTCATGAGCG GATACATATT TGAATGTATT TAGAAAAA        3900

AACAAATAGG GGTTCCGCGC ACATTTCCCC GAAAAGTGCC ACCTGACGTC TAAGAAAC        3960

TTATTATCAT GACATTAACC TATAAAAATA GGCGTATCAC GAGGCCCTTT CGTCTTCA        4019
```

(2) INFORMATION FOR SEQ ID NO: 40:

(i) SEQUENCE CHARACTERISTICS:
        (A) LENGTH: 3999 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

```
CTCGAGAAAT CATAAAAAAT TTATTTGCTT TGTGAGCGGA TAACAATTAT AATAGATTCA      60

ATTGTGAGCG GATAACAATT TCACACAGAA TTCATTAAAG AGGAGAAATT AACTATGAG       120

GGATCGCATC ACCATCACCA TCACACGGAT CCGCATGCGA GCTCCCAGTG GGAGGTGAG       180

CAGGTGCCCC TGGACCTGTG TGAGGTCTAT GGCGGGGGCT GCCACGGTTG CCTCATGTC       240

CGAGACCCCT ACTGCGGCTG GACCAGGGC CGCTGCATCT CCATCTACAG CTCCGAACG        300

TCAGTGCTGC AATCCATTAA TCCAGCCGAG CCACACAAGG AGTGTCCCAA CCCCAAACC       360

GACAAGGCCC CACTGCAGAA GGTTTCCCTG GCCCCAAACT CTCGCTACTA CCTGAGCTG       420

CCCATGGAAT CCCGCCACGC CACCTACTCA TGGCGCCACA AGGAGAACGT GGAGCAGAG       480

TGCGAACCTG GTCACCAGAG CCCCAACTGC ATCCTGTTCA TCGAGAACCT CACGGCGCA       540

CAGTACGGCC ACTACTTCTG CGAGGCCCAG GAGGGCTCCT ACTTCCGCGA GGCTCAGCA       600

TGGCAGCTGC TGCCCGAGGA CGGCATCATG GCCGAGCACC TGCTGGGTCA TGCCTGTGC       660

CTGGCTGCCT CCCTCTGGCT GGGGGTGCTG CCCACACTCA CTCTTGGCTT GCTGGTCCA       720

GTGAAGCTTA ATTAGCTGAG CTTGGACTCC TGTTGATAGA TCCAGTAATG ACCTCAGAA       780

TCCATCTGGA TTTGTTCAGA ACGCTCGGTT GCCGCCGGGC GTTTTTTATT GGTGAGAAT       840

CAAGCTAGCT TGGCGAGATT TTCAGGAGCT AAGGAAGCTA AAATGGAGAA AAAAATCAC       900

GGATATACCA CCGTTGATAT ATCCCAATGG CATCGTAAAG AACATTTTGA GGCATTTCA       960

TCAGTTGCTC AATGTACCTA TAACCAGACC GTTCAGCTGG ATATTACGGC CTTTTTAA       1020

ACCGTAAAGA AAAATAAGCA CAAGTTTTAT CCGGCCTTTA TTCACATTCT TGCCCGCC       1080

ATGAATGCTC ATCCGGAATT TCGTATGGCA ATGAAAGACG GTGAGCTGGT GATATGGG       1140

AGTGTTCACC CTTGTTACAC CGTTTTCCAT GAGCAAACTG AAACGTTTTC ATCGCTCT       1200

AGTGAATACC ACGACGATTT CCGGCAGTTT CTACACATAT ATTCGCAAGA TGTGGCGT       1260

TACGGTGAAA ACCTGGCCTA TTTCCCTAAA GGGTTTATTG AGAATATGTT TTTCGTCT       1320

GCCAATCCCT GGGTGAGTTT CACCAGTTTT GATTTAAACG TGGCCAATAT GGACAACT       1380
```

```
TTCGCCCCCG TTTTCACCAT GGGCAAATAT TATACGCAAG GCGACAAGGT GCTGATGC      1440

CTGGCGATTC AGGTTCATCA TGCCGTCTGT GATGGCTTCC ATGTCGGCAG AATGCTTA      1500

GAATTACAAC AGTACTGCGA TGAGTGGCAG GGCGGGGCGT AATTTTTTTA AGGCAGTT      1560

TGGTGCCCTT AAACGCCTGG GGTAATGACT CTCTAGCTTG AGGCATCAAA TAAAACGA      1620

GGCTCAGTCG AAAGACTGGG CCTTTCGTTT TATCTGTTGT TTGTCGGTGA ACGCTCTC      1680

GAGTAGGACA AATCCGCCGC TCTAGAGCTG CCTCGCGCGT TTCGGTGATG ACGGTGAA      1740

CCTCTGACAC ATGCAGCTCC CGGAGACGGT CACAGCTTGT CTGTAAGCGG ATGCCGGG      1800

CAGACAAGCC CGTCAGGGCG CGTCAGCGGG TGTTGGCGGG TGTCGGGGCG CAGCCATG      1860

CCAGTCACGT AGCGATAGCG GAGTGTATAC TGGCTTAACT ATGCGGCATC AGAGCAGA      1920

GTACTGAGAG TGCACCATAT GCGGTGTGAA ATACCGCACA GATGCGTAAG GAGAAAAT      1980

CGCATCAGGC GCTCTTCCGC TTCCTCGCTC ACTGACTCGC TGCGCTCGGT CTGTCGGC      2040

CGGCGAGCGG TATCAGCTCA CTCAAAGGCG GTAATACGGT TATCCACAGA ATCAGGGG      2100

AACGCAGGAA AGAACATGTG AGCAAAAGGC CAGCAAAAGG CCAGGAACCG TAAAAAGG      2160

GCGTTGCTGG CGTTTTTCCA TAGGCTCCGC CCCCCTGACG AGCATCACAA AAATCGAC      2220

TCAAGTCAGA GGTGGCGAAA CCCGACAGGA CTATAAAGAT ACCAGGCGTT TCCCCCTG      2280

AGCTCCCTCG TGCGCTCTCC TGTTCCGACC CTGCCGCTTA CCGGATACCT GTCCGCCT      2340

CTCCCTTCGG GAAGCGTGGC GCTTTCTCAA TGCTCACGCT GTAGGTATCT CAGTTCGG      2400

TAGGTCGTTC GCTCCAAGCT GGGCTGTGTG CACGAACCCC CCGTTCAGCC CGACCGCT      2460

GCCTTATCCG GTAACTATCG TCTTGAGTCC AACCCGGTAA GACACGACTT ATCGCCAC      2520

GCAGCAGCCA CTGGTAACAG GATTAGCAGA GCGAGGTATG TAGGCGGTGC TACAGAGT      2580

TTGAAGTGGT GGCCTAACTA CGGCTACACT AGAAGGACAG TATTTGGTAT CTGCGCTC      2640

CTGAAGCCAG TTACCTTCGG AAAAAGAGTT GGTAGCTCTT GATCCGGCAA ACAAACCA      2700

GCTGGTAGCG GTGGTTTTTT TGTTTGCAAG CAGCAGATTA CGCGCAGAAA AAAAGGAT      2760

CAAGAAGATC CTTTGATCTT TTCTACGGGG TCTGACGCTC AGTGGAACGA AAACTCAC      2820

TAAGGGATTT TGGTCATGAG ATTATCAAAA AGGATCTTCA CCTAGATCCT TTTAAATT      2880

AAATGAAGTT TTAAATCAAT CTAAAGTATA TATGAGTAAA CTTGGTCTGA CAGTTACC      2940

TGCTTAATCA GTGAGGCACC TATCTCAGCG ATCTGTCTAT TTCGTTCATC CATAGCTG      3000

TGACTCCCCG TCGTGTAGAT AACTACGATA CGGGAGGGCT TACCATCTGG CCCCAGTG      3060

GCAATGATAC CGCGAGACCC ACGCTCACCG GCTCCAGATT TATCAGCAAT AAACCAGC      3120

GCCGAAGGG CCGAGCGCAG AAGTGGTCCT GCAACTTTAT CCGCCTCCAT CCAGTCTA      3180

AATTGTTGCC GGGAAGCTAG AGTAAGTAGT TCGCCAGTTA ATAGTTTGCG CAACGTTG      3240

GCCATTGCTA CAGGCATCGT GGTGTCACGC TCGTCGTTTG GTATGGCTTC ATTCAGCT      3300

GGTTCCCAAC GATCAAGGCG AGTTACATGA TCCCCCATGT TGTGCAAAAA AGCGGTTA      3360

TCCTTCGGTC CTCCGATCGT TGTCAGAAGT AAGTTGGCCG CAGTGTTATC ACTCATGG      3420

ATGGCAGCAC TGCATAATTC TCTTACTGTC ATGCCATCCG TAAGATGCTT TTCTGTGA      3480

GGTGAGTACT CAACCAAGTC ATTCTGAGAA TAGTGTATGC GGCGACCGAG TTGCTCTT      3540

CCGGCGTCAA TACGGGATAA TACCGCGCCA CATAGCAGAA CTTTAAAAGT GCTCATCA      3600

GGAAAACGTT CTTCGGGGCG AAAACTCTCA AGGATCTTAC CGCTGTTGAG ATCCAGTT      3660

ATGTAACCCA CTCGTGCACC CAACTGATCT TCAGCATCTT TTACTTTCAC CAGCGTTT      3720
```

-continued

```
GGGTGAGCAA AAACAGGAAG GCAAAATGCC GCAAAAAAGG GAATAAGGGC GACACGGA      3780

TGTTGAATAC TCATACTCTT CCTTTTTCAA TATTATTGAA GCATTTATCA GGGTTATT      3840

CTCATGAGCG GATACATATT TGAATGTATT TAGAAAAATA AACAAATAGG GGTTCCGC      3900

ACATTTCCCC GAAAAGTGCC ACCTGACGTC TAAGAAACCA TTATTATCAT GACATTAA      3960

TATAAAAATA GGCGTATCAC GAGGCCCTTT CGTCTTCAC                           3999
```

(2) INFORMATION FOR SEQ ID NO: 41:

(i) SEQUENCE CHARACTERISTICS:
        (A) LENGTH: 8888 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

```
GAGCCGCACA CGGTGCTTTT CCACGAGCCA GGCAGCTCCT CTGTGTGGGT GGGAGGACGT      60

GGCAAGGTCT ACCTCTTTGA CTTCCCCGAG GGCAAGAACG CATCTGTGCG CACGGTGAG      120

CTCTCTCTTC CCCCAACACC CCCCCTACCC TCTTATCTCC CCTCTGGCCC TGCCAAGGG      180

CCTCAGGGAA TCCAGGGGAG CTGGCTTCTC TTCCTAAACT GCCCCCACCT CCGTATCCT      240

TAAATGGCTC CTGGGGGAGG CTCCCTAAAG GTAGTCCAGA TTGGAGTGGG GAGCTGGGG      300

GGTGTGGAGA AAAACAGGAG CTAATGGGCC TGGCCAGCTG GGCAGCGCTG CTGCGGAAA      360

CCCAGGCTGG AAGCTGGGCC CCAGAGCCCA TGCCTGGTCT TCTGAACCCT CTGGGCCTC      420

GCTCTGGATA TGAGACCCTG TTTGACCTCA GGTAGATCAC TCACCCTCTC AGAGCCCCA      480

TTGCTCATCT GTCAGATGAG AATAATGGTT GCTTCCTTTG GGGCTTATCC TGAGGCTGT      540

TGGAAAGCAT TTCAGGGGTA CCTCACCCCT GGCAGATTGA ACTAATGCTT CTCCCCTTC      600

CCAGGTGAAT ATCGGCTCCA CAAAGGGGTC CTGTCTGGAT AAGCGGGTGA GCGGGGGAG      660

GATCTGGAGG GGTCTGAGCC ACTTGGTAAA GGGAGAGGAG ACCCTGAGGG TCTAAGGAA      720

GAAGCATGGC CCTGCCCCAC GAGTCCCAGA CTGATGGGGA GACGTGGTCC TCTGTGCTT      780

GGGGATGGCG TCAGCTGCAC ACACTCTGGG CTGTCCCGGG AGGCTGTCAC CTATGCTAA      840

CCCTTCTGAC ACCTTCTTCC CTGATCCTGG GGGTCCTAGT GCTAGGCTTG CCAGGGCCT      900

CCAGCAACCA ATTTCTCTCC TCCCTTCTCT CTTCCCCGGG CAGGACTGCG AGAACTACA      960

CACTCTCCTG GAGAGGCGGA GTGAGGGGCT GCTGGCCTGT GGCACCAACG CCCGGCAC       1020

CAGCTGCTGG AACCTGGTGA GAAGGCTGCT CCCCATGTGC CTGATCAGCT CACCTTCT       1080

TGCGTGGGCT TCTGCCCCTC ATGGTGGGAA GGAGATGGCG AGACTCCAAT GCTGGCCT       1140

CCCTGGGAGG ATGGGGCTCC TGGCCGAGAA ACTGGCCGTC ATGGGAGGCA GTGGCTGT       1200

GATTATGTGG CCATCCAACC CTCTGGATCT CCCACAGGTG AATGGCACTG TGGTGCCA       1260

TGGCGAGATG AGAGGCTACG CCCCCTTCAG CCCGGACGAG AACTCCCTGG TTCTGTTT       1320

AGGTTGGGGC ATGCTTCGGA ACTGGGCTGG GAGCAGGATG GTCAGCTCTT TGTCCAGT       1380

CCGGAGGAGG GACTTCCAGG AGCTGCCTGC CCTTACTCAT TTCTCCCTCC CACTGACC       1440

AGGGGACGAG GTGTATTCCA CCATCCGGAA GCAGGAATAC AATGGGAAGA TCCCTCGG       1500

CCGCCGCATC CGGGGCGAGA GTGAGCTGTA CACCAGTGAT ACTGTCATGC AGAGTGAG       1560

AGGCTCCGGC TGGGCTGAGG GTGGGCAAGG GGGTGTGAGC ACTTAAGGTG GCAGATGG       1620

TCCTGATGTT TCTGGGAGGG CTCCCTGAGG GCCGCTGGGG CCATGCAGGA AAGCAGGA       1680
```

| | |
|---|---|
| TTGGTATAGG CCTGAGAAGT TAGGGTTGGC TGGGAGCAGA GGAACAGACA AGGTATAG | 1740 |
| GTGGGATGGG CCCAGCCCTC TTCAGGAACA CAAACAGAGG GAGCCCCAGA CCCAGTGC | 1800 |
| GGTCCCCAGG AGCCAAAGTT TATCCTCTGC TGAGTTCACG TGGAGGCAGC CCCCCAAC | 1860 |
| CCTCCTCATC AGGGCTCTGC CAATTGAGCA GAAGTGACAT AGGGGCCCCC AGGGACCT | 1920 |
| CCCCACTCCC CAGGCATGAA GTCATTGCTC CTGGGCCGAT GACATCTTTG TAGGAAGA | 1980 |
| GCAAAACAGG TGTGGGGTGG AGGTGCAGGG TCTAGGGCCC CTCGGGGAGT TGGACCTG | 2040 |
| GTTATGAGTC CTATTCCAGA TCTGATTTGC CATGGTTTGT GCAGACCCGA AGGAGGGA | 2100 |
| AGAGTGTGCA GGGTTGGAAT GGTCTCCCGG GCAAGCTTCC CAGCCTTACG CCCATTCG | 2160 |
| TCTGTGCCCT GGCAGACCCA CAGTTCATCA AAGCCACCAT CGTGCACCAA GACCAGGC | 2220 |
| ACGATGACAA GATCTACTAC TTCTTCCGAG AGGACAATCC TGACAAGAAT CCTGAGGC | 2280 |
| CTCTCAATGT GTCCCGTGTG GCCCAGTTGT GCAGGGTGAA CACGGGCGTG AGGGCTGC | 2340 |
| GCTACGTGTC TGTGCATGAA TAGGCCTGAG TGAGGGTGAG TTCTGTGTGT CCGTGTGC | 2400 |
| GTAGAAGTTG TGTGGATGTA TGAGTGGGTC TGTGTCAGGG ACTGTGGGAG CAGCTGTG | 2460 |
| TGCATGGAGC ATCATGTGTC TGTGTGTGGG TAAAGGTGGC TGAGCTCCTG TGCACGTA | 2520 |
| ATGGCGTGTG AGCGTGTGTA TGATGGGGTG TGTGTGTGTG TGTGTGTGTG TGTTTTGC | 2580 |
| GTGTGAATGT GCTGTGCCAC GTATGTGGGT GCGTGAGTCA GTAAATGTGT GTCTGAGT | 2640 |
| GTCTGCTCTG TGGGGACCTG GCACTCTCAC CTGCCCTGAC CCTGGGCACT GCTGGCCC | 2700 |
| GGCTCTGGAT CAGCCAGGCC TGCTTGCAGG AGTCTCATCT GGAGACCTGC CCTGAGTC | 2760 |
| GGGGCACCCC CGGCAGGTCC TGGCCCCTCG CAGCCTGCCT TCCTCCTCTG GGCCCAGG | 2820 |
| TTGATATTGC TGGCAGTGGT TTCCTGGGGT GTGTGGGGAA GCCCGGGCAG GTGCTGAG | 2880 |
| GCCTCTTCTC CCCTCTACCC TTCCAGGGGG ACCAGGGTGG GGAAAGTTCA CTGTCAGT | 2940 |
| CCAAGTGGAA CACTTTTCTG AAAGCCATGC TGGTATGCAG TGATGCTGCC ACCAACAA | 3000 |
| ACTTCAACAG GCTGCAAGAC GTCTTCCTGC TCCCTGACCC CAGCGGCCAG TGGAGGGA | 3060 |
| CCAGGGTCTA TGGTGTTTTC TCCAACCCCT GGTGAGTGGC CCTTGTCCTG GGCCGGG | 3120 |
| TGGCATTGGT TCAGTGTCCA GTAGGGACAG GAGGCCTTGG GCCCTGCTGA GGGCCTCC | 3180 |
| GGTGTGGCAG GAGCAGGGGC TGCAGGCTCA AGAGGCTGGG CTGTTGCTGG GTGTGGGG | 3240 |
| GGGGACAGC CAGTGCGATG TATGTACTGT TGTGTGAGTG AGTCTGCACT CATGGGTG | 3300 |
| TGTGCATGCC CTATATGCAC ACTCATGACT GCACTTGTGC CTGTGTGTCC CACCACCT | 3360 |
| TTGTGCCGAG AGTGGACACT GGGCCCAGGA GGAAGCTGCT GAAGCATCTC TCGGGGAG | 3420 |
| GGGTGCTATT ACACCTGCTC AGGCACTGCC TGAGCCCGAT AATTCACACT TCTTAATC | 3480 |
| TCTCATTGAT TGAACACACG GCAGGCGGAA GTGTTGGGTG TGTGTGGGA GAGTTAGG | 3540 |
| TAGAGTGGAG GAAGCCAAGA CCCTGCTCTG TGGCTCCTGG GTGAGTGGGT CCCCCAGG | 3600 |
| GGGAAGGGGT TGGGGGTCTG GCCTCCTGGG GCATCAGCAC CCCACAGCCT GTGCCCAG | 3660 |
| AGGGCTAGAG AACTGCTCAG CCTATGATGG GGTTCCTCCT GCCTTGGGGT TGGGTAGA | 3720 |
| AGATGGCCTC TAGACTCAGT GATTCTGTAA CAGGATACAA GTTTGTGGTT TTAAATTG | 3780 |
| GCACAAAGAA ATTAGGCTGA ACTCCTCTCC TTCCTCCTCT CCATCCCTCC CCATTTTC | 3840 |
| TGGTGGTTGG CAACTCAGTG CCAGGCACAA GGCTGGCCTG GGTGAGTGGA GGTGGATG | 3900 |
| TGGGTTCTGG GCCCCCCATT GAGCTGGTCT CCATGTCACT GCAGGAACTA CTCAGCCG | 3960 |
| TGTGTGTATT CCCTCGGTGA CATTGACAAG GTCTTCCGTA CCTCCTCACT CAAGGGCT | 4020 |
| CACTCAAGCC TTCCCAACCC GCGGCCTGGC AAGGTGAGCG TGACACCAGC CGTGGCCC | 4080 |

-continued

```
GCCCAGCCCT CCTTCTGCCT CACCTCCCAC CACCCCACTG ACCTGGGCCT GCTCTCCT      4140
CCCAGTGCCT CCCAGACCAG CAGCCGATAC CCACAGAGAC CTTCCAGGTG GCTGACCG      4200
ACCCAGAGGT GGCGCAGAGG GTGGAGCCCA TGGGGCCTCT GAAGACGCCA TTGTTCCA      4260
CTAAATACCA CTACCAGAAA GTGGCCGTCC ACCGCATGCA AGCCAGCCAC GGGGAGAC      4320
TTCATGTGCT TTACCTAACT ACAGGTGAGA GGCTACCCCG GGACCCTCAG TTTGCTTT      4380
AAAAACGGGC ATGAAAGGTG TAAGGAATAA TGTAGTTAAC ATCTGGTTGG ATCTTTAC      4440
GTGGAAGGAA TAATTGAGTG ACTGGAGTTG TCAGGGGTTA ATGTGTGTGG GTGTGGAA      4500
GCCAGGCAGG GAGAGCTTCC TGGAGGAGGT AGGGGCAAGA GGGAAGGGGG GATGGGAG      4560
AAGCAAGCAC TGGGATTTGG AGGCGGAAAT CTGGAGAGTC TGAGCAAAGC CAGGTGCA      4620
TTTGGTCCAG ATGTCTGACT CAGGGAAGAA GATGGTAGGA AGAGACGTGG CAAATGAG      4680
GGAGGGGCCT GAACCACAGG GATACTGGCC TCTGCCAGGC AGAATGAGGG AGTCAGGC      4740
TGCGCCTGTC TTTGGGATTG TGCAGGTGAG AAGAAACATT TGAGGAGTTG ATGGGGCA      4800
AATTAGGTAT GGGGAAGGAG TTCCAGGGGG CAGAACCTTT GCCATCTCAC AGAGGACA      4860
GGCAGCTTCT CTTCTTCCCT GGAGTAGGCC CTGCTGGGGG AAGCTGGGTG GAATGCCG      4920
GGAGATGCTC CTGCTTTCTG GAAAGCCACA GGACACGGAG GAGCCAGTCC TGAGTTGG      4980
TTGTCGCAGC TTCCCATGCC AGCTGCCTTC CTTGAGACTG GAAAGGGCCT CTAGCACC      5040
TGGGGCCATT CAATTCAGGC CCAGGCGCCC AACCTCAGTT GTTCACATTC CCCATGTG      5100
CTCCTGTTGC TGCTTCACCT TGGGACTGTC TCGGCTTTGG TGACCTTGTA GGAAACTG      5160
ACCCCAGCAC CATTGTTTGG CTCCTGGAAG CCTTGGGGAG AGGAATTTCC CACAGGGC      5220
GGCCTGGGTC CTGATTCCCT GCCTCTTTAC TCCCTATTCA TCCCGGCTAC ACCCTTGG      5280
CCCCATCCTT GCTTGGCTCC AGTACTGGCT GGCACAGCTG TTGTGGTCAT CCAGGGAT      5340
CAGGGCACTG GGAACAGAA GAGAGAGGTC ACACAGTGCG GAACTGGGAG CAGGAGCT      5400
GACAAGGAAG GCTGGACTTG GCCATGGAT TCCCTTCCTG CAGACTTGGG AAGTGAGC      5460
ACTTGAGTGA TTAGAGAAGG TGTCTTCGTT CTAAGGGCAG TGGAGGAGGC ACCATTTT      5520
AGCCTGCATC ATTCGTATTT GGGCTAGATT GAAAAATAGA GCTTTCTAAG TCCTCTGC      5580
AGAATGGGAG GCTCTCACAA CTGGGAGAAG TATTGGCTCT TTTCCTGAGA ATTTGCC       5640
GGGTATGCTG TTACTGGGGC TGGTTTGGAA GGAGTATAGG GCATTATGTC TGTGAAGG      5700
GTGGCTGGGG TGGGGCCTTA TCAGGCCCAA GGAGCATCTG GCCACATCTC AGAGTCCA      5760
GATGAGGATC ACGGATGTGT AGAGGAAACA TCCTAGGCAG GCAATCATCT GACTGCTT      5820
TTGGGGCAGG TGATGCCCTG GGAAATTGGG AGGGAGGGAG AGAGGGAGGT AGGCTATT      5880
AGAAACTGGG AGAGCAGGTG AGGTAGGATT GGGAGGACCA GGGGTCAGGG TCCCCATT      5940
TCCCTAATTG AGAACGGAGA GAGCATTGGT CTAGGAGGCA GGCAGCTCGG TTATAAGA      6000
TTGGGAACTC TTGATTTAGA ATCCAAGATC CTTTTTAGAT CTAGGATTTT ATAAAATT      6060
GATATCCCCT AAGATCAAAT GCAACGTGGA GTCCTGAATT GGATCCTAGA ACAGAAGA      6120
GACATTTGTG GAAAAACTAG TGAAATCCAA ATAAAGTCTG TAGTTTTGTT AATAGTAA      6180
CACCAATGTC AGTTGCCTAG TTGTGACAAA TATACCGTGG TTATGTAAGA TGGTAACA      6240
AGGGGGAACT GGAGAAGGGT AGATTGGAGC TCTCTGTACT ATCTTTGCAA CTTTTCTG      6300
AATCTAAAAT TACTCCAAAA TAAAAAAAAA ATGTATTTAA AGTAAATATA TTCCCTAA      6360
GTCCAGGAGG CAGGGGAGTT GTAGAAGCAG CTGAGTGGTT GGGTTCTGAC AGATTTGG      6420
```

| | |
|---|---|
| CCAACTCGGT CTCTGCTGCT CACCAGCTGT GTGACCTTGA GCAAGTGGCT TAGCCTTT | 6480 |
| GAGCCTGATT TCCTTATCTG TGGAGTGGGG AAGATGACAG CCACCTCGCA GGGCTGTG | 6540 |
| GGGTTAAACG AGGTGATGCA TGGACAGCAG CCGCACTGAC CTTGCTGGTG TGGGGCTC | 6600 |
| GCTTCTGTTC TTCCCGTGCA GCCTTGGGAA TGTTGGAGGC CGTATCCAGG GACCCCTG | 6660 |
| CCTCCTGGGA TGGCCTCTCT GGATCAGCCT TGGAAGGTTC CAGGCTGCCC TTAGGCTC | 6720 |
| ACATTCTTCC CCAGTCACGC TCTCCTCGCC CTGCCCACAC CAGTCCTGTG ACCCTTGC | 6780 |
| GAGTTGTGAC TTCCCACCCC TCCCCGGCCT AGAGGAAAGC TGCCTGGCCC CTCAGTGG | 6840 |
| CTCCCGCCCA CTGACCCTCT GTCCACCATA CACAGACAGG GGCACTATCC ACAAGGTG | 6900 |
| GGAACCGGGG GAGCAGGAGC ACAGTTCGC CTTCAACATC ATGGAGATCC AGCCCTTC | 6960 |
| CCGCGCGGCT GCCATCCAGA CCATGTCGCT GGATGCTGAG CGGGTGAGCC TTCCCCCA | 7020 |
| GCGTCCCATG GGCTATGCAG TGACTGCAGC TGAGGACAGG GCTCCTTTGC ATGTGATT | 7080 |
| TGTGTTCTTT TAAGAGCTTC TAGGCCTTAG GGCCTGGACA TTTAGGACTG AGTGTGGG | 7140 |
| GGGGCCCGGG CCTGACCCAA TCCTGCTGTC CTTCCAGAGG AAGCTGTATG TGAGCTCC | 7200 |
| GTGGGAGGTG AGCCAGGTGC CCCTGGACCT GTGTGAGGTC TATGGCGGGG GCTGCCAC | 7260 |
| TTGCCTCATG TCCCGAGACC CCTACTGCGG CTGGGACCAG GGCCGCTGCA TCTCCATC | 7320 |
| CAGCTCCGAA CGGTACGTTG GCCGGGATCC CTCCGTCCCT GGGACAAGGT GGGCATGG | 7380 |
| CAGGGGGAGG TGTTGTCGGG CTGGAAGAGG TGGCGGTACT GGGCCTTTCT TGTGGGAC | 7440 |
| CCTCTCTACT GGAACTGCAC TAGGGGTAAG GATATGAGGG TCAGGTCTGC AGCCTTGT | 7500 |
| CTGCTGATCC TCTTTCGTCC TTCCCACTCC AGGTCAGTGC TGCAATCCAT TAATCCAG | 7560 |
| GAGCCACACA AGGAGTGTCC CAACCCCAAA CCAGGTACCT GATCTGGCCC TGCTGGCG | 7620 |
| TGTGGCCCAA TGAGTGGGGT ACTGCCCTGC CCTGATTGTC CTGGTCTGAG GAAACAT | 7680 |
| CCTTGTCCTG TGGGCCCCAG GTACATGGGG CAGGATACAG TCCTGCAGAG GGAGCCCT | 7740 |
| TGGTGGGATG AGCGAGACGG GAGAAAAAAG GAGGACGCTG AGGGCTGGGT TCCCCACG | 7800 |
| CATTCAGAAG CCTTGTCCTG GGATCCCAGT CGGTGGGGAG GACACATCCT CCCCTGGG | 7860 |
| CTCTTTGTCC CTCCTCACGG CTGCTTCCCC ACTGCCTCCC CAGACAAGGC CCCACTGC | 7920 |
| AAGGTTTCCC TGGCCCCAAA CTCTCGCTAC TACCTGAGCT GCCCCATGGA ATCCCGCC | 7980 |
| GCCACCTACT CATGGCGCCA CAAGGAGAAC GTGGAGCAGA GCTGCGAACC TGGTCACC | 8040 |
| AGCCCCAACT GCATCCTGTT CATCGAGAAC CTCACGGCGC AGCAGTACGG CCACTACT | 8100 |
| TGCGAGGCCC AGGAGGGCTC CTACTTCCGC GAGGCTCAGC ACTGGCAGCT GCTGCCCG | 8160 |
| GACGGCATCA TGGCCGAGCA CCTGCTGGGT CATGCCTGTG CCCTGGCCGC CTCCCTCT | 8220 |
| CTGGGGGTGC TGCCCACACT CACTCTTGGC TTGCTGGTCC ACTAGGGCCT CCCGAGGC | 8280 |
| GGCATGCCTC AGGCTTCTGC AGCCCAGGGC ACTAGAACGT CTCACACTCA GAGCCGGC | 8340 |
| GCCCGGGAGC TCCTTGCCTG CCACTTCTTC CAGGGGACAG AATAACCCAG TGGAGGAT | 8400 |
| CAGGCCTGGA GACGTCCAGC CGCAGGCGGC TGCTGGGCCC CAGGTGGCGC ACGGATGG | 8460 |
| AGGGGCTGAG AATGAGGGCA CCGACTGTGA AGCTGGGGCA TCGATGACCC AAGACTTT | 8520 |
| CTTCTGGAAA ATATTTTTCA GACTCCTCAA ACTTGACTAA ATGCAGCGAT GCTCCCAG | 8580 |
| CAAGAGCCCA TGGGTCGGGG AGTGGGTTTG GATAGGAGAG CTGGGACTCC ATCTCGAC | 8640 |
| TGGGGCTGAG GCCTGAGTCC TTCTGGACTC TTGGTACCCA CATTGCCTCC TTCCCCTC | 8700 |
| TCTCTCATGG CTGGGTGGCT GGTGTTCCTG AAGACCCAGG GCTACCCTCT GTCCAGCC | 8760 |
| GTCCTCTGCA GCTCCCTCTC TGGTCCTGGG TCCCACAGGA CAGCCGCCTT GCATGTTT | 8820 |

```
TGAAGGATGT TGCTTTCCG GACGGAAGGA CGGAAAAAGC TCTGAAAAAA AAAAAAAA         8880

AAAAAAAA                                                               8888

(2) INFORMATION FOR SEQ ID NO: 42:

(i) SEQUENCE CHARACTERISTICS:
        (A) LENGTH: 6622 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

GATATCATGG AGATAATTAA AATGATAACC ATCTCGCAAA TAAATAAGTA TTTTACTGTT         60

TTCGTAACAG TTTTGTAATA AAAAAACCTA TAAATATGAA ATTCTTAGTC AACGTTGCC        120

TTGTTTTTAT GGTCGTATAC ATTTCTTACA TCTATGCGGA TCGATGGGGA TCCGCCCAG        180

GCCACCTAAG GAGCGGACCC CGCATCTTCG CCGTCTGGAA AGGCCATGTA GGGCAGGAC        240

GGGTGGACTT TGGCCAGACT GAGCCGCACA CGGTGCTTTT CCACGAGCCA GGCAGCTCC        300

CTGTGTGGGT GGGAGGACGT GGCAAGGTCT ACCTCTTTGA CTTCCCCGAG GCAAGAAC        360

CATCTGTGCG CACGGTGAAT ATCGGCTCCA CAAAGGGGTC CTGTCTGGAT AAGCGGGAC        420

GCGAGAACTA CATCACTCTC CTGGAGAGGC GGAGTGAGGG GCTGCTGGCC TGTGGCACC        480

ACGCCCGGCA CCCCAGCTGC TGGAACCTGG TGAATGGCAC TGTGGTGCCA CTTGGCGAG        540

TGAGAGGCTA TGCCCCCTTC AGCCCGGACG AGAACTCCCT GGTTCTGTTT GAAGGGGAC        600

AGGTGTATTC CACCATCCGG AAGCAGGAAT ACAATGGGAA GATCCCTCGG TTCCGCCGC        660

TCCGGGCGA GAGTGAGCTG TACACCAGTG ATACTGTCAT GCAGAACCCA CAGTTCATC         720

AAGCCACCAT CGTGCACCAA GACCAGGCTT ACGATGACAA GATCTACTAC TTCTTCCGA        780

AGGACAATCC TGACAAGAAT CCTGAGGCTC CTCTCAATGT GTCCCGTGTG GCCCAGTTG        840

GCAGGGGGA CCAGGGTGGG GAAAGTTCAC TGTCAGTCTC CAAGTGGAAC ACTTTTCTG         900

AAGCCATGCT GGTATGCAGT GATGCTGCCA CCAACAAGAA CTTCAACAGG CTGCAAGAC        960

TCTTCCTGCT CCCTGACCCC AGCGGCCAGT GGAGGGACAC CAGGGTCTAT GGTGTTTT        1020

CCAACCCCTG GAACTACTCA GCCGTCTGTG TGTATTCCCT CGGTGACATT GACAAGGT        1080

TCCGTACCTC CTCACTCAAG GGCTACCACT CAAGCCTTCC CAACCCGCGG CCTGGCAA        1140

GCCTCCCAGA CCAGCAGCCG ATACCCACAG AGACCTTCCA GGTGGCTGAC CGTCACCC        1200

AGGTGGCGCA GAGGGTGGAG CCCATGGGGC CTCTGAAGAC GCCATTGTTC CACTCTAA        1260

ACCACTACCA GAAAGTGGCC GTTCACCGCA TGCAAGCCAG CCACGGGGAG ACCTTTCA        1320

TGCTTTACCT AACTACAGAC AGGGGCACTA TCCACAAGGT GGTGGAACCG GGGGAGCA        1380

AGCACAGCTT CGCCTTCAAC ATCATGGAGA TCCAGCCCTT CCGCCGCGCG GCTGCCAT        1440

AGACCATGTC GCTGGATGCT GAGCGGAGGA AGCTGTATGT GAGCTCCCAG TGGGAGGT        1500

GCCAGGTGCC CCTGGACCTG TGTGAGGTCT ATGGCGGGGG CTGCCACGGT TGCCTCAT        1560

CCCGAGACCC CTACTGCGGC TGGGACCAGG GCCGCTGCAT CTCCATCTAC AGCTCCGA        1620

GGTCAGTGCT GCAATCCATT AATCCAGCCG AGCCACACAA GGAGTGTCCC AACCCCAA        1680

CAGACAAGGC CCCACTGCAG AAGGTTTCCC TGGCCCCAAA CTCTCGCTAC TACCTGAG        1740

GCCCCATGGA ATCCCGCCAC GCCACCTACT CATGGCGCCA CAAGGAGAAC GTGGAGCA        1800

GCTGCGAACC TGGTCACCAG AGCCCCAACT GCATCCTGTT CATCGAGAAC CTCACGGC        1860
```

```
AGCAGTACGG CCACTACTTC TGCGAGGCCC AGGAGGGCTC CTACTTCCGC GAGGCTCA      1920

ACTGGCAGCT GCTGCCCGAG GACGGCATCA TGGCCGAGCA CCTGCTGGGT CATGCCTG      1980

CCCTGGCTGC CTGAATTCGA AGCTTGGAGT CGACTCTGCT GAAGAGGAGG AAATTCTC      2040

TGAAGTTTCC CTGGTGTTCA AGTAAAGGA GTTTGCACCA GACGCACCTC TGTTCACT       2100

TCCGGCGTAT TAAAACACGA TACATTGTTA TTAGTACATT TATTAAGCGC TAGATTCT      2160

GCGTTGTTGA TTTACAGACA ATTGTTGTAC GTATTTTAAT AATTCATTAA ATTTATAA      2220

TTTAGGGTGG TATGTTAGAG CGAAAATCAA ATGATTTTCA GCGTCTTTAT ATCTGAAT      2280

AAATATTAAA TCCTCAATAG ATTTGTAAAA TAGGTTTCGA TTAGTTTCAA ACAAGGGT      2340

TTTTTCCGAA CCGATGGCTG GACTATCTAA TGGATTTTCG CTCAACGCCA CAAAACTT      2400

CAAATCTTGT AGCAGCAATC TAGCTTTGTC GATATTCGTT TGTGTTTTGT TTTGTAAT      2460

AGGTTCGACG TCGTTCAAAA TATTATGCGC TTTTGTATTT CTTTCATCAC TGTCGTTA      2520

GTACAATTGA CTCGACGTAA ACACGTTAAA TAAAGCCTGG ACATATTTAA CATCGGGC      2580

GTTAGCTTTA TTAGGCCGAT TATCGTCGTC GTCCCAACCC TCGTCGTTAG AAGTTGCT      2640

CGAAGACGAT TTTGCCATAG CCACACGACG CCTATTAATT GTGTCGGCTA ACACGTCC      2700

GATCAAATTT GTAGTTGAGC TTTTTGGAAT TATTTCTGAT GCGGGCGTT TTTGGGCG       2760

TTTCAATCTA ACTGTGCCCG ATTTTAATTC AGACAACACG TTAGAAAGCG ATGGTGCA      2820

CGGTGGTAAC ATTTCAGACG GCAAATCTAC TAATGGCGGC GGTGGTGGAG CTGATGAT      2880

ATCTACCATC GGTGGAGGCG CAGGCGGGGC TGGCGGCGGA GGCGGAGGCG GAGGTGGT      2940

CGGTGATGCA GACGGCGGTT TAGGCTCAAA TTGTCTCTTT CAGGCAACAC AGTCGGCA      3000

TCAACTATTG TACTGGTTTC GGGCGTATGG TGCACTCTCA GTACAATCTG CTCTGATG      3060

GCATAGTTAA GCCAGCCCCG ACACCCGCCA ACACCCGCTG ACGCGCCCTG ACGGGCTT      3120

CTGCTCCCGG CATCCGCTTA CAGACAAGCT GTGACCGTCT CCGGGAGCTG CATGTGTC      3180

AGGTTTTCAC CGTCATCACC GAAACGCGCG AGACGAAAGG GCCTCGTGAT ACGCCTAT      3240

TTATAGGTTA ATGTCATGAT AATAATGGTT TCTTAGACGT CAGGTGGCAC TTTTCGGG      3300

AATGTGCGCG GAACCCCTAT TTGTTTATTT TTCTAAATAC ATTCAAATAT GTATCCGC      3360

ATGAGACAAT AACCCTGATA AATGCTTCAA TAATATTGAA AAAGGAAGAG TATGAGTA      3420

CAACATTTCC GTGTCGCCCT TATTCCCTTT TTTGCGGCAT TTTGCCTTCC TGTTTTTG      3480

CACCCAGAAA CGCTGGTGAA AGTAAAAGAT GCTGAAGATC AGTTGGGTGC ACGAGTGG      3540

TACATCGAAC TGGATCTCAA CAGCGGTAAG ATCCTTGAGA GTTTTCGCCC CGAAGAAC      3600

TTTCCAATGA TGAGCACTTT TAAAGTTCTG CTATGTGGCG CGGTATTATC CCGTATTG      3660

GCCGGGCAAG AGCAACTCGG TCGCCGCATA CACTATTCTC AGAATGACTT GGTTGAGT      3720

TCACCAGTCA CAGAAAAGCA TCTTACGGAT GGCATGACAG TAAGAGAATT ATGCAGTG      3780

GCCATAACCA TGAGTGATAA CACTGCGGCC AACTTACTTC TGACAACGAT CGGAGGAC      3840

AAGGAGCTAA CCGCTTTTTT GCACAACATG GGGGATCATG TAACTCGCCT TGATCGTT      3900

GAACCGGAGC TGAATGAAGC CATACCAAAC GACGAGCGTG ACACCACGAT GCCTGTAG      3960

ATGGCAACAA CGTTGCGCAA ACTATTAACT GGCGAACTAC TTACTCTAGC TTCCCGGC      4020

CAATTAATAG ACTGGATGGA GGCGGATAAA GTTGCAGGAC CACTTCTGCG CTCGGCCC      4080

CCGGCTGGCT GGTTTATTGC TGATAAATCT GGAGCCGGTG AGCGTGGGTC TCGCGGTA      4140

ATTGCAGCAC TGGGGCCAGA TGGTAAGCCC TCCCGTATCG TAGTTATCTA CACGACGG      4200
```

```
AGTCAGGCAA CTATGGATGA ACGAAATAGA CAGATCGCTG AGATAGGTGC CTCACTGA      4260

AAGCATTGGT AACTGTCAGA CCAAGTTTAC TCATATATAC TTTAGATTGA TTTAAAAC      4320

CATTTTTAAT TTAAAAGGAT CTAGGTGAAG ATCCTTTTTG ATAATCTCAT GACCAAAA      4380

CCTTAACGTG AGTTTCGTT CCACTGAGCG TCAGACCCCG TAGAAAAGAT CAAAGGAT       4440

TCTTGAGATC CTTTTTTTCT GCGCGTAATC TGCTGCTTGC AAACAAAAAA ACCACCGC      4500

CCAGCGGTGG TTTGTTTGCC GGATCAAGAG CTACCAACTC TTTTTCCGAA GGTAACTG      4560

TTCAGCAGAG CGCAGATACC AAATACTGTT CTTCTAGTGT AGCCGTAGTT AGGCCACC      4620

TTCAAGAACT CTGTAGCACC GCCTACATAC CTCGCTCTGC TAATCCTGTT ACCAGTGG      4680

GCTGCCAGTG GCGATAAGTC GTGTCTTACC GGGTTGGACT CAAGACGATA GTTACCGG      4740

AAGGCGCAGC GGTCGGGCTG AACGGGGGGT TCGTGCACAC AGCCCAGCTT GGAGCGAA      4800

ACCTACACCG AACTGAGATA CCTACAGCGT GAGCTATGAG AAAGCGCCAC GCTTCCCG      4860

GGGAGAAAGG CGGACAGGTA TCCGGTAAGC GGCAGGGTCG AACAGGAGA GCGCACGA      4920

GAGCTTCCAG GGGGAAACGC CTGGTATCTT TATAGTCCTG TCGGGTTTCG CCACCTCT      4980

CTTGAGCGTC GATTTTTGTG ATGCTCGTCA GGGGGGCGGA GCCTATGGAA AAACGCCA      5040

AACGCGGCCT TTTTACGGTT CCTGGCCTTT TGCTGGCCTT TTGCTCACAT GTTCTTTC      5100

GCGTTATCCC CTGATTCTGT GGATAACCGT ATTACCGCCT TTGAGTGAGC TGATACCG      5160

CGCCGCAGCC GAACGACCGA GCGCAGCGAG TCAGTGAGCG AGGAAGCATC CTGCACCA      5220

GTCTGCTCAT CCATGACCTG ACCATGCAGA GGATGATGCT CGTGACGGTT AACGCCTC      5280

ATCAGCAACG GCTTGCCGTT CAGCAGCAGC AGACCATTTT CAATCCGCAC CTCGCGGA      5340

CCGACATCGC AGGCTTCTGC TTCAATCAGC GTGCCGTCGG CGGTGTGCAG TTCAACCA      5400

GCACGATAGA GATTCGGGAT TTCGGCGCTC CACAGTTTCG GGTTTTCGAC GTTCAGAC      5460

AGTGTGACGC GATCGGTATA ACCACCACGC TCATCGATAA TTTCACCGCC GAAAGGCG      5520

GTGCCGCTGG CGACCTGCGT TTCACCCTGC CATAAAGAAA CTGTTACCCG TAGGTAGT      5580

CGCAACTCGC CGCACATCTG AACTTCAGCC TCCAGTACAG CGCGGCTGAA ATCATCAT      5640

AAGCGAGTGG CAACATGGAA ATCGCTGATT TGTGTAGTCG GTTTATGCAG CAACGAGA      5700

TCACGGAAAA TGCCGCTCAT CCGCCACATA TCCTGATCTT CCAGATAACT GCCGTCAC      5760

CAACGCAGCA CCATCACCGC GAGGCGGTTT TCTCCGGCGC GTAAAAATGC GCTCAGGT      5820

AATTCAGACG GCAAACGACT GTCCTGGCCG TAACCGACCC AGCGCCCGTT GCACCACA      5880

TGAAACGCCG AGTTAACGCC ATCAAAAATA ATTCGCGTCT GGCCTTCCTG TAGCCAGC      5940

TCATCAACAT TAAATGTGAG CGAGTAACAA CCCGTCGGAT TCTCCGTGGG AACAAACG      6000

GGATTGACCG TAATGGGATA GGTCACGTTG GTGTAGATGG GCGCATCGTA ACCGTGCA      6060

TGCCAGTTTG AGGGGACGAC GACAGTATCG GCCTCAGGAA GATCGCACTC CAGCCAGC      6120

TCCGGCACCG CTTCTGGTGC CGGAAACCAG GCAAAGCGCC ATTCGCCATT CAGGCTGC      6180

AACTGTTGGG AAGGGCGATC GGTGCGGGCC TCTTCGCTAT TACGCCAGCT GGCGAAAG      6240

GGATGTGCTG CAAGGCGATT AAGTTGGGTA ACGCCAGGGT TTTCCCAGTC ACGACGTT      6300

AAAACGACGG GATCTATCAT TTTTAGCAGT GATTCTAATT GCAGCTGCTC TTTGATAC      6360

CTAATTTTAC GACGACGATG CGAGCTTTTA TTCAACCGAG CGTGCATGTT TGCAATCG      6420

CAAGCGTTAT CAATTTTTCA TTATCGTATT GTTGCACATC AACAGGCTGG ACACCACG      6480

GAACTCGCCG CAGTTTTGCG GCAAGTTGGA CCCGCCGCGC ATCCAATGCA AACTTTCC      6540
```

-continued

```
CATTCTGTTG CCTACGAACG ATTGATTCTT TGTCCATTGA TCGAAGCGAG TGCCTTCG      6600

TTTTTCGTGT CCAGTGTGGC TT                                             6622

(2) INFORMATION FOR SEQ ID NO: 43:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

CCGGATCCGC CCAGGGCCAC CTAAGGAGCG G                                    31

(2) INFORMATION FOR SEQ ID NO: 44:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

CTGAATTCAG GAGCCAGGGC ACAGGCATG                                       29
```

HUMAN SEMAPHORIN L (H-SEMAL) AND CORRESPONDING SEMAPHORINS IN OTHER SPECIES

RELATED APPLICATIONS

This application is a continuation of U.S. application Ser. No. 09/836,077, filed Apr. 16, 2001, now abandoned which is a continuation of U.S. application Ser. No. 09/112,904, filed Jul. 9, 1998, now abandoned which claims priority to German Application Nos. 19729211.9 and 19805371.1, filed Jul. 9, 1997 and Feb. 11, 1998, respectively, each incorporated herein by reference.

BACKGROUND OF THE INVENTION

1. Field of the Invention

The invention relates to novel semaphorins which are distinguished by a particular domain structure and derivatives thereof, nucleic acids (DNA, RNA, cDNA) which code for these semaphorins, and derivatives thereof, and the preparation and use thereof.

2. Description of the Related Art

The publications which are referenced in this application describe the state of the art to which this invention pertains. These references are incorporated herein by references.

Semaphorins were described for the first time by Kolodkin {Kolodkin et al. (1993) Cell 75:1389-1399} as members of a conserved gene family.

The genes or parts of the genes of other semaphorins have now been cloned and, in some cases, characterized. To date, a total of 5 human (H-Sema III, H-Sema V, H-Sema IV, H-SemaB and H-SemaE) {Kolodkin et al. (1993); Roche et al. (1996) Onkogene 12:1289-1297; Sekido et al. (1996) Proc. Natl. Acad. Sci. USA 93:4120-4125; Xiang et al. (1996) Genomics 32:39-48; Hall et al. (1996) Proc. Natl. Acad. Sci. USA 39:11780-11785; Yamada et al. (1997) (GenBank Accession No. AB000220)}, 8 murine (mouse genes; M-Sema A to M-Sema-H) {Püschel et al. (1995) Neuron 14:941-948; Messerschmidt et al. (1995) Neuron 14:949-959; Inigaki et al. (1995) FEBS Letters 370:269-272; Adams et al. (1996) Mech. Dev. 57:3345; Christensen et al. (1996)(GenBank Accession No. Z80941, Z93948)}, 5 galline (chicken) (collapsin-1 to -5) {Luo et al. (1993); Luo et al. (1995) Neuron 14:1131-1140}, and genes from rats (R-Sema-III) {Giger et al. (1996) J. Comp. Neurol. 375: 378-392}, zebra fish, insects (fruit fly (*Drosophila melanogaster*: D-Sema I and D-Sema II), beetles (*Tribolium confusum*: T-Sema-I), grasshoppers (*Schistocerca americana*: G-Sema-I)) {Kolodkin et al. (1993)}, and nematodes (*C. elegans*: Ce-Sema) {Roy et al. (1994) (GenBank Accession No. U15667)} have been disclosed. In addition, two poxviruses (vaccinia (ORF-A39) and variola (ORFA39-homologous)) {Kolodkin et al. (1993)} and alcelaphine herpesvirus Type 1 (AHV-1) (AHV-Sema) {Ensser and Fleckenstein (1995) Gen. Virol. 76:1063-1067} have genes homologous to semaphorins.

Table 1 summarizes the semaphorins identified to date in various species. Table 1 indicates the names of the semaphorins (column 1), the synonyms used (column 2), the species from which the particular semaphorin has been isolated (column 3) and, where known, data on the domain structure of the encoded protein and on the chromosomal location (column 4 in Table 1), the accession number under which the sequence of the gene is stored in gene databanks (for example in an EST (expressed sequence tags) databank, EMBL (European Molecular Biology Laboratory, Heidelberg) or NCBI (National Center for Biotechnology Information, Maryland, USA), and the corresponding reference under which these data have been published (column 5 in Table 1).

All the gene products (encoded semaphorins) of the semaphorin genes disclosed to date have an N-terminal signal peptide which has at its C-terminal end a characteristic Sema domain with a length of about 450 to 500 amino acids. Highly conserved amino acid motifs and a number of highly conserved cysteine residues are located within the Sema domains. The gene products (semaphorins) differ in the C-terminal sequences which follow the Sema domains and are composed of one or more domains. They have, for example, in these C-terminal amino acid sequences transmembrane domains (TM), immunoglobulin-like domains (Ig) (constant part of the immunoglobulin), cytoplasmic sequences (CP), processing signals (P) (for example having the consensus sequence (RXR) where R is the amino acid arginine and X is any amino acid) and/or hydrophilic C termini (HPC). The semaphorins disclosed to date can be divided on the basis of the differences in the domain structure in the C terminus into 5 different subgroups (I to V):

| | | |
|---|---|---|
| I | | Secreted, without other domains (for example ORF-A49) |
| II | Ig | Secreted (without transmembrane domain) for example AHV-Sema) |
| III | Ig, TM, CP | Membrane-anchored with cytoplasmic sequence (for example CD100) |
| IV | Ig, (P), HPC | Secreted with hydrophilic C terminus (for example H-Sema III, M-SemaD, collapsin-1) |
| V | Ig, TM, CP | Membrane-anchored with C-terminal 7 thrombospondin motif (for example M-SemaF and G) |

A receptor or extracellular ligand for semaphorins has not been described to date. Intracellular, heterotrimeric GTP-binding protein complexes have been described in connection with semaphorin-mediated effects. One component of these protein complexes which has been identified in chickens is called CRMP (collapsin response mediator protein) and is presumed to be a component of the semaphorin-induced intracellular signal cascade (Goshima et al. (1995) Nature 376: 509-514). CRMP62, for example, has homology with unc-33, a nematode protein which is essential for directed growth of axons. A human protein with 98% amino acid identity with CRMP62 is likewise known (Hamajima et al. (1996) Gene 180: 157-163). Several CRMP-related genes have likewise been described in rats (Wang et al. (1996) Neurosci. 16: 6197-6207).

The secreted or transmembrane semaphorins convey repulsive signals for growing nerve buds. They play a part in the development of the central nervous system (CNS) and are expressed in particular in muscle and nerve tissues (Kolodkin et al. (1993); Luo et al. (1993) Cell 75:217-227).

Pronounced expression of M-SemaG has been observed not only in the CNS but also in cells of the lymphatic and hematopoietic systems, in contrast to the closely related M-SemaF {Furuyima et al. (1996) J. Biol. Chem. 271: 33376-33381}.

Recently, two other human semaphorins have been identified, H-Sema IV and H-Sema V, specifically in a region on chromosome 3p21.3, whose deletion is associated with various types of bronchial carcinomas. H-Sema IV {Roche et al. (1996), Xiang et al. (1996), Sekido et al. (1996)} is about 50% identical at the amino acid level with M-SemaE, whereas H-Sema V {Sekido et al. (1996)} is the direct homolog of M-SemaA (86% amino acid identity). Since these genes (H-Sema IV and V) were found during DNA sequencing projects on the deleted 3p21.3 loci, the complex intron-exon structure of these two genes is known. Both genes are expressed in various neuronal and non-neuronal tissues.

Likewise only recently, the cellular surface molecule CD100 (human), expressed and induced on activated T cells, has been identified as a semaphorin (likewise listed in Table 1). It assists interaction with B cells via the CD40 receptor and the corresponding ligand CD40L. CD100 is a membrane-anchored glycoprotein dimer of 150 kd (kilodaltons). An association of the intracytoplasmic C-terminus of CD100 with an as yet unknown kinase has been described {Hall et al. (1996)}. This means that CD100 is the first and to date only semaphorin whose expression in cells of the immune system has been demonstrated.

In the "transforming genes of rhadinoviruses" project, the complete genome of alcelaphine herpesvirus Type 1 (AHV-1) has been cloned and sequenced {Ensser et al. (1995)}. AHV-1 is the causative agent of malignant catarrhal fever, a disease of various ruminants which is associated with a lymphoproliferative syndrome and is usually fatal. On analysis, an open reading frame was found, at one end of the viral genome, having remote but significant homology with a gene of vaccinia-virus (ORF-A39 corresponds to VAC-A39 in Ensser et al. (1995) J. Gen. Virol. 76:1063-1067) which has been assigned to the semaphorin gene family. Whereas the AHV-1 semaphorin (AHV-Sema) has a well-conserved semaphorin structure, the poxvirus genes (ORF-A39 and ORF-A39-homologous, see Table 1) have C-terminal truncations, i.e. the conserved Sema domain is present in them only incompletely.

Databank comparison of the found AHV-Sema with dbEST (EST (expressed sequence tags) databank (db)) provided in each case 2 EST sequences from 2 independent cDNA clones from human placenta (accession numbers H02902, H03806 (clone 151129), accession numbers R33439 and R33537 (clone 135941)). These display distinctly greater homology with AHV-1 semaphorin than with the neuronal semaphorins hitherto described.

SUMMARY OF THE INVENTION

The present invention relates to semaphorins which have a novel, as yet undisclosed and unexpected domain structure and which possess a biochemical function in the immune system (immunomodulating semaphorins). The novel semaphorins are referred to as type L semaphorins (SemaL). They comprise an N-terminal signal peptide, a characteristic Sema domain and, in the C-terminal region of the protein, an immunoglobulin-like domain and a hydrophobic domain which represents a potential transmembrane domain.

The amino acid sequence of the signal peptide may have fewer than 70, preferably fewer than 60 amino acids and more than 20, preferably more than 30 amino acids, and a particularly preferred length is of about 40 to 50 amino acids. In a specific embodiment of the invention, the signal peptide has a length of 44 amino acids, i.e. a cleavage site for a signal peptidase is located between amino acids 44 and 45.

The Sema domain may have a length of from 300 to 700 or more, preferably of about 400 to 600, amino acids. Preferred Sema domains have a length of 450 to 550 amino acids, preferably of about 500 amino acids. In a preferred embodiment of the invention, the Sema domain is joined to the signal peptide, in which case the Sema domain preferably extends up to amino acid 545.

The immunoglobulin-like domain may have a length of about 30 to 110 or more amino acids, and preferred lengths are between 50 and 90, particularly preferably about 70, amino acids.

The transmembrane domain may have a length of about 10 to 35, preferably of about 15 to 30, particularly preferably of about 20 to 25, amino acids.

The invention relates to type L semaphorins from various species, in particular from vertebrates, for example from birds and/or fishes, preferably from mammals, for example from primates, rat, rabbit, dog, cat, sheep, goat, cow, horse, pig, particularly preferably from human and mouse. The invention also relates to corresponding semaphorins from microorganisms, especially from pathogenic microorganisms, for example from bacteria, yeasts and/or viruses, for example from retroviruses, especially from human-pathogenic microorganisms.

DESCRIPTION OF THE DRAWINGS

The invention will be described in greater detail with the aid of the following figures:

FIG. 4 is a FACS analysis of H-SEMAL expression in various cell lines.

FIG. 5 is a comparative analysis of CD 100 and H-SemaL expression.

FIG. 6 is the expression of secretable human SEMA-L (H-SemaL) in HiFive and SC3 cells.

DETAILED DESCRIPTION OF THE INVENTION

Figure 1:
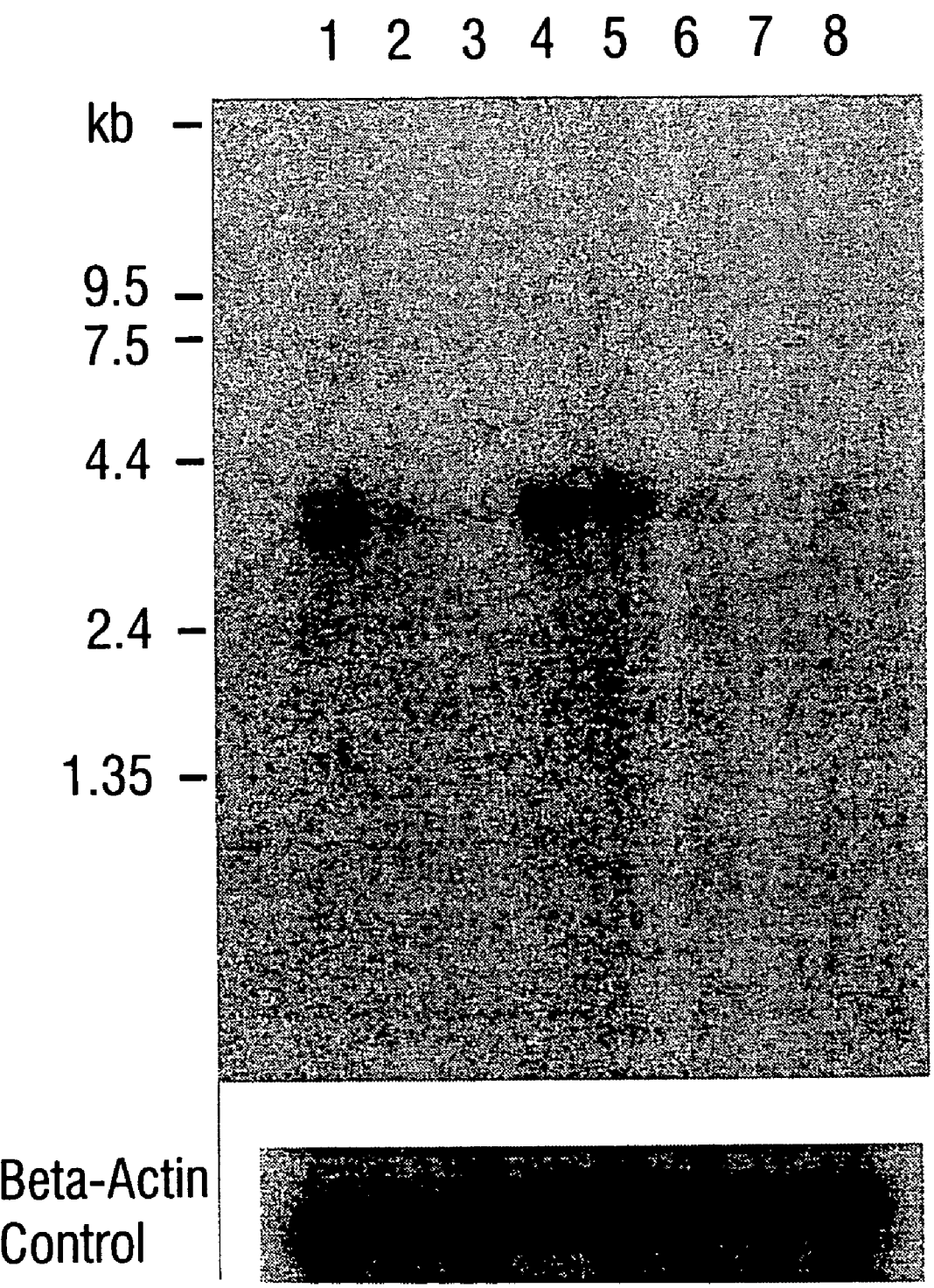
FIG. 1 is a Multiple tissue Northern blot for the tissue-specific expression of H-SemaL.
Figure 2:
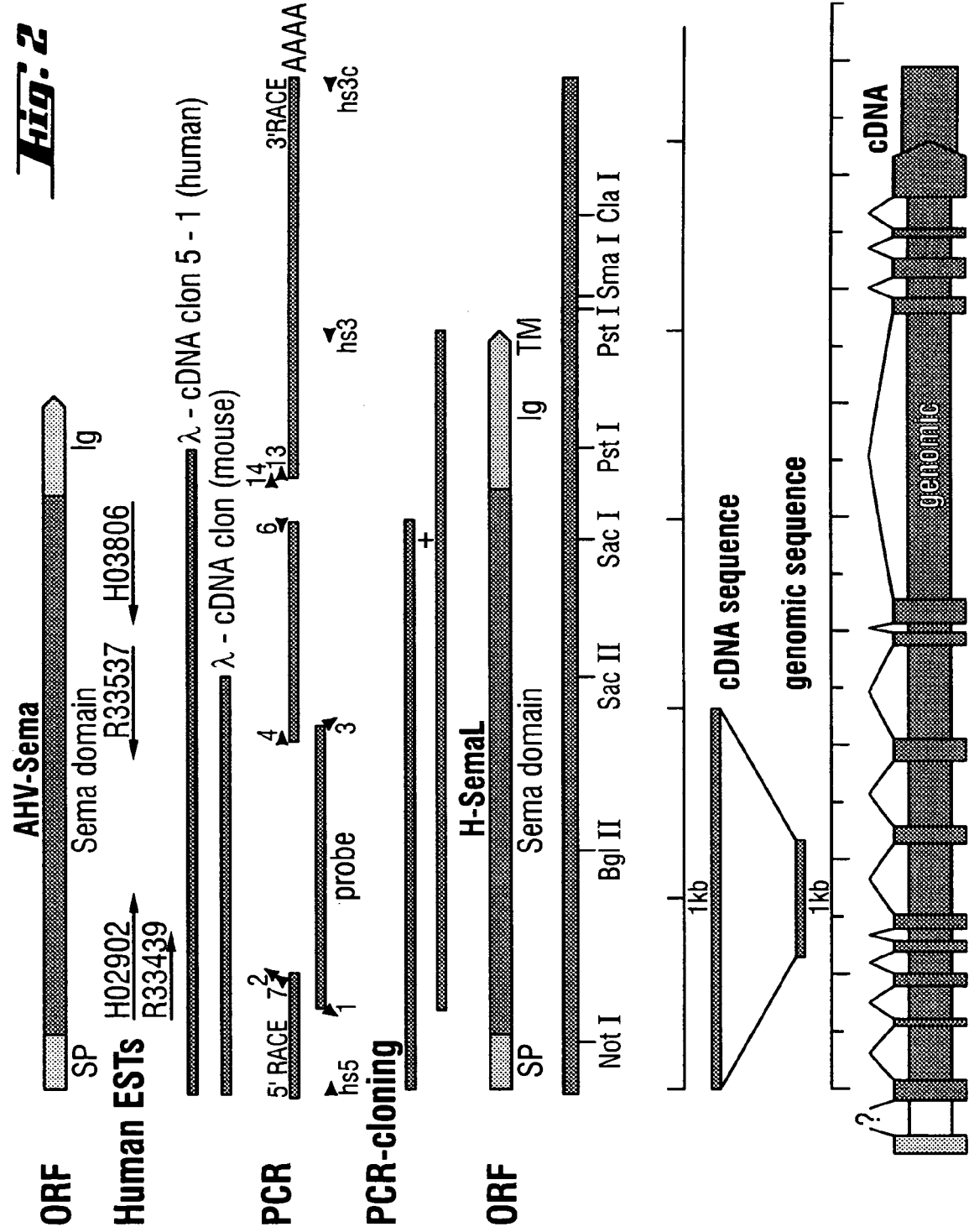
FIG. 2 is a diagrammic representation of the cloning of the H-SemaL cDNA and of the genomic organization of the H-SemaL encoding sequence.

One embodiment of the invention is a corresponding human semaphorin (H-SemaL) which has a signal peptide, a Sema domain, an immunoglobulin-like domain and a transmembrane domain. A specific embodiment is the semaphorin which is given by the amino acid sequence shown in Table 4.

Another embodiment of the invention comprises corresponding semaphorins in other species which have, in the region of the Sema domain, an amino acid identity greater than 40%, preferably greater than 50%, particularly preferably greater than 60%, in relation to the Sema domain of H-SemaL (amino acids 45 to 545 of the sequence in Table 4). The corresponding semaphorins from closely related species (for example primates, mouse) may perfectly-well have amino acid identities of greater than 70%, preferably greater than 80%, particularly preferably greater than 90%. Percentage homologies can be determined or calculated for example using the GAP program (GCG program package, Genetice Computer Group (1991)).

Such an embodiment of the invention is a corresponding mouse semaphorin (murine semaphorin (M-SemaL)). This contains, for example, the partial amino acid sequence shown in Table 5 (murine semaphorin (M-SemaL)).

The invention also relates to corresponding semaphorins which have an amino acid identity (considered over the entire length of the amino acid sequence of the protein) of only about 15 to 20% in the case of less related species (very remote from one another phylogenetically), preferably 25 to 30%, particularly preferably 35 to 40%, or a higher identity in relation to the complete amino acid sequence of H-SemaL shown in Table 4.

The genes which code for type L semaphorins have a complex exon-intron structure. These genes may have, for example, between 10 and 20 exons, preferably about 11 to 18, particularly preferably 12 to 16, exons and a corresponding number of introns. However, they may also have the same number of exons and introns as does the gene of H-SemaL (13 or 15 exons, preferably 14 exons). A particular embodiment of the invention relates to the gene of H-SemaL. This gene preferably has a length of 8888 to 10,000 or more nucleotides. The human semaphorin gene preferably contains the nucleotide sequence given in Table 14 or the nucleotide sequence which has been deposited at the GenBank® databank under accession number AF030697. These nucleotide sequences contain at least 13 introns. In addition, the human semaphorin gene has at the 5' end an additional sequence region. This region contains, where appropriate, further coding and uncoding sequences, for example one or two further introns or exons.

Attempts to locate the human type L semaphorin on the chromosome revealed that the corresponding gene is located at position 15q22.3-23. The gene for M-SemaL has correspondingly been located at position 9A3.3-B.

As a consequence of the complex intron-exon structure, the splicing of the primary transcript of the semaphorin mRNA may vary, resulting in different splicing variants of the semaphorins. The proteins translated from these splicing variants are derivatives of the semaphorins according to the invention. They correspond in their amino acid sequence and also substantially in their domain structure to the described type L semaphorins according to the invention, but are truncated by comparison with the latter where appropriate. For example, splicing variants wholly or partly lacking the transmembrane domain may be formed. A semaphorin derivative which contains an incomplete, or no, transmembrane domain, but contains a signal peptide, may be secreted and in this way have effects outside the cell, locally or else over relatively large distances, for example on other cells. Another splicing variant may, for example, no longer contain a sequence which codes for a signal peptide and, where appropriate, also no sequence which codes for a hydrophobic amino acid sequence representing a potential transmembrane domain. One consequence would be that this semaphorin derivative is neither incorporated into the membrane nor secreted (unless through secretory vesicles). Such a semaphorin derivative may be involved in intracellular processes, for example in signal transduction processes. It is possible in this way for a wide variety of intra- and extracellular processes to be controlled and/or harmonized with the same basic molecule (type L semaphorins) and the derivatives derived therefrom (for example splicing variants).

A particular embodiment of the invention relates to semaphorin derivatives which are derived from the type L semaphorins according to the invention but which contain an incomplete, or no, transmembrane domain.

Another embodiment of the invention relates to semaphorin derivatives which are derived from the type L semaphorins according to the invention but which contain no signal peptide.

The signal peptide may also undergo post-translational elimination. This forms a membrane-bound (with TM domain) or a secreted (splicing variant without TM domain) semaphorin derivative with truncated domain structure. A semaphorin derivative which has undergone post-translational processing in this way now contains only Sema domain, Ig domain and, where appropriate, transmembrane domain. A signal peptide cleavage site can be located, for example, right at the end of the signal peptide, but it may, for example, be located 40 to 50 amino acids or more away from the amino terminus.

A "truncated" (i.e. containing fewer domains) semaphorin L derivative can be distinguished from other semaphorins which are not derived from type L semaphorins in that there is a very great (>90%) amino acid identity or an identical amino acid sequence with the type L semaphorins in the domains which are present.

The semaphorins according to the invention may also have undergone post-translational modification in other ways. For example, they may be glycosylated (N- and/or O-glycosylated) once, twice, three, four, five, six, seven, eight, nine, ten or more times. The amino acid sequences of the semaphorins may then have an equal number of or more consensus sequences for potential glycosylation sites, preferably five such sites. One embodiment of the invention relates to semaphorins in which the glycosylation sites are located at positions which correspond to positions 105, 157, 258, 330 and 602 of the H-SemaL amino acid sequence (Table 4).

In addition, the semaphorins may be in the form of their phosphorylated derivatives. Semaphorins may be the substrates of various kinases, for example the amino acid sequences may have consensus sequences for protein kinase C, tyrosine kinase and/or creatine kinases. In addition, the amino acid sequences of the semaphorins may have consensus sequences for potential myristylation sites. Corresponding semaphorin derivatives may be esterified with myristic acid at these sites.

The type L semaphorins according to the invention and their derivatives may be in the form of monomers, dimers and/or multimers, for example two or more semaphorins or their derivatives can be linked together by intermolecular disulfide bridges. It is also possible for intramolecular disulfide bridges to be formed.

Further derivatives of the semaphorins according to the invention are fusion proteins. A fusion protein of this type contains, on the one hand, a type L semaphorin or parts thereof and, in addition, another peptide or protein or a part thereof. Peptides or proteins or parts thereof may be, for example, epitope tags (for example His tag (6× histidine), Myc tag, flu tag) which can be used, for example, for purifying the fusion proteins, or those which can be used for labeling the fusion proteins, for example GFP (green fluorescent protein). Examples of derivatives of the type L semaphorins are given for example by the constructs described in the examples. The sequences of these constructs can be found in Tables 7 to 15, where appropriate taking account of the annotations relating to the plasmids.

The invention further relates to nucleic acid sequences, preferably DNA and RNA sequences, which code for the type L semaphorins according to the invention and/or their derivatives, for example the corresponding genes, the various splicing variants of the mRNA, the cDNAs corresponding thereto, and derivatives thereof, for example salts of the DNA or RNA. Derivatives for the purpose of the inventions are sequences or parts thereof which have been modified, for example, by methods of molecular biology and adapted to the particular requirements, for example truncated genes or parts of genes (for example promoter sequences, terminator sequences), cDNAs or chimeras thereof, constructs for expression and cloning and salts thereof.

One embodiment relates to the genomic sequences (genes) of the type L semaphorins. The invention relates to the intron and exon sequences and gene-regulatory sequences, for example promoter, enhancer and silencer sequences.

This embodiment relates on the one hand to the gene of H-SemaL or its derivatives. The invention relates on the one hand to a gene which comprises the nucleotide sequence given in Table 14. The invention further relates to the gene which comprises the nucleotide sequence which is deposited in the GenBank® databank under accession number AF030697.

This embodiment further relates to the gene of M-SemaL and its derivatives.

The invention further relates to the cDNA of H-SemaL or its derivatives (for example parts of the cDNA). A particular embodiment is the cDNA of H-SemaL according to the nucleotide sequence in Table 2. The invention further relates to the cDNA of H-SemaL which is deposited in the GenBank® databank under accession number AF030698. The invention also relates to the mRNAs corresponding to these cDNAs, or parts thereof.

The invention further relates to the cDNA of M-SemaL or its derivatives (for example parts of the cDNA). A particular embodiment is the partial cDNA sequence of M-SemaL shown in Table 3, and cDNA sequences which comprise this partial cDNA sequence. Another embodiment of the invention relates to the cDNA of M-SemaL which is deposited in the GenBank databank under accession number AF030699. The invention also relates to the mRNAs corresponding to these cDNAs, or parts thereof.

The invention also comprises alleles and/or individual expression forms of the genes/mRNAs/cDNAs which differ only slightly from the semaphorin sequences described herein and code for an identical or only slightly modified protein (difference in the amino acid sequence less than or equal to 10%) (further example of derivatives). Further examples of the derivatives are given by the constructs indicated in the examples. The sequences of these constructs are depicted in Tables 7 to 14 and can be interpreted taking account of the annotation for plasmids.

The invention further relates to plasmids which comprise DNA which codes for the type L semaphorins or derivatives thereof. Plasmids of this type may be, for example, plasmids with high replication rates suitable for amplification of the DNA, for example in *E. coli*.

A specific embodiment comprises expression plasmids with which the semaphorins or parts thereof or their derivatives can be expressed in prokaryotic and/or eukaryotic expression systems. Both constitutive expression plasmids and those containing inducible promoters are suitable.

The invention also relates to processes for preparing nucleic acids which code for type L semaphorins or derivatives thereof.

These nucleic acids, for example DNA or RNA, can be synthesized, for example, by chemical means. In particular, it is possible for these nucleic acids, for example the corresponding genes or cDNAs or parts thereof, to be amplified by PCR using specific primers and suitable starting material as template. (For example cDNA from a suitable tissue or genomic DNA).

A specific process for preparing semaphorin L cDNA and the H-SemaL gene is described in the examples.

The invention also relates to processes for preparing type L semaphorins. For example, a semaphorin L or a derivative thereof can be prepared by cloning a corresponding nucleic acid sequence which codes for a type L semaphorin or a derivative thereof into an expression vector and using the latter recombinant vector to transform a suitable cell. It is possible to use, for example, prokaryotic or eukaryotic cells. The type L semaphorins or derivatives thereof may also, where appropriate, be prepared by chemical means.

In addition, the type L semaphorins and derivatives thereof can be expressed as fusion proteins, for example with proteins or peptides which permit detection of the expressed fusion protein, for example as fusion protein with GFP (green fluorescent protein). The semaphorins may also be expressed as fusion proteins with one, two, three or more epitope tags, for example with Myc and/or His (6× histidine) and/or flu tags. It is correspondingly possible to use or prepare plasmids which comprise DNA sequences which code for these fusion proteins. For example, semaphorin-encoding sequences can be cloned into plasmids which contain DNA sequences which code for GFP and/or epitope tags, for example Myc tag, His tag, flu tag. Specific examples thereof are given by the examples and the sequences listed in the tables, where appropriate with the assistance of the annotation relating to the plasmids.

The invention further relates to antibodies which specifically bind or recognize the type L semaphorins, derivatives thereof or parts thereof. Possible examples thereof are polyclonal or monoclonal antibodies which can be produced, for example, in mouse, rabbit, goat, sheep, chicken etc.

A particular embodiment of this subject-matter of the invention comprises antibodies directed against the epitopes which correspond to the amino acid sequences from position 179 to 378 or 480 to 666 of the H-SemaL sequence shown in Table 4. The invention also relates to a process for preparing specific anti-semaphorin L antibodies, using for the preparation antigens comprising said epitopes.

The invention also relates to processes for preparing the antibodies, preferably using for this purpose a fusion protein consisting of a characteristic semaphorin epitope and an epitope tag which can be used for the subsequent purification of the recombinant fusion protein. The purified fusion protein can subsequently be used for the immunization. To prepare the recombinant fusion protein, a corresponding recombinant expression vector is prepared and used to transform a suitable cell. The recombinant fusion protein can be isolated from this cell. The procedure can be, for example, like that described in Example 8.

These antibodies can be used, for example, for purifying the corresponding semaphorins, for example H-SemaL and its derivatives, for example on affinity columns, or for the immunological detection of the proteins, for example in an ELISA, in a Western blot and/or in immunohistochemistry. The antibodies can also be used to analyze the expression of H-SemaL, for example in various cell types or cell lines.

The cDNA of H-SemaL has a length of 2636 nucleotides (Table 2). The gene product of the H-SemaL cDNA has a length of about 666 amino acids (Table 4) and displays the typical domain structure of a type L semaphorin. The gene product has an N-terminal signal peptide (amino acids 1 to 44), Sema domain (amino acid 45 to approximately amino acid 545), and Ig (immunoglobulin) domain (approximately amino acids 550 to 620) and, at the C-terminal end, a hydrophobic amino acid sequence which represents a potential transmembrane domain. This domain structure has never previously been described for semaphorins. It relates to a membrane-associated glycoprotein which is probably located on the cell surface and belongs to a new subgroup.

On the basis of this previously unknown domain structure, the semaphorins can now be divided into VI subgroups:

| | | |
|---|---|---|
| I | | Secreted, without other domains (for example ORF-A49) |
| II | Ig | Secreted (without transmembrane domain) (for example AHV-Sema) |
| III | Ig, TM, CP | Membrane-anchored with cytoplasmic sequence (for example CD100) |
| IV | Ig, (P), HPC | Secreted with hydrophilic C terminus (for example H-Sema-III, M-SemaD, collapsin-1) |
| V | Ig, TM, CP | Membrane-anchored with C-terminal 7 thrombospondin motif (for example M-SemaF and G) |
| VI | Ig, TM | Membrane-anchored (for example H-SemaL, M-SemaL) |

The unglycosylated, unprocessed form of H-SemaL has a calculated molecular weight of about 74.8 kd (74823 dalton) (calculated using Peptide-Sort, GCG program package). The isoelectric point is calculated to be pH=7.56.

A possible signal peptide cleavage site is located between amino acids 44 and 45 (Table 3; calculated with SignalP, a program based on neural networks for analyzing signal sequences {Nielsen H. et. al. (1997) Protein Engineering 10:1-6}). This gives for the processed protein (without signal peptide) a molecular weight (MW) of 70.3 kd (70323 dalton) and an isoelectric point of pH=7.01.

The genomic structure is likewise substantially elucidated. The H-SemaL gene has 13 or 15 or more exons, preferably 14 exons, and 12 or 14 introns, preferably. 13 introns. Because of this complex exon-intron structure, various splicing variants are possible. The mRNA of the transcribed H-SemaL gene is found in the Northern blot particularly in placenta, gonads, thymus and spleen. No mRNA has been detected in neuronal tissue or in muscle tissue. There is evidence of specifically regulated expression in endothelial cells.

Alternative splicing may also result in forms of H-SemaL with intracytoplasmic sequences which are involved in intracellular signal transduction, similar to, for example, CD100. It would likewise be possible for alternative splicing to result in secreted forms of H-SemaL, analogous to viral AHV-Sema.

Nucleotide and amino acid sequence analyses were performed with the aid of the GCG program package (Genetics Computer Group (1991) Program manual for the GCG package, Version 7, 575 Science Drive, Wisconsin, USA 53711), FASTA (Pearson and Lipman (1988) Proc. Natl. Acad. Sci. 85, 2444-2448) and BLAST program (Gish and States (1993) Nat. Genet. 3, 266-272; Altschul et al. (1990) J. Mol. Biol. 215, 403-410). These programs were also used for sequence comparisons with GenBank (Version 102.0) and Swiss Prot (Version 34.0).

Post-translational modifications such as glycosylation and myristylation of H-SemaL are likewise possible. Consensus sequences for N-glycosylation sites were found with the aid of the Prosite program (GCG program package) at positions 105, 157, 258, 330 and 602 of the amino acid sequence of H-SemaL (shown in Table 4), and those for myristylation were found at positions 114, 139, 271, 498, 499, 502 and 654 (consensus sequence: G~(E, D, R, K, H, P, F, Y, W)×(S, T, A, G, C, N)~(P)). In addition, the amino acid sequence of H-SemaL contains several consensus sequences for potential phosphorylation sites for various kinases. It can therefore be assumed that H-SemaL can be the substrate of various kinases, for example phosphorylation sites for creatine kinase 2, protein kinase C and tyrosine kinase.

Predicted creatine kinase 2 phosphorylation sites (consensus sequence Ck2: (S,T)×2(D,E)) (Prosite, GCG) at positions 119, 131, 173, 338, 419 and 481 of the amino acid sequence.

Predicted protein kinase C phosphorylation sites (consensus sequence PkC: (S,T)×(R,K)) (Prosite, GCG) at positions 107, 115, 190, 296, 350, 431, 524 and 576 of the amino acid sequence.

Predicted tyrosine kinase phosphorylation site (consensus sequence: (R,K)×{2,3}(D,E)×{2,3}Y) (Prosite, GCG) at position 205 of the amino acid sequence.

The consensus sequences are indicated in the single letter code for amino acids.

An "RGD" motif (arginine-glycine-aspartic acid) characteristic of integrins is located at position 267.

The glycosylation sites are highly conserved between viral AHV-Sema, H-SemaL and (as far as is known) M-SemaL.

Di- or multimerization of H-SemaL is possible and has been described for other semaphorins such as CD100 {Hall et al. (1996)}. The CD100 molecule is likewise a membrane-anchored glycoprotein dimer of 150 kd. However, CD100 is not closely related to the human semaphorin (H-SemaL) according to the invention.

The partial cDNA sequence of M-SemaL has a length of 1195 nucleotides. This sequence codes for a protein having 394 amino acids. These 394 amino acids correspond to amino acids 1 to 396 of H-SemaL. The signal peptide in M-SemaL extends over amino acids 1 to 44 (exactly as in H-SemaL). The Sema domain starts at amino acid 45 and extends up to the end or probably beyond the end of the sequence shown in Table 4.

Multiple alignments were carried-out using the Clustal W program (Thompson et al. (1994)). These alignments were processed further manually using SEAVIEW (Galtier et al. (1996) Comput. Appl. Biosci 12, 543-548). The phylogenetic distances were determined using Clustal W (Thompson et al. (1994)).

Comparison of the protein sequences of the known and of the novel semaphorins and phylogenetic analysis of these sequences shows that the genes can be categorized according to their phylogenetic relationship. The C-terminal domain structure of the corresponding semaphorin subtypes is, of course, involved in this as a factor deciding why semaphorins in the same subgroups are, as a rule, also more closely related phylogenetically than are semaphorins in different subgroups. The species from which the semaphorin was isolated also has an influence, i.e. whether the corresponding species are phylogenetically closely related to one another or not.

Figure 3:
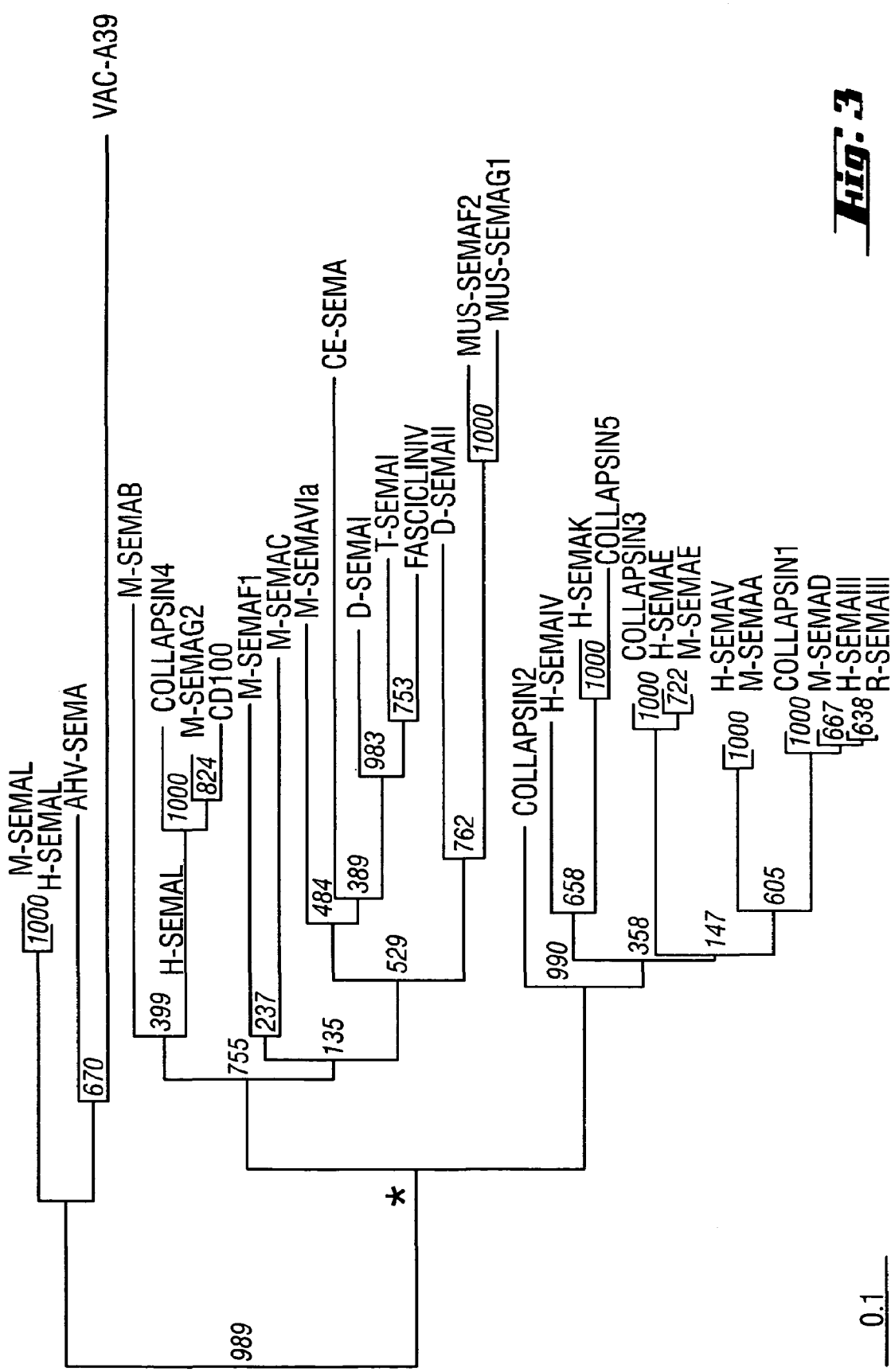
FIG. 3 is a phylogenetic tree.

A phylogenetic analysis (compare FIG. 3) of the known semaphorin amino acid sequences (complete sequences and/or part-sequences, using the amino acid sequences for H-SemaL and M-SemaL shown in Tables 4 and 5 and for all other sequences the sequences stored under the accession numbers or the encoded amino acid sequences derived from these sequences) using the CLUSTAL W program {Thompson J. D. et al. (1994) Nucleic Acids Res. 22:4673-4680} shows that the amino acid sequences of H-SemaL and M-SemaL are phylogenetically closely related to one another and form a separate phylogenetic group. H-SemaL and M-SemaL in turn are phylogenetically most closely related to AHV-Sema and Vac-A39. The are distinctly more closely related to one another than to any other previously disclosed semaphorin. The analysis also shows that other semaphorins are also phylogenetically closely related to one another and form separate groups within the semaphorins. For example, the semaphorins which are secreted, for example H-Sema III, -IV, -V and -E belong in one phylogenetic group. Their homologs in other species also belong to this subfamily, whereas the human (transmembrane) CD100 belongs in one phylogenetic group together with the corresponding mouse homolog (M-SemaG2) and with Collapsin-4.

In relation to the complete amino acid sequences, the observed homologies within the phylogenetic groups are between about 90% and 80% amino acid identity in relation to very closely related genes such as, for example, H- and M-SemaE or -III/D and somewhat less than 40% in the case of less related genes of the semaphorins. Within the Sema domain, the observed amino acid identity is a few percent higher, and, owing to its great contribution to the total protein (50-80% of the protein belong to the Sema domain) of the amino acid sequence, this considerably influences the overall identity.

H-SemaL is, calculated for the complete protein, 46% identical with AHV-Sema, but if the Sema domain is considered on its own, then the amino acid identity is 53%. This is higher than, for example, between the related M-Sema-B and -C (37% identity in relation to the complete protein, 43% identity in relation to the Sema domain), similar to M-SemaA and -E (43% complete protein, 53% Sema domain). The amino acid identity between the partial M-SemaL sequence (Table 6) and H-SemaL (Table 5) in the region of the Sema domain is 93% so that it can be assumed that the correspondingly homologous mouse gene is involved.

Semaphorins corresponding to H-SemaL and M-SemaL in other species may have an amino acid identity within the Sema domain of more than 40% in relation to H-SemaL. In closely related vertebrates (mammals, birds) amino acid identities above 70% may even be found.

The semaphorins belong to a new subfamily with greater amino acid identity to the viral AHV-Sema than to the previously disclosed human and murine semaphorins, and with a C-terminal structure not previously disclosed for human semaphorins. These novel semaphorins (members of the subfamily) are distinguished by belonging, because of their domain structure, to subgroup IV and/or to the same phylogenetic group as H-SemaL and M-SemaL and/or have, in relation to the complete amino acid sequence, an amino acid identity of at least 30 to 40%, preferably 50 to 60%, particularly preferably 70 to 80%, or a greater identity, to H-SemaL and/or have, in relation to the Sema domain, an amino acid identity of at least 70%, preferably greater than 80%, particularly preferably greater than 90%, to H-SemaL.

The type L semaphorins also have a different type of biochemical function. One novel function of these semaphorins is modulation of the immune system.

The closest relative of H-SemaL is the viral AHV semaphorin (AHV-Sema). The latter has a similar size but, in contrast to H-SemaL, has no transmembrane domain. AHV-Sema is presumably secreted by virus-infected cells in order to block the H-SemaL equivalent receptor (type L semaphorin in the blue wildebeest) in the natural host (blue wildebeest) and thus elude the attack of the immune system. It is also conceivable that there is a function as repulsive agent (chemorepellant) for cells of the immune system.

The biochemical function of the novel type L semaphorins and derivatives thereof is to be regarded as generally immunomodulating and/or inflammation-modulating. They are able on the one hand A) as molecules inhibiting the immune response to display their effect as chemorepellant and/or immunosuppressant either locally, for example as transmembrane protein on the surface of cells, or else over larger distances, for example if they are secreted due to processing (for example proteases) or alternative splicing, for example by diffusion in the tissue.

For example, expression of these novel type L semaphorins for example on the surface of the cells of the vascular endothelium can prevent leukocyte attachment and migration thereof through the vessel wall. The novel semaphorins may play a part in maintenance of barrier effects, for example to prevent infections in particularly "important" or exposed organs, for example to maintain the blood-brain barrier, the placental circulation and/or other immunologically privileged locations (for example pancreatic islets) and/or in prevention of autoimmune diseases. In addition, the novel semaphorins and/or their derivatives may also be involved in repulsive signals in various tissues, for example for cells of the immune system (for example leukocytes) to prevent inadvertent activation of defense mechanisms.

B) In addition, the novel semaphorins and/or derivatives thereof may have functions as accessory molecules. Expressed on the cell surface, they may, for example, be involved in the interaction with cells of the immune system as part of the activation of defense mechanisms, for example in cases of virus infection.

This reveals several possible uses of the novel type L semaphorins and derivatives thereof, and the nucleic acids coding for these proteins.

Function A): This comprises an immunosuppressant and/or anti-inflammatory principle: there are numerous potential possibilities of use in the areas of organ transplantation, therapy of inflammations, immunotherapy and gene therapy.

For example, nonhuman, transgenic animals can be produced with the aid of the semaphorin-encoding DNA or derivatives thereof.

One possible use of these animals is in the inhibition of transplant rejection in transgenic models of organ transplantations. For example, transgenic animal organs protected against rejection can be produced for xenotransplantations. This ought to be possible for example also together with other transgenes (for example complement regulators such as DAF or CD59). Another use is in the production of nonhuman knock-out animals, for example knock-out mice ("Laboratory Protocols for Gene-Targeting", Torres and Kujhn (1997) Oxford University Press, ISBN 0-19-963677-X): it is possible by knocking out the mouse M-SemaL gene for example to find other functions of the gene. They also represent potential model systems for inflammatory diseases if the mice can survive without semaphorin gene. If M-SemaL is important for immunomodulation, a plurality of such mice is to be expected. In addition, nonhuman knock-in animals, for example mice, can be produced. This entails, for example, replacing M-SemaL by normal/modified H-SemaL or modified M-SemaL (for example integration of the novel semaphorin subtypes under the control of constitutive and/or inducible promoters). Animals of this type can be used, for example, for looking for further functions of the novel semaphorins, for example functions of the human gene or derivatives of these genes, or be used for identifying and characterizing immunomodulating agents.

Use of, for example, nucleic acids which code for type L semaphorins or derivatives thereof for producing, for example, recombinant immunosuppressants, other soluble proteins or peptides derived from the amino acid sequence of type L semaphorins, for example from H-SemaL or the corresponding nucleic acids, for example genes. It is also possible in a similar way to produce agonists with structural similarity. These immunosuppressant agents or agonists may be used for autoimmune diseases and inflammatory disorders and/or organ transplantations too.

Gene therapy with type L semaphorins, for example with nucleic acids which code for H-SemaL or derivatives thereof, for example using viral or nonviral methods. Use in autoimmune diseases and inflammatory disorders, the transduction of organs and before/during/after transplantations to prevent transplant rejection.

It is particularly possible to employ the novel semaphorins and/or the nucleic acids coding for these semaphorins, and derivatives thereof, in particular H-SemaL, DNA coding for H-SemaL, and derivatives thereof, in a method for screening for agents, in particular for identifying and characterizing immunomodulating agents.

Function B): H-SemaL is an accessory molecule which is expressed on the cell surface and is involved in the interaction with cells, for example of the immune system, for example as accessory molecule in the activation of signal pathways. A viral gene or the gene product of a viral or other pathogenic gene, for example of microbiological origin, might act, for example, as competitive inhibitor of this accessory molecule. One use of the novel semaphorins with this function is likewise in the area of organ transplantation, therapy of inflammation, immunotherapy and/or gene therapy.

For example, the novel semaphorins can be used in a method for screening for antagonistic agents or inhibitors. Agents identified in this way can then be employed, for example, for blocking the semaphorin receptor. Soluble and/or secreted H-SemaL antagonists or inhibitors may be, for example, chemical substances or the novel semaphorins or derivatives thereof themselves (for example parts/truncated forms thereof, for example without membrane domain or as Ig fusion proteins or peptides derived from the latter, which are suitable for blocking the corresponding receptor). Specific antagonists and/or inhibitors identified in this way may, for example, have competitive effects and be employed for inhibiting rejection, for example in transgenic models of organ transplantations and for autoimmune diseases, inflammatory disorders and organ transplantations. Nucleic acids, for example DNA, which code for the novel semaphorins, or derivatives thereof produced with the aid of methods of molecular biology, may be used, for example, for producing nonhuman transgenic animals. Overexpression of H-SemaL in these transgenic animals may lead to increased susceptibility to autoimmune diseases and/or inflammatory disorders. Such transgenic animals are thus suitable for screening for novel specific immunomodulating agents.

Such nucleic acids can likewise be used to produce nonhuman knock-out animals, for example knock-out mice in which the mouse M-SemaL gene is switched off. Such knock-out animals can be employed to search for further biochemical functions of the gene. They also represent potential model systems for inflammatory disorders if the mice are able to survive without the M-SemaL gene.

This DNA can likewise be used to produce nonhuman knock-in animals, for example mice. This entails the M-SemaL gene being replaced by a modified M-SemaL gene/cDNA or an optionally modified, for example mutated, type L semaphorin gene/cDNA of another species, for example H-SemaL. Such transgenic animals can be used to look for further functions of the semaphorins according to the invention.

The invention also relates to the use of the type L semaphorins and derivatives thereof, and of the nucleic acids coding for these proteins, for example genes/cDNAs and derivatives thereof and/or agents identified with the aid of these semaphorins for producing pharmaceuticals. It is possible, for example, to produce pharmaceuticals which can be used in gene therapy and which comprise agonists and/or antagonists of the expression of the type L semaphorins, for example of H-SemaL. It is possible to use for this purpose, for example, viral and/or nonviral methods. These pharmaceuticals can be employed, for example, for autoimmune diseases and inflammatory disorders, organ transplantations before and/or during and/or after the transplantation to prevent rejection.

The nucleic acids coding for the novel semaphorins, for example genes, cDNAs and derivatives thereof, can also be employed as aids in molecular biology.

In addition, the novel semaphorins, especially H-SemaL and nucleic acids, for example genes/cDNAs thereof can be employed in methods for screening for novel agents. Modified proteins and/or peptides derived, for example, from H-SemaL and/or M-SemaL can be used to look for the corresponding receptor and/or its antagonists or agonist in functional assays, for example using expression constructs of H-SemaL and homologs.

The invention also relates to the use of a type L semaphorin or a nucleic acid sequence which codes for a type L semaphorin in a method for identifying pharmacological agents, especially immunomodulating agents.

The invention also relates to methods for identifying agents employing a type L semaphorin or a derivative thereof or a nucleic acid sequence which codes for a type L semaphorin, or a derivative thereof, in order to identify pharmacological agents, for example immunomodulating agents. The invention relates, for example, to a method in which a type L semaphorin is incubated under defined conditions with an agent to be investigated and, in parallel, a second batch is carried out without the agent to be investigated but under conditions which are otherwise the same, and then the inhibiting or activating effect of the agent to be investigated is determined.

The invention also relates, for example, to methods for identifying agents where a nucleic acid sequence which codes for a type L semaphorin or a derivative thereof is expressed under defined conditions in the presence of an agent to be investigated, and the extent of the expression is determined. It is also possible, where appropriate, in such a method to carry out two or more batches in parallel under the same conditions but with the batches containing different amounts of the agent to be investigated.

For example, the agent to be investigated may inhibit or activate transcription and/or translation.

The type L semaphorin can, like its viral homologs, bind to the newly described receptor molecule VESPR (Comeau et al, (1998) Immunity, Vol. 8, 473-482) and in monocytes can presumably cause induction of cell adhesion molecules such as ICAM-1 and cytokines such as interleukin-6 and interleukin-8. This may lead to activation thereof and to cell aggregation. The expression pattern of the VESPR receptor shows some interesting parallels with H-SemaL, for example strong expression in placenta and pronounced expression in spleen tissue. Interactions with other as yet unknown receptors of the plexin family or other receptors are possible. It may also interact with itself or other semaphorin-like molecules. Interaction of the type L semaphorins may take place in particular via a conserved domain in the C-terminal region of the Sema domain.

Concerning the annotation on plasmids:

pMelBacA-H-SemaL (6622 bp) in pMelBacA (Invitrogen, De Schelp, N L) (SEQ ID NO.42). Nucleotide 96-98 ATG—start codon, nucleotide 96-168 mellitin signal sequence, nucleotide 168-173 BamHI cleavage site (PCR/cloning), nucleotide 171-1998 reading frame SEMA-L amino acids 42-649 (without own signal sequence and without transmembrane sequence), nucleotide 1993-1998 EcoRI cleavage site (PCR/cloning) and nucleotide 1992-1994 stop codon Plasmid pCDNA3.1-H-SemaL-MychisA (7475 bp) (SEQ ID NO. 35): nucleotide 954-959 BamHI cleavage site (cloning), nucleotide 968-970 ATG SEMAL, nucleotide 968-2965 reading frame SEMAL, nucleotide 2963-2968 Pml I cleavage site, nucleotide 2969-2974 HindIII cleavage site, nucleotide 2981-3013 Myc tag, nucleotide 3026-3033 6×His tag, nucleotide 3034-3036 stop codon, Plasmid pCDNA3.1-H-SemaL-EGFP-MychisA (8192 bp):(SEQ ID NO. 36): nucleotide 954-959 BamHI cleavage site (cloning), nucleotide 968-970 ATG SEMA-L, nucleotide 968-2965 reading frame SEMA-L, nucleotide 2963-2965 half Pml I cleavage site, nucleotide 2966-3682 reading frame EGFP (cloned in Pml I), nucleotide 3683-3685 half Pml I cleavage site, nucleotide 3685-3691 HindIII, nucleotide 3698-3730 Myc tag, nucleotide 3743-3760 6×His tag, and nucleotide 3761-3763 stop codon Plasmid pIND-H-SemaL-EA (7108 bp) in vector pIND (Invitrogen, De Schelp, N L) (SEQ ID No. 38): nucleotide 533-538 BamHI cleavage site (cloning), nucleotide 546-548 ATG SEMA-L, nucleotide 546-reading frame SEMA-L, nucleotide 2542-2547 Pml I cleavage site, nucleotide 2548-2553 HindIII cleavage site and nucleotide 2563-2565 stop codon.

Plasmid pIND-H-SemaL-EE (total length 7102 bp) in vector pIND (Invitrogen, De Schelp, N L) (SEQ ID No. 37): nucleotide 533-538 BamHI cleavage site (cloning), nucleotide 546-548 ATG SEMA-L, nucleotide 546- reading frame SEMA-L, nucleotide 2542-2547 Pml I cleavage site, nucleotide 2548-2553 HindIII cleavage site, nucleotide 2560-2592 Myc tag, nucleotide 2605-2622 6×His tag and nucleotide 2623-2625 stop codon.

Plasmid pQE30-H-SemaL-179-378.seq (4019 bp) in vector pQE30 (Qiagen, Hilden) corresponds to pQE30-H-SemaLBH (SEQ ID No. 39): nucleotide 115-117 ATG, nucleotide 127-144 6×His tag, nucleotide 145-750 BamHI-HindIII PCR fragment SEMA-L amino acids (aa) 179-378 and nucleotide 758-760 stop codon.

Plasmid pQE31-H-SemaL-(SH (3999 bp) in vector pQE31 (Qiagen, Hilden) (SEQ ID No. 40): nucleotide 115-117 ATG, nucleotide 127-144 6×His tag, nucleotide (147-152 BamHI), nucleotide 159-729 SacI-HindIII fragment SEMA-L (C-terminal) aa480666 and nucleotide 734-736 stop codon.

EXAMPLES

Experimental conditions used in the examples:
PCR programs used:

| Taq52-60 (with Ampli-Taq$^R$ polymerase, Perkin Elmer, Weil der Stadt, Germany) | |
|---|---|
| 96° C./60 s | 1 cycle |
| 96° C./15 s-52° C./20 s-70° C./60 s | 40 cycles |
| 70° C./60 s | 1 cycle |
| Taq60-30 | |
| 96° C./60 s | 1 cycle |
| 96° C./15 s-60° C./20 s-70° C./30 s | 35 cycles |
| 70° C./60 s | 1 cycle |
| Taq60-60 | |
| 96° C./60 s | 1 cycle |
| 96° C./15 s-60° C./20 s-70° C./60 s | 35 cycles |
| 70° C./60 s | 1 cycle |

| Taq62-40 | |
|---|---|
| 96° C./60 s | 1 cycle |
| 96° C./15 s-62° C./20 s-70° C./40 s | 35 cycles |
| 70° C./60 s | 1 cycle |

Reaction conditions used for PCR with Taq polymerase: 50 µl reaction mixtures with 100-200 ng of template, 200 µM dNTP, 0.2-0.4 µM each primer, 2.5U of Ampli-Taq®, 5 µl of the 10× reaction buffer supplied Programs used for:

| 1. XL62-6 (with expand-long template PCR System$^R$, Boehringer Mannheim, Germany) | |
|---|---|
| 94° C./60 s | 1 cycle |
| 94° C./15 s-62° C./30 s-68° C./6 min | 10 cycles |
| 94° C./15 s-62° C./30 s-68° C./(6 min + 15 s/cycle) | 25 cycles |
| 68° C./7 min | 1 cycle |
| 2. XL62-12 (with expand-long template PCR System$^R$, Boehringer Mannheim, Germany) | |
| 94° C./60 s | 1 cycle |
| 94° C./15 s-62° C./30 s-68° C./12 min | 10 cycles |
| 94° C./15 s-62° C./30 s-68° C./(12 min + 15 s/cycle) | 25 cycles |
| 68° C./7 min | 1 cycle |

Reaction conditions for PCR with expand-long template PCR System 50 µl reaction mixtures with 100-200 ng of template, 500 µM dNTP, 0.2-0.4 µM each primer, 0.75 µl of enzyme mix, 5 µl of the 10× reaction buffer No. 2 supplied.

Example 1

Starting from AHV-Sema sequences (Ensser & Fleckenstein (1995), J. General Virol. 76: 1063-1067), PCRs and RACE-PCRs were carried out. The starting material used for this was human cDNA from placental tissue onto which adaptors had been ligated for the RACE amplification (Marathon™ -cDNA Amplification Kit, Clontech Laboratories GmbH, Tullastraβe 4, 69126 Heidelberg, Germany). Firstly specific primers (No. 121234+No. 121236, Table 6) were used to amplify a PCR fragment with a length of about 800 bp (base pairs) (PCR program: (Taq60-60)). This was cloned and sequenced (Taq dye-deoxy terminator sequencing kit, Applied Biosystems, Foster City, Calif., USA/Brunnenweg 13, Weil der Stadt). Sequencing of the PCR product revealed a sequence which has a high degree of homology with the DNA sequence of AHV-Sema, identical to the sequence of the two ESTs.

A PCR fragment of 600 bp was identified using the primer pair (No. 121237+No. 121239, Table 6). It emerged that they were clones with DNA sequences from the same gene.

Example 2

The 800 bp PCR fragment from Example 1 was radiolabeled (random priming by the method of {Feinberg (1983) Anal. Biochem. 132:6-13}, with $^{32}$P-α-dCTP) and used as probe for a multitissue Northern blot (Human Multiple Tissue Northern Blot II, Clontech, Heidelberg, Germany) which contains mRNA samples from the tissues spleen, thymus, prostate, testes, ovaries, small intestine, large intestine and leukocytes (PBL). This clearly showed expression of an mRNA with a length of about 3.3 kb in spleen and gonads (testes, ovaries), and less strongly in the thymus and intestine. Hybridization of a master blot (dot-blot with RNA from numerous tissues (Human RNA Master Blot™, Clontech)) confirmed this result and also showed strong expression in placental tissue.

Hybridization was carried out under stringent conditions (5× SSC, 50 mM Na phosphate pH 6.8, 50% formamide, 100 µg/ml yeast RNA) at 42° C. for 16 hours. The blots were washed stringently (65° C., 0.2× SSC, 0.1% SDS) and exposed to a Fuji BAS2000 Phosphoimager™.

Example 3

A cDNA library from human spleen, cloned in the bacteriophage Lambda gt10 (Human Spleen 5' STRETCH PLUS cDNA, Clontech), was screened with this probe, and a lambda clone was identified. The cDNA with a length of 1.6 kb inserted in this clone was amplified by PCR (Expand™ Long Template PCR System, Boehringer Mannheim GmbH, Sandhofer Straße 116, 68305 Mannheim) using the vector-specific primers No. 207608+No. 207609 (Table 6) (flanking the EcoRI cloning site), and the resulting PCR fragment was sequenced, This clone contained the 5' end of the cDNA and also extended the known cDNA sequence in the 3' direction. Starting from the new part-sequences of the cDNA, new primers for the RACE-PCR were developed (No. 232643, No. 232644, No. 233084, Table 6). Together with an improved thermocycler technique (PTC-200 from MJ-Research, Biozym Diagnostik GmbH, 31833 Hess. Oldendort) with distinctly better performance data (heating and cooling rates), a 3' RACE-PCR product was amplified using the primers No. 232644 and No. 232643 and AP1, and was cloned into the vector pCR2.1 (Invitrogen, De Schelp 12, 9351 NV Leek, The Netherlands). The 3' RACE-PCR product was sequenced and the 3' end of the cDNA was identified in this way. A RACE amplification in the 5' direction (primers No. 131990 and No. 233084 and AP1) extended the 5' end of the cDNA by a few nucleotides and confirmed the amino terminus of H-SemaL found in the identified lambda clone.

Example 4

Starting from a short murine EST (Accession No. AA260340) and a primer derived therefrom, No. 260813 (Table 6) and the H-SemaL specific primer No. 121234 (Table 6), PCR (conditions: Taq52-60) was used to amplify a DNA fragment with a length of about 840 bp of murine cDNA, followed by cloning into the vector pCR2.1. The gene containing this DNA fragment was called M-SemaL. The resulting M-SemaL DNA fragment was used to investigate a cDNA bank from mouse spleen (Mouse Spleen 5' STRETCH cDNA, Clontech), identification of several clones being possible.

PCR (Taq60-30) with the primers No. 260812 and No. 260813 from murine endothelial cDNA provided a PCR fragment with a length of 244 base pairs. The PCR results showed that there is distinct baseline expression in murine endothelial cells which declines after stimulation with the cytokine interferon-γ and lipopolysaccharides.

Example 5

Investigations on the location in the chromosome were carried out by fluorescence in situ hybridization (FISH). For this purpose, human and murine metaphase chromosomes were prepared starting from a human blood sample and the mouse cell line BINE 4.8 (Keyna et al. (1995) J. Immunol. 155, 5536-5542), respectively (Kraus et al. (1994) Genomics 23, 272-274). The slides were treated with RNase and pepsin (Liehr et al. (1995) Appl. Cytogenetics 21, 185-188). For the hybridization, 120 mg of human nick-translated semaphorin sample and 200 mg of a corresponding mouse sample were used. The hybridization was in each case carried out in the presence of 4.0 µg of COT1-DNA and 20 µg of STD at 37° C. (3 days) in a moistened chamber.

The slides were washed with 50% formamide/2× SSC (3 times for 5 min each time at 45° C.) and then with 2× SSC (3 times for 5 min each time at 37° C.), and the biotinylated sample was detected using the FITC-avidin system (Liehr et al. (1995)). The slides were evaluated using a fluorescence microscope. 25 metaphases/sample were evaluated, carrying out each experiment in duplicate. It emerged that H-SemaL is located on chromosome 15q23. Located adjacent in the chromosome is the locus for Bardet-Biedis syndrome and Tay-Sachs disease (hexosaminidase A).

Example 6

The genomic intron-exon structure of the H-SemaL gene is for the most part elucidated.

Genomic DNA fragments were amplified starting from 250 mg of human genomic DNA which had been isolated from PHA-stimulated peripheral lymphocytes (blood). Shorter fragments were amplified using Ampli Taq® (Perkin Elmer), and longer fragments were amplified using the expanded long template PCR System® (Boehringer Mannheim).

It has been possible by PCR amplification to date to clone and characterize almost the complete genomic locus of H-SemaL. It has already been possible in total to determine more than 8888 bp of the genomic sequence and thus substantially to elucidate the intron-exon structure of the gene.

Example 7

Expression Clonings:

Since no complete clone of the semaphorin gene could be isolated from the lambda-gt10 cDNA bank, and no complete clone was obtainable by PCR either, the coding region of the cDNA was amplified in 2 overlapping subfragments by PCR (XL62-6) using the primers No. 240655 and No. 121339 for the N-terminal DNA fragment, and the primers No. 240656 (contains HindIII and PmeI cleavage sites) and No. 121234 for the C-terminal DNA fragment. The resulting DNA fragments (subfragments) were cloned into the vector pCR21. The two subfragments were completely sequenced and finally the complete H-SemaL cDNA was prepared by inserting a 0.6 kb C-terminal SstI-HindIII restriction fragment into the plasmid which contained the N-terminal DNA fragment and had been cut with the restriction enzymes SstI and HindIII. From this plasmid pCR2.1-H-SemaL (sequence shown in Table 7, SEQ ID NO. 34), the complete gene was cut out using the EcoRI cleavage site (in pCR2.1) and HindIII cleavage site (in primer No. 240656, Table 6) and ligated into a correspondingly cut constitutive expression vector pCDNA3.1(−)MycHisA (Invitrogen). The EcoRI-ApaI fragment (without Myc-His tag) was cut out of the resulting recombinant plasmid pCDNA3.1(−)H-SemaL-MycHisA (sequence shown in Table 8) and ligated into the inducible vector pIND (Ecdysone-Inducible Mammalian Expression System, Invitrogen) which had previously likewise been cut with EcoRI-ApaI. The recombinant plasmid was called pIND-H-SemaLEA (sequence shown in Table 11). An EcoRI-PmeI fragment (with Myc-His tag) from pCDNA3.1(-)H-SemaL-Myc-HisA (sequence shown in Table 9) was inserted into an EcoRI-EcoRV-cut vector pIND. The recombinant plasmid was called pIND-H-SemaL-EE (sequence shown in Table 10).

A fusion gene of H-SemaL with enhanced green fluorescent protein (EGFP) was prepared by ligating the PCR-amplified EGFP reading frame (from the vector pEGFP-C1 (Clontech), using the primers No. 243068+No. 243069, Taq52-60) into the PmeI cleavage site of the plasmid pCDNA3.1(-)H-SemaL-MycHisA, resulting in the plasmid pCDNA3.1(-)H-SemaL-EGFP-MycHisA (sequence shown in Table 9).

Small letters in Tables 7 to 13 and Table 15 denote the sequence of H-SemaL, parts or derivatives thereof, and large letters denote the sequence of the plasmid.

Example 8

To prepare H-SemaL-specific antibodies, cDNA fragments of H-SemaL were integrated into prokaryotic expression vectors and expressed in *E. coli*, and the semaphorin derivatives were purified. The semaphorin derivatives were expressed as fusion proteins with a His tag. Accordingly, vectors containing the sequence for a His tag and permitting integration of the semaphorin cDNA fragment into the reading frame were used. An N-terminal 6× histidine tag makes it possible, for example, to purify by nickel chelate affinity chromatography (Qiagen GmbH, Max-Volmer Straße 4, 40724 Hilden):

1. The part of the H-SemaL cDNA coding for amino acids 179-378 was amplified by PCR using the primers No. 150788 and No. 150789, and this DNA fragment was ligated into the vector pQE30 (Qiagen) which had previously been cut with the restriction enzymes BamHI and HindIII (construct pQE30-H-SemaL-BH (sequence shown in Table 12)).
2. The section of the H-SemaL cDNA coding for the C-terminal amino acids 480-666 was cut with the restriction enzymes SstI and HindIII out of the plasmid pCR 2.1 and ligated into the vector pQE31 (Qiagen) which had previously been cut with SstI and HindIII (construct pQE31-H-SemaL-SH (sequence shown in Table 13)).

Correct integration of the sequences in the correct reading frame was checked by DNA sequencing. The fusion proteins consisting of an N-terminal 6× histidine tag and a part of the semaphorin H-SemaL were purified by $Ni^{2+}$ affinity chromatography. The purified fusion proteins were used to immunize various animals (rabbit, chicken, mouse).

Example 9

FACS analysis of various cell types (FIGS. 4 and 5)

The cells (about $0.2-0.5 \times 10^6$) were washed with FACS buffer (phosphate-buffered saline (PBS) with 5% fetal calf serum (FCS) and 0.1% Na azide) and then incubated with the antisera (on ice) for 1 hour in each case.

The primary antibodies used for the control (overlay chicken preimmune serum (1:50)) and for the specific detection (specific staining) comprised an H-SemaL-specific chicken antiserum (1:50). The specific antiserum with antibodies against amino acids (Aa) 179-378 (with N-terminal His tag) of H-SemaL was generated by immunizing chickens with the protein purified by Ni chelate affinity, chromatography (as described in Example 8). The second antibody used was an FITC-labeled anti-chicken F(ab') antibody from rabbits (Dianova Jackson Laboratories, Order No. 303-095-006, Hamburg, Germany) (1 mg/ml). A rabbit anti-mouse IgG, FITC-labeled, was used for the CD100 staining. The second antibody was employed in each case in 1:50 dilution in FACS buffer.

The cells were then washed, resuspended in PBS and analyzed in the FACS. The FACS analysis was carried out using a FACS-track instrument (Becton-Dickinson). Principle: a single cell suspension is passed through a measuring channel where the cells are irradiated with laser light of 488 nm and thus fluorescent dyes (FITC) are excited. The measurements are of the light scattered forward (forward scatter, FSC: correlates with the cell size), and to the side (sideward scatter, SSC: correlates with the granular content: different in different cell types) and fluorescence in channel 1 (FL 1) (for wavelengths in the FITC emission range, max. at 530 nm). 10,000 events (cells) were measured in this way each time.

The dot plot (FIGS. 4*a-k*) (figure on the left in each case): FSC against SSC (size against granular content/scatter) with, inside the boundary, the (uniform) cell population of similar size and granular content analyzed in the right-hand window (relevant right-hand figure in each case). The right-hand window shows the intensity of FL 1 (X axis) against the number of events (Y axis), that is to say a frequency distribution.

In each of these, the result with the control serum (unfilled curve) is superimposed on the result of the specific staining (filled curve). A shift of the curve for the specific staining to the right compared with the control corresponds to an expression of H-SemaL in the corresponding cells. A larger shift means stronger expression.

Cell Lines Used for FACS Analysis:

a) U937 cell line
   American Type Culture Collection ATCC; ATCC number: CRL-1593
   Name: U-937
   Tissue: lymphoma; histiocytic; monocyte-like
   Species: human;
   Depositor: H. Koren
b) THP-1 cell line
   ATCC number: TIB-202
   Tissue: monocyte; acute monocytic leukemia
   Species: human
   Depositor: S. Tsuchiya
c) K-562 cell line
   ATCC number: CCL-243
   Tissue: chronic myelogenous leukemia
   Species: human;
   Depositor: H. T. Holden
d) L428 cell line
   DSMZ-Deutsche Sammlung von Mikroorganismen und Zelikulturen GmbH,
   DSMZ No: ACC 197
   Cell type: human Hodgkin's lymphoma
e) Jurkat cell line
   DSMZ-Deutsche Sammlung von Mikroorganismen und zelikulturen GmH,
   DSMZ No: ACC 282
   Cell type: human T cell leukemia
f) Daudi cell line
   ATCC number: CCL-213
   Tissue: Burkitt's lymphoma; B lymphoblast; B cells
   Species: human
   Depositor: G. Klein g) LCL cell line
EBV-transformed lymphoblastoid B-cell line.
h) Jiyoye (P-2003) cell line
ATCC number: CCL-87
Tissue: Burkitt's lymphoma; B cells, B lymphocyte
Species: human
Depositor: W. Henle
i) CBL-Mix57
Human T-cell line (isolated from blood) transformed with recombinant H. Saimiri (wild-type without deletion)
j) CBL-Mix59
Human T-cell line (isolated from blood) transformed with H. Saimiri (deletion of ORF71).

Example 10

Protein Gel and Western Blot

Figure 8:
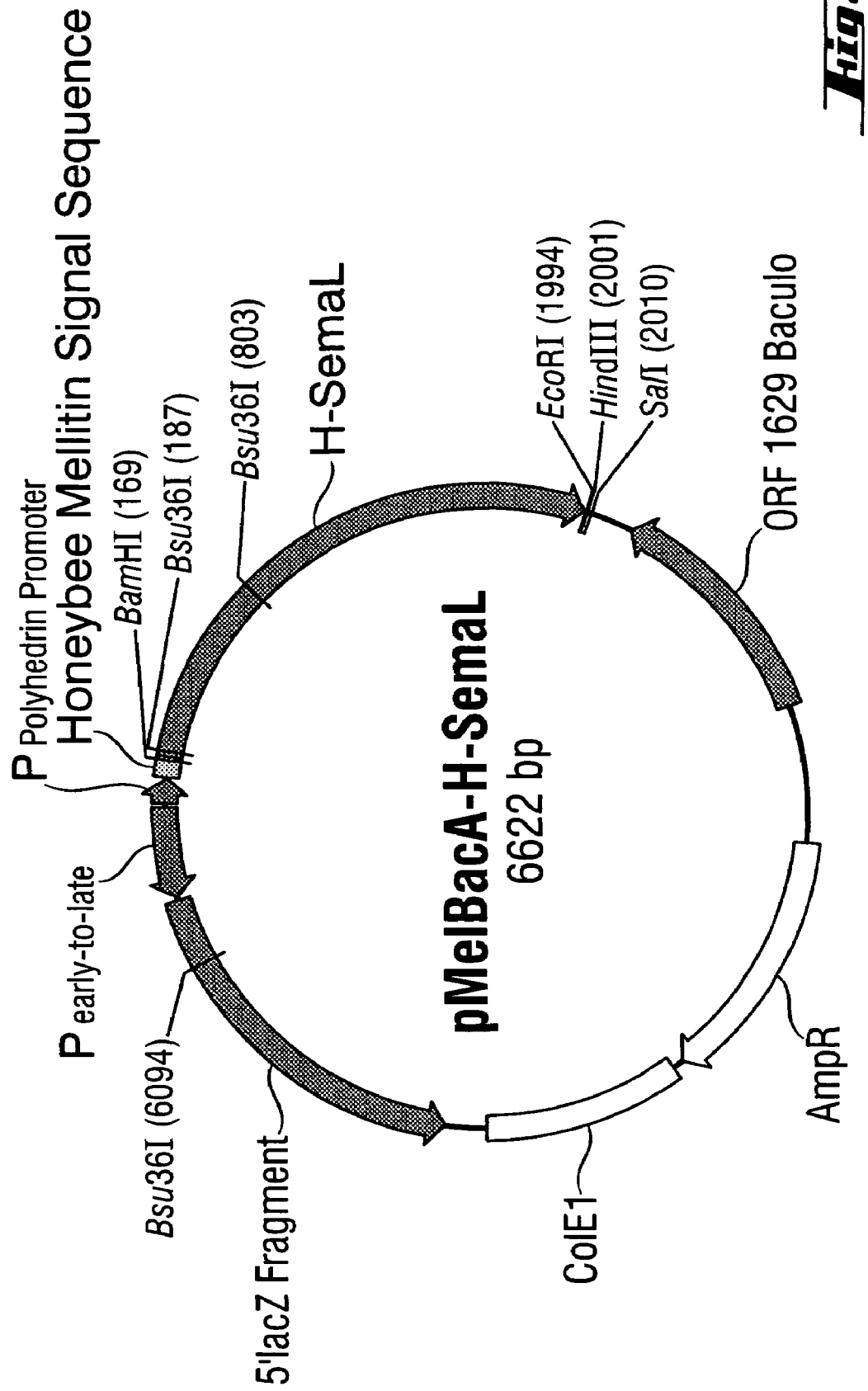
FIG. 8 is a plasmid map of pMelBacA-H-SEMAL.

Secretable human SEMA-L (amino acids 42-649 in Table 4 (without signal peptide and without transmembrane domain)) was cloned into the plasmid pMelBac-A (Invitrogen, De Schelp, Leck, The Netherlands, Cv 1950-20) and, in this way, the plasmid pMelBacA-H-SemaL (length 6622 bp) was generated (FIG. 8). The H-SemaL derivative was expressed in the baculovirus system (Bac-N-Blue, Invitrogen). Expression was carried out in the cell lines derived from insect egg cells Sf9 (from *Spodoptera frugiperda*) and High Five™ (from *Trichoplusia ni*, U.S. Pat. No. 5,300,435, purchased from Invitrogen) by infection with the recombinant, plaque-purified baculoviruses.

The expression was carried out in accordance with the manufacturer's instructions.

The proteins were then fractionated in a gel, and the H-SemaL derivative was detected in a Western blot. Detection was carried out with H-SemaL-specific chicken antiserum (compare Example 8 and FIG. 7) (dilution 1:100). The specific chicken antibody was detected using anti-IgY-HRP conjugate (dilution: 1:3000, from donkey; Dianova Jackson Laboratories) in accordance with the manufacturer's instructions.

Example 11

Preparation of pMelBacA-H-SEMAL

The recombinant vector (pMelBacA-H-SEMAL, 6622 bp) was prepared by cloning an appropriate DNA fragment which codes for amino acids 42-649 of H-SemaL into the vector pMelBacA (4.8 kb Invitrogen) (compare annotation for pMelBacA-H-SEMAL). The cloning took place via BamHI and EcoRI in frame behind the signal sequence present in the vector ("honeybee melittin signal sequence"). A corresponding H-SemaL DNA fragment was amplified using the primer pair h-sema-1 baculo 5' and h-sema-1 baculo 3'.

Primers for amplification (TaKaRa Ex Ta9 polymerase) and cloning: "h-sema-1 baculo 5'" for amplification without signal sequence and for introducing a BamHI cleavage site 5'-CCGGATCCGCCCAGGGCCACCTAAGGAGCGG-3' (SEQ ID NO: 43) "h-sema-1 baculo 3'" for amplification without transmembrane domain and for introducing an EcoRI cleavage site 5'-CTGAATTCAGGAGCCAGGGCA-CAGGCATG-3' (SEQ ID NO: 44).

DETAILED DESCRIPTION OF THE DRAWINGS

FIG. 1:
Tissue-specific expression of H-Sema-L
A) Multiple tissue Northern blot (Clontech, Heidelberg, Germany). Loadings from left to right: 2 µg in each lane of Poly-A-RNA from spleen, thymus, prostate, testes, ovanes, small intestine, large intestinal mucosa, peripheral (blood) leukocytes. Size standards are marked.

The blots were hybridized under stringent conditions with an H-SemaL probe 800 base-pairs long.

FIG. 2:

Diagrammatic representation of the cloning of the H-SemaL cDNA and of the genomic organization of the H-SemaL encoding sequences (H-SemaL gene) Top: Location of the EST sequences (accession numbers; location of the EST sequences is shown relative to the AHV-Sema sequence).

Below: Amplified PCR and RACE products and the position of the cDNA clones in relation to the location in the complete H-SemaL cDNA and the open reading frame (ORF) for the encoded protein.

Bottom: Relative position of the exons in the H-SemaL gene in relation to the genomic sequence. The position of the oligonucleotide primer used is indicated by arrows.

FIG. 3:

Phylogenetic tree: Obtained by multiple alignment of the listed semaphorin sequences. The phylogenetic relationship of the semaphorins can be deduced from their grouping in the phylogenetic tree.

FIG. 4:

FACS analysis of H-SemaL expression in various cell lines and various cell types (compare Example 8).

FIG. 5:

Comparative analysis of CD100 and H-SemaL expression (compare Example 9).

FIG. 6:

Expression of secretable human SEMA-L (H-SemaL) in HiFive and Sf3 cells (compare Example 10).

Aa 42-649 in pMelBac-A (Invitrogen) in the baculovirus system (Bac-N-Blue, Invitrogen)

Detection with specific chicken antiserum (1:100) and anti-IgY-HRP conjugate (1:3000, from rabbits, Jackson Lab.)

1,4,6 uninfected HiFive cells (serum-free)

2,3,5,7,8 HiFive cells infected with recombinant baculovirus (serum-free)

M Rainbow molecular weight marker (Amersham RPN756)

9,10 infected Sf9 cells (serum-containing medium).

Figure 7:
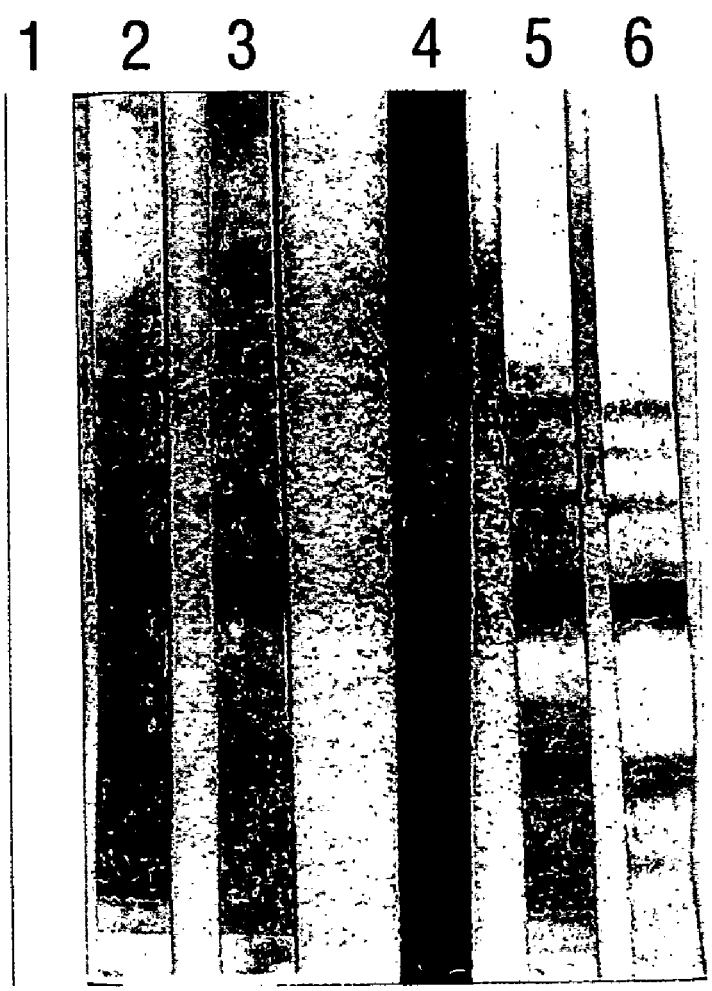
FIG. 7 depicts the specificity of the antiserum.

FIG. 7: Specificity of the antiserum

Lanes 1-3: chicken 1; lanes 46: chicken 2

Lanes 1 and 4: Preimmune serum

Lanes 2 and 5: $60^{th}$ day of immunization

Lanes 4 and 6: $105^{th}$ day of immunization

Immunization was carried out with amino acids 179-378 of H-SemaL (with amino-terminal His tag) (compare Example 8, Section 1.)

FIG. 8: Depiction of the plasmid map of pMelBacA-H-SEMAL.

The recombinant plasmid was prepared as described in Example 11.

TABLES

TABLE 1

Various subtypes of semaphorins from various species

| Name | Synonym | Species | | Reference |
|---|---|---|---|---|
| H-Sema III | (H-SemaD) | Human | Sec. | (Kolodkin et al. 1993) |
| CD-100 | | Human | TM, IC; CD45 associated, expressed in T cells | (Hall et al. 1996) |
| H-Sema V | (H-SemaA) | Human | Sec.; Locus 3p21.3 | (Sekido et al. 1996; Roche et al. 1996) |
| H-Sema IV | (H-Sema3F) | Human | Sec.; Locus 3p21.3 | (Xiang et al. 1996; Sekido et al. 1996) |
| H-SemaE | | Human | Sec.; divergent from M-Sema-E at the 3' end (alignment of reading frame improved) | AB000220 (Yamada 1997 unpublished) |
| H-SemaK | KIAA0331 | Human | Sec.; | (Nagase et al. 1997) |
| H-SemaL | SEMAL | Human | TM, no IC | This application |
| M-SemaA | | Mouse | Sec. | (Püschel et al. 1995) |
| M-SemaB | | Mouse | TM, IC | (Püschel et al. 1995) |
| M-SemaC | | Mouse | TM, IC | (Püschel et al. 1995) |
| M-SemaD | M-Sema III | Mouse | Sec. | (Messersmith et al. 1995; Püschel et al. 1995) |
| M-SemaE | | Mouse | Sec.; 5' partial sequence | (Püschel et al. 1995) |
| M-SemaF1 | M-SemaF | Mouse | TM, IC | (Inagaki et al. 1995) |
| M-SemaG2 | M-SemaG | Mouse | TM, IC; expressed in lymphoid cells, mouse homolog of CD100 | (Furuyama et al. 1996) |
| M-SemaF2 | M-SemaF | Mouse | TM, IC; Thrombospondin motif | (Adams et al. 1996) |
| M-SemaG1 | M-SemaG | Mouse | TM, IC; Thrombospondin motif | (Adams et al. 1996) |
| M-SemaH | | Mouse | Sec. | (Christensen 1996 unpub) Z80941 |
| M-Sema VIa | | Mouse | TM, IC | (Zhou et al. 1997) |
| M-SemaL | Semal | Mouse | Partial sequence | This application |
| Collapsin-1 | | Chicken | Sec. | (Luo et al. 1993) |
| Collapsin-2 | | Chicken | Sec. | (Luo et al. 1995) |
| Collapsin-3 | | Chicken | Sec. | (Luo et al. 1995) |
| Collapsin-4 | | Chicken | Partial sequence | (Luo et al. 1995) |
| Collapsin-5 | | Chicken | Sec. | (Luo et al. 1995) |
| R-Sema III | | Rat | Sec. | (Giger et al. 1996) |
| T-Sema I | | Tribolium confusum | TM, IC | (Kolodkin et al. 1993) |
| Ce-Sema I | | C. elegans | TM, IC | U15667 (Roy1994 unpublished) |
| G-Sema I | Fasciclin-IV | Grasshopper | TM, IC | (Kolodkin et al. 1992) |
| D-Sema I | | Drosophila | TM, IC | (Kolodkin et al. 1993) |
| D-Sema II | | Drosophila | Sec. | (Kolodkin et al. 1993) |
| AHV-Sema | | AHV-1 | Sec. | (Ensser and Fleckenstein, 1995) |
| ORF-A39 | | Vaccinia | Sec. | (Kolodkin et al. 1993) |
| ORF-A39 homologous | | Variola | Sec.; | (Kolodkin et al. 1993) |

TM: transmembrane domain
Sec.: secreted
IC: presumably intracellular cytoplasmic sequence motif

TABLE 2 cDNA sequence of H-SemaL (2636 nucleotides) (SEQ ID NO.:1)

```
  1 cggggccacg ggatgacgcc tcctccgccc ggacgtgccg cccccagcgc 51 accgcgcgcc cgcgtccctg gcccgccggc tcggttgggg cttccgctgc 101 ggctgcggct gctgctgctg ctctgggcgg ccgccgcctc cgcccagggc 151 cacctaagga gcggacccccg catcttcgcc gtctggaaag gccatgtagg 201 gcaggaccgg gtggactttg gccagactga gccgcacacg gtgcttttcc 251 acgagccagg cagctcctct gtgtgggtgg gaggacgtgg caaggtctac 301 ctctttgact cccccgaggg caagaacgca tctgtgcgca cggtgaatat 351 cggctccaca aagggggtcct gtctggataa gcgggactgc gagaactaca 401 tcactctcct ggagaggcgg agtgaggggc tgctggcctg tggcaccaac 451 gcccggcacc ccagctgctg gaacctggtg aatggcactg tggtgccact 501 tggcgagatg agaggctacg cccccttcag cccggacgag aactccctgg 551 ttctgtttga aggggacgag gtgtattcca ccatccggaa gcaggaatac 601 aatgggaaga tccctcggtt ccgccgcatc cggggcgaga gtgagctgta
```

TABLE 2-continued

| cDNA sequence of H-SemaL (2636 nucleotides) (SEQ ID NO.:1) |
|---|
| 651 caccagtgat actgtcatgc agaacccaca gttcatcaaa gccaccatcg |
| 701 tgcaccaaga ccaggcttac gatgacaaga tctactactt cttccgagag |
| 751 gacaatcctg acaagaatcc tgaggctcct ctcaatgtgt cccgtgtggc |
| 801 ccagttgtgc agggggggacc agggtgggga aagttcactg tcagtctcca |
| 851 agtggaacac ttttctgaaa gccatgctgg tatgcagtga tgctgccacc |
| 901 aacaagaact tcaacaggct gcaagacgtc ttcctgctcc ctgacccccag |
| 951 cggccagtgg agggacacca gggtctatgg tgttttctcc aaccccctgga |
| 1001 actactcagc cgtctgtgtg tattccctcg gtgacattga caaggtcttc |
| 1051 cgtacctcct cactcaaggg ctaccactca agccttccca cccgcggcc |
| 1101 tggcaagtgc ctcccagacc agcagccgat acccacagag accttccagg |
| 1151 tggctgaccg tcacccagag gtggcgcaga gggtggagcc catggggcct |
| 1201 ctgaagacgc cattgttcca ctctaaatac cactaccaga aagtggccgt |
| 1251 tcaccgcatg caagccagcc acggggagac ctttcatgtg cttttacctaa |
| 1301 ctacagacag gggcactatc acaaggtgg tggaaccggg ggagcaggag |
| 1351 cacagcttcg ccttcaacat catggagatc cagcccttcc gccgcgcggc |
| 1401 tgccatccag accatgtcgc tggatgctga gcggaggaag ctgtatgtga |
| 1451 gctcccagtg ggaggtgagc caggtgcccc tggacctgtg tgaggtctat |
| 1501 ggcgggggct gccacggttg cctcatgtcc cgagacccct actgcggctg |
| 1551 ggaccagggc cgctgcatct ccatctacag ctccgaacgg tcagtgctgc |
| 1601 aatccattaa tccagccgag ccacacaagg agtgtcccaa ccccaaacca |
| 1651 gacaaggccc cactgcagaa ggtttccctg gccccaaaact ctcgctacta |
| 1701 cctgagctgc cccatggaat cccgccacgc cacctactca tggcgccaca |
| 1751 aggagaacgt ggagcagagc tgcgaacctg gtcaccagag ccccaactgc |
| 1801 atcctgttca tcgagaacct cacggcgcag cagtacggcc actacttctg |
| 1851 cgaggcccag gagggctcct acttccgcga ggctcagcac tggcagctgc |
| 1901 tgcccgagga cggcatcatg ccgagcacc tgctgggtca tgcctgtgcc |
| 1951 ctggctgcct ccctctggct gggggtgctg cccacactca ctcttggctt |
| 2001 gctggtccac tagggcctcc cgaggctggg catgcctcag gcttctgcag |
| 2051 cccagggcac tagaacgtct cacactcaga gccggctggc ccgggagctc |
| 2101 cttgcctgcc acttcttcca ggggacagaa taacccagtg gaggatgcca |
| 2151 ggcctggaga cgtccagccg caggcggctg ctgggcccca ggtggcgcac |
| 2201 ggatggtgag gggctgagaa tgagggcacc gactgtgaag ctggggcatc |
| 2251 gatgacccaa gactttatct tctggaaaat attttttcaga ctcctcaaac |
| 2301 ttgactaaat gcagcgatgc tcccagccca agagcccatg ggtcggggag |
| 2351 tgggttttgga taggagagct gggactccat ctcgaccctg ggctgaggc |
| 2401 ctgagtcctt ctggactctt ggtacccaca ttgcctcctt cccctccctc |
| 2451 tctcatggct gggtgctgg tgttcctgaa gacccagggc taccctctgt |
| 2501 ccagccctgt cctctgcagc tccctctctg gtcctgggtc ccacaggaca |

TABLE 2-continued cDNA sequence of H-SemaL (2636 nucleotides) (SEQ ID NO.:1)

2551 gccgccttgc atgtttattg aaggatgttt gctttccgga cggaaggacg 2601 gaaaaagctc tgaaaaaaaa aaaaaaaaaa aaaaaa

TABLE 3

Nucleotide sequence of the cDNA of M-SemaL
(partial, 1195 nucleotides) (SEQ ID NO.:2)

1    cggggctgcg ggatgacgcc tcctcctccc ggacgtgccg ccccccagcgc
51   accgcgcgcc cgcgtcctca gcctgccggc tcggttcggg ctcccgctgc
101  ggctgcggct tctgctggtg ttctgggtgg ccgccgcctc cgcccaaggc
151  cactcgagga gcggaccccg catctccgcc gtctggaaag ggcaggacca
201  tgtggacttt agccagcctg agccacacac cgtgcttttc catgagccgg
251  gcagcttctc tgtctgggtg ggtggacgtg caaggtcta ccacttcaac
301  ttccccgagg gcaagaatgc ctctgtgcgc acggtgaaca tcggctccac
351  aaagggtcc tgtcaggaca acaggactg tgggaattac atcactcttc
401  tagaaaggcg gggtaatggg ctgctggtct gtggcaccaa tgcccggaag
451  cccagctgct ggaacttggt gaatgacagt gtggtgatgt cacttggtga
501  gatgaaaggc tatgccccct tcagcccgga tgagaactcc ctggttctgt
551  ttgaaggaga tgaagtgtac tctaccatcc ggaagcagga atacaacggg
601  aagatccctc ggtttcgacg cattcggggc gagagtgaac tgtacacaag
651  tgatacagtc atgcagaacc cacagttcat caaggccacc attgtgcacc
701  aagaccaagc ctatgatgat aagatctact acttcttccg agaagacaac
751  cctgacaaga accccgaggc tcctctcaat gtgtcccgag tagcccagtt
801  gtgcagggg gaccagggtg gtgagagttc gttgtctgtc tccaagtgga
851  acaccttcct gaaagccatg ttggtctgca gcgatgcagc caccaacagg
901  aacttcaatc ggctgcaaga tgtcttcctg ctccctgacc ccagtggcca
951  gtggagagat accagggtct atggcgtttt ctccaacccc tggaactact
1001 cagctgtctg cgtgtattcg cttggtgaca ttgacagagt cttccgtacc
1051 tcatcgctca aaggctacca catgggcctt tccaaccctc gacctggcat
1101 gtgcctccca aaaagcagc ccatacccac agaaaccttc caggtagctg
1151 atagtcaccc agaggtggct cagagggtgg aacctatggg gcccc

TABLE 4

Amino acid sequence of H-SemaL (666 amino acids)
(SEQ ID NO.:3)

1    MTPPPPGRAA PSAPRARVPG PPARLGLPLR LRLLLLLWAA AASAQGHLRS
51   GPRIFAVWKG HVGQDRVDFG QTEPHTVLFH EPGSSSVWVG GRGKVYLFDF
101  PEGKNASVRT VNIGSTKGSC LDKRDCENYI TLLERRSEGL LACGTNARHP
151  SCWNLVNGTV VPLGEMRGYA PFSPDENSLV LFEGDEVYST IRKQEYNGKI

TABLE 4-continued

Amino acid sequence of H-SemaL (666 amino acids)
(SEQ ID NO.:3)

```
201 PRFRRIRGES ELYTSDIVMQ NPQFIKATIV HQDQAYDDKI YYFFREDNPD
251 KNPEAPLNVS RVAQLCRGDQ GGESSLSVSK WNTFLKAMLV CSDAATNKNF
301 NRLQDVFLLP DPSGQWRDTR VYGVFSNPWN YSAVCVYSLG DIDKVFRTSS
351 LKGYHSSLPN PRPGKCLPDQ QPIPTETFQV ADRHPEVAQR VEPMGPLKTP
401 LFHSKYHYQK VAVHRMQASH GETFHVLYLT TDRGTIHKVV EPGEQEHSFA
451 FNIMEIQPFR RAAAIQTMSL DAERRKLYVS SQWEVSQVPL DLCEVYGGGC
501 HGCLMSRDPY CGWDQGRCIS IYSSERSVLQ SINPAEPHKE CPNPKPDKAP
551 LQKVSLAPNS RYYLSCPMES RHATYSWRHK ENVEQSCEPG HQSPNCILFI
601 ENLTAQQYGH YFCEAQEGSY FREAQHWQLL PEDGIMAEHL LGHACALAAS
651 LWLGVLPTLT LGLLVH
```

TABLE 5

(Partial) amino acid sequence of M-SemaL (394 amino acids,
corresponding to position 1-396 of H-SemaL)
(SEQ ID NO.:4)

```
  1 MTPPPPGRAA PSAPRARVLS LPARFGLPLR LRLLLVFWVA AASAQGHSRS
 51 GPRISAVWKG QDHVDFSQPE PHTVLFHEPG SFSVWVGGRG KVYHFNFPEG
101 KNASVRTVNI GSTKGSCQDK QDCGNYITLL ERRGNLLVC GTNARKPSCW
151 NLVNDSVVMS LGEMKGYAPF SPDENSLVLF EGDEVYSTIR KQEYNGKIPR
201 FRRIRGESEL YTSDTVMQNP QFIKATIVHQ DQAYDDKIYY FFREDNPDKN
251 PEAPLNVSRV AQLCRGDQGG ESSLSVSKWN TFLKAMLVCS DAATNRNFNR
301 LQDVFLLPDP SGQWRDTRVY GVFSNPWNYS AVCVYSLGDI DRVFRTSSLK
351 GYHMGLSNPR PGMCLPKKQP IPTETFQVAD SHPEVAQRVE PMGP
```

TABLE 6

Synthetic oligonucleotides (Eurogentec, Seraing, Belgium)

| Number of the primer/name | Nucleotide sequence of the primer (of the synthetic oligonucleotides) | |
|---|---|---|
| 91506/AP2 | actcactatagggctcgagcggc | (SEQ ID NO.:5) |
| 121234 | agccgcacacggtgcttttc | (SEQ ID NO.:6) |
| 121235/Est 2 | gcacagatgcgttcttgccc | (SEQ ID NO.:7) |
| 121236/Est 3 | accatagaccctggtgtccc | (SEQ ID NO.:8) |
| 121237/Est 4 | gcagtgatgctgccaccaac | (SEQ ID NO.:9) |
| 121238 | ccagaccatgtcgctggatg | (SEQ ID NO.:10) |
| 121239/Est 6 | acatgaggcaaccgtggcag | (SEQ ID NO.:11) |
| 131989/Ap1 | ccatcctaatacgactcactatagggc | (SEQ ID NO.:12) |
| 131990/Est 7 | aggtagaccttgccacgtcc | (SEQ ID NO.:13) |
| 131991 | gaacttcaacaggctgcaagacg | (SEQ ID NO.:14) |
| 131992 | atgctgagcggaggaagctg | (SEQ ID NO.:15) |

TABLE 6-continued

Synthetic oligonucleotides (Eurogentec, Seraing, Belgium)

| Number of the primer/name | Nucleotide sequence of the primer (of the synthetic oligonucleotides) | |
|---|---|---|
| 131993 | ccgccatacacctcacacag | (SEQ ID NO.:16) |
| 150788 | ctggaagctttctgtgggtatcggctgc | (SEQ ID NO.:17) |
| 150789 | tttggatccctggttctgtttgaag | (SEQ ID NO.:18) |
| 167579/cDNA Synthesis primer | ttctagaattcagcggccgcttttttttttttttttttttttttttvn | (SEQ ID NO.:19) |
| 168421 | ggggaaagttcactgtcagtctccaag | (SEQ ID NO.:20) |
| 168422 | gggaatacacacagacggctgagtag | (SEQ ID NO.:21) |
| 207608/ Amplification of λgt10 insert | agcaagttcagcctggttaagt | (SEQ ID NO.:22) |
| 207609/ Amplification of λgt10 insert | ttatgagtatttcttccaggg | (SEQ ID NO.:23) |
| 232643/Est 13 | ccattaatccagccgagccacacaag | (SEQ ID NO.:24) |
| 232644/Est 14 | catctacagctccgaacggtcagtg | (SEQ ID NO.:25) |
| 233084 | cagcggaagccccaaccgag | (SEQ ID NO.:26) |
| 240655/hs 5 | gggatgacgcctcctccgcccgg | (SEQ ID NO.:27) |
| 240656/hs 3 | aagcttcacgtggaccagcaagccaagagtg | (SEQ ID NO.:28) |
| 240657/hs 3c | aagcttttccgtccttccgtccgg | (SEQ ID NO.:29) |
| 243068 | atggtgagcaagggcgaggagctg | (SEQ ID NO.:30) |
| 243069 | cttgtacagctcgtccatgccgag | (SEQ ID NO.:31) |
| 260812 | GGGTGGTGAGAGTTCGTTGTCTGTC | (SEQ ID NO.:32) |
| 260813 | GAGCGATGAGGTACGGAAGACTCTG | (SEQ ID NO.:33) |

TABLE 7

Nucleotide sequence of the recombinant plasmid pCR2.1-H-SemaL (SEQ ID NO.:34)

```
  1 AGCGCCCAAT ACGCAAACCG CCTCTCCCCG CGCGTTGGCC GATTCATTAA
 51 TGCAGCTGGC ACGACAGGTT TCCCGACTGG AAAGCGGGCA GTGAGCGCAA
101 CGCAATTAAT GTGAGTTAGC TCACTCATTA GGCACCCCAG GCTTTACACT
151 TTATGCTTCC GGCTCGTATG TTGTGTGGAA TTGTGAGCGG ATAACAATTT
201 CACACAGGAA ACAGCTATGA CCATGATTAC GCCaagcttc acgtggacca
251 gcaagccaag agtgagtgtg ggcagcaccc ccagccagag ggaggcagcc
301 agggcacagg catgacccag caggtgctcg gccatgatgc cgtcctcggg
351 cagcagctgc cagtgctgag cctcgcggaa gtaggagccc tcctgggcct
401 cgcagaagta gtggccgtac tgctgcgccg tgaggttctc gatgaacagg
451 atggcagttgg ggctctggtg accaggttcg cagctctgct ccacgttctc
```

TABLE 7-continued

Nucleotide sequence of the recombinant plasmid pCR2.1-H-SemaL (SEQ ID NO.:34)

```
 501 cttgtggcgc catgagtagg tggcgtggcg ggattccatg gggcagctca
 551 ggtagtagcg agagtttggg gccagggaaa ccttctgcag tggggccttg
 601 tctggtttgg ggttgggaca ctccttgtgt ggctcggctg gattaatgga
 651 ttgcagcact gaccgttcgg agctgtagat ggagatgcag cggccctggt
 701 cccagccgca gtagggtct cgggacatga ggcaaccgtg gcagccccg
 751 ccatagacct cacacaggtc caggggcacc tggctcacct cccactggga
 801 gctcacatac agcttcctcc gctcagcatc cagcgacatg gtctggatgg
 851 cagccgcgcg gcggaagggc tggatctcca tgatgttgaa ggcgaagctg
 901 tgctcctgct ccccggttc caccaccttg tggatagtgc ccctgtctgt
 951 agttaggtaa agcacatgaa aggtctcccc gtggctggct tgcatgcggt
1001 gaacggccac tttctggtag tggtatttag agtggaacaa tggcgtcttc
1051 agaggcccca tgggctccac cctctgcgcc acctctgggt gacggtcagc
1101 cacctggaag gtctctgtgg gtatcggctg ctggtctggg aggcacttgc
1151 caggccgcgg gttgggaagg cttgagtggt agcccttgag tgaggaggta
1201 cggaagacct tgtcaatgtc accgagggaa tacacacaga cggctgagta
1251 gttccagggg ttggagaaaa caccatagac cctggtgtcc ctccactggc
1301 cgctggggtc agggagcagg aagacgtctt gcagcctgtt gaagttcttg
1351 ttggtggcag catcactgca taccagcatg gctttcagaa aagtgttcca
1401 cttggagact gacagtgaac tttccccacc ctggtccccc ctgcacaact
1451 gggccacacg gacacattg agaggagcct caggattctt gtcaggattg
1501 tcctctcgga agaagtagta gatcttgtca tcgtaagcct ggtcttggtg
1551 cacgatggtg gctttgatga actgtgggtt ctgcatgaca gtatcactgg
1601 tgtacagctc actctcgccc cggatgcggc ggaaccgagg gatcttccca
1651 ttgtattcct gcttccggat ggtggaatac acctcgtccc cttcaaacag
1701 aaccagggag ttctcgtccg ggctgaaggg gcgtagcct ctcatctcgc
1751 caagtggcac cacagtgcca ttcaccaggt tccagcagct ggggtgccgg
1801 gcgttggtgc cacaggccag cagcccctca ctccgcctct ccaggagagt
1851 gatgtagttc tcgcagtccc gcttatccag acaggacccc tttgtggagc
1901 cgatattcac cgtgcgcaca gatgcgttct tgccctcggg gaagtcaaag
1951 aggtagacct tgccacgtcc tcccacccac acagaggagc tgcctggctc
2001 gtggaaaagc accgtgtgcg gctcagtctg gccaaagtcc acccggtcct
2051 gccctacatg gcctttccag acggcgaaga tgcggggtcc gctccttagg
2101 tggccctggg cggaggcggc ggccgcccag agcagcagca gcagccgcag
2151 ccgcagcgga agcccaacc gagccggcgg gccagggacg cgggcgcgcg
2201 gtgcgctggg ggcggcacgt ccgggcggag gaggcgtcat cccaagccga
2251 attcTGCAGA TATCCATCAC ACTGGCGGCC GCTCGAGCAT GCATCTAGAG
2301 GGCCCAATTC GCCCTATAGT GAGTCGTATT ACAATTCACT GGCCGTCGTT
2351 TTACAACGTC GTGACTGGGA AAACCCTGGC GTTACCCAAC TTAATCGCCT
```

TABLE 7-continued

Nucleotide sequence of the recombinant plasmid pCR2.1-H-SemaL (SEQ ID NO.:34)

```
2401 TGCAGCACAT CCCCCTTTCG CCAGCTGGCG TAATAGCGAA GAGGCCCGCA
2451 CCGATCGCCC TTCCCAACAG TTGCGCAGCC TGAATGGCGA ATGGGACGCG
2501 CCCTGTAGCG GCGCATTAAG CGCGGCGGGT GTGGTGGTTA CGCGCAGCGT
2551 GACCGCTACA CTTGCCAGCG CCCTAGCGCC CGCTCCTTTC GCTTTCTTCC
2601 CTTCCTTTCT CGCCACGTTC GCCGGCTTTC CCCGTCAAGC TCTAAATCGG
2651 GGGCTCCCTT TAGGGTTCCG ATTTAGAGCT TTACGGCACC TCGACCGCAA
2701 AAAACTTGAT TTGGGTGATG GTTCACGTAG TGGGCCATCG CCCTGATAGA
2751 CGGTTTTTCG CCCTTTGACG TTGGAGTCCA CGTTCTTTAA TAGTGGACTC
2801 TTGTTCCAAA CTGGAACAAC ACTCAACCCT ATCGCGGTCT ATTCTTTTGA
2851 TTTATAAGGG ATTTTGCCGA TTTCGGCCTA TTGGTTAAAA AATGAGCTGA
2901 TTTAACAAAT TCAGGGCGCA AGGGCTGCTA AAGGAACCGG AACACGTAGA
2951 AAGCCAGTCC GCAGAAACGG TGCTGACCCC GGATGAATGT CAGCTACTGG
3001 GCTATCTGGA CAAGGGAAAA CGCAAGCGCA AAGAGAAAGC AGGTAGCTTG
3051 CAGTGGGCTT ACATGGCGAT AGCTAGACTG GGCGGTTTTA TGGACAGCAA
3101 GCGAACCGGA ATTGCCAGCT GGGGCGCCCT CTGGTAAGGT TGGGAAGCCC
3151 TGCAAAGTAA ACTGGATGGC TTTCTTGCCG CCAAGGATCT GATGGCGCAG
3201 GGGATCAAGA TCTGATCAAG AGACAGGATG AGGATCGTTT CGCATGATTG
3251 AACAAGATGG ATTGCACGCA GGTTCTCCGG CCGCTTGGGT GGAGAGGCTA
3301 TTCGGCTATG ACTGGGCACA ACAGACAATC GGCTGCTCTG ATGCCGCCGT
3351 GTTCCGGCTG TCAGCGCAGG GGCGCCCGGT TCTTTTTGTC AAGACCGACC
3401 TGTCCGGTGC CCTGAATGAA CTGCAGGACG AGGCAGCGCG GCTATCGTGG
3451 CTGGCCACGA CGGGCGTTCC TTGCGCAGCT GTGCTCGACG TTGTCACTGA
3501 AGCGGGAAGG GACTGGCTGC TATTGGGCGA AGTGCCGGGG CAGGATCTCC
3551 TGTCATCTCG CCTTGCTCCT GCCGAGAAAG TATCCATCAT GGCTGATGCA
3601 ATGCGGCGGC TGCATACGCT TGATCCGGCT ACCTGCCCAT TCGACCACCA
3651 AGCGAAACAT CGCATCGAGC GAGCACGTAC TCGGATGGAA GCCGGTCTTG
3701 TCGATCAGGA TGATCTGGAC GAAGAGCATC AGGGGCTCGC GCCAGCCGAA
3751 CTGTTCGCCA GGCTCAAGGC GCGCATGCCC GACGGCGAGG ATCTCGTCGT
3801 GATCCATGGC GATGCCTGCT TGCCGAATAT CATGGTGGAA AATGGCCGCT
3851 TTTCTGGATT CAACGACTGT GGCCGGCTGG GTGTGGCGGA CCGCTATCAG
3901 GACATAGCGT TGGATACCCG TGATATTGCT GAAGAGCTTG GCGGCGAATG
3951 GGCTGACCGC TTCCTCGTGC TTTACGGTAT CGCCGCTCCC GATTCGCAGC
4001 GCATCGCCTT CTATCGCCTT CTTGACGAGT TCTTCTGAAT TGAAAAGGA
4051 AGAGTATGAG TATTCAACAT TTCCGTGTCG CCCTTATTCC CTTTTTTGCG
4101 GCATTTTGCC TTCCTGTTTT TGCTCACCCA GAAACGCTGG TGAAAGTAAA
4151 AGATGCTGAA GATCAGTTGG GTGCACGAGT GGGTTACATC GAACTGGATC
4201 TCAACAGCGG TAAGATCCTT GAGAGTTTTC GCCCCGAAGA ACGTTTTCCA
4251 ATGATGAGCA CTTTTAAAGT TCTGCTATGT CATACACTAT TATCCCGTAT
```

TABLE 7-continued

Nucleotide sequence of the recombinant plasmid pCR2.1-H-SemaL (SEQ ID NO.:34)

```
4301 TGACGCCGGG CAAGAGCAAC TCGGTCGCCG GGCGCGGTAT TCTCAGAATG
4351 ACTTGGTTGA GTACTCACCA GTCACAGAAA AGCATCTTAC GGATGGCATG
4401 ACAGTAAGAG AATTATGCAG TGCTGCCATA ACCATGAGTG ATAACACTGC
4451 GGCCAACTTA CTTCTGACAA CGATCGGAGG ACCGAAGGAG CTAACCGCTT
4501 TTTTGCACAA CATGGGGGAT CATGTAACTC GCCTTGATCG TTGGGAACCG
4551 GAGCTGAATG AAGCCATACC AAACGACGAG AGTGACACCA CGATGCCTGT
4601 AGCAATGCCA ACAACGTTGC GCAAACTATT AACTGGCGAA CTACTTACTC
4651 TAGCTTCCCG GCAACAATTA ATAGACTGGA TGGAGGCGGA TAAAGTTGCA
4701 GGACCACTTC TGCGCTCGGC CCTTCCGGCT GGCTGGTTTA TTGCTGATAA
4751 ATCTGGAGCC GGTGAGCGTG GGTCTCGCGG TATCATTGCA GCACTGGGGC
4801 CAGATGGTAA GCCCTCCCGT ATCGTAGTTA TCTACACGAC GGGGAGTCAG
4851 GCAACTATGG ATGAACGAAA TAGACAGATC GCTGAGATAG GTGCCTCACT
4901 GATTAAGCAT TGGTAACTGT CAGACCAAGT TTACTCATAT ATACTTTAGA
4951 TTGATTTAAA ACTTCATTTT TAATTTAAAA GGATCTAGGT GAAGATCCTT
5001 TTTGATAATC TCATGACCAA AATCCCTTAA CGTGAGTTTT CGTTCCACTG
5051 AGCGTCAGAC CCCGTAGAAA AGATCAAAGG ATCTTCTTGA GATCCTTTTT
5101 TTCTGCGCGT AATCTGCTGC TTGCAAACAA AAAAACCACC GCTACCAGCG
5151 GTGGTTTGTT TGCCGGATCA AGAGCTACCA ACTCTTTTTC CGAAGGTAAC
5201 TGGCTTCAGC AGAGCGCAGA TACCAAATAC TGTCCTTCTA GTGTAGCCGT
5251 AGTTAGGCCA CCACTTCAAG AACTCTGTAG CACCGCCTAC ATACCTCGCT
5301 CTGCTAATCC TGTTACCAGT GGCTGCTGCC AGTGGCGATA AGTCGTGTCT
5351 TACCGGGTTG GACTCAAGAC GATAGTTACC GGATAAGGCG CAGCGGTCGG
5401 GCTGAACGGG GGGTTCGTGC ACACAGCCCA GCTTGGAGCG AACGACCTAC
5451 ACCGAACTGA GATACCTACA GCGTGAGCAT TGAGAAAGCG CCACGCTTCC
5501 CGAAGGGAGA AAGGCGGACA GGTATCCGGT AAGCGGCAGG GTCGGAACAG
5551 GAGAGCGCAC GAGGGAGCTT CCAGGGGGAA ACGCCTGGTA TCTTTATAGT
5601 CCTGTCGGGT TTCGCCACCT CTGACTTGAG CGTCGATTTT TGTGATGCTC
5651 GTCAGGGGGG CGGAGCCTAT GGAAAAACGC CAGCAACGCG GCCTTTTTAC
5701 GGTTCCTGGC CTTTTGCTGG CCTTTTGCTC ACATGTTCTT TCCTGCGTTA
5751 TCCCCTGATT CTGTGGATAA CCGTATTACC GCCTTTGAGT GAGCTGATAC
5801 CGCTCGCCGC AGCCGAACGA CCGAGCGCAG CGAGTCAGTG AGCGAGGAAG
5851 CGGAAG
```

TABLE 8

Nucleotide sequence of the recombinant expression plasmid pCDNA3.1(−)H-SemaL-MycHisA (SEQ ID NO.:35)

```
  1 GACGGATCGG GAGATCTCCC GATCCCCTAT GGTCGACTCT CAGTACAATC
 51 TGCTCTGATG CCGCATAGTT AAGCCAGTAT CTGCTCCCTG CTTGTGTGTT
```

TABLE 8-continued

Nucleotide sequence of the recombinant expression plasmid
pCDNA3.1(-)H-SemaL-MycHisA (SEQ ID NO.:35)

```
 101 GGAGGTCGCT GAGTAGTGCG CGAGCAAAAT TTAAGCTACA CAAGGCAAG
 151 GCTTGACCGA CAATTGCATG AAGAATCTGC TTAGGGTTAG GCGTTTTGCG
 201 CTGCTTCGCG ATGTACGGGC CAGATATACG CGTTGACATT GATTATTGAC
 251 TAGTTATTAA TAGTAATCAA TTACGGGGTC ATTAGTTCAT AGCCCATATA
 301 TGGAGTTCCG CGTTACATAA CTTACGGTAA ATGGCCCGCC TGGCTGACCG
 351 CCCAACGACC CCCGCCCATT GACGTCAATA ATGACGTATG TTCCCATAGT
 401 AACGCCAATA GGGACTTTCC ATTGACGTCA ATGGGTGGAC TATTTACGGT
 451 AAACTGCCCA CTTGGCAGTA CATCAAGTGT ATCATATGCC AAGTACGCCC
 501 CCTATTGACG TCAATGACGG TAAATGGCCC GCCTGGCATT ATGCCCAGTA
 551 CATGACCTTA TGGGACTTTC CTACTTGGCA GTACATCTAC GTATTAGTCA
 601 TCGCTATTAC CATGGTGATG CGGTTTTGGC AGTACATCAA TGGGCGTGGA
 651 TAGCGGTTTG ACTCACGGGG ATTTCCAAGT CTCCACCCCA TTGACGTCAA
 701 TGGGAGTTTG TTTTGGCACC AAAATCAACG GGACTTTCCA AAATGTCGTA
 751 ACAACTCCGC CCCATTGACG CAAATGGGCG GTAGGCGTGT ACGGTGGGAG
 801 GTCTATATAA GCAGAGCTCT CTGGCTAACT AGAGAACCCA CTGCTTACTG
 851 GCTTATCGAA ATTAATACGA CTCACTATAG GGAGACCCAA GCTGGCTAGC
 901 GTTTAAACGG GCCCTCTAGA CTCGAGCGGC CGCCACTGTG CTGGATATCT
 951 GCAgaattcg gcttgggatg acgcctcctc cgcccggacg tgccgccccc
1001 agcgcaccgc gcgcccgcgt ccctggcccg ccggctcggt tggggcttcc
1051 gctgcggctg cggctgctgc tgctgctctg ggcggccgcc gcctccgccc
1101 agggccacct aaggagcgga ccccgcatct tcgccgtctg gaaaggccat
1151 gtagggcagg accgggtgga ctttggccag actgagccgc acacggtgct
1201 tttccacgag ccaggcagct cctctgtgtg ggtgggagga cgtggcaagg
1251 tctacctctt tgacttcccc gagggcaaga acgcatctgt gcgcacggtg
1301 aatatcggct ccacaaaggg gtcctgtctg gataagcggg actgcgagaa
1351 ctacatcact ctcctggaga ggcggagtga ggggctgctg gcctgtggca
1401 ccaacgcccg gcaccccagc tgctggaacc tggtgaatgg cactgtggtg
1451 ccacttggcg agatgagagg ctacgccccc ttcagcccgg acgagaactc
1501 cctggttctg tttgaagggg acgaggtgta ttccaccatc cggaagcagg
1551 aatacaatgg gaagatccct cggttccgcc gcatccgggg cgagagtgag
1601 ctgtacacca gtgatactgt catgcagaac ccacagttca tcaaagccac
1651 catcgtgcac aagaccaggc cttacgatga caagatctac tacttcttcc
1701 gagaggacaa tcctgacaag aatcctgagg ctcctctcaa tgtgtcccgt
1751 gtggcccagt gtgcaggggg ggaccagggt ggggaaagtt cactgtcagt
1801 ctccaagtgg aacactttc tgaaagccat gctggtatgc agtgatgctg
1851 ccaccaacaa gaacttcaac aggctgcaag acgtcttcct gctccctgac
1901 cccagcggcc agtggaggga caccagggtc tatggtgttt tctccaaccc
1951 ctggaactac tcagccgtct gtgtgtattc cctcggtgac attgacaagg
```

TABLE 8-continued

Nucleotide sequence of the recombinant expression plasmid
pCDNA3.1(-)H-SemaL-MycHisA (SEQ ID NO.:35)

```
2001 tcttccgtac ctcctcactc aagggctacc actcaagcct tcccaacccg
2051 cggcctggca agtgcctccc agaccagcag ccgatacccg cagagacctt
2101 ccaggtggct gaccgtcacc cagaggtggc gcagagggtg gagcccatgg
2151 ggcctctgaa acgccattg ttccactcta ataccacta ccagaaagtg
2201 gccgttcacc gcatgcaagc cagccacggg gagacctttc atgtgcttta
2251 cctaactaca gacagggggca ctatccacaa ggtggtggaa ccgggggagc
2301 aggagcacag cttcgccttc aacatcatgg agatccagcc cttccgccgc
2351 gcggctgcca tccagaccat gtcgctggat gctgagcgga ggaagctgta
2401 tgtgagctcc cagtgggagg tgagccaggt gcccctggac ctgtgtgagg
2451 tctatggcgg gggctgccac ggttgcctca tgtcccgaga cccctactgc
2501 ggctgggacc agggccgctg catctccatc tacagctccg aacggtcagt
2551 gctgcaatcc attaatccag ccgagccaca caaggagtgt cccaacccca
2601 aaccagacaa ggcccactg cagaaggttt ccctggcccc aaactctcgc
2651 tactacctga gctgccccat ggaatcccgc cacgccacct actcatggcg
2701 ccacaaggag aacgtggagc agagctgcga acctggtcac cagagcccca
2751 actgcatcct gttcatcgag aacctcacgg cgcagcagta cggccactac
2801 ttctgcgagg cccaggaggg ctcctacttc cgcgaggctc agcactggca
2851 gctgctgccc gaggacggca tcatggccga gcacctgctg ggtcatgcct
2901 gtgcccctgggc tgcctccctc tggctggggg tgctgcccac actcactctt
2951 ggcttgctgg tccacgtgaa gcttGGGCCC GAACAAAAAC TCATCTCAGA
3001 AGAGGATCTG AATAGCGCCG TCGACCATCA TCATCATCAT CATTGAGTTT
3051 AAACCGCTGA TCAGCCTCGA CTGTGCCTTC TAGTTGCCAG CCATCTGTTG
3101 TTTGCCCCTC CCCCGTGCCT TCCTTGACCC TGGAAGGTGC CACTCCCACT
3151 GTCCTTTCCT AATAAAATGA GGAAATTGCA TCGCATTGTC TGAGTAGGTG
3201 TCATTCTATT CTGGGGGGTG GGGTGGGGCA GGACAGCAAG GGGGAGGATT
3251 GGGAAGACAA TAGCAGGCAT GCTGGGGATG CGGTGGGCTC TATGGCTTCT
3301 GAGGCGGAAA GAACCAGCTG GGGCTCTAGG GGGTATCCCC ACGCGCCCTG
3351 TAGCGGCGCA TTAAGCGCGG CGGGTGTGGT GGTTACGCGC AGCGTGACCG
3401 CTACACTTGC CAGCGCCCTA GCGCCCGCTC CTTTCGCTTT CTTCCCTTCC
3451 TTTCTCGCCA CGTTCGCCGG CTTTCCCCGT CAAGCTCTAA ATCGGGGCAT
3501 CCCTTTAGGG TTCCGATTTA GTGCTTTACG GCACCTCGAC CCCAAAAAAC
3551 TTGATTAGGG TGATGGTTCA CGTAGTGGGC CATCGCCCTG ATAGACGGTT
3601 TTTCGCCCTT TGACGTTGGA GTCCACGTTC TTTAATAGTG GACTCTTGTT
3651 CCAAACTGGA ACAACACTCA ACCCTATCTC GGTCTATTCT TTTGATTTAT
3701 AAGGGATTTT GGGGATTTCG GCCTATTGGT TAAAAAATGA GCTGATTTAA
3751 CAAAATTTTA ACGCGAATTA ATTCTGTGGA ATGTGTGTCA GTTAGGGTGT
3801 GGAAAGTCCC CAGGCTCCCC AGGCAGGCAG AAGTATGCAA AGCATGCATC
3851 TCAATTAGTC AGCAACCAGG TGTGGAAAGT CCCCAGGCTC CCCAGCAGGC
```

TABLE 8-continued

Nucleotide sequence of the recombinant expression plasmid pCDNA3.1(-)H-SemaL-MycHisA (SEQ ID NO.:35)

```
3901 AGAAGTATGC AAAGCATGCA TCTCAATTAG TCAGCAACCA TAGTCCCGCC
3951 CCTAACTCCG CCCATCCCGC CCCTAACTCC GCCCAGTTCC GCCCATTCTC
4001 CGCCCCATGG CTGACTAATT TTTTTTATTT ATGCAGAGGC CGAGGCCGCC
4051 TCTGCCTCTG AGCTATTCCA GAAGTAGTGA GGAGGCTTTT TTGGAGGCCT
4101 AGGCTTTTGC AAAAAGCTCC CGGGAGCTTG TATATCCATT TTCGGATCTG
4151 ATCAAGAGAC AGGATGAGGA TCGTTTCGCA TGATTGAACA AGATGGATTG
4201 CACGCAGGTT CTCCGGCCGC TTGGGTGGAG AGGCTATTCG GCTATGACTG
4251 GGCACAACAG ACAATCGGCT GCTCTGATGC CGCCGTGTTC CGGCTGTCAG
4301 CGCAGGGGCG CCCGGTTCTT TTTGTCAAGA CCGACCTGTC CGGTGCCCTG
4351 AATGAACTGC AGGACGAGGC AGCGCGGCTA TCGTGGCTGG CCACGACGGG
4401 CGTTCCTTGC GCAGCTGTGC TCGACGTTGT CACTGAAGCG GGAAGGGACT
4451 GGCTGCTATT GGGCGAAGTG CCGGGGCAGG ATCTCCTGTC ATCTCACCTT
4501 GCTCCTGCCG AGAAAGTATC CATCATGGCT GATGCAATGC GGCGGCTGCA
4551 TACGCTTGAT CCGGCTACCT GCCCATTCGA CCACCAAGCG AAACATCGCA
4601 TCGAGCGAGC ACGTACTCGG ATGGAAGCCG GTCTTGTCGA TCAGGATGAT
4651 CTGGACGAAG AGCATCAGGG GCTCGCGCCA GCCGAACTGT TCGCCAGGCT
4701 CAAGGCGCGC ATGCCCGACG GCGAGGATCT CGTCGTGACC CATGGCGATG
4751 CCTGCTTGCC GAATATCATG GTGGAAAATG GCCGCTTTTC TGGATTCATC
4801 GACTGTGGCC GGCTGGGTGT GGCGGACCGC TATCAGGACA TAGCGTTGGC
4851 TACCCGTGAT ATTGCTGAAG AGCTTGGCGG CGAATGGGCT GACCGCTTCC
4901 TCGTGCTTTA CGGTATCGCC GCTCCCGATT CGCAGCGCAT CGCCTTCTAT
4951 CGCCTTCTTG ACGAGTTCTT CTGAGCGGGA CTCTGGGGTT CGAAATGACC
5001 GACCAAGCGA CGCCCAACCT GCCATCACGA GATTTCGATT CCACCGCCGC
5051 CTTCTATGAA AGGTTGGGCT TCGGAATCGT TTTCCGGGAC GCCGGCTGGA
5101 TGATCCTCCA GCGCGGGGAT CTCATGCTGG AGTTCTTCGC CCACCCCAAC
5151 TTGTTTATTG CAGCTTATAA TGGTTACAAA TAAAGCAATA GCATCACAAA
5201 TTTCACAAAT AAAGCATTTT TTCACTGCA TTCTAGTTGT GGTTTGTCCA
5251 AACTCATCAA TGTATCTTAT CATGTCTGTA TACCGTCGAC CTCTAGCTAG
5301 AGCTTGGCGT AATCATGGTC ATAGCTGTTT CCTGTGTGAA ATTGTTATCC
5351 GCTCACAATT CCACACAACA TACGAGCCGG AAGCATAAAG TGTAAAGCCT
5401 GGGGTGCCTA ATGAGTGAGC TAACTCACAT TAATTGCGTT GCGCTCACTG
5451 CCCGCTTTCC AGTCGGGAAA CCTGTCGTGC CAGCTGCATT AATGAATCGG
5501 CCAACGCGCG GGGAGAGGCG GTTTGCGTAT TGGGCGCTCT TCCGCTTCCT
5551 CGCTCACTGA CTCGCTGCGC TCGGTCGTTC GGCTGCGGCG AGCGGTATCA
5601 GCTCACTCAA AGGCGGTAAT ACGGTTATCC ACAGAATCAG GGGATAACGC
5651 AGGAAAGAAC ATGTGAGCAA AAGGCCAGCA AAAGGCCAGG AACCGTAAAA
5701 AGGCCGCGTT GCTGGCGTTT TTCCATAGGC TCCGCCCCCC TGACGAGCAT
5751 CACAAAAATC GACGCTCAAG TCAGAGGTGG CGAAACCCGA CAGGACTATA
```

TABLE 8-continued

Nucleotide sequence of the recombinant expression plasmid
pCDNA3.1(-)H-SemaL-MycHisA (SEQ ID NO.:35)

```
5801 AAGATACCAG GCGTTTCCCC CTGGAAGCTC CCTCGTGCGC TCTCCTGTTC

5851 CGACCCTGCC GCTTACCGGA TACCTGTCCG CCTTTCTCCC TTCGGGAAGC

5901 GTGGCGCTTT CTCAATGCTC ACGCTGTAGG TATCTCAGTT CGGTGTAGGT

5951 CGTTCGCTCC AAGCTGGGCT GTGTGCACGA ACCCCCCGTT CAGCCCGACC

6001 GCTGCGCCTT ATCCGGTAAC TATCGTCTTG AGTCCAACCC GGTAAGACAC

6051 GACTTATCGC CACTGGCAGC AGCCACTGGT AACAGGATTA GCAGAGCGAG

6101 GTATGTAGGC GGTGCTACAG AGTTCTTGAA GTGGTGGCCT AACTACGGCT

6151 ACACTAGAAG GACAGTATTT GGTATCTGCG CTCTGCTGAA GCCAGTTACC

6201 TTCGGAAAAA GAGTTGGTAG CTCTTGATCC GGCAAACAAA CCACCGCTGG

6251 TAGCGGTGGT TTTTTTGTTT GCAAGCAGCA GATTACGCGC AGAAAAAAAG

6301 GATCTCAAGA AGATCCTTTG ATCTTTTCTA CGGGGTCTGA CGCTCAGTGG

6351 AACGAAAACT CACGTTAAGG GATTTTGGTC ATGAGATTAT CAAAAAGGAT

6401 CTTCACCTAG ATCCTTTTAA ATTAAAAATG AAGTTTTAAA TCAATCTAAA

6451 GTATATATGA GTAAACTTGG TCTGACAGTT ACCAATGCTT AATCAGTGAG

6501 GCACCTATCT CAGCGATCTG TCTATTTCGT TCATCCATAG TTGCCTGACT

6551 CCCCGTCGTG TAGATAACTA CGATACGGGA GGGCTTACCA TCTGGCCCCA

6601 GTGCTGCAAT GATACCGCGA GACCCACGCT CACCGGCTCC AGATTTATCA

6651 GCAATAAACC AGCCAGCCGG AAGGGCCGAG CGCAGAAGTG GTCCTGCAAC

6701 TTTATCCGCC TCCATCCAGT CTATTAATTG TTGCCGGGAA GCTAGAGTAA

6751 GTAGTTCGCC AGTTAATAGT TTGCGCAACG TTGTTGCCAT TGCTACAGGC

6801 ATCGTGGTGT CACGCTCGTC GTTTGGTATG GCTTCATTCA GCTCCGGTTC

6851 CCAACGATCA AGGCGAGTTA CATGATCCCC CATGTTGTGC AAAAAAGCGG

6901 TTAGCTCCTT CGGTCCTCCG ATCGTTGTCA GAAGTAAGTT GGCCGCAGTG

6951 TTATCACTCA TGGTTATGGC AGCACTGCAT AATTCTCTTA CTGTCATGCC

7001 ATCCGTAAGA TGCTTTTCTG TGACTGGTGA GTACTCAACC AAGTCATTCT

7051 GAGAATAGTG TATGCGGCGA CCGAGTTGCT CTTGCCCGGC GTCAATACGG

7101 GATAATACCG CGCCACATAG CAGAACTTTA AAAGTGCTCA TCATTGGAAA

7151 ACGTTCTTCG GGGCGAAAAC TCTCAAGGAT CTTACCGCTG TTGAGATCCA

7201 GTTCGATGTA ACCCACTCGT GCACCCAACT GATCTTCAGC ATCTTTTACT

7251 TTCACCAGCG TTTCTGGGTG AGCAAAAACA GGAAGGCAAA ATGCCGCAAA

7301 AAAGGGAATA AGGGCGACAC GGAAATGTTG AATACTCATA CTCTTCCTTT

7351 TTCAATATTA TTGAAGCATT TATCAGGGTT ATTGTCTCAT GAGCGGATAC

7401 ATATTTGAAT GTATTTAGAA AAATAAACAA ATAGGGGTTC CGCGCACATT

7451 TCCCCGAAAA GTGCCACCTG ACGTC
```

TABLE 9

Nucleotide sequence of the recombinant plasmid pcDNA3.1-H-SemaL-EGFP-MychisA (SEQ ID NO.:36)

```
   1 GACGGATCGG GAGATCTCCC GATCCCCTAT GGTCGACTCT CAGTACAATC
  51 TGCTCTGATG CCGCATAGTT AAGCCAGTAT CTGCTCCCTG CTTGTGTGTT
 101 GGAGGTCGCT GAGTAGTGCG CGAGCAAAAT TAAGCTACA ACAAGGCAAG
 151 GCTTGACCGA CAATTGCATG AAGAATCTGC TTAGGGTTAG GCGTTTTGCG
 201 CTGCTTCGCG ATGTACGGGC CAGATATACG CGTTGACATT GATTATTGAC
 251 TAGTTATTAA TAGTAATCAA TTACGGGGTC ATTAGTTCAT AGCCCATATA
 301 TGGAGTTCCG CGTTACATAA CTTACGGTAA ATGGCCCGCC TGGCTGACCG
 351 CCCAACGACC CCCGCCCATT GACGTCAATA ATGACGTATG TTCCCATAGT
 401 AACGCCAATA GGGACTTTCC ATTGACGTCA ATGGGTGGAC TATTTACGGT
 451 AAACTGCCCA CTTGGCAGTA CATCAAGTGT ATCATATGCC AAGTACGCCC
 501 CCTATTGACG TCAATGACGG TAAATGGCCC GCCTGGCATT ATGCCCAGTA
 551 CATGACCTTA TGGGACTTTC CTACTTGGCA GTACATCTAC GTATTAGTCA
 601 TCGCTATTAC CATGGTGATG CGGTTTTGGC AGTACATCAA TGGGCGTGGA
 651 TAGCGGTTTG ACTCACGGGG ATTTCCAAGT CTCCACCCCA TTGACGTCAA
 701 TGGGAGTTTG TTTTGGCACC AAAATCAACG GGACTTTCCA AAATGTCGTA
 751 ACAACTCCGC CCCATTGACG CAAATGGGCG GTAGGCGTGT ACGGTGGGAG
 801 GTCTATATAA GCAGAGCTCT CTGGCTAACT AGAGAACCCA CTGCTTACTG
 851 GCTTATCGAA ATTAATACGA CTCACTATAG GGAGACCCAA GCTGGCTAGC
 901 GTTTAAACGG GCCCTCTAGA CTCGAGCGGC CGCCACTGTG CTGGATATCT
 951 GCAgaattcg gcttgggatg acgcctcctc cgcccggacg tgccgccccc
1001 agcgcaccgc gcgcccgcgt ccctggcccg ccggctcggt tggggcttcc
1051 gctgcggctg cggctgctgc tgctgctctg ggcggccgcc gcctccgccc
1101 agggccacct aaggagcgga ccccgcatct tcgccgtctg gaaaggccat
1151 gtagggcagg accgggtgga ctttggccag actgagccgc acacggtgct
1201 tttccacgag ccaggcagct cctctgtgtg ggtgggagga cgtggcaagg
1251 tctacctctt tgacttcccc gagggcaaga acgcatctgt gcgcacggtg
1301 aatatcggct ccacaaaggg gtcctgtctg gataagcggg actgcgagaa
1351 ctacatcact ctcctggaga ggcggagtga ggggctgctg gcctgtggca
1401 ccaacgcccg gcaccccagc tgctggaacc tggtgaatgg cactgtggtg
1451 ccacttggcg agatgagagg ctacgccccc ttcagcccgg acgagaactc
1501 cctggttctg tttgaagggg acgaggtgta ttccaccatc cggaagcagg
1551 aatacaatgg gaagatccct cggttccgcc gcatccgggg cgagagtgag
1601 ctgtacacca gtgatactgt catgcagaac ccacagttca tcaaagccac
1651 catcgtgcac caagaccagg cttacgatga caagatctac tacttcttcc
1701 gagaggacaa tcctgacaag aatcctgagg ctcctctcaa tgtgtcccgt
1751 gtggcccagt gtgcaggggg gaccagggt ggggaaagtt cactgtcagt
1801 ctccaagtgg aacactttc tgaaagccat gctggtatgc agtgatgctg
1851 ccaccaacaa gaacttcaac aggctgcaag acgtcttcct gctccctgac
```

TABLE 9-continued

Nucleotide sequence of the recombinant plasmid pcDNA3.1-H-SemaL-EGFP-MychisA (SEQ ID NO.:36)

```
1901 cccagcggcc agtggaggga caccaggtc tatggtgttt tctccaaccc
1951 ctggaactac tcagccgtct gtgtgtattc cctcggtgac attgacaagg
2001 tcttccgtac ctcctcactc aagggctacc actcaagcct tcccaacccg
2051 cggcctggca agtgcctccc agaccagcag ccgatacccca cagagacctt
2101 ccaggtggct gaccgtcacc cagaggtggc gcagagggtg gagcccatgg
2151 ggcctctgaa gacgccattg ttccactcta ataccacta ccagaaagtg
2201 gccgttcacc gcatgcaagc cagccacggg gagacctttc atgtgctta
2251 cctaactaca gacaggggca ctatccacaa ggtggtggaa ccggggagc
2301 aggagcacag cttcgccttc aacatcatgg agatccagcc cttccgccgc
2351 gcggctgcca tccagaccat gtcgctggat gctgagcgga ggaagctgta
2401 tgtgagctcc cagtgggagg tgagccaggt gcccctggac ctgtgtgagg
2451 tctatggcgg gggctgccac ggttgcctca tgtcccgaga ccctactgc
2501 ggctgggacc agggccgctg catctccatc tacagctccg aacggtcagt
2551 gctgcaatcc attaatccag ccgagccaca aaggagtgt cccaacccca
2601 aaccagacaa ggccccactg cagaaggttt ccctggcccc aaactctcgc
2651 tactacctga gctgccccat ggaatcccgc cacgccacct actcatggcg
2701 ccacaaggag atcgtggagc agagctgcga acctggtcac cagagcccca
2751 actgcatcct gttcatcgag aacctcacgg cgcagcagta cggccactac
2801 ttctgcgagg cccaggaggg ctcctacttc cgcgaggctc agcactggca
2851 gctgctgccc gaggacggca tcatggccga gcacctgctg ggtcatgcct
2901 gtgccctggc tgcctccctc tggctggggg tgctgcccac actcactctt
2951 ggcttgctgg tccacATGGT GAGCAAGGGC GAGGAGCTGT TCACCGGGGT
3001 GGTGCCCATC CTGGTCGAGC TGGACGGCGA CGTAAACGGC CACAAGTTCA
3051 GCGTGTCCGG CGAGGGCGAG GGCGATGCCA CCTACGGCAA GCTGACCCTG
3101 AAGTTCATCT GCACCACCGG CAAGCTGCCC GTGCCCTGGC CCACCCTCGT
3151 GACCACCCTG ACCTACGGCG TGCAGTGCTT CAGCCGCTAC CCCGACCACA
3201 TGAAGCAGCA CGACTTCTTC AAGTCCGCCA TGCCCGAAGG CTACGTCCAG
3251 GAGCGCACCA TCTTCTTCAA GGACGACGGC AACTACAAGA CCCGCGCCGA
3301 GGTGAAGTTC GAGGGCGACA CCCTGGTGAA CCGCATCGAG CTGAAGGGCA
3351 TCGACTTCAA GGAGGACGGC AACATCCTGG GCACAAGCT GGAGTACAAC
3401 TACAACAGCC ACAACGTCTA TATCATGGCC GACAAGCAGA AGAACGGCAT
3451 CAAGGTGAAC TTCAAGATCC GCCACAACAT CGAGGACGGC AGCGTGCAGC
3501 TCGCCGACCA CTACCAGCAG AACACCCCCA TCGGCGACGG CCCCGTGCTG
3551 CTGCCCGACA ACCACTACCT GAGCACCCAG TCCGCCCTGA GCAAAGACCC
3601 CAACGAGAAG CGCGATCACA TGGTCCTGCT GGAGTTCGTG ACCGCCGCCG
3651 GGATCACTCT CGGCATGGAC GAGCTGTACA Aggtgaagct tGGGCCCGAA
3701 CAAAAACTCA TCTCAGAAGA GGATCTGAAT AGCGCCGTCG ACCATCATCA
3751 TCATCATCAT TGAGTTTAAA CCGCTGATCA GCCTCGACTG TGCCTTCTAG
```

TABLE 9-continued

Nucleotide sequence of the recombinant plasmid pcDNA3.1-H-SemaL-EGFP-MychisA (SEQ ID NO.:36)

3801 TTGCCAGCCA TCTGTTGTTT GCCCCTCCCC CGTGCCTTCC TTGACCCTGG

3851 AAGGTGCCAC TCCCACTGTC CTTTCCTAAT AAAATGAGGA AATTGCATCG

3901 CATTGTCTGA GTAGGTGTCA TTCTATTCTG GGGGGTGGGG TGGGGCAGGA

3951 CAGCAAGGGG GAGGATTGGG AAGACAATAG CAGGCATGCT GGGGATGCGG

4001 TGGGCTCTAT GGCTTCTGAG GCGGAAAGAA CCAGCTGGGG CTCTAGGGGG

4051 TATCCCCACG CGCCCTGTAG CGGCGCATTA AGCGCGGCGG GTGTGGTGGT

4101 TACGCGCAGC GTGACCGCTA CACTTGCCAG CGCCCTAGCG CCCGCTCCTT

4151 TCGCTTTCTT CCCTTCCTTT CTCGCCACGT TCGCCGGCTT TCCCCGTCAA

4201 GCTCTAAATC GGGGCATCCC TTTAGGCTTC CGATTTAGTG CTTTACGGCA

4251 CCTCGACCCC AAAAAACTTG ATTAGGGTGA TGGTTCACGT AGTGGGCCAT

4301 CGCCCTGATA GACGGTTTTT CGCCCTTTGA CGTTGGAGTC CACGTTCTTT

4351 AATAGTGGAC TCTTGTTCCA AACTGGAACA ACACTCAACC CTATCTCGGT

4401 CTATTCTTTT GATTTATAAG GGATTTTGGG GATTTCGGCC TATTGGTTAA

4451 AAAATGAGCT GATTTAACAA AAATTTAACG CGAATTAATT CTGTGGAATG

4501 TGTGTCAGTT AGGGTGTGGA AAGTCCCCAG GCTCCCCAGG CAGGCAGAAG

4551 TATGCAAAGC ATGCATCTCA ATTAGTCAGC AACCAGGTGT GGAAAGTCCC

4601 CAGGCTCCCC AGCAGGCAGA AGTATGCAAA GCATGCATCT CAATTAGTCA

4651 GCAACCATAG TCCCGCCCCT AACTCCGCCC ATCCCGCCCC TAACTCCGCC

4701 CAGTTCCGCC CATTCTCCGC CCCATGGCTG ACTAATTTTT TTTATTTATG

4751 CAGAGGCCGA GGCCGCCTCT GCCTCTGAGC TATTCCAGAA GTAGTGAGGA

4801 GGCTTTTTTG GAGGCCTAGG CTTTTGCAAA AAGCTCCCGG GAGCTTGTAT

4851 ATCCATTTTC GGATCTGATC AAGAGACAGG ATGAGGATCG TTTCGCATGA

4901 TTGAACAAGA TGGATTGCAC GCAGGTTCTC CGGCCGCTTG GGTGGAGAGG

4951 CTATTCGGCT ATGACTGGGC ACAACAGACA ATCGGCTGCT CTGATGCCGC

5001 CGTGTTCCGG CTGTCAGCGC AGGGGCGCCC GGTTCTTTTT GTCAAGACCG

5051 ACCTGTCCGG TGCCCTGAAT GAACTGCAGG ACGAGGCAGC GCGGCTATCG

5101 TGGCTGGCCA CGACGGGCGT TCCTTGCGCA GCTGTGCTCG ACGTTGTCAC

5151 TGAAGCGGGA AGGGACTGGC TGCTATTGGG CGAAGTGCCG GGGCAGGATC

5201 TCCTGTCATC TCACCTTGCT CCTGCCGAGA AGTATCCAT CATGGCTGAT

5251 GCAATGCGGC GGCTGCATAC GCTTGATCCG GCTACCTGCC CATTCGACCA

5301 CCAAGCGAAA CATCGCATCG AGCGAGCACG TACTCGGATG GAAGCCGGTC

5351 TTGTCGATCA GGATGATCTG GACGAAGAGC ATCAGGGGCT CGCGCCAGCC

5401 GAACTGTTCG CCAGGCTCAA GGCGCGCATG CCCGACGGCG AGGATCTCGT

5451 CGTGACCCAT GGCGATGCCT GCTTGCCGAA TATCATGGTG AAAATGGCC

5501 GCTTTTCTGG ATTCATCGAC TGTGGCCGGC TGGGTGTGGC GGACCGCTAT

5551 CAGGACATAG CGTTGGCTAC CCGTGATATT GCTGAAGAGC TTGGCGGCGA

5601 ATGGGCTGAC CGCTTCCTCG TGCTTTACGG TATCGCCGCT CCCGATTCGC

5651 AGCGCATCGC CTTCTATCGC CTTCTTGACG AGTTCTTCTG AGCGGGACTC

TABLE 9-continued

Nucleotide sequence of the recombinant plasmid pcDNA3.1-H-SemaL-EGFP-MychisA (SEQ ID NO.:36)

```
5701 TGGGGTTCGA AATGACCGAC CAAGCGACGC CCAACCTGCC ATCACGAGAT
5751 TTCGATTCCA CCGCCGCCTT CTATGAAAGG TTGGGCTTCG GAATCGTTTT
5801 CCGGGACGCC GGCTGGATGA TCCTCCAGCG CGGGGATCTC ATGCTGGAGT
5851 TCTTCGCCCA CCCCAACTTG TTTATTGCAG CTTATAATGG TTACAAATAA
5901 AGCAATAGCA TCACAAATTT CACAAATAAA GCATTTTTTT CACTGCATTC
5951 TAGTTGTGGT TTGTCCAAAC TCATCAATGT ATCTTATCAT GTCTGTATAC
6001 CGTCGACCTC TAGCTAGAGC TTGGCGTAAT CATGGTCATA GCTGTTTCCT
6051 GTGTGAAATT GTTATCCGCT CACAATTCCA CACAACATAC GAGCCGGAAG
6101 CATAAAGTGT AAAGCCTGGG GTGCCTAATG AGTGAGCTAA CTCACATTAA
6151 TTGCGTTGCG CTCACTGCCC GCTTTCCAGT CGGGAAACCT GTCGTGCCAG
6201 CTGCATTAAT GAATCGGCCA ACGCGCGGGG AGAGGCGGTT TGCGTATTGG
6251 GCGCTCTTCC GCTTCCTCGC TCACTGACTC GCTGCGCTCG GTCGTTCGGC
6301 TGCGGCGAGC GGTATCAGCT CACTCAAAGG CGGTAATACG GTTATCCACA
6351 GAATCAGGGG ATAACGCAGG AAAGAACATG TGAGCAAAAG GCCAGCAAAA
6401 GGCCAGGAAC CGTAAAAAGG CCGCGTTGCT GGCGTTTTTC CATAGGCTCC
6451 GCCCCCCTGA CGAGCATCAC AAAAATCGAC GCTCAAGTCA GAGGTGGCGA
6501 AACCCGACAG GACTATAAAG ATACCAGGCG TTTCCCCCTG GAAGCTCCCT
6551 CGTGCGCTCT CCTGTTCCGA CCCTGCCGCT TACCGGATAC CTGTCCGCCT
6601 TTCTCCCTTC GGGAAGCGTG GCGCTTTCTC AATGCTCACG CTGTAGGTAT
6651 CTCAGTTCGG TGTAGGTCGT TCGCTCCAAG CTGGGCTGTG TGCACGAACC
6701 CCCCGTTCAG CCCGACCGCT GCGCCTTATC CGGTAACTAT CGTCTTGAGT
6751 CCAACCCGGT AAGACACGAC TTATCGCCAC TGGCAGCAGC CACTGGTAAC
6801 AGGATTAGCA GAGCGAGGTA TGTAGGCGGT GCTACAGAGT TCTTGAAGTG
6851 GTGGCCTAAC TACGGCTACA CTAGAAGGAC AGTATTTGGT ATCTGCGCTC
6901 TGCTGAAGCC AGTTACCTTC GGAAAAAGAG TTGGTAGCTC TTGATCCGGC
6951 AAACAAACCA CCGCTGGTAG CGGTGGTTTT TTTGTTTGCA AGCAGCAGAT
7001 TACGCGCAGA AAAAAGGAT CTCAAGAAGA TCCTTTGATC TTTTCTACGG
7051 GGTCTGACGC TCAGTGGAAC GAAAACTCAC GTTAAGGGAT TTTGGTCATG
7101 AGATTATCAA AAAGGATCTT CACCTAGATC CTTTTAAATT AAAAATGAAG
7151 TTTTAAATCA ATCTAAAGTA TATATGAGTA AACTTGGTCT GACAGTTACC
7201 AATGCTTAAT CAGTGAGGCA CCTATCTCAG CGATCTGTCT ATTTCGTTCA
7251 TCCATAGTTG CCTGACTCCC CGTCGTGTAG ATAACTACGA TACGGGAGGG
7301 CTTACCATCT GGCCCCAGTG CTGCAATGAT ACCGCGAGAC CCACGCTCAC
7351 CGGCTCCAGA TTTATCAGCA ATAAACCAGC CAGCCGGAAG GGCCGAGCGC
7401 AGAAGTGGTC CTGCAACTTT ATCCGCCTCC ATCCAGTCTA TTAATTGTTG
7451 CCGGGAAGCT AGAGTAAGTA GTTCGCCAGT TAATAGTTTG CGCAACGTTG
7501 TTGCCATTGC TACAGGCATC GTGGTGTCAC GCTCGTCGTT TGGTATGGCT
7551 TCATTCAGCT CCGGTTCCCA ACGATCAAGG CGAGTTACAT GATCCCCCAT
```

TABLE 9-continued

Nucleotide sequence of the recombinant plasmid pcDNA3.1-H-SemaL-EGFP-MychisA (SEQ ID NO.:36)

```
7601 GTTGTGCAAA AAAGCGGTTA GCTCCTTCGG TCCTCCGATC GTTGTCAGAA
7651 GTAAGTTGGC CGCAGTGTTA TCACTCATGG TTATGGCAGC ACTGCATAAT
7701 TCTCTTACTG TCATGCCATC CGTAAGATGC TTTTCTGTGA CTGGTGAGTA
7751 CTCAACCAAG TCATTCTGAG AATAGTGTAT GCGGCGACCG AGTTGCTCTT
7801 GCCCGGCGTC AATACGGGAT AATATCGCGC CACATAGCAG AACTTTAAAA
7851 GTGCTCATCA TTGGAAAACG TTCTTCGGGG CGAAAACTCT CAAGGATCTT
7901 ACCGCTGTTG AGATCCAGTT CGATGTAACC CACTCGTGCA CCCAACTGAT
7951 CTTCAGCATC TTTTACTTTC ACCAGCGTTT CTGGGTGAGC AAAAACAGGA
8001 AGGCAAAATG CCGCAAAAAA GGGAATAAGG GCGACACGGA AATGTTGAAT
8051 ACTCATACTC TTCCTTTTTC AATATTATTG AAGCATTTAT CAGGGTTATT
8101 GTCTCATGAG CGGATACATA TTTGAATGTA TTTAGAAAAA TAAACAAATA
8151 GGGGTTCCGC GCACATTTCC CCGAAAAGTG CCACCTGACG TC
```

TABLE 10

Nucleotide sequence of the recombinant plasmid pIND-H-SemaL-EE (SEQ ID NO.:37)

```
   1 AGATCTCGGC CGCATATTAA GTGCATTGTT CTCGATACCG CTAAGTGCAT
  51 TGTTCTCGTT AGCTCGATGG ACAAGTGCAT TGTTCTCTTG CTGAAAGCTC
 101 GATGGACAAG TGCATTGTTC TCTTGCTGAA AGCTCGATGG ACAAGTGCAT
 151 TGTTCTCTTG CTGAAAGCTC AGTACCCGGG AGTACCCTCG ACCGCCGGAG
 201 TATAAATAGA GGCGCTTCGT CTACGGAGCG ACAATTCAAT TCAAACAAGC
 251 AAAGTGAACA CGTCGCTAAG CGAAAGCTAA GCAAATAAAC AAGCGCAGCT
 301 GAACAAGCTA AACAATCTGC AGTAAAGTGC AAGTTAAAGT GAATCAATTA
 351 AAAGTAACCA GCAACCAAGT AAATCAACTG CAACTACTGA AATCTGCCAA
 401 GAAGTAATTA TTGAATACAA GAAGAGAACT CTGAATACTT TCAACAAGTT
 451 ACCGAGAAAG AAGAACTCAC ACACAGCTAG CGTTTAAACT TAAGCTTGGT
 501 ACCGAGCTCG GATCCACTAG TCCAGTGTGG TGgaattcgg cttgggatga
 551 cgcctcctcc gcccggacgt gccgccccca gcgcaccgcg cgcccgcgtc
 601 cctggcccgc cggctcggtt ggggcttccg ctgcggctgc ggctgctgct
 651 gctgctctgg gcggccgccg cctccgccca gggccaccta aggagcggac
 701 cccgcatctt cgccgtctgg aaaggccatg tagggcagga ccgggtggac
 751 tttggccaga ctgagccgca cacggtgctt ttccacgagc caggcagctc
 801 ctctgtgtgg gtgggaggac gtggcaaggt ctacctcttt gacttccccg
 851 agggcaagaa cgcatctgtg cgcacggtga atatcggctc cacaaagggg
 901 tcctgtctga taagcggga ctgcgagaac tacatcactc tcctggagag
 951 gcggagtgag gggctgctgg cctgtggcac caacgcccgg caccccagct
1001 gctggaacct ggtgaatggc actgtggtgc cacttggcga gatgagaggc
1051 tacgccccct tcagcccgga cgagaactcc ctggttctgt ttgaagggga
```

TABLE 10-continued

Nucleotide sequence of the recombinant plasmid pIND-H-SemaL-EE (SEQ ID NO.:37)

```
1101 cgaggtgtat tccaccatcc ggaagcagga atacaatggg aagatccctc
1151 ggttccgccg catccggggc gagagtgagc tgtacaccag tgatactgtc
1201 atgcagaacc cacagttcat caaagccacc atcgtgcacc aagaccaggc
1251 ttacgatgac aagatctact acttcttccg agaggacaat cctgacaaga
1301 atcctgaggc tcctctcaat gtgtcccgtg tggcccagtt gtgcaggggg
1351 gaccagggtg gggaaagttc actgtcagtc tccaagtgga acacttttct
1401 gaaagccatg ctggtatgca gtgatgctgc caccaacaag aacttcaaca
1451 ggctgcaaga cgtcttcctg ctccctgacc ccagcggcca gtggagggac
1501 accagggtct atggtgtttt ctccaacccc tggaactact cagccgtctg
1551 tgtgtattcc ctcggtgaca ttgacaaggt cttccgtacc tcctcactca
1601 agggctacca ctcaagcctt cccaacccgc ggcctggcaa gtgcctccca
1651 gaccagcagc cgatacccac agagaccttc caggtggctg accgtcaccc
1701 agaggtggcg cagagggtgg agcccatggg gcctctgaag acgccattgt
1751 tccactctaa ataccactac cagaaagtgg ccgttcaccg catgcaagcc
1801 agccacgggg agaccttttca tgtgctttac ctaactacag acaggggcac
1851 tatccacaag gtggtggaac cgggggagca ggagcacagc ttcgccttca
1901 acatcatgga gatccagccc ttccgccgcg cggctgccat ccagaccatg
1951 tcgctggatg ctgagcggag gaagctgtat gtgagctccc agtgggaggt
2001 gagccaggtg cccctggacc tgtgtgaggt ctatggcggg ggctgccacg
2051 gttgcctcat gtcccgagac ccctactgcg gctgggacca gggccgctgc
2101 atctccatct acagctccga acggtcagtg ctgcaatcca ttaatccagc
2151 cgagccacac aaggagtgtc ccaaccccaa accagacaag gccccactgc
2201 agaaggtttc cctggcccca aactctcgct actacctgag ctgccccatg
2251 gaatcccgcc acgccaccta tcatggcgcc cacaaggaga acgtggagca
2301 gagctgcgaa cctggtcacc agagccccaa ctgcatcctg ttcatcgaga
2351 acctcacggc gcagcagtac ggccactact tctgcgaggc ccaggagggc
2401 tcctacttcc gcgaggctca gcactggcag ctgctgcccg aggacggcat
2451 catggccgag cacctgctgg gtcatgcctg tgccctggct gcctccctct
2501 ggctggggggt gctgcccaca ctcactcttg gcttgctggt ccacgtgaag
2551 cttGGGCCCG TTTAAACCCG CTGATCAGCC TCGACTGTGC CTTCTAGTTG
2601 CCAGCCATCT GTTGTTTGCC CCTCCCCCGT GCCTTCCTTG ACCCTGGAAG
2651 GTGCCACTCC CACTGTCCTT TCCTAATAAA ATGAGGAAAT TGCATCGCAT
2701 TGTCTGAGTA GGTGTCATTC TATTCTGGGG GGTGGGGTGG GGCAGGACAG
2751 CAAGGGGGAG GATTGGGAAG ACAATAGCAG GCATGCTGGG GATGCGGTGG
2801 GCTCTATGGC TTCTGAGGCG GAAAGAACCA GCTGGGGCTC TAGGGGGTAT
2851 CCCCACGCGC CCTGTAGCGG CGCATTAAGC GCGGCGGGTG TGGTGGTTAC
2901 GCGCAGCGTG ACCGCTACAC TTGCCAGCGC CCTAGCGCCC GCTCCTTTCG
2951 CTTTCTTCCC TTCCTTTCTC GCCACGTTCG CCGGCTTTCC CCGTCAAGCT
```

TABLE 10-continued

Nucleotide sequence of the recombinant plasmid pIND-H-SemaL-EE (SEQ ID NO.:37)

```
3001 CTAAATCGGG GCATCCCTTT AGGGTTCCGA TTTAGTGCTT TACGGCACCT
3051 CGACCCCAAA AAACTTGATT AGGGTGATGG TTCACGTAGT GGGCCATCGC
3101 CCTGATAGAC GGTTTTTCGC CCTTTGACGT TGGAGTCCAC GTTCTTTAAT
3151 AGTGGACTCT TGTTCCAAAC TGGAACAACA CTCAACCCTA TCTCGGTCTA
3201 TTCTTTTGAT TTATAAGGGA TTTTGGGGAT TTCGGCCTAT TGGTTAAAAA
3251 ATGAGCTGAT TTAACAAAAA TTTAACGCGA ATTAATTCTG TGGAATGTGT
3301 GTCAGTTAGG GTGTGGAAAG TCCCCAGGCT CCCCAGGCAG GCAGAAGTAT
3351 GCAAAGCATG CATCTCAATT AGTCAGCAAC CAGGTGTGGA AAGTCCCCAG
3401 GCTCCCCAGC AGGCAGAAGT ATGCAAAGCA TGCATCTCAA TTAGTCAGCA
3451 ACCATAGTCC CGCCCCTAAC TCCGCCCATC CCGCCCCTAA CTCCGCCCAG
3501 TTCCGCCCAT TCTCCGCCCC ATGGCTGACT AATTTTTTTT ATTTATGCAG
3551 AGGCCGAGGC CGCCTCTGCC TCTGAGCTAT TCCAGAAGTA GTGAGGAGGC
3601 TTTTTTGGAG GCCTAGGCTT TTGCAAAAAG CTCCCGGGAG CTTGTATATC
3651 CATTTTCGGA TCTGATCAAG AGACAGGATG AGGATCGTTT CGCATGATTG
3701 AACAAGATGG ATTGCACGCA GGTTCTCCGG CCGCTTGGGT GGAGAGGCTA
3751 TTCGGCTATG ACTGGGCACA ACAGACAATC GGCTGCTCTG ATGCCGCCGT
3801 GTTCCGGCTG TCAGCGCAGG GGCGCCCGGT TCTTTTTGTC AAGACCGACC
3851 TGTCCGGTGC CCTGAATGAA CTGCAGGACG AGGCAGCGCG GCTATCGTGG
3901 CTGGCCACGA CGGGCGTTCC TTGCGCAGCT GTGCTCGACG TTGTCACTGA
3951 AGCGGGAAGG GACTGGCTGC TATTGGGCGA AGTGCCGGGG CAGGATCTCC
4001 TGTCATCTCA CCTTGCTCCT GCCGAGAAAG TATCCATCAT GGCTGATGCA
4051 ATGCGGCGGC TGCATACGCT TGATCCGGCT ACCTGCCCAT TCGACCACCA
4101 AGCGAAACAT CGCATCGAGC GAGCACGTAC TCGGATGGAA GCCGGTCTTG
4151 TCGATCAGGA TGATCTGGAC GAAGAGCATC AGGGGCTCGC GCCAGCCGAA
4201 CTGTTCGCCA GGCTCAAGGC GCGCATGCCC GACGGCGAGG ATCTCGTCGT
4251 GACCCATGGC GATGCCTGCT TGCCGAATAT CATGGTGGAA AATGGCCGCT
4301 TTTCTGGATT CATCGACTGT GGCCGGCTGG GTGTGGCGGA CCGCTATCAG
4351 GACATAGCGT TGGCTACCCG TGATATTGCT GAAGAGCTTG GCGGCGAATG
4401 GGCTGACCGC TTCCTCGTGC TTTACGGTAT CGCCGCTCCC GATTCGCAGC
4451 GCATCGCCTT CTATCGCCTT CTTGACGAGT TCTTCTGAGC GGGACTCTGG
4501 GGTTCGAAAT GACCGACCAA GCGACGCCCA ACCTGCCATC ACGAGATTTC
4551 GATTCCACCG CCGCCTTCTA TGAAAGGTTG GGCTTCGGAA TCGTTTTCCG
4601 GGACGCCGGC TGGATGATCC TCCAGCGCGG GGATCTCATG CTGGAGTTCT
4651 TCGCCCACCC CAACTTGTTT ATTGCAGCTT ATAATGGTTA CAAATAAAGC
4701 AATAGCATCA CAAATTTCAC AAATAAAGCA TTTTTTTCAC TGCATTCTAG
4751 TTGTGGTTTG TCCAAACTCA TCAATGTATC TTATCATGTC TGTATACCGT
4801 CGACCTCTAG CTAGAGCTTG GCGTAATCAT GGTCATAGCT GTTTCCTGTG
4851 TGAAATTGTT ATCCGCTCAC AATTCCACAC AACATACGAG CCGGAAGCAT
```

TABLE 10-continued

Nucleotide sequence of the recombinant plasmid pIND-H-SemaL-EE (SEQ ID NO.:37)

```
4901 AAAGTGTAAA GCCTGGGGTG CCTAATGAGT GAGCTAACTC ACATTAATTG

4951 CGTTGCGCTC ACTGCCCGCT TTCCAGTCGG AAACCTGTC GTGCCAGCTG

5001 CATTAATGAA TCGGCCAACG CGCGGGGAGA GGCGGTTTGC GTATTGGGCG

5051 CTCTTCCGCT TCCTCGCTCA CTGACTCGCT GCGCTCGGTC GTTCGGCTGC

5101 GGCGAGCGGT ATCAGCTCAC TCAAAGGCGG TAATACGGTT ATCCACAGAA

5151 TCAGGGGATA ACGCAGGAAA GAACATGTGA GCAAAAGGCC AGCAAAAGGC

5201 CAGGAACCGT AAAAAGGCCG CGTTGCTGGC GTTTTTCCAT AGGCTCCGCC

5251 CCCCTGACGA GCATCACAAA AATCGACGCT CAAGTCAGAG GTGGCGAAAC

5301 CCGACAGGAC TATAAAGATA CCAGGCGTTT CCCCCTGGAA GCTCCCTCGT

5351 GCGCTCTCCT GTTCCGACCC TGCCGCTTAC CGGATACCTG TCCGCCTTTC

5401 TCCCTTCGGG AAGCGTGGCG CTTTCTCAAT GCTCACGCTG TAGGTATCTC

5451 AGTTCGGTGT AGGTCGTTCG CTCCAAGCTG GGCTGTGTGC ACGAACCCCC

5501 CGTTCAGCCC GACCGCTGCG CCTTATCCGG TAACTATCGT CTTGAGTCCA

5551 ACCCGGTAAG ACACGACTTA TCGCCACTGG CAGCAGCCAC TGGTAACAGG

5601 ATTAGCAGAG CGAGGTATGT AGGCGGTGCT ACAGAGTTCT TGAAGTGGTG

5651 GCCTAACTAC GGCTACACTA GAAGGACAGT ATTTGGTATC TGCGCTCTGC

5701 TGAAGCCAGT TACCTTCGGA AAAAGAGTTG GTAGCTCTTG ATCCGGCAAA

5751 CAAACCACCG CTGGTAGCGG TGGTTTTTTT GTTTGCAAGC AGCAGATTAC

5801 GCGCAGAAAA AAAGGATCTC AAGAAGATCC TTTGATCTTT TCTACGGGGT

5851 CTGACGCTCA GTGGAACGAA AACTCACGTT AAGGGATTTT GGTCATGAGA

5901 TTATCAAAAA GGATCTTCAC CTAGATCCTT TTAAATTAAA AATGAAGTTT

5951 TAAATCAATC TAAAGTATAT ATGAGTAAAC TTGGTCTGAC AGTTACCAAT

6001 GCTTAATCAG TGAGGCACCT ATCTCAGCGA TCTGTCTATT TCGTTCATCC

6051 ATAGTTGCCT GACTCCCCGT CGTGTAGATA ACTACGATAC GGGAGGGCTT

6101 ACCATCTGGC CCCAGTGCTG CAATGATACC GCGAGACCCA CGCTCACCGG

6151 CTCCAGATTT ATCAGCAATA AACCAGCCAG CCGGAAGGGC CGAGCGCAGA

6201 AGTGGTCCTG CAACTTTATC CGCCTCCATC CAGTCTATTA ATTGTTGCCG

6251 GGAAGCTAGA GTAAGTAGTT CGCCAGTTAA TAGTTTGCGC AACGTTGTTG

6301 CCATTGCTAC AGGCATCGTG GTGTCACGCT CGTCGTTTGG TATGGCTTCA

6351 TTCAGCTCCG GTTCCCAACG ATCAAGGCGA GTTACATGAT CCCCCATGTT

6401 GTGCAAAAAA GCGGTTAGCT CCTTCGGTCC TCCGATCGTT GTCAGAAGTA

6451 AGTTGGCCGC AGTGTTATCA CTCATGGTTA TGGCAGCACT GCATAATTCT

6501 CTTACTGTCA TGCCATCCGT AAGATGCTTT TCTGTGACTG GTGAGTACTC

6551 AACCAAGTCA TTCTGAGAAT AGTGTATGCG GCGACCGAGT TGCTCTTGCC

6601 CGGCGTCAAT ACGGGATAAT ACCGCGCCAC ATAGCAGAAC TTTAAAAGTG

6651 CTCATCATTG GAAAACGTTC TTCGGGGCGA AAACTCTCAA GGATCTTACC

6701 GCTGTTGAGA TCCAGTTCGA TGTAACCCAC TCGTGCACCC AACTGATCTT

6751 CAGCATCTTT TACTTTCACC AGCGTTTCTG GGTGAGCAAA AACAGGAAGG
```

TABLE 10-continued

Nucleotide sequence of the recombinant plasmid pIND-H-SemaL-EE (SEQ ID NO.:37)

```
6801 CAAAATGCCG CAAAAAAGGG AATAAGGGCG ACACGGAAAT GTTGAATACT
6851 CATACTCTTC CTTTTTCAAT ATTATTGAAG CATTTATCAG GGTTATTGTC
6901 TCATGAGCGG ATACATATTT GAATGTATTT AGAAAAATAA ACAAATAGGG
6951 GTTCCGCGCA CATTTCCCCG AAAAGTGCCA CCTGACGTCG ACGGATCGGG
```

TABLE 11

Nucleotide sequence of the recombinant plasmid pIND-H-SemaL-EA (SEQ ID NO.:38)

```
   1 AGATCTCGGC CGCATATTAA GTGCATTGTT CTCGATACCG CTAAGTGCAT
  51 TGTTCTCGTT AGCTCGATGG ACAAGTGCAT TGTTCTCTTG CTGAAAGCTC
 101 GATGGACAAG TGCATTGTTC TCTTGCTGAA AGCTCGATGG ACAAGTGCAT
 151 TGTTCTCTTG CTGAAAGCTC AGTACCCGGG AGTACCCTCG ACCGCCGGAG
 201 TATAAATAGA GGCGCTTCGT CTACGGAGCG ACAATTCAAT TCAAACAAGC
 251 AAAGTGAACA CGTCGCTAAG CGAAAGCTAA GCAAATAAAC AAGCGCAGCT
 301 GAACAAGCTA AACAATCTGC AGTAAAGTGC AAGTTAAAGT GAATCAATTA
 351 AAAGTAACCA GCAACCAAGT AAATCAACTG CAACTACTGA AATCTGCCAA
 401 GAAGTAATTA TTGAATACAA GAAGAGAACT CTGAATACTT TCAACAAGTT
 451 ACCGAGAAAG AAGAACTCAC ACACAGCTAG CGTTTAAACT TAAGCTTGGT
 501 ACCGAGCTCG GATCCACTAG TCCAGTGTGG TGgaattcgg cttgggatga
 551 cgcctcctcc gcccggacgt gccgccccca gcgcaccgcg cgcccgcgtc
 601 cctggcccgc cggctcggtt ggggcttccg ctgcggctgc ggctgctgct
 651 gctgctctgg gcggccgccg cctccgccca gggccaccta aggagcggac
 701 cccgcatctt cgccgtctgg aaaggccatg tagggcagga ccgggtggac
 751 tttggccaga ctgagccgca cacggtgctt ttccacgagc caggcagctc
 801 ctctgtgtgg gtgggaggac gtggcaaggt ctacctcttt gacttccccg
 851 agggcaagaa cgcatctgtg cgcacggtga atatcggctc cacaaagggg
 901 tcctgtctgg ataagcggga ctgcgagaac tacatcactc tcctggagag
 951 gcggagtgag gggctgctgg cctgtggcac caacgcccgg cacccccagct
1001 gctgaaacct ggtgaatggc actgtggtgc cacttggcga gatgagaggc
1051 tacgcccccT tcagcccgga cgagaactcc ctggttctgt ttgaagggga
1101 cgaggtgtat tccaccatcc ggaagcagga atacaatggg aagatccctc
1151 ggttccgccg catccggggc gagagtgagc tgtacaccag tgatactgtc
1201 atgcagaacc cacagttcat caaagccacc atcgtgcacc aagaccaggc
1251 ttacgatgac aagatctact acttcttccg agaggacaat cctgacaaga
1301 atcctgaggc tcctctcaat gtgtcccgtg tggcccagtt gtgcaggggg
1351 gaccagggtg gggaaagttc actgtcagtc tccaagtgga cacttttct
1401 gaaagccatg ctggtatgca gtgatgctgc caccaacaag aacttcaaca
1451 ggctgcaaga cgtcttcctg ctccctgacc ccagcggcca gtggagggac
```

TABLE 11-continued

Nucleotide sequence of the recombinant plasmid pIND-H-SemaL-EA (SEQ ID NO.:38)

```
1501 accagggtct atgtgtttt ctccaacccc tggaactact cagccgtctg
1551 tgtgtattcc ctcggtgaca ttgacaaggt cttccgtacc tcctcactca
1601 agggctacca ctcaagcctt cccaacccgc ggcctggcaa gtgcctccca
1651 gaccagcagc cgatacccac agagaccttc caggtggctg accgtcaccc
1701 agaggtggcg cagagggtgg agcccatggg gcctctgaag acgccattgt
1751 tccactctaa ataccactac cagaaagtgg ccgttcaccg catgcaagcc
1801 agccacgggg agacctttca tgtgctttac ctaactacag acaggggcac
1851 tatccacaag gtggtggaac cgggggagca ggagcacagc ttcgccttca
1901 acatcatgga gatccagccc ttccgccgcg cggctgccat ccagaccatg
1951 tcgctggatg ctgagcggag gaagctgtat gtgagctccc agtgggaggt
2001 gagccaggtg cccctggacc tgtgtgaggt ctatggcggg ggctgccacg
2051 gttgcctcat gtcccgagac ccctactgcg gctgggacca gggccgctgc
2101 atctccatct acagctccga acggtcagtg ctgcaatcca ttaatccagc
2151 cgagccacac aaggagtgtc ccaaccccaa accagacaag gccccactgc
2201 agaaggtttc cctggcccca aactctcgct actacctgag ctgccccatg
2251 gaatcccgcc acgccaccta ctcatggcgc cacaaggaga acgtggagca
2301 gagctgcgaa cctggtcacc agagcccaa ctgcatcctg ttcatcgaga
2351 acctcacggc gcagcagtac ggccactact tctgcgaggc ccaggagggc
2401 tcctacttcc gcgaggctca gcactggcag ctgctgcccg aggacggcat
2451 catggccgag cacctgctgg gtcatgcctg tgccctggct gcctccctct
2501 ggctgggggt gctgcccaca ctcactcttg gcttgctggt ccacgtgaag
2551 cttGGGCCCG AACAAAAACT CATCTCAGAA GAGGATCTGA ATAGCGCCGT
2601 CGACCATCAT CATCATCATC ATTGAGTTTA TCCAGCACAG TGGCGGCCGC
2651 TCGAGTCTAG AGGGCCCGTT TAAACCCGCT GATCAGCCTC GACTGTGCCT
2701 TCTAGTTGCC AGCCATCTGT TGTTTGCCCC TCCCCCGTGC CTTCCTTGAC
2751 CCTGGAAGGT GCCACTCCCA CTGTCCTTTC CTAATAAAAT GAGGAAATTG
2801 CATCGCATTG TCTGAGTAGG TGTCATTCTA TTCTGGGGGG TGGGGTGGGG
2851 CAGGACAGCA AGGGGGAGGA TTGGGAAGAC AATAGCAGGC ATGCTGGGGA
2901 TGCGGTGGGC TCTATGGCTT CTGAGGCGGA AAGAACCAGC TGGGGCTCTA
2951 GGGGGTATCC CCACGCGCCC TGTAGCGGCG CATTAAGCGC GGCGGGTGTG
3001 GTGGTTACGC GCAGCGTGAC CGCTACACTT GCCAGCGCCC TAGCGCCCGC
3051 TCCTTTCGCT TTCTTCCCTT CCTTTCTCGC CACGTTCGCC GGCTTTCCCC
3101 GTCAAGCTCT AAATCGGGGC ATCCCTTTAG GGTTCCGATT TAGTGCTTTA
3151 CGGCACCTCG ACCCCAAAAA ACTTGATTAG GGTGATGGTT CACGTAGTGG
3201 GCCATCGCCC TGATAGACGG TTTTTCGCCC TTTGACGTTG GAGTCCACGT
3251 TCTTTAATAG TGGACTCTTG TTCCAAACTG GAACAACACT CAACCCTATC
3301 TCGGTCTATT CTTTTGATTT ATAAGGGATT TTGGGGATTT CGGCCTATTG
3351 GTTAAAAAAT GAGCTGATTT AACAAAAATT TAACGCGAAT TAATTCTGTG
```

TABLE 11-continued

Nucleotide sequence of the recombinant plasmid pIND-H-SemaL-EA (SEQ ID NO.:38)

```
3401 GAATGTGTGT CAGTTAGGGT GTGGAAAGTC CCCAGGCTCC CCAGGCAGGC
3451 AGAAGTATGC AAAGCATGCA TCTCAATTAG TCAGCAACCA GGTGTGGAAA
3501 GTCCCCAGGC TCCCCAGCAG GCAGAAGTAT GCAAAGCATG CATCTCAATT
3551 AGTCAGCAAC CATAGTCCCG CCCCTAACTC CGCCCATCCC GCCCCTAACT
3601 CCGCCCAGTT CCGCCCATTC TCCGCCCCAT GGCTGACTAA TTTTTTTTAT
3651 TTATGCAGAG GCCGAGGCCG CCTCTGCCTC TGAGCTATTC CAGAAGTAGT
3701 GAGGAGGCTT TTTTGGAGGC CTAGGCTTTT GCAAAAAGCT CCCGGGAGCT
3751 TGTATATCCA TTTTCGGATC TGATCAAGAG ACAGGATGAG GATCGTTTCG
3801 CATGATTGAA CAAGATGGAT TGCACGCAGG TTCTCCGGCC GCTTGGGTGG
3851 AGAGGCTATT CGGCTATGAC TGGGCACAAC AGACAATCGG CTGCTCTGAT
3901 GCCGCCGTGT TCCGGCTGTC AGCGCAGGGG CGCCCGGTTC TTTTTGTCAA
3951 GACCGACCTG TCCGGTGCCC TGAATGAACT GCAGGACGAG GCAGCGCGGC
4001 TATCGTGGCT GGCCACGACG GGCGTTCCTT GCGCAGCTGT GCTCGACGTT
4051 GTCACTGAAG CGGGAAGGGA CTGGCTGCTA TTGGGCGAAG TGCCGGGGCA
4101 GGATCTCCTG TCATCTCACC TTGCTCCTGC CGAGAAAGTA TCCATCATGG
4151 CTGATGCAAT GCGGCGGCTG CATACGCTTG ATCCGGCTAC CTGCCCATTC
4201 GACCACCAAG CGAAACATCG CATCGAGCGA GCACGTACTC GGATGGAAGC
4251 CGGTCTTGTC GATCAGGATG ATCTGGACGA AGAGCATCAG GGGCTCGCGC
4301 CAGCCGAACT GTTCGCCAGG CTCAAGGCGC GCATGCCCGA CGGCGAGGAT
4351 CTCGTCGTGA CCCATGGCGA TGCCTGCTTG CCGAATATCA TGGTGGAAAA
4401 TGGCCGCTTT TCTGGATTCA TCGACTGTGG CCGGCTGGGT GTGGCGGACC
4451 GCTATCAGGA CATAGCGTTG GCTACCCGTG ATATTGCTGA AGAGCTTGGC
4501 GGCGAATGGG CTGACCGCTT CCTCGTGCTT TACGGTATCG CCGCTCCCGA
4551 TTCGCAGCGC ATCGCCTTCT ATCGCCTTCT TGACGAGTTC TTCTGAGCGG
4601 GACTCTGGGG TTCGAAATGA CCGACCAAGC GACGCCCAAC CTGCCATCAC
4651 GAGATTTCGA TTCCACCGCC GCCTTCTATG AAAGGTTGGG CTTCGGAATC
4701 GTTTTCCGGG ACGCCGGCTG GATGATCCTC CAGCGCGGGG ATCTCATGCT
4751 GGAGTTCTTC GCCCACCCCA ACTTGTTTAT TGCAGCTTAT AATGGTTACA
4801 AATAAAGCAA TAGCATCACA AATTTCACAA ATAAAGCATT TTTTTCACTG
4851 CATTCTAGTT GTGGTTTGTC CAAACTCATC AATGTATCTT ATCATGTCTG
4901 TATACCGTCG ACCTCTAGCT AGAGCTTGGC GTAATCATGG TCATAGCTGT
4951 TTCCTGTGTG AAATTGTTAT CCGCTCACAA TTCCACACAA CATACGAGCC
5001 GGAAGCATAA AGTGTAAAGC CTGGGGTGCC TAATGAGTGA GCTAACTCAC
5051 ATTAATTGCG TTGCGCTCAC TGCCCGCTTT CCAGTCGGGA AACCTGTCGT
5101 GCCAGCTGCA TTAATGAATC GGCCAACGCG CGGGGAGAGG CGGTTTGCGT
5151 ATTGGGCGCT CTTCCGCTTC CTCGCTCACT GACTCGCTGC GCTCGGTCGT
5201 TCGGCTGCGG CGAGCGGTAT CAGCTCACTC AAAGGCGGTA ATACGGTTAT
5251 CCACAGAATC AGGGGATAAC GCAGGAAAGA ACATGTGAGC AAAAGGCCAG
```

TABLE 11-continued

Nucleotide sequence of the recombinant plasmid pIND-H-SemaL-EA (SEQ ID NO.:38)

```
5301 CAAAAGGCCA GGAACCGTAA AAAGGCCGCG TTGCTGGCGT TTTTCCATAG

5351 GCTCCGCCCC CCTGACGAGC ATCACAAAAA TCGACGCTCA AGTCAGAGGT

5401 GGCGAAACCC GACAGGACTA TAAAGATACC AGGCGTTTCC CCCTGGAAGC

5451 TCCCTCGTGC GCTCTCCTGT TCCGACCCTG CCGCTTACCG GATACCTGTC

5501 CGCCTTTCTC CCTTCGGGAA GCGTGGCGCT TTCTCAATGC TCACGCTGTA

5551 GGTATCTCAG TTCGGTGTAG GTCGTTCGCT CCAAGCTGGG CTGTGTGCAC

5601 GAACCCCCCG TTCAGCCCGA CCGCTGCGCC TTATCCGGTA ACTATCGTCT

5651 TGAGTCCAAC CCGGTAAGAC ACGACTTATC GCCACTGGCA GCAGCCACTG

5701 GTAACAGGAT TAGCAGAGCG AGGTATGTAG GCGGTGCTAC AGAGTTCTTG

5751 AAGTGGTGGC CTAACTACGG CTACACTAGA AGGACAGTAT TTGGTATCTG

5801 CGCTCTGCTG AAGCCAGTTA CCTTCGGAAA AAGAGTTGGT AGCTCTTGAT

5851 CCGGCAAACA AACCACCGCT GGTAGCGGTG GTTTTTTTGT TTGCAAGCAG

5901 CAGATTACGC GCAGAAAAAA AGGATCTCAA GAAGATCCTT TGATCTTTTC

5951 TACGGGGTCT GACGCTCAGT GGAACGAAAA CTCACGTTAA GGGATTTTGG

6001 TCATGAGATT ATCAAAAAGG ATCTTCACCT AGATCCTTTT AAATTAAAAA

6051 TGAAGTTTTA PATCAATCTA AAGTATATAT GAGTAAACTT GGTCTGACAG

6101 TTACCAATGC TTAATCAGTG AGGCACCTAT CTCAGCGATC TGTCTATTTC

6151 GTTCATCCAT AGTTGCCTGA CTCCCCGTCG TGTAGATAAC TACGATACGG

6201 GAGGGCTTAC CATCTGGCCC CAGTGCTGCA ATGATACCGC GAGACCCACG

6251 CTCACCGGCT CCAGATTTAT CAGCAATAAA CCAGCCAGCC GGAAGGGCCG

6301 AGCGCAGAAG TGGTCCTGCA ACTTTATCCG CCTCCATCCA GTCTATTAAT

6351 TGTTGCCGGG AAGCTAGAGT AAGTAGTTCG CCAGTTAATA GTTTGCGCAA

6401 CGTTGTTGCC ATTGCTACAG GCATCGTGGT GTCACGCTCG TCGTTTGGTA

6451 TGGCTTCATT CAGCTCCGGT TCCCAACGAT CAAGGCGAGT TACATGATCC

6501 CCCATGTTGT GCAAAAAAGC GGTTAGCTCC TTCGGTCCTC CGATCGTTGT

6551 CAGAAGTAAG TTGGCCGCAG TGTTATCACT CATGGTTATG GCAGCACTGC

6601 ATAATTCTCT TACTGTCATG CCATCCGTAA GATGCTTTTC TGTGACTGGT

6651 GAGTACTCAA CCAAGTCATT CTGAGAATAG TGTATGCGGC GACCGAGTTG

6701 CTCTTGCCCG GCGTCAATAC GGGATAATAC CGCGCCACAT AGCAGAACTT

6751 TAAAAGTGCT CATCATTGGA AAACGTTCTT CGGGGCGAAA ACTCTCAAGG

6801 ATCTTACCGC TGTTGAGATC CAGTTCGATG TAACCCACTC GTGCACCCAA

6851 CTGATCTTCA GCATCTTTTA CTTTCACCAG CGTTTCTGGG TGAGCAAAAA

6901 CAGGAAGGCA AAATGCCGCA AAAAAGGGAA TAAGGGCGAC ACGGAAATGT

6951 TGAATACTCA TACTCTTCCT TTTTCAATAT TATTGAAGCA TTTATCAGGG

7001 TTATTGTCTC ATGAGCGGAT ACATATTTGA ATGTATTTAG AAAAATAAAC

7051 AAATAGGGGT TCCGCGCACA TTTCCCCGAA AAGTGCCACC TGACGTCGAC

7101 GGATCGGG
```

TABLE 12

Sequence of the recombinant plasmid pQE30-H-SemaL-BH
(SEQ ID NO.:39)

```
   1 CTCGAGAAAT CATAAAAAAT TTATTTGCTT TGTGAGCGGA TAACAATTAT
  51 AATAGATTCA ATTGTGAGCG GATAACAATT TCACACAGAA TTCATTAAAG
 101 AGGAGAAATT AACTATGAGA GGATCGCATC ACCATCACCA TCACGGAtcc
 151 ctggttctgt ttgaagggga cgaggtgtat tccaccatcc ggaagcagga
 201 atacaatggg aagatccctc ggttccgccg catccggggc gagagtgagc
 251 tgtacaccag tgatactgtc atgcagaacc cacagttcat caaagccacc
 301 atcgtgcacc aagaccaggc ttacgatgac aagatctact acttcttccg
 351 agaggacaat cctgacaaga atcctgaggc tcctctcaat gtgtcccgtg
 401 tggcccagtt gtgcagggggg gaccagggtg gggaaagttc actgtcagtc
 451 tccaagtgga acacttttct gaaagccatg ctggtatgca gtgatgctgc
 501 caccaacaag aacttcaaca ggctgcaaga cgtcttcctg ctccctgacc
 551 ccagcggcca gtggagggac accagggtct atggtgtttt ctccaacccc
 601 tggaactact cagccgtctg tgtgtattcc ctcggtgaca ttgacaaggt
 651 cttccgtacc tcctcactca agggctacca ctcaagcctt cccaacccgc
 701 ggcctggcaa gtgcctccca gaccagcagc cgatacccac agaAAGCTTA
 751 ATTAGCTGAG CTTGGACTCC TGTTGATAGA TCCAGTAATG ACCTCAGAAC
 801 TCCATCTGGA TTTGTTCAGA ACGCTCGGTT GCCGCCGGGC GTTTTTTATT
 851 GGTGAGAATC CAAGCTAGCT TGGCGAGATT TTCAGGAGCT AAGGAAGCTA
 901 AAATGGAGAA AAAAATCACT GGATATACCA CCGTTGATAT ATCCCAATGG
 951 CATCGTAAAG AACATTTTGA GGCATTTCAG TCAGTTGCTC AATGTACCTA
1001 TAACCAGACC GTTCAGCTGG ATATTACGGC CTTTTTAAAG ACCGTAAAGA
1051 AAAATAAGCA CAAGTTTTAT CCGGCCTTTA TTCACATTCT TGCCCGCCTG
1101 ATGAATGCTC ATCCGGAATT TCGTATGGCA ATGAAAGACG GTGAGCTGGT
1151 GATATGGGAT AGTGTTCACC CTTGTTACAC CGTTTTCCAT GAGCAAACTG
1201 AAACGTTTTC ATCGCTCTGG AGTGAATACC ACGACGATTT CCGGCAGTTT
1251 CTACACATAT ATTCGCAAGA TGTGGCGTGT TACGGTGAAA ACCTGGCCTA
1301 TTTCCCTAAA GGGTTTATTG AGAATATGTT TTTCGTCTCA GCCAATCCCT
1351 GGGTGAGTTT CACCAGTTTT GATTTAAACG TGGCCAATAT GGACAACTTC
1401 TTCGCCCCCG TTTTCACCAT GGGCAAATAT TATACGCAAG GCGACAAGGT
1451 GCTGATGCCG CTGGCGATTC AGGTTCATCA TGCCGTCTGT GATGGCTTCC
1501 ATGTCGGCAG AATGCTTAAT GAATTACAAC AGTACTGCGA TGAGTGGCAG
1551 GGCGGGGCGT AATTTTTTTA AGGCAGTTAT TGGTGCCCTT AAACGCCTGG
1601 GGTAATGACT CTCTAGCTTG AGGCATCAAA TAAAACGAAA GGCTCAGTCG
1651 AAAGACTGGG CCTTTCGTTT TATCTGTTGT TTGTCGGTGA ACGCTCTCCT
1701 GAGTAGGACA AATCCGCCGC TCTAGAGCTG CCTCGCGCGT TTCGGTGATG
1751 ACGGTGAAAA CCTCTGACAC ATGCAGCTCC CGGAGACGGT CACAGCTTGT
1801 CTGTAAGCGG ATGCCGGGAG CAGACAAGCC CGTCAGGGCG CGTCAGCGGG
1851 TGTTGGCGGG TGTCGGGGCG CAGCCATGAC CCAGTCACGT AGCGATAGCG
```

TABLE 12-continued

Sequence of the recombinant plasmid pQE30-H-SemaL-BH
(SEQ ID NO.:39)

```
1901 GAGTGTATAC TGGCTTAACT ATGCGGCATC AGAGCAGATT GTACTGAGAG
1951 TGCACCATAT GCGGTGTGAA ATACCGCACA GATGCGTAAG GAGAAAATAC
2001 CGCATCAGGC GCTCTTCCGC TTCCTCGCTC ACTGACTCGC TGCGCTCGGT
2051 CTGTCGGCTG CGGCGAGCGG TATCAGCTCA CTCAAAGGCG GTAATACGGT
2101 TATCCACAGA ATCAGGGGAT AACGCAGGAA AGAACATGTG AGCAAAAGGC
2151 CAGCAAAAGG CCAGGAACCG TAAAAAGGCC GCGTTGCTGG CGTTTTTCCA
2201 TAGGCTCCGC CCCCCTGACG AGCATCACAA AAATCGACGC TCAAGTCAGA
2251 GGTGGCGAAA CCCGACAGGA CTATAAAGAT ACCAGGCGTT TCCCCCTGGA
2301 AGCTCCCTCG TGCGCTCTCC TGTTCCGACC CTGCCGCTTA CCGGATACCT
2351 GTCCGCCTTT CTCCCTTCGG AAGCGTGGC GCTTTCTCAA TGCTCACGCT
2401 GTAGGTATCT CAGTTCGGTG TAGGTCGTTC GCTCCAAGCT GGGCTGTGTG
2451 CACGAACCCC CCGTTCAGCC CGACCGCTGC GCCTTATCCG GTAACTATCG
2501 TCTTGAGTCC AACCCGGTAA GACACGACTT ATCGCCACTG GCAGCAGCCA
2551 CTGGTAACAG GATTAGCAGA GCGAGGTATG TAGGCGGTGC TACAGAGTTC
2601 TTGAAGTGGT GGCCTAACTA CGGCTACACT AGAAGGACAG TATTTGGTAT
2651 CTGCGCTCTG CTGAAGCCAG TTACCTTCGG AAAAAGAGTT GGTAGCTCTT
2701 GATCCGGCAA ACAAACCACC GCTGGTAGCG GTGGTTTTTT TGTTTGCAAG
2751 CAGCAGATTA CGCGCAGAAA AAAAGGATCT CAAGAAGATC CTTTGATCTT
2801 TTCTACGGGG TCTGACGCTC AGTGGAACGA AAACTCACGT TAAGGGATTT
2851 TGGTCATGAG ATTATCAAAA AGGATCTTCA CCTAGATCCT TTTAAATTAA
2901 AAATGAAGTT TTAAATCAAT CTAAAGTATA TATGAGTAAA CTTGGTCTGA
2951 CAGTTACCAA TGCTTAATCA GTGAGGCACC TATCTCAGCG ATCTGTCTAT
3001 TTCGTTCATC CATAGCTGCC TGACTCCCCG TCGTGTAGAT AACTACGATA
3051 CGGGAGGGCT TACCATCTGG CCCCAGTGCT GCAATGATAC CGCGAGACCC
3101 ACGCTCACCG GCTCCAGATT TATCAGCAAT AAACCAGCCA GCCGGAAGGG
3151 CCGAGCGCAG AAGTGGTCCT GCAACTTTAT CCGCCTCCAT CCAGTCTATT
3201 AATTGTTGCC GGGAAGCTAG AGTAAGTAGT TCGCCAGTTA ATAGTTTGCG
3251 CAACGTTGTT GCCATTGCTA CAGGCATCGT GGTGTCACGC TCGTCGTTTG
3301 GTATGGCTTC ATTCAGCTCC GGTTCCCAAC GATCAAGGCG AGTTACATGA
3351 TCCCCCATGT TGTGCAAAAA AGCGGTTAGC TCCTTCGGTC CTCCGATCGT
3401 TGTCAGAAGT AAGTTGGCCG CAGTGTTATC ACTCATGGTT ATGGCAGCAC
3451 TGCATAATTC TCTTACTGTC ATGCCATCCG TAAGATGCTT TTCTGTGACT
3501 GGTGAGTACT CAACCAAGTC ATTCTGAGAA TAGTGTATGC GGCGACCGAG
3551 TTGCTCTTGC CCGGCGTCAA TACGGGATAA TACCGCGCCA CATAGCAGAA
3601 CTTTAAAAGT GCTCATCATT GGAAAACGTT CTTCGGGGCG AAAACTCTCA
3651 AGGATCTTAC CGCTGTTGAG ATCCAGTTCG ATGTAACCCA CTCGTGCACC
3701 CAACTGATCT TCAGCATCTT TTACTTTCAC CAGCGTTTCT GGGTGAGCAA
3751 AAACAGGAAG GCAAAATGCC GCAAAAAAGG GAATAAGGGC GACACGGAAA
```

TABLE 12-continued

Sequence of the recombinant plasmid pQE30-H-SemaL-BH
(SEQ ID NO.:39)

3801 TGTTGAATAC TCATACTCTT CCTTTTTCAA TATTATTGAA GCATTTATCA

3851 GGGTTATTGT CTCATGAGCG ATACATATT TGAATGTATT TAGAAAAATA

3901 AACAAATAGG GGTTCCGCGC ACATTTCCCC GAAAAGTGCC ACCTGACGTC

3951 TAAGAAACCA TTATTATCAT GACATTAACC TATAAAAATA GGCGTATCAC

4001 GAGGCCCTTT CGTCTTCAC

TABLE 13

Sequence of the recombinant plasmid pQE31-H-SemaL-SH
(SEQ ID NO.:40)

1 CTCGAGAAAT CATAAAAAAT TTATTTGCTT TGTGAGCGGA TAACAATTAT

51 AATAGATTCA ATTGTGAGCG GATAACAATT TCACACAGAA TTCATTAAAG

101 AGGAGAAATT AACTATGAGA GGATCGCATC ACCATCACCA TCACACGGAT

151 CCGCATGCga gctcccagtg ggaggtgagc caggtgcccc tggacctgtg 201 tgaggtctat ggcgggggct gccacggttg cctcatgtcc cgagacccct 251 actgcggctg ggaccagggc cgctgcatct ccatctacag ctccgaacgg 301 tcagtgctgc aatccattaa tccagccgag ccacacaagg agtgtcccaa 351 ccccaaacca gacaaggccc cactgcagaa ggtttccctg gccccaaact 401 ctcgctacta cctgagctgc cccatggaat cccgccacgc cacctactca 451 tggcgccaca aggagaacgt ggagcagagc tgcgaacctg gtcaccagag 501 ccccaactgc atcctgttca tcgagaacct cacggcgcag cagtacggcc 551 actacttctg cgaggcccag gagggctcct acttccgcga ggctcagcac 601 tggcagctgc tgcccgagga cggcatcatg gccgagcacc tgctgggtca 651 tgcctgtgcc ctggctgcct ccctctggct gggggtgctg cccacactca 701 ctcttggctt gctggtccac gtgaagcttA ATTAGCTGAG CTTGGACTCC

751 TGTTGATAGA TCCAGTAATG ACCTCAGAAC TCCATCTGGA TTTGTTCAGA

801 ACGCTCGGTT GCCGCCGGGC GTTTTTTATT GGTGAGAATC CAAGCTAGCT

851 TGGCGAGATT TTCAGGAGCT AAGGAAGCTA AAATGGAGAA AAAATCACT

901 GGATATACCA CCGTTGATAT ATCCCAATGG CATCGTAAAG AACATTTTGA

951 GGCATTTCAG TCAGTTGCTC AATGTACCTA TAACCAGACC GTTCAGCTGG

1001 ATATTACGGC CTTTTTAAAG ACCGTAAAGA AAAATAAGCA CAAGTTTTAT

1051 CCGGCCTTTA TTCACATTCT TGCCCGCCTG ATGAATGCTC ATCCGGAATT

1101 TCGTATGGCA ATGAAAGACG GTGAGCTGGT GATATGGGAT AGTGTTCACC

1151 CTTGTTACAC CGTTTTCCAT GAGCAAACTG AAACGTTTTC ATCGCTCTGG

1201 AGTGAATACC ACGACGATTT CCGGCAGTTT CTACACATAT ATTCGCAAGA

1251 TGTGGCGTGT TACGGTGAAA ACCTGGCCTA TTTCCCTAAA GGGTTTATTG

1301 AGAATATGTT TTTCGTCTCA GCCAATCCCT GGGTGAGTTT CACCAGTTTT

1351 GATTTAAACG TGGCCAATAT GGACAACTTC TTCGCCCCCG TTTTCACCAT

1401 GGGCAAATAT TATACGCAAG GCGACAAGGT GCTGATGCCG CTGGCGATTC

TABLE 13-continued

Sequence of the recombinant plasmid pQE31-H-SemaL-SH
(SEQ ID NO.:40)

```
1451 AGGTTCATCA TGCCGTCTGT GATGGCTTCC ATGTCGGCAG AATGCTTAAT

1501 GAATTACAAC AGTACTGCGA TGAGTGGCAG GGCGGGGCGT AATTTTTTTA

1551 AGGCAGTTAT TGGTGCCCTT AAACGCCTGG GGTAATGACT CTCTAGCTTG

1601 AGGCATCAAA TAAAACGAAA GGCTCAGTCG AAAGACTGGG CCTTTCGTTT

1651 TATCTGTTGT TTGTCGGTGA ACGCTCTCCT GAGTAGGACA AATCCGCCGC

1701 TCTAGAGCTG CCTCGCGCGT TTCGGTGATG ACGGTGAAAA CCTCTGACAC

1751 ATGCAGCTCC CGGAGACGGT CACAGCTTGT CTGTAAGCGG ATGCCGGGAG

1801 CAGACAAGCC CGTCAGGGCG CGTCAGCGGG TGTTGGCGGG TGTCGGGGCG

1851 CAGCCATGAC CCAGTCACGT AGCGATAGCG GAGTGTATAC TGGCTTAACT

1901 ATGCGGCATC AGAGCAGATT GTACTGAGAG TGCACCATAT GCGGTGTGAA

1951 ATACCGCACA GATGCGTAAG GAGAAAATAC CGCATCAGGC GCTCTTCCGC

2001 TTCCTCGCTC ACTGACTCGC TGCGCTCGGT CGTTCGGCTG CGGCGAGCGG

2051 TATCAGCTCA CTCAAAGGCG GTAATACGGT TATCCACAGA ATCAGGGGAT

2101 AACGCAGGAA AGAACATGTG AGCAAAAGGC CAGCAAAAGG CCAGGAACCG

2151 TAAAAAGGCC GCGTTGCTGG CGTTTTTCCA TAGGCTCCGC CCCCCTGACG

2201 AGCATCACAA AAATCGACGC TCAAGTCAGA GGTGGCGAAA CCCGACAGGA

2251 CTATAAAGAT ACCAGGCGTT TCCCCCTGGA AGCTCCCTCG TGCGCTCTCC

2301 TGTTCCGACC CTGCCGCTTA CCGGATACCT GTCCGCCTTT CTCCCTTCGG

2351 GAAGCGTGGC GCTTTCTCAA TGCTCACGCT GTAGGTATCT CAGTTCGGTG

2401 TAGGTCGTTC GCTCCAAGCT GGGCTGTGTG CACGAACCCC CCGTTCAGCC

2451 CGACCGCTGC GCCTTATCCG GTAACTATCG TCTTGAGTCC AACCCGGTAA

2501 GACAGGACTT ATCGCCACTG GCAGCAGCCA CTGGTAACAG GATTAGGAGA

2551 GCGAGGTATG TAGGCGGTGC TACAGAGTTC TTGAAGTGGT GGCCTAACTA

2601 CGGCTACACT AGAAGGACAG TATTTGGTAT CTGCGCTCTG CTGAAGCCAG

2651 TTACCTTCGG AAAAAGAGTT GGTAGCTCTT GATCCGGCAA ACAAACCACC

2701 GCTGGTAGCG GTGGTTTTTT TGTTTGCAAG CAGCAGATTA CGCGCAGAAA

2751 AAAAGGATCT CAAGAAGATC CTTTGATCTT TTCTACGGGG TCTGACGCTC

2801 AGTGGAACGA AAACTCACGT TAAGGGATTT TGGTCATGAG ATTATCAAAA

2851 AGGATCTTCA CCTAGATCCT TTTAAATTAA AAATGAAGTT TTAAATCAAT

2901 CTAAAGTATA TATGAGTAAA CTTGGTCTGA CAGTTACCAA TGCTTAATCA

2951 GTGAGGCACC TATCTCAGCG ATCTGTCTAT TTCGTTCATC CATAGCTGCC

3001 TGACTCCCCG TCGTGTAGAT AACTACGATA CGGGAGGGCT TACCATCTGG

3051 CCCCAGTGCT GCAATGATAC CGCGAGACCC ACGCTCACCG GCTCCAGATT

3101 TATCAGCAAT AAACCAGCCA GCCGGAAGGG CCGAGCGCAG AAGTGGTCCT

3151 GCAACTTTAT CCGCCTCCAT CCAGTCTATT AATTGTTGCC GGGAAGCTAG

3201 AGTAAGTAGT TCGCCAGTTA ATAGTTTGCG CAACGTTGTT GCCATTGCTA

3251 CAGGCATCGT GGTGTCACGC TCGTCGTTTG GTATGGCTTC ATTCAGCTCC

3301 GGTTCCCAAC GATCAAGGCG AGTTACATGA TCCCCCATGT TGTGCAAAAA
```

TABLE 13-continued

Sequence of the recombinant plasmid pQE31-H-SemaL-SH
(SEQ ID NO.:40)

```
3351 AGCGGTTAGC TCCTTCGGTC CTCCGATCGT TGTCAGAAGT AAGTTGGCCG
3401 CAGTGTTATC ACTCATGGTT ATGGCAGCAC TGCATAATTC TCTTACTGTC
3451 ATGCCATCCG TAAGATGCTT TTCTGTGACT GGTGAGTACT CAACCAAGTC
3501 ATTCTGAGAA TAGTGTATGC GGCGACCGAG TTGCTCTTGC CCGGCGTCAA
3551 TACGGGATAA TACCGCGCCA CATAGCAGAA CTTTAAAAGT GCTCATCATT
3601 GGAAAACGTT CTTCGGGGCG AAAACTCTCA AGGATCTTAC CGCTGTTGAG
3651 ATCCAGTTCG ATGTAACCCA CTCGTGCACC CAACTGATCT TCAGCATCTT
3701 TTACTTTCAC CAGCGTTTCT GGGTGAGCAA AAACAGGAAG GCAAAATGCC
3751 GCAAAAAAGG GAATAAGGGC GACACGGAAA TGTTGAATAC TCATACTCTT
3801 CCTTTTTCAA TATTATTGAA GCATTTATCA GGGTTATTGT CTCATGAGCG
3851 GATACATA1T TGAATGTATT TAGAAAAATA AACAAATAGG GGTTCCGCGC
3901 ACATTTCCCC GAAAAGTGCC ACCTGACGTC TAAGAAACCA TTATTATCAT
3951 GACATTAACC TATAAAAATA GGCGTATCAC GAGGCCCTTT CGTCTTCAC
```

TABLE 14

(Partial) nucleotide sequence of the human semaphorin L gene.
(8888 nucleotides) (SEQ ID NO.:41):

```
GAGCCGCACACGGTGCTTTTCCACGAGCCAGGCAGCTCCTCTGTGTGGGTGGGAGGACGT
GGCAAGGTCTACCTCTTTGACTTCCCCGAGGGCAAGAACGCATCTGTGCGCACGGTGAGC
CTCTCTCTTCCCCCAACACCCCCCCTACCCTCTTATCTCCCCTCTGGCCCTGCCAAGGGT
CCTCAGGGAATCCGAGGGAGCTGGCTTCTCTTCCTAAACTGCCCCCACCTCCGTATCCTA
TAAATGGCTCCTGGGGGAGGCTCCCTAAAGGTAGTCCAGATTGGAGTGGGGAGCTGGGGC
GGTGTGGAGAAAAACAGGAGCTAATGGGCCTGGCCAGCTGGGCAGCGCTGCTGCGGAAAG
CCCAGGCTGGAAGCTGGGCCCCAGAGCCCATGCCTGGTCTTCTGAACCCTCTGGGCCTCA
GCTCTGGATATGAGACCCTGTTTGACCTCAGGTAGATCACTCACCCTCTCAGAGCCCCAG
TTGCTCATCTGTCAGATGAGAATAATGGTTGCTTCCTTTGGGGCTTATCCTGAGGCTGTG
TGGAAAGCATTTCAGGGGTACCTCACCCCTGGCAGATTGAACTAATGCTTCTCCCCTTCC
CCAGGTGAATATCGGCTCCACAAAGGGGTCCTGTCTGGATAAGCGGGTGAGCGGGGGAGG
GATCTGGAGGGGTCTGAGCCACTTGGTAAAGGGAGAGGAGACCCTGAGGGTCTAAGGAAG
GAAGCATGGCCCTGCCCCACGAGTCCCAGACTGATGGGGAGACGTGGTCCTCTGTGCTTA
GGGGATGGCGTCAGCTGCACACACTCTGGGCTGTCCCGGAGGCTGTCACCTATGCTAAG
CCCTTCTGACACCTTCTTCCCTGATCCTGGGGGTCCTAGTGCTAGGCTTGCCAGGGCCTT
CCAGCAACCAATTTCTCTCCTCCCTTCTCTCTTCCCCGGGCAGGACTGCGAGAACTACAT
CACTCTCCTGGAGAGGCGGAGTGAGGGCTGCTGGCCTGTGGCACCAACGCCCGGCACCC
CAGCTGCTGGAACCTGGTGAGAAGGCTGCTCCCCATGTGCCTGATCAGCTCACCTTCTAC
TGCGTGGGCTTCTGCCCCTCATGGTGGGAAGGAGATGGCGAGACTCCAATGCTGGCCTTG
CCCTGGGAGGATGGGGCTCCTGGCCGAGAAACTGGCCGTCATGGGAGGCAGTGGCTGTGG
GATTATGTGGCCATCCAACCCTCTGGATCTCCCACAGGTGAATGGCACTGTGGTGCCACT
```

TABLE 14-continued (Partial) nucleotide sequence of the human semaphorin L gene.
(8888 nucleotides) (SEQ ID NO.:41):

TGGCGAGATGAGAGGCTACGCCCCCTTCAGCCCGGACGAGAACTCCCTGGTTCTGTTTGA

AGGTTGGGGCATGCTTCGGAACTGGGCTGGGAGCAGGATGGTCAGCTCTTTGTCCAGTGT

CCGGAGGAGGGACTTCCAGGAGCTGCCTGCCCTTACTCATTTCTCCCTCCCACTGACCCC

AGGGGACGAGGTGTATTCCACCATCCGGAAGCAGGAATACAATGGGAAGATCCCTCGGTT

CCGCCGCATCCGGGGCGAGAGTGAGCTGTACACCAGTGATACTGTCATGCAGAGTGAGTC

AGGCTCCGGCTGGGCTGAGGGTGGGCAAGGGGGTGTGAGCACTTAAGGTGGCAGATGGGA

TCCTGATGTTTCTGGGAGGGCTCCCTGAGGGCCGCTGGGGCCATGCAGGAAAGCAGGACC

TTGGTATAGGCCTGAGAAGTTAGGGTTGGCTGGGAGCAGAGGAACAGACAAGGTATAGCA

GTGGGATGGGCCCAGCCCTCTTCAGGAACACAAACAGAGGGAGCCCCAGACCCAGTGCAG

GGTCCCCAGGAGCCAAAGTTTATCCTCTGCTGAGTTCACGTGGAGGCAGCCCCCCAACTC

CCTCCTCATCAGGGCTCTGCCAATTGAGCAGAAGTGACATAGGGGCCCCAGGGACCTTC

CCCCACTCCCCAGGCATGAAGTCATTGCTCCTGGGCCGATGACATCTTTGTAGGAAGAGG

GCAAAACAGGTGTGGGGTGGAGGTGCAGGGTCTAGGGCCCCTCGGGGAGTTGGACCTGAT

GTTATGAGTCCTATTCCAGATCTGATTTGCCATGGTTTGTGCAGACCCGAAGGAGGGAGG

AGAGTGTGCAGGGTTGGAATGGTCTCCCGGGCAAGCTTCCCAGCCTTACGCCCATTCGCT

TCTGTGCCCTGGCAGACCCACAGTTCATCAAAGCCACCATCGTGCACCAAGACCAGGCTT

ACGATGACAAGATCTACTACTTCTTCCGAGAGGACAATCCTGACAAGAATCCTGAGGCTC

CTCTCAATGTGTCCCGTGTGGCCCAGTTGTGCAGGGTGAACACGGGCGTGAGGGCTGCTG

GCTACGTGTCTGTGCATGAATAGGCCTGAGTGAGGGTGAGTTCTGTGTGTCCGTGTGCAT

GTAGAAGTTGTGTGGATGTATGAGTGGGTCTGTGTCAGGGACTGTGGGAGCAGCTGTGTG

TGCATGGAGCATCATGTGTCTGTGTGTGGGTAAAGGTGGCTGAGCTCCTGTGCACGTATG

ATGGCGTGTGAGCGTGTGTATGATGGGGTGTGTGTGTGTGTGTGTGTGTTTTGCCT

GTGTGAATGTGCTGTGCCACGTATGTGGGTGCGTGAGTCAGTAAATGTGTGTCTGAGTCC

GTCTGCTCTGTGGGGACCTGGCACTCTCACCTGCCCTGACCCTGGGCACTGCTGGCCCTG

GGCTCTGGATCAGCCAGGCCTGCTTGCAGGAGTCTCATCTGGAGACCTGCCCTGAGTCCT

GGGGCACCCCCGGCAGGTCCTGGCCCCTCGCAGCCTGCCTTCCTCCTCTGGGCCCAGGTG

TTGATATTGCTGGCAGTGGTTTCCTGGGGTGTGTGGGGAAGCCCGGGCAGGTGCTGAGGG

GCCTCTTCTCCCCTCTACCCTTCCAGGGGGACCAGGGTGGGGAAAGTTCACTGTCAGTCT

CCAAGTGGAACACTTTTCTGAAAGCCATGCTGGTATGCAGTGATGCTGCCACCAACAAGA

ACTTCAACAGGCTGCAAGACGTCTTCCTGCTCCCTGACCCCAGCGGCCAGTGGAGGGACA

CCAGGGTCTATGGTGTTTTCTCCAACCCCTGGTGAGTGGCCCTTGTCCTGGGCCGGGGC

TGGCATTGGTTCAGTGTCCAGTAGGGACAGGAGGCCTTGGGCCCTGCTGAGGGCCTCCCT

GGTGTGGCAGGAGCAGGGGCTGCAGGCTCAAGAGGCTGGGCTGTTGCTGGGTGTGGGGTG

GGGGGACAGCCAGTGCGATGTATGTACTGTTGTGTGAGTGAGTCTGCACTCATGGGTGTG

TGTGCATGCCCTATATGCACACTCATGACTGCACTTGTGCCTGTGTGTCCCACCACCTGC

TTGTGCCGAGAGTGGACACTGGGCCCAGGAGGAAGCTGCTGAAGCATCTCTCGGGGAGCT

GGGTGCTATTACACCTGCTCAGGCACTGCCTGAGCCCGATAATTCACACTTCTTAATCAC

TCTCATTGATTGAACACACGGCAGGCGGAAGTGTTGGGTGTGTGTGGGGAGAGTTAGGGA

TABLE 14-continued (Partial) nucleotide sequence of the human semaphorin L gene.
(8888 nucleotides) (SEQ ID NO.:41):

TAGAGTGGAGGAAGCCAAGACCCTGCTCTGTGGCTCCTGGGTGAGTGGGTCCCCCAGGCT

GGGAAGGGGTTGGGGGTCTGGCCTCCTGGGGCATCAGCACCCCACAGCCTGTGCCCAGGG

AGGGCTAGAGAACTGCTCAGCCTATGATGGGGTTCCTCCTGCCTTGGGGTTGGGTAGAGC

AGATGGCCTCTAGACTCAGTGATTCTGTAACAGGATACAAGTTTGTGGTTTTAAATTGCA

GCACAAAGAAATTAGGCTGAACTCCTCTCCTTCCTCCTCTCCATCCCTCCCCATTTTCAG

TGGTGGTTGGCAACTCAGTGCCAGGCACAAGGCTGGCCTGGGTGAGTGGAGGTGGATGGG

TGGGTTCTGGGCCCCCCATTGAGCTGGTCTCCATGTCACTGCAGGAACTACTCAGCCGTC

TGTGTGTATTCCCTCGGTGACATTGACAAGGTCTTCCGTACCTCCTCACTCAAGGGCTAC

CACTCAAGCCTTCCCAACCCGCGGCCTGGCAAGGTGAGCGTGACACCAGCCGTGGCCCAG

GCCCAGCCCTCCTTCTGCCTCACCTCCCACCACCCCACTGACCTGGGCCTGCTCTCCTTG

CCCAGTGCCTCCCAGACCAGCAGCCGATACCCACAGAGACCTTCCAGGTGGCTGACCGTC

ACCCAGAGGTGGCGCAGAGGGTGGAGCCCATGGGGCCTCTGAAGACGCCATTGTTCCACT

CTAAATACCACTACCAGAAAGTGGCCGTCCACCGCATGCAAGCCAGCCACGGGGAGACCT

TTCATGTGCTTTACCTAACTACAGGTGAGAGGCTACCCCGGGACCCTCAGTTTGCTTTGT

AAAAACGGGCATGAAAGGTGTAAGGAATAATGTAGTTAACATCTGGTTGGATCTTTACAT

GTGGAAGGAATAATTGAGTGACTGGAGTTGTCAGGGGTTAATGTGTGTGGGTGTGGAAGA

GCCAGGCAGGGAGAGCTTCCTGGAGGAGGTAGGGGCAAGAGGGAAAGGGGGATGGGAGAA

AAGCAAGCACTGGGATTTGGAGGCGGAAATCTGGAGAGTCTGAGCAAAGCCAGGTGCACC

TTTGGTCCAGATGTCTGACTCAGGGAAGAAGATGGTAGGAAGAGACGTGGCAAATGAGGA

GGAGGGGCCTGAACCACAGGGATACTGGCCTCTGCCAGGCAGAATGAGGGAGTCAGGCCC

TGCGCCTGTCTTTGGGATTGTGCAGGTGAGAAGAAACATTTGAGGAGTTGATGGGGCACA

AATTAGGTATGGGAAGGAGTTCCAGGGGGCAGAACCTTTGCCATCTCACAGAGGACAGG

GGCAGCTTCTCTTCTTCCCTGGAGTAGGCCCTGCTGGGGGAAGCTGGGTGGAATGCCGTG

GGAGATGCTCCTGCTTTCTGGAAAGCCACAGGACACGGAGGAGCCAGTCCTGAGTTGGGT

TTGTCGCAGCTTCCCATGCCAGCTGCCTTCCTTGAGACTGGAAAGGGCCTCTAGCACCCC

TGGGGCCATTCAATTCAGGCCCAGGCGCCCAACCTCAGTTGTTCACATTCCCCATGTGAT

CTCCTGTTGCTGCTTCACCTTGGGACTGTCTCGGCTTTGGTGACCTTGTAGGAAACTGGA

ACCCCAGCACCATTGTTTGGCTCCTGGAAGCCTTGGGGAGAGGAATTTCCCACAGGGCAG

GGCCTGGGTCCTGATTCCCTGCCTCTTTACTCCCTATTCATCCCGGCTACACCCTTGGGC

CCCCATCCTTGCTTGGCTCCAGTACTGGCTGGCACAGCTGTTGTGGTCATCCAGGGATGG

CAGGGCACTGGGGAACAGAAGAGAGAGGTCACACAGTGCGGAACTGGGAGCAGGAGCTAG

GACAAGGAAGGCTGGACTTGGGCCATGGATTCCCTTCCTGCAGACTTGGGAAGTGAGCAC

ACTTGAGTGATTAGAGAAGGTGTCTTCGTTCTAAGGGCAGTGGAGGAGGCACCATTTTGG

AGCCTGCATCATTCGTATTTGGGCTAGATTGAAAAATAGAGCTTTCTAAGTCCTCTGCAG

AGAATGGAGGCTCTCACAACTGGGAGAAGTATTGGCTCTTTTCCTGAGAATTTTGCCAA

GGGTATGCTGTTACTGGGGCTGGTTTGGAAGGAGTATAGGGCATTATGTCTGTGAAGGCA

GTGGCTGGGTGGGGCCTTATCAGGCCCAAGGAGCATCTGGCCACATCTCAGAGTCCACA

GATGAGGATCACGGATGTGTAGAGGAAACATCCTAGGCAGGCAATCATCTGACTGCTTTT

TABLE 14-continued (Partial) nucleotide sequence of the human semaphorin L gene.
(8888 nucleotides) (SEQ ID NO.:41):

TTGGGGCAGGTGATGCCCTGGGAAATTGGGAGGGAGGGAGAGAGGGAGGTAGGCTATTCT

AGAAACTGGGAGAGCAGGTGAGGTAGGATTGGGAGGACCAGGGGTCAGGGTCCCCATTGG

TCCCTAATTGAGAACGGAGAGAGCATTGGTCTAGGAGGCAGGCAGCTCGGTTATAAGACC

TTGGGAACTCTTGATTTAGAATCCAAGATCCTTTTTAGATCTAGGATTTTATAAAATTAA

GATATCCCCTAAGATCAAATGCAACGTGGAGTCCTGAATTGGATCCTAGAACAGAAGAAG

GACATTTGTGGAAAAACTAGTGAAATCCAAATAAAGTCTGTAGTTTTGTTAATAGTAATG

CACCAATGTCAGTTGCCTAGTTGTGACAAATATACCGTGGTTATGTAAGATGGTAACATT

AGGGGGAACTGGAGAAGGGTAGATTGGAGCTCTCTGTACTATCTTTGCAACTTTTCTGGG

AATCTAAAATTACTCCAAAATAAAAAAAAAATGTATTTAAAGTAAATATATTCCCTAAGA

GTCCAGGAGGCAGGGGAGTTGTAGAAGCAGCTGAGTGGTTGGGTTCTGACAGATTTGGTT

CCAACTCGGTCTCTGCTGCTCACCAGCTGTGTGACCTTGAGCAAGTGGCTTAGCCTTTCT

GAGCCTGATTTCCTTATCTGTGGAGTGGGGAAGATGACAGCCACCTCGCAGGGCTGTGGA

GGGTTAAACGAGGTGATGCATGGACAGCAGCCGCACTGACCTTGCTGGTGTGGGGCTCCT

GCTTCTGTTCTTCCCGTGCAGCCTTGGGAATGTTGGAGGCCGTATCCAGGGACCCCTGGG

CCTCCTGGGATGGCCTCTCTGGATCAGCCTTGGAAGGTTCCAGGCTGCCCTTAGGCTCCC

ACATTCTTCCCCAGTCACGCTCTCCTCGCCCTGCCCACACCAGTCCTGTGACCCTTGCCT

GAGTTGTGACTTCCCACCCCTCCCCGGCCTAGAGGAAAGCTGCCTGGCCCCTCAGTGGGA

CTCCCGCCCACTGACCCTCTGTCCACCATACACAGACAGGGGCACTATCCACAAGGTGGT

GGAACCGGGGAGCAGGAGCACAGCTTCGCCTTCAACATCATGGAGATCCAGCCCTTCCG

CCGCGCGGCTGCCATCCAGACCATGTCGCTGGATGCTGAGCGGGTGAGCCTTCCCCCACT

GCGTCCCATGGGCTATGCAGTGACTGCAGCTGAGGACAGGGCTCCTTTGCATGTGATTTG

TGTGTTCTTTTAAGAGCTTCTAGGCCTTAGGGCCTGGACATTTAGGACTGAGTGTGGGGT

GGGGCCCGGGCCTGACCCAATCCTGCTGTCCTTCCAGAGGAAGCTGTATGTGAGCTCCCA

GTGGGAGGTGAGCCAGGTGCCCCTGGACCTGTGTGAGGTCTATGGCGGGGGCTGCCACGG

TTGCCTCATGTCCCGAGACCCCTACTGCGGCTGGGACCAGGGCCGCTGCATCTCCATCTA

CAGCTCCGAACGGTACGTTGGCCGGGATCCCTCCGTCCCTGGGACAAGGTGGGCATGGGA

CAGGGGGAGGTGTTGTCGGGCTGGAAGAGGTGGCGGTACTGGGCCTTCTTTGTGGGACCT

CCTCTCTACTGGAACTGCACTAGGGGTAAGGATATGAGGGTCAGGTCTGCAGCCTTGTAT

CTGCTGATCCTCTTTCGTCCTTCCCACTCCAGGTCAGTGCTGCAATCCATTAATCCAGCC

GAGCCACACAAGGAGTGTCCCAACCCCAAACCAGGTACCTGATCTGGCCCTGCTGGCGGC

TGTGGCCCAATGAGTGGGGTACTGCCCTGCCCTGATTGTCCTGGTCTGAGGGAAACATGG

CCTTGTCCTGTGGGCCCCAGGTACATGGGCAGGATACAGTCCTGCAGAGGGAGCCCTCT

TGGTGGGATGAGCGAGACGGGAGAAAAAAGGAGGACGCTGAGGGCTGGGTTCCCCACGTT

CATTCAGAAGCCTTGTCCTGGGATCCCAGTCGGTGGGGAGGACACATCCTCCCCTGGGAG

CTCTTTGTCCCTCCTCACGGCTGCTTCCCCACTGCCTCCCCAGACAAGGCCCCACTGCAG

AAGGTTTCCCTGGCCCCAAACTCTCGCTACTACCTGAGCTGCCCCATGGAATCCCGCCAC

GCCACCTACTCATGGCGCCACAAGGAGAACGTGGAGCAGAGCTGCGAACCTGGTCACCAG

AGCCCCAACTGCATCCTGTTCATCGAGAACCTCACGGCGCAGCAGTACGCCACTACTTC

TABLE 14-continued (Partial) nucleotide sequence of the human semaphorin L gene.
(8888 nucleotides) (SEQ ID NO.:41):

TGCGAGGCCCAGGAGGGCTCCTACTTCCGCGAGGCTCAGCACTGGCAGCTGCTGCCCGAG

GACGGCATCATGGCCGAGCACCTGCTGGGTCATGCCTGTGCCCTGGCCGCCTCCCTCTGG

CTGGGGGTGCTGCCCACACTCACTCTTGGCTTGCTGGTCCACTAGGGCCTCCCGAGGCTG

GGCATGCCTCAGGCTTCTGCAGCCCAGGGCACTAGAACGTCTCACACTCAGAGCCGGCTG

GCCCGGGAGCTCCTTGCCTGCCACTTCTTCCAGGGGACAGAATAACCCAGTGGAGGATGC

CAGGCCTGGAGACGTCCAGCCGCAGGCGGCTGCTGGGCCCCAGGTGGCGCACGGATGGTG

AGGGGCTGAGAATGAGGGCACCGACTGTGAAGCTGGGGCATCGATGACCCAAGACTTTAT

CTTCTGGAAAATATTTTTCAGACTCCTCAAACTTGACTAAATGCAGCGATGCTCCCAGCC

CAAGAGCCCATGGGTCGGGGAGTGGGTTTGGATAGGAGAGCTGGGACTCCATCTCGACCC

TGGGGCTGAGGCCTGAGTCCTTCTGGACTCTTGGTACCCACATTGCCTCCTTCCCCTCCC

TCTCTCATGGCTGGGTGGCTGGTGTTCCTGAAGACCCAGGGCTACCCTCTGTCCAGCCCT

GTCCTCTGCAGCTCCCTCTCTGGTCCTGGGTCCCACAGGACAGCCGCCTTGCATGTTTAT

TGAAGGATGTTTGCTTTCCGGACGGAAGGACGGAAAAAGCTCTGAAAAAAAAAAAAAAA

AAAAAAA

TABLE 15

Nucleotide sequence of pMelBacA-H-SEMAL (6622 bp) (SEQ ID
NO:42)

```
  1 GATATCATGG AGATAATTAA AATGATAACC ATCTCGCAAA TAAATAAGTA
 51 TTTTACTGTT TTCGTAACAG TTTTGTAATA AAAAAACCTA TAAATATGAA
101 ATTCTTAGTC AACGTTGCCC TTGTTTTTAT GGTCGTATAC ATTTCTTACA
151 TCTATGCGGA TCGATGG
                         gga tccgcccagg gccacctaag gagcggaccc
201 cgcatcttcg ccgtctggaa aggccatgta gggcaggacc gggtggactt
251 tggccagact gagccgcaca cggtgctttt ccacgagcca ggcagctcct
301 ctgtgtgggt gggaggacgt ggcaaggtct acctctttga cttccccgag
351 ggcaagaacg catctgtgcg cacggtgaat atcggctcca caaaggggtc
401 ctgtctggat aagcgggact gcgagaacta catcactctc ctggagaggc
451 ggagtgaggg gctgctggcc tgtggcacca acgcccggca ccccagctgc
501 tggaacctgg tgaatggcac tgtggtgcca cttggcgaga tgagaggcta
551 tgcccccttc agcccggacg agaactccct ggttctgttt gaaggggacg
601 aggtgtattc caccatccgg aagcaggaat acaatgggaa gatccctcgg
651 ttccgccgca tccggggcga gagtgagctg tacaccagtg atactgtcat
701 gcagaaccca cagttcatca agccaccat cgtgcaccaa gaccaggctt
751 acgatgacaa gatctactac ttcttccgag aggacaatcc tgacaagaat
801 cctgaggctc ctctcaatgt gtcccgtgtg gcccagttgt gcaggggga
851 ccagggtggg gaaagttcac tgtcagtctc caagtggaac acttttctga
901 aagccatgct ggtatgcagt gatgctgcca ccaacaagaa cttcaacagg
```

TABLE 15-continued

| Nucleotide sequence of pMelBacA-H-SEMAL (6622 bp) (SEQ ID NO:42) |
| --- |
| 951 ctgcaagacg tcttcctgct ccctgacccc agcggccagt ggagggacac |
| 1001 cagggtctat ggtgttttct ccaacccctg gaactactca gccgtctgtg |
| 1051 tgtattccct cggtgacatt gacaaggtct tccgtacctc ctcactcaag |
| 1101 ggctaccact caagccttcc caacccgcgg cctggcaagt gcctcccaga |
| 1151 ccagcagccg atacccacag agaccttcca ggtggctgac cgtcacccag |
| 1201 aggtggcgca gagggtggag cccatggggc tctgaagac gccattgttc |
| 1251 cactctaaat accactacca gaaagtggcc gttcaccgca tgcaagccag |
| 1301 ccacggggag acctttcatg tgctttacct aactacagac aggggcacta |
| 1351 tccacaaggt ggtggaaccg ggggagcagg agcacagctt cgccttcaac |
| 1401 atcatggaga tccagcccct ccgccgcgcg gctgccatcc agaccatgtc |
| 1451 gctggatgct gagcggagga agctgtatgt gagctcccag tgggaggtga |
| 1501 gccaggtgcc cctggacctg tgtgaggtct atggcggggg ctgccacggt |
| 1551 tgcctcatgt cccgagaccc ctactgcggc tgggaccagg gccgctgcat |
| 1601 ctccatctac agctccgaac ggtcagtgct gcaatccatt aatccagccg |
| 1651 agccacacaa ggagtgtccc aaccccaaac cagacaaggc cccactgcag |
| 1701 aaggtttccc tggccccaaa ctctcgctac tacctgagct gccccatgga |
| 1751 atcccgccac gccacctact catggcgcca caaggagaac gtggagcaga |
| 1801 gctgcgaacc tggtcaccag agccccaact gcatcctgtt catcgagaac |
| 1851 ctcacggcgc agcagtacgg ccactacttc tgcgaggccc aggagggctc |
| 1901 ctacttccgc gaggctcagc actggcagct gctgcccgag gacggcatca |
| 1951 tggccgagca cctgctgggt catgcctgtg ccctggctgc ctgaattc |
| 2001 AGCTTGGAGT CGACTCTGCT GAAGAGGAGG AAATTCTCCT TGAAGTTTCC |
| 2051 CTGGTGTTCA AGTAAAGGA GTTTGGACCA GACGCACCTC TGTTCACTGG |
| 2101 TCCGGCGTAT TAAAACACGA TACATTGTTA TTAGTACATT TATTAAGCGC |
| 2151 TAGATTCTGT GCGTTGTTGA TTTACAGACA ATTGTTGTAC GTATTTTAAT |
| 2201 AATTCATTAA ATTTATAATC TTTAGGGTGG TATGTTAGAG CGAAAATCAA |
| 2251 ATGATTTTCA GCGTCTTTAT ATCTGAATTT AAATATTAAA TCCTCAATAG |
| 2301 ATTTGTAAAA TAGGTTTGGA TTAGTTTCAA ACAAGGGTTG TTTTTCCGAA |
| 2351 CCGATGGCTG GACTATCTAA TGGATTTTCG CTCAACGCCA CAAAACTTGC |
| 2401 CAAATCTTGT AGCAGCAATC TAGCTTTGTC GATATTCGTT TGTGTTTTGT |
| 2451 TTTGTAATAA AGGTTCGACG TCGTTCAAAA TATTATGCGC TTTTGTATTT |
| 2501 CTTTCATCAC TGTCGTTAGT GTACAATTGA CTCGACGTAA ACACGTTAAA |
| 2551 TAAAGCCTGG ACATATTTAA CATCGGGCGT GTTAGCTTTA TTAGGCCGAT |
| 2601 TATCGTCGTC GTCCCAACCC TCGTCGTTAG AAGTTGCTTC CGAAGACGAT |
| 2651 TTTGCCATAG CCACACGACG CCTATTAATT GTGTCGGCTA ACACGTCCGC |
| 2701 GATCAAATTT GTAGTTGAGC TTTTTGGAAT TATTTCTGAT TGCGGGCGTT |
| 2751 TTTGGGCGGG TTTCAATCTA ACTGTGCCCG ATTTTAATTC AGACAACACG |
| 2801 TTAGAAAGCG ATGGTGCAGG CGGTGGTAAC ATTTCAGACG GCAAATCTAC |

TABLE 15-continued

Nucleotide sequence of pMelBacA-H-SEMAL (6622 bp) (SEQ ID NO:42)

```
2851 TAATGGCGGC GGTGGTGGAG CTGATGATAA ATCTACCATC GGTGGAGGCG

2901 CAGGCGGGGC TGGCGGCGGA GGCGGAGGCG GAGGTGGTGG CGGTGATGCA

2951 GACGGCGGTT TAGGCTCAAA TTGTCTCTTT CAGGCAACAC AGTCGGCACC

3001 TCAACTATTG TACTGGTTTC GGGCGTATGG TGCACTCTCA GTACAATCTG

3051 CTCTGATGCC GCATAGTTAA GCCAGCCCCG ACACCCGCCA ACACCCGCTG

3101 ACGCGCCCTG ACGGGCTTGT CTGCTCCCGG CATCCGCTTA CAGACAAGCT

3151 GTGACCGTCT CCGGGAGCTG CATGTGTCAG AGGTTTTCAC CGTCATCACC

3201 GAAACGCGCG AGACGAAAGG GCCTCGTGAT ACGCCTATTT TTATAGGTTA

3251 ATGTCATGAT AATAATGGTT TCTTAGACGT CAGGTGGCAC TTTTCGGGGA

3301 AATGTGCGCG GAACCCCTAT TTGTTTATTT TTCTAAATAC ATTCAAATAT

3351 GTATCCGCTC ATGAGACAAT AACCCTGATA AATGCTTCAA TAATATTGAA

3401 AAAGGAAGAG TATGAGTATT CAACATTTCC GTGTCGCCCT TATTCCCTTT

3451 TTTGCGGCAT TTTGCCTTCC TGTTTTTGCT CACCCAGAAA CGCTGGTGAA

3501 AGTAAAAGAT GCTGAAGATC AGTTGGGTGC ACGAGTGGGT TACATCGAAC

3551 TGGATCTCAA CAGCGGTAAG ATCCTTGAGA GTTTTCGCCC CGAAGAACGT

3601 TTTCCAATGA TGAGCACTTT TAAAGTTCTG CTATGTGGCG CGGTATTATC

3651 CCGTATTGAC GCCGGGCAAG AGCAACTCGG TCGCCGCATA CACTATTCTC

3701 AGAATGACTT GGTTGAGTAC TCACCAGTCA CAGAAAAGCA TCTTACGGAT

3751 GGCATGACAG TAAGAGAATT ATGCAGTGCT GCCATAACCA TGAGTGATAA

3801 CACTGCGGCC AACTTACTTC TGACAACGAT CGGAGGACCG AAGGAGCTAA

3851 CCGCTTTTTT GGACAACATG GGGGATCATG TAACTCGCCT TGATCGTTGG

3901 GAACCGGAGC TGAATGAAGC CATACCAAAC GACGAGCGTG ACACCAGGAT

3951 GCCTGTAGCA ATGGCAACAA CGTTGCGCAA ACTATTAACT GGCGAACTAC

4001 TTACTCTAGC TTCCCGGCAA CAATTAATAG ACTGGATGGA GGCGGATAAA

4051 GTTGCAGGAC CACTTCTGCG CTCGGCCCTT CCGGCTGGCT GGTTTATTGC

4101 TGATAAATCT GGAGCCGGTG AGCGTGGGTC TCGCGGTATC ATTGCAGCAC

4151 TGGGGCCAGA TGGTAAGCCC TCCCGTATCG TAGTTATCTA CACGACGGGG

4201 AGTCAGGCAA CTATGGATGA ACGAAATAGA CAGATCGCTG AGATAGGTGC

4251 CTCACTGATT AAGCATTGGT AACTGTCAGA CCAAGTTTAC TCATATATAC

4301 TTTAGATTGA TTTAAAACTT CATTTTTAAT TTAAAAGGAT CTAGGTGAAG

4351 ATCCTTTTTG ATAATCTCAT GACCAAAATC CCTTAACGTG AGTTTTCGTT

4401 CCACTGAGCG TCAGACCCCG TAGAAAAGAT CAAAGGATCT TCTTGAGATC

4451 CTTTTTTTCT GCGCGTAATC TGCTGCTTGC AAACAAAAAA ACCACCGCTA

4501 CCAGCGGTGG TTTGTTTGCC GGATCAAGAG CTACCAACTC TTTTTCCGAA

4551 GGTAACTGGC TTCAGCAGAG CGCAGATACC AAATACTGTT CTTCTAGTGT

4601 AGCCGTAGTT AGGCCACCAC TTCAAGAACT CTGTAGCACC GCCTACATAC

4651 CTCGCTCTGC TAATCCTGTT ACCAGTGGCT GCTGCCAGTG GCGATAAGTC

4701 GTGTCTTACC GGGTTGGACT CAAGACGATA GTTACCGGAT AAGGCGCAGC
```

TABLE 15-continued

| Nucleotide sequence of pMelBacA-H-SEMAL (6622 bp) (SEQ ID NO:42) |
|---|
| 4751 GGTCGGGCTG AACGGGGGGT TCGTGCACAC AGCCCAGCTT GGAGCGAACG |
| 4801 ACCTACACCG AACTGAGATA CCTACAGCGT GAGCTATGAG AAAGCGCCAC |
| 4851 GCTTCCCGAA GGGAGAAAGG CGGACAGGTA TCCGGTAAGC GGCAGGGTCG |
| 4901 GAACAGGAGA GCGCACGAGG GAGCTTCCAG GGGGAAACGC CTGGTATCTT |
| 4951 TATAGTCCTG TCGGGTTTCG CCACCTCTGA CTTGAGCGTC GATTTTTGTG |
| 5001 ATGCTCGTCA GGGGGGCGGA GCCTATGGAA AAACGCCAGC AACGCGGCCT |
| 5051 TTTTACGGTT CCTGGCCTTT TGCTGGCCTT TTGCTCACAT GTTCTTTCCT |
| 5101 GCGTTATCCC CTGATTCTGT GGATAACCGT ATTACCGCCT TTGAGTGAGC |
| 5151 TGATACCGCT CGCCGCAGCC GAACGACCGA GCGCAGCGAG TCAGTGAGCG |
| 5201 AGGAAGCATC CTGCACCATC GTCTGCTCAT CCATGACCTG ACCATGCAGA |
| 5251 GGATGATGCT CGTGACGGTT AACGCCTCGA ATCAGCAACG GCTTGCCGTT |
| 5301 CAGCAGCAGC AGACCATTTT CAATCCGCAC CTCGCGGAAA CCGACATCGC |
| 5351 AGGCTTCTGC TTCAATCAGC GTGCCGTCGG CGGTGTGCAG TTCAACCACC |
| 5401 GCACGATAGA GATTCGGGAT TTCGGCGCTC CACAGTTTCG GGTTTTCGAC |
| 5451 GTTCAGACGT AGTGTGACGC GATCGGTATA ACCACCACGC TCATCGATAA |
| 5501 TTTCACCGCC GAAAGGCGCG GTGCCGCTGG CGACCTGCGT TTCACCCTGC |
| 5551 CATAAAGAAA CTGTTACCCG TAGGTAGTCA CGCAACTCGC CGCACATCTG |
| 5601 AACTTCAGCC TCCAGTACAG CGCGGCTGAA ATCATCATTA AAGCGAGTGG |
| 5651 CAACATGGAA ATCGCTGATT TGTGTAGTCG GTTTATGCAG CAACGAGACG |
| 5701 TCACGGAAAA TGCCGCTCAT CCGCCACATA TCCTGATCTT CCAGATAACT |
| 5751 GCCGTCACTC AACGCAGCA CCATCACCGC GAGGCGGTTT TCTCCGGCGC |
| 5801 GTAAAAATGC GCTCAGGTCA AATTCAGACG GCAAACGACT GTCCTGGCCG |
| 5851 TAACCGACCC AGCGCCCGTT GCACCACAGA TGAAACGCCG AGTTAACGCC |
| 5901 ATCAAAAATA ATTCGCGTCT GGCCTTCCTG TAGCCAGCTT TCATCAACAT |
| 5951 TAAATGTGAG CGAGTAACAA CCCGTCGGAT TCTCCGTGGG AACAAACGGC |
| 6001 GGATTGACCG TAATGGGATA GGTCACGTTG GTGTAGATGG GCGCATCGTA |
| 6051 ACCGTGCATC TGCCAGTTTG AGGGGACGAC GACAGTATCG GCCTCAGGAA |
| 6101 GATCGCACTC CAGCCAGCTT TCCGGCACCG CTTCTGGTGC CGGAAACCAG |
| 6151 GCAAAGCGCC ATTCGCCATT CAGGCTGCGC AACTGTTGGG AAGGGCGATC |
| 6201 GGTGCGGGCC TCTTCGCTAT TACGCCAGCT GGCGAAAGGG GGATGTGCTG |
| 6251 CAAGGCGATT AAGTTGGGTA ACGCCAGGGT TTTCCCAGTC ACGACGTTGT |
| 6301 AAAACGACGG GATCTATCAT TTTTAGCAGT GATTCTAATT GCAGCTGCTC |
| 6351 TTTGATACAA CTAATTTTAC GACGACGATG CGAGCTTTTA TTCAACCGAG |
| 6401 CGTGCATGTT TGCAATCGTG CAAGCGTTAT CAATTTTTCA TTATCGTATT |
| 6451 GTTGCACATC AACAGGCTGG ACACCACGTT GAACTCGCCG CAGTTTTGCG |
| 6501 GCAAGTTGGA CCCGCCGCGC ATCCAATGCA AACTTTCCGA CATTCTGTTG |
| 6551 CCTACGAACG ATTGATTCTT TGTCCATTGA TCGAAGCGAG TGCCTTCGAC |
| 6601 TTTTTCGTGT CCAGTGTGGC TT |

The above description of the invention is intended to be illustrative and not limiting. Various changes or modifications in the embodiments described may occur to those skilled in the art. These can be made without departing from the spirit or scope of the invention. Accordingly, it is intended that the invention be limited only to the extent required by the claims and the applicable rules of law.

The invention claimed is:

1. An isolated semaphorin protein comprising a Sema domain having at least 90% identity to amino acids 45 to 545 of SEQ ID NO: 3.

2. The isolated semaphorin protein as claimed in claim 1 having an amino acid sequence of SEQ ID NO: 3.

3. The isolated semaphorin protein as claimed in claim 1, wherein the protein further comprises an immunoglobulin domain.

4. The isolated semaphorin protein as claimed in claim 1, wherein the protein further comprises a transmembrane domain.

* * * * *